US012612658B2

(12) United States Patent
Jain et al.

(10) Patent No.: US 12,612,658 B2
(45) Date of Patent: Apr. 28, 2026

(54) RNA REPLICATION USING TRANSCRIPTION POLYMERASES

(71) Applicant: The Board of Trustees of the Leland Stanford Junior University, Stanford, CA (US)

(72) Inventors: Nimit Jain, Redwood City, CA (US); Andrew Z. Fire, Redwood City, CA (US); Lucas R. Blauch, Redwood City, CA (US); Sindy K. Y. Tang, Redwood City, CA (US); Karen L Artiles, Redwood City, CA (US); Julia T. Garcia-Daou, Redwood City, CA (US); Y. Whitney Yin, Redwood City, CA (US); Michal R. Szymanski, Redwood City, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 842 days.

(21) Appl. No.: 17/624,782

(22) PCT Filed: Jul. 7, 2020

(86) PCT No.: PCT/US2020/041046
§ 371 (c)(1),
(2) Date: Jan. 4, 2022

(87) PCT Pub. No.: WO2021/007233
PCT Pub. Date: Jan. 14, 2021

(65) Prior Publication Data
US 2022/0259645 A1 Aug. 18, 2022

Related U.S. Application Data

(60) Provisional application No. 62/872,540, filed on Jul. 10, 2019.

(51) Int. Cl.
*C12Q 1/68* (2018.01)
*C12P 19/34* (2006.01)
*C12Q 1/6853* (2018.01)

(52) U.S. Cl.
CPC ............ *C12Q 1/6853* (2013.01); *C12P 19/34* (2013.01); *C12Y 207/07006* (2013.01)

(58) Field of Classification Search
CPC .............................. C12Q 1/6853; C12P 19/34; C12Y 207/07006
See application file for complete search history.

(56) References Cited

U.S. PATENT DOCUMENTS 4,957,858 A 9/1990 Chu et al.
5,665,545 A 9/1997 Malek et al.
5,869,320 A 2/1999 Studier et al.
6,300,074 B1 10/2001 Gold et al.
6,828,127 B2 12/2004 Cheynet-Sauvion et al.
7,323,310 B2 1/2008 Peters et al.
2011/0300554 A1 12/2011 Joyce

OTHER PUBLICATIONS

Biebricher (Biebricher & Luce; EMBO journal, vol. 15, pp. 3458-3465, 1996) (Year: 1996).*
Konarska (Konarska & Sharp; Cell, vol. 63, pp. 609-618, Nov. 2, 1990) (Year: 1990).*
Sarcar (Sarcar & Miller; Scientific Reports, vol. 8, pp. 1-13, Sep. 17, 2018 (Year: 2018).*
Tao (Tao et al.; Lab Chip; vol. 15, pp. 3934-3940, 2015) (Year: 2015).*
Biebricher et al. (1996) Template-free generation of RNA species that replicate with bacteriophage T7 RNA polymerase. EMBO J. 15(13):3458-3465.
Davanloo et al. (1984) Cloning and expression of the gene for bacteriophage T7 RNA polymerase. Proc Natl Acad Sci USA 81(7):2035-2039.
Konarska et al. (1990) Structure of RNAs replicated by the DNA-dependent T7 RNA polymerase. Cell 63(3):609-618.
Wang et al. (2017) Lirex: A Package for Identification of Long Inverted Repeats in Genomes. Genomics Proteomics Bioinformatics 15(2):141-146.
Watanabe et al. (2018) Complex repeat structure promotes hyper-amplification and amplicon evolution through rolling-circle replication. Nucleic Acids Res. 46(10):5097-5108.
Jain et al. (2020) Transcription polymerase-catalyzed emergence of novel RNA replicons. Science 368, vol. 153, p. 1; and vol. 368(6487):eaay0688. PDF File: pp. 1-11.
Konarska et al. (1989) Replication of RNA by the DNA-dependent RNA polymerase of phage T7. Cell 57(3):423-431.
Horning et al. (2016) Amplification of RNA by an RNA polymerase ribozyme Proc Natl Acad Sci U.S.A. 113(35):9786-9791.
Biebricher et al. (1973) An RNA that Multiplies Indefinitely with DNA-Dependent RNA Polymerase: Selection from a Random Copolymer. Proc. Natl. Acad. Sci. 70:934-938.
Wettich et al. (2001) RNA Species that Replicate with DNA-Dependent RNA Polymerase from *Escherichia coli*. Biochemistry. 40:3308-3315.
Kakimoto et al. (2015) Abnormal rapid non-linear RNA production induced by T7 RNA polymerase in the absence of an exogenous DNA template. AIP Conf. Proc. 1649:113-115.
Gholamalipour et al. (2018) 3' end additions by T7 RNA polymerase are RNA self-templated, distributive and diverse in character-RNA-Seq analyses. Nucleic Acids Res. 46:9253-9263.

(Continued)

*Primary Examiner* — Jehanne S Sitton
*Assistant Examiner* — Bailey Buchanan
(74) *Attorney, Agent, or Firm* — Jenny L. Buchbinder; Bozicevic, Field & Francis LLP

(57) ABSTRACT

Compositions and methods for amplifying RNA by replication using transcription polymerases are disclosed. Such replicated RNAs can be used in various applications such as RNAi therapeutics, diagnostic probes, RNA sequencing, directed evolution of RNA aptamers without intermediate conversion to DNA, and RNA vaccines. The transcription polymerases comprise T7 bacteriophage RNA polymerase.

18 Claims, 48 Drawing Sheets

Specification includes a Sequence Listing.

(56) References Cited

OTHER PUBLICATIONS

Priano et al. (1987) Evolution of the RNA Coliphages: The Role of Secondary Structures during RNA Replication. Cold Spring Harb. Symp. Quant. Biol. 52:321-330.
Cazenave et al. (1994) RNA template-directed RNA synthesis by T7 RNA polymerase. Proc. Natl. Acad. Sci. U.S.A. 91:6972-6976.
Sumper et al. (1975) Evidence for de novo production of self-replicating and environmentally adapted RNA structures by bacteriophage Qbeta replicase. Proc. Natl. Acad. Sci. 72:162-166.
Arnaud-Barbe et al. (1998) "Transcription of RNA templates by T7 RNA polymerase", Nucleic Acids Res., 26(15):3550-3554.

* cited by examiner

Experimental design

No-template-added, high concentration T7 RNAP reactions in parallel

**Visible turbidity
at 24 hours indicates
RNA synthesis**

Effect of extra 3' base addition on replication of chemically synthesized Y2 RNA

G strand
5' GG━━GG 3'    GGAAAAUUUCAAGAUCAGGGCUUGAAAUUUUACAAAAUUUCAAGCCCUGAUCUUGAAAUUUUGG C strand
5' CC━━CC 3'    CCAAAAUUUCAAGAUCAGGGCUUGAAAUUUUGUAAAAUUUCAAGCCCUGAUCUUGAAAUUUUCC Model for RNA replication by T7 RNAP with subterminal *de novo* initiation

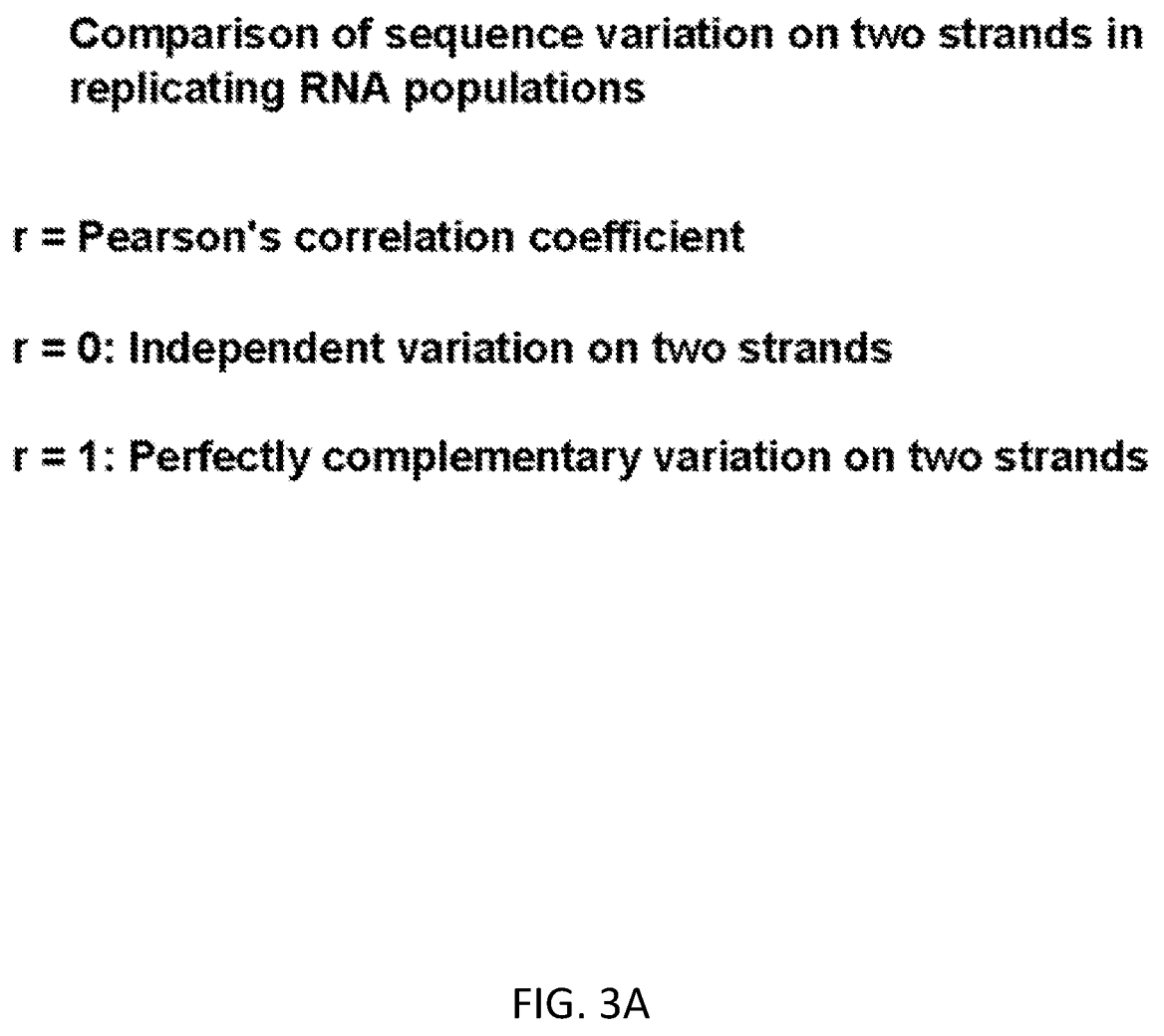

Comparison of sequence variation on two strands in replicating RNA populations r = Pearson's correlation coefficient r = 0: Independent variation on two strands r = 1: Perfectly complementary variation on two strands

FIG. 3A

Sequences of X RNA and Y2 RNA used to test structural requirements for RNA replication
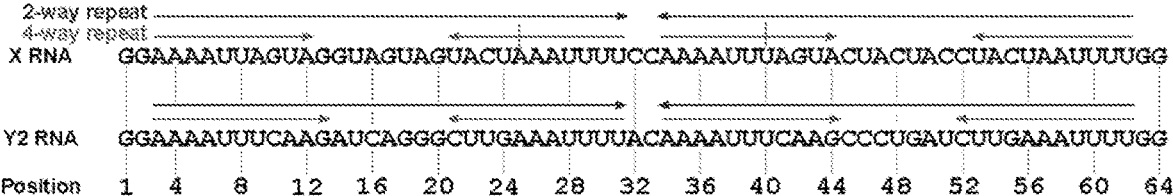
Test of 2-way repeat requirement
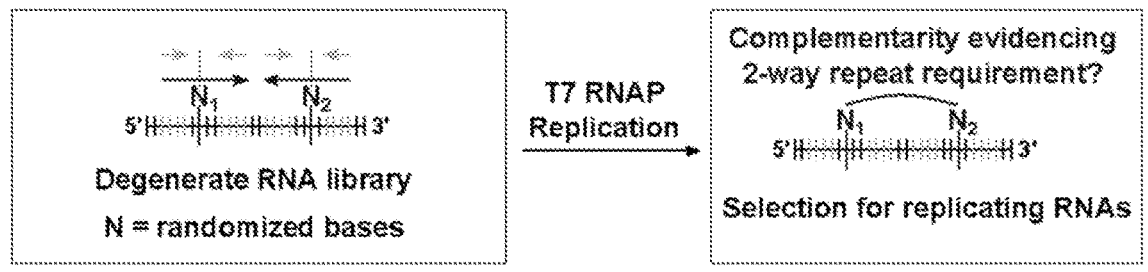
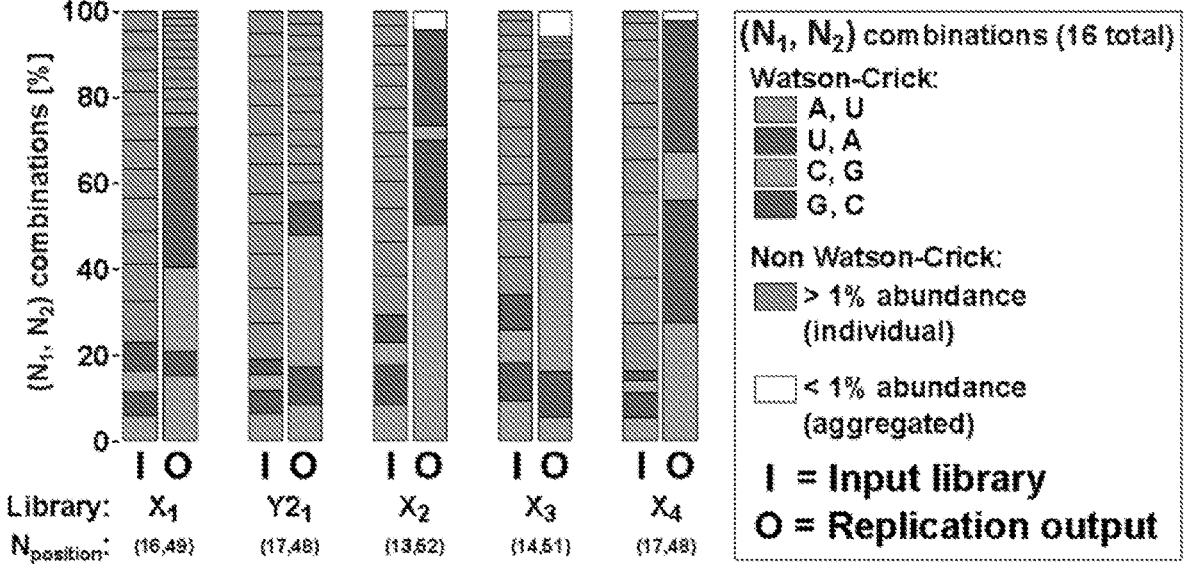
FIG. 4A Test of 4-way repeat requirement
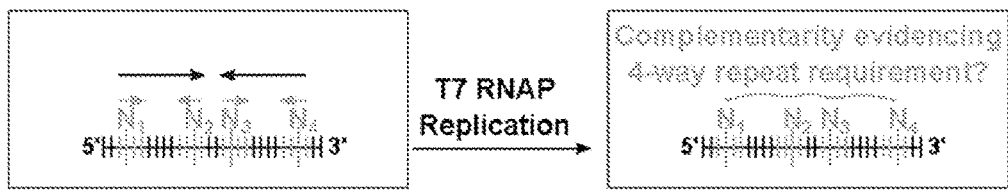
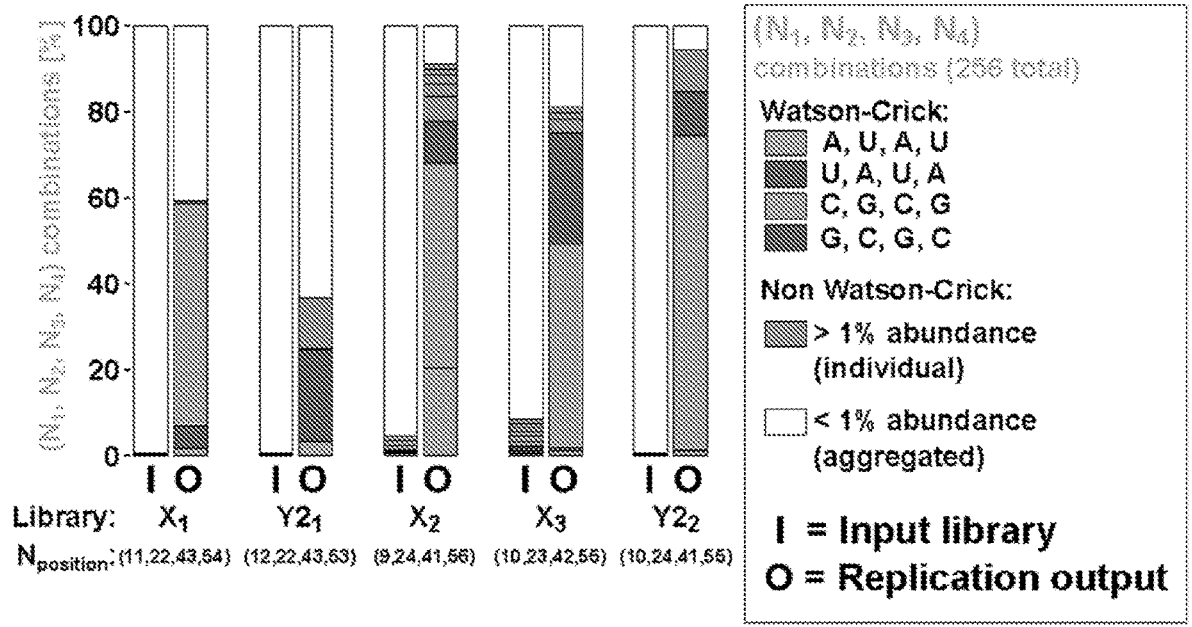
FIG. 4B Additional test of 4-way repeat
requirement
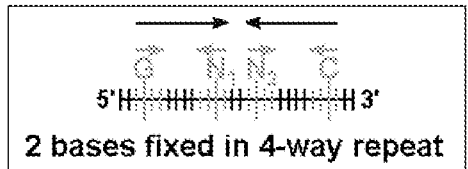
2 bases fixed in 4-way repeat
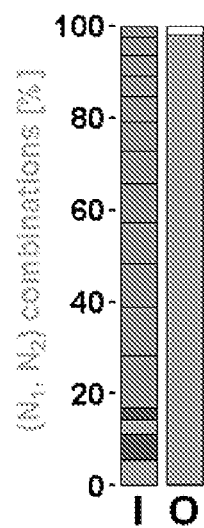
Library:    $X_4$
$N_{position}$:    (23,42)
$(N_1, N_2)$ combinations (16 total)
Watson-Crick:
A, U
U, A
C, G
G, C
Non Watson-Crick:
> 1% abundance
(individual)
< 1% abundance
(aggregated)
I   = Input library
O = Replication output
FIG. 4C Schematic for test of dimer formation mechanism

Sequence agreement between dimer halves (bulk analysis)

| Starting diverse template pool | $X_1$ | | $Y2_1$ | |
|---|---|---|---|---|
| Experimental replicate | 1 | 2 | 1 | 2 |
| Dimers with A=B [%] | 87 | 88 | 88 | 88 |

FIG. 5C

Model for interrupted rolling circle synthesis

Continued RNA synthesis after T7 RNAP jumps from 5' to 3' end of template

RNA Template     RNA Product

Testing the hypothesis that replicating RNAs can originate from DNA seeds

Complex DNA pool

High concentration T7 RNAP reactions
for 4 conditions in parallel:

i.   Unseeded
ii.  Seeded with DNA pool
iii. Seeded with DNase-treated DNA pool
iv.  Seeded with hot alkali-treated DNA pool Drop
reactions → RNA-Seq →

Tube
reactions → RNA-Seq →

Are there novel
RNA species
that match
DNA pool?

Amplification of RNA species upon dilution into fresh T7 RNAP reactions
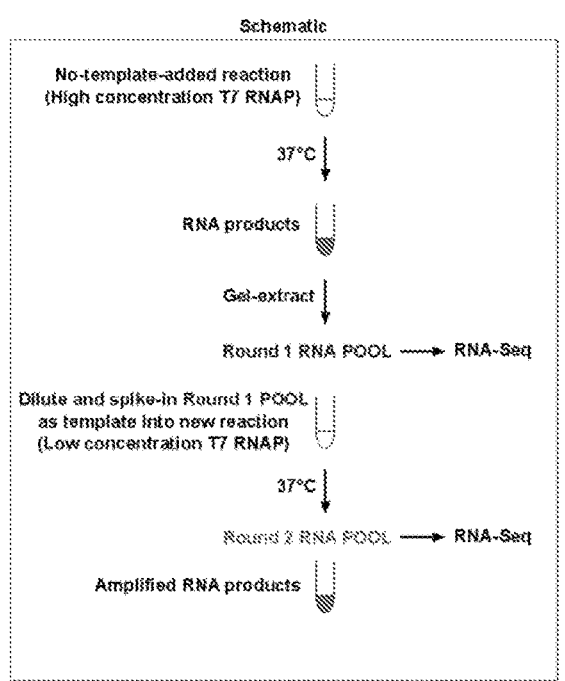
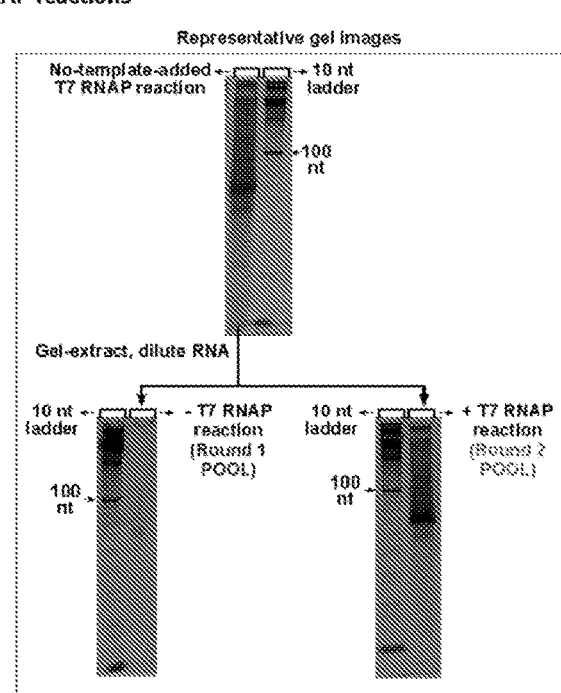
FIG. 8A Sequence correspondence between Round 1 POOL and
Round 2 POOL when distinct RNA species amplified in parallel Schematic Quantification for the most abudant Round 2 POOL RNA species

| Output Pool | % Output reads from most abundant RNA species | Specificity of most abudant output RNA species to input pools (scale from 0 to 1) | | |
|---|---|---|---|---|
| | | 1A | 1B | 1C |
| 2A | 85% | 0.995 | 0.002 | 0.002 |
| 2B | 62% | 0.003 | 0.994 | 0.003 |
| 2C | 87% | 0.001 | 0.011 | 0.988 |

Analysis of junction sequences in RNA dimers
*RNA dimer*
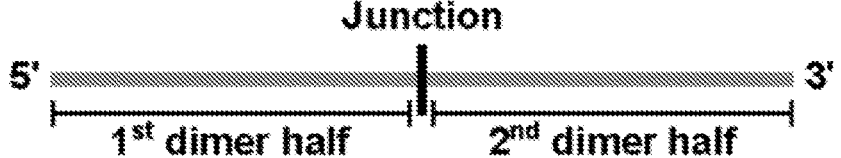
Sequence agreement between dimer junction and dimer 3' end is close to expectation based on random chance
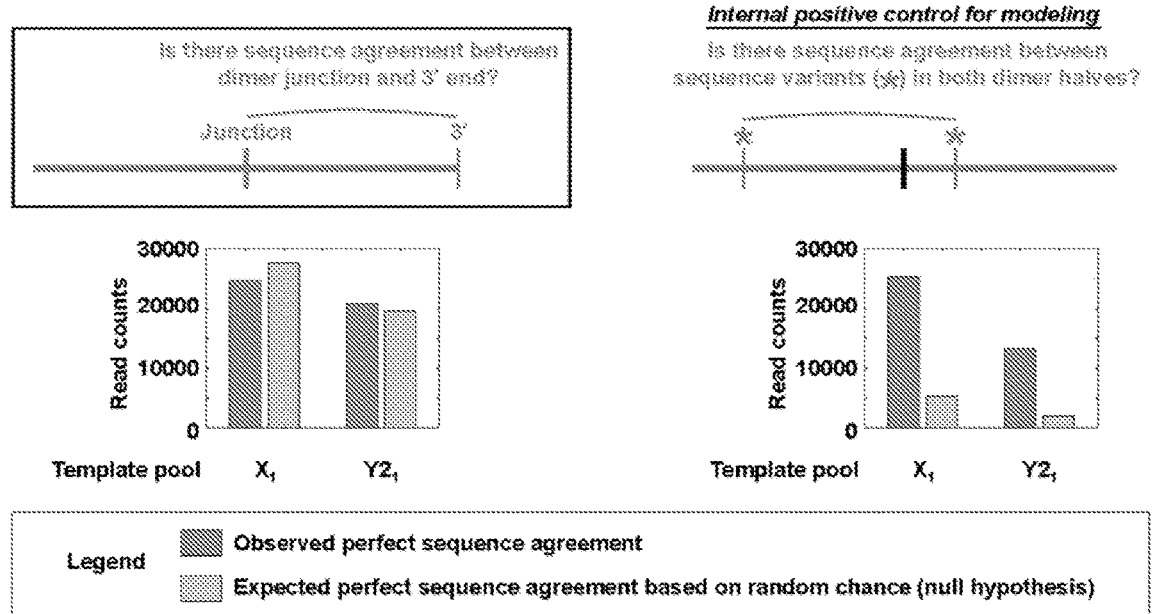
FIG. 14A Example of RNA dimer junction sequences for a particular template in the X₁ diverse pool

|  | | Abbreviation |
|---|---|---|
| G strand sequence | GGAAAGUUAGCAGUGGUAGUGCUAAAUUUCCAAAGUUUAGCACUACCACUGCUAAUUUGG | ━━━━━━━ |
| C strand sequence | CCAAAUUAGCAGUGGUAGUGCUAAAUUUCCAAAGUUUAGCACUACCACUGCUAAUUUCC | ∿∿∿∿∿∿∿ |

G strand dimers (10 most abundant shown, sorted by decreasing counts)

| Junction | 3' end | Counts |
|---|---|---|
| ∿∿∿UU GGGUG  AA∿∿∿UU GGA | | 517 |
| ∿∿∿UU GGGUG  AA∿∿∿UU GGG | | 376 |
| ∿∿∿UU GGGUG  AA∿∿∿UU GG | | 320 |
| ∿∿∿UU GGGUG  AA∿∿∿UU GGGG | | 307 |
| ∿∿∿UU GGGUG  AA∿∿∿UU GGC | | 274 |
| ∿∿∿UU GGGUGG AA∿∿∿UU GGA | | 247 |
| ∿∿∿UU GGGAGG AA∿∿∿UU GGA | | 241 |
| ∿∿∿UU GGCGG  AA∿∿∿UU GGA | | 239 |
| ∿∿∿UU GGGUGG AA∿∿∿UU GGG | | 238 |
| ∿∿∿UU GGUGG  AA∿∿∿UU GGG | | 224 |

C strand dimers (10 most abundant shown, sorted by decreasing counts)

| Junction | 3' end | Counts |
|---|---|---|
| ∿∿∿UU CCUCCC AA∿∿∿UU CC | | 3401 |
| ∿∿∿UU CCUCCC AA∿∿∿UU CCC | | 3198 |
| ∿∿∿UU CCUCCC AA∿∿∿UU CCA | | 1680 |
| ∿∿∿UU CCCCC  AA∿∿∿UU CC | | 1467 |
| ∿∿∿UU CCUCCC AA∿∿∿UU CCG | | 1434 |
| ∿∿∿UU CCCCCC AA∿∿∿UU CC | | 930 |
| ∿∿∿UU CCUCCC AA∿∿∿UU CCCC | | 749 |
| ∿∿∿UU CCCCC  AA∿∿∿UU CCA | | 686 |
| ∿∿∿UU CCCCC  AA∿∿∿UU CCC | | 680 |
| ∿∿∿UU CCCCC  AA∿∿∿UU CCG | | 605 |

FIG. 14B

Digital readout of templated RNA replication catalyzed by T7 RNAP in drop format +T7 RNAP, Template targeted at 3.31 copies/drop +T7 RNAP, Template targeted at 0.39 copies/drop

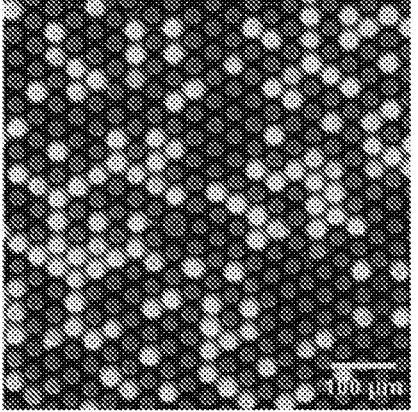
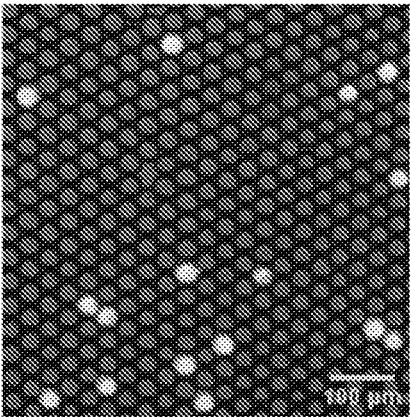

% drops fluorescent = 36.3 ± 3.2
(n=16 images with ~430 drops each)

% drops fluorescent = 6.6 ± 1.1
(n=12 images with ~540 drops each)

Negative controls

No T7 RNAP, Template targeted at 3.49 copies/drop

+T7 RNAP, No template added

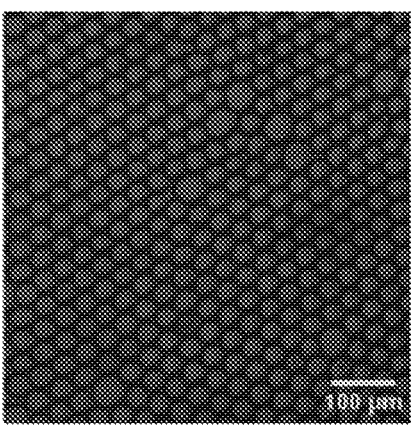
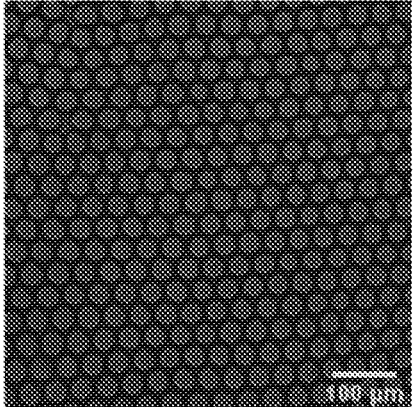

% drops fluorescent = 0.0 ± 0.0
(n=13 images with ~575 drops each)

% drops fluorescent = 0.1 ± 0.1
(n=16 images with ~570 drops each)

Another example of an RNA species which matches a known genome and was isolated from a no-template-added T7 RNAP reaction

FIG. 20B

RNA REPLICATION USING TRANSCRIPTION POLYMERASES

FEDERALLY SPONSORED RESEARCH AND DEVELOPMENT

This invention was made with Government support under contracts GM037706 and GM130366 awarded by the National Institutes of Health. The Government has certain rights in the invention.

BACKGROUND

Transcription polymerases (DNA-dependent RNA polymerases) mediate information transfer from DNA to RNA across the tree of life. In addition to their expected activity to linearly amplify RNA from DNA templates, some transcription polymerases can also exponentially replicate particular RNA templates, as has been demonstrated in vitro for transcription polymerases from *Escherichia coli* (Biebricher et al. (1973) Proc. Natl. Acad. Sci. 70:934-938, Wettich et al. (2001) Biochemistry 40:3308-3315) and bacteriophage T7 (Konarska et al. (1989) Cell 57:423-431, Konarska et al. (1990) Cell 63:609-618, Biebricher et al. (1996) EMBO J. 15:3458-3465, Kakimoto et al. (2015) AIP Conf. Proc. 1649:113-115). By RNA replication is meant a template-regenerating process that includes (i) full-length copying of an RNA template followed by (ii) the resulting RNA copy serving as template for new synthesis of full-length RNA copies. Importantly, such an RNA replication process does not involve DNA.

Historically, the transcription polymerase of T7 bacteriophage (T7 RNAP) has served as a model enzyme for its DNA-dependent RNA polymerase activity (Steitz (2004) Curr. Opin. Struct. Biol. 14:4-9). T7 RNAP also provides a paradigm for investigating RNA replication by transcription polymerases at the molecular level (Konarska et al. (1989), supra; Konarska et al. (1990), supra; Biebricher, et al. (1996), supra). Of note, a chloroplastic transcription polymerase similar to T7 RNAP may be the enzyme that replicates ASBVd, the canonical member of the Avsunviroidae family of viroids (Navarro et al. (2000) Virology 268:218-225).

There remains a need for improved methods of producing RNA for various applications.

SUMMARY

The present invention is based, in part, on the discovery that RNA can be replicated using transcription polymerases. Thus, the present disclosure further pertains to compositions and methods for replicating RNAs of interest for use in various applications such as RNAi therapeutics, diagnostic probes, RNA sequencing, directed evolution of RNA aptamers without intermediate conversion to DNA, and RNA vaccines.

In one aspect, a method of amplifying RNA is provided, the method comprising replicating the RNA in a reaction mixture comprising an RNA polymerase; a set of ribonucleoside triphosphates comprising ATP, CTP, GTP, and UTP, or analogues or derivatives thereof; and an RNA template comprising (i) a 2-way repeat configuration comprising a first inverted repeat, and (ii) a 4-way repeat configuration comprising a second inverted repeat that is shorter than the first inverted repeat, wherein each arm of the 2-way repeat comprises the second inverted repeat.

In certain embodiments, the transcription polymerase is a bacteriophage transcription polymerase, for example, including without limitation a T7 bacteriophage RNA polymerase such as encoded by gene 1 of the T7 bacteriophage. In some embodiments, the reaction mixture contains no DNA.

In other embodiments, a method of amplifying RNA is provided, the method comprising replicating the RNA in a reaction mixture comprising: an RNA polymerase; a set of ribonucleoside triphosphates comprising ATP, CTP, GTP, and UTP, or analogues or derivatives thereof; and a DNA seed, wherein an RNA template for replication is generated by transcription of the DNA seed. In some embodiments, the DNA seed comprises a nucleotide sequence of interest and a 4-way repeat unit. In certain embodiments, the DNA seed is added to the reaction mixture such that the RNA polymerase generates a first RNA comprising the 4-way repeat unit by transcription of the DNA seed. In some embodiments, the method further comprises carrying out a first round of 3'-extension of the first RNA to produce a second RNA comprising a second 4-way repeat unit; and carrying out a second round of 3'-extension of the second RNA to produce the RNA template comprising the 4-way repeat configuration.

In certain embodiments, the RNA template ranges from 50 to 120 nucleotides in length.

In certain embodiments, each repeat region within the 2-way repeat configuration ranges from 10 to 60 nucleotides in length, or any length within this range such as 10, 15, 20, 25, 30, 35, 40, 45, 50, 55, or 60 nucleotides in length. In certain embodiments, each repeat region within the 2-way repeat configuration ranges from about 20% to about 50% of the total length of the replicating RNA, or any length within this range such as 20%, 22%, 23%, 24%, 26%, 28%, 30%, 32%, 34%, 36%, 38%, 40%, 42%, 44%, 46%, 48%, or 50% of the total length of the replicating RNA.

In certain embodiments, each repeat region within the 4-way repeat configuration ranges from about 5 to about 25 nucleotides in length, or any length within this range such as 5, 6, 7, 8, 9, 10, 11, 12, 13, 14, 15, 16, 17, 18, 19, 20, 21, 22, 23, 24, or 25 nucleotides in length. In certain embodiments, each repeat region within the 4-way repeat configuration ranges from about 5% to about 20% of the total length of the replicating RNA, or any length within this range such as 5%, 6%, 7%, 8%, 9%, 10%, 11%, 12%, 13%, 14%, 15%, 16%, 17%, 18%, 19%, or 20% of the total length of the replicating RNA.

In certain embodiments, the replicating RNA in the reaction comprises a G RNA strand comprising two G bases at or close to the 5' end and two G bases at or close to the 3' end, and a complementary C RNA strand comprising two C bases at or close to the 5' end and two C bases at or close to the 3' end.

In certain embodiments, the method further comprises adding at least one base to the 3' ends of the G RNA strand or the C RNA strand. In some embodiments, an adenine base is added to the 3' end of the G RNA strand or the C RNA strand. In some embodiments, one to three bases are added to the 3' end of the G RNA strand or the C RNA strand.

In certain embodiments, the RNA template is linear.

In certain embodiments, a single RNA or a plurality of RNAs are replicated in the reaction mixture. In some embodiments, the plurality of RNAs are RNA variants.

In certain embodiments, the methods described herein are performed in a microfluidic device. In some embodiments, the microfluidic device comprises a droplet generator. In some embodiments, the method further comprises partitioning a plurality of RNAs into a plurality of droplets. In some embodiments, the RNA is replicated using digital droplet RNA replication.

In certain embodiments, the method further comprises using the amplified RNA for RNA interference, sequencing, expression profiling, a vaccine, or directed evolution of RNA aptamers without intermediate conversion to DNA.

In certain embodiments, the replicating RNA comprises a nucleotide sequence selected from Tables 1, 2, or 4, or a sequence displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto. In some embodiments, the replicating RNA comprises i) a 2-way repeat configuration comprising a first inverted repeat, and (ii) a 4-way repeat configuration comprising a second inverted repeat that is shorter than the first inverted repeat, wherein each arm of the 2-way repeat comprises the second inverted repeat. In some embodiments, the RNA template comprises a G RNA strand comprising two G bases at or close to a 5' end and two G bases at or close to a 3' end of the G RNA strand, or a C RNA strand comprising two C bases at or close to a 5' end and two C bases at or close to a 3' end of the C RNA strand.

In certain embodiments, the method further comprises isolating a replicated RNA from the reaction mixture.

In certain embodiments, the method further comprises substantially purifying a replicated RNA from the reaction mixture.

In certain embodiments, the RNA polymerase is at concentration of at least about 1 nM in the reaction mixture.

In another aspect, a composition for generating replicating RNA templates is provided, the composition comprising: a) an RNA template for RNA replication, wherein the RNA template comprises (i) a 2-way repeat configuration comprising a first inverted repeat, and (ii) a 4-way repeat configuration comprising a second inverted repeat that is shorter than the first inverted repeat, wherein each arm of the 2-way repeat comprises the second inverted repeat; b) an RNA polymerase; c) a DNA seed comprising a nucleotide sequence of interest and a 4-way repeat unit; and d) a set of ribonucleoside triphosphates comprising ATP, CTP, GTP, and UTP, or analogues or derivatives thereof. In some embodiments, the set of ribonucleoside triphosphates further comprises a modified nucleotide or nucleotide analogue.

In another aspect, a composition for generating replicating RNA templates is provided, the composition comprising: a) an RNA polymerase; b) a DNA seed; and c) a set of ribonucleoside triphosphates comprising ATP, CTP, GTP, and UTP, or analogues or derivatives thereof. In some embodiments, the DNA seed comprises a nucleotide sequence of interest and a 4-way repeat unit.

BRIEF DESCRIPTION OF THE DRAWINGS

FIG. 1A) Experimental scheme. No DNA or RNA template was explicitly added to any reaction. FIG. 1B) Representative denaturing gel image illustrates the different migration of products from no-template T7 RNAP reactions that had been set up in parallel. M=marker (denatured 10 base-pair DNA ladder), nt=nucleotides. FIG. 1C) Results from high-throughput sequencing of 24 reactions which were set up in parallel. Sequenced pools were dominated by 1 to 3 RNA species, with a species referring to a heterogenous population of closely related RNA sequences. RNA species constituting >5% of any sequenced pool are depicted. FIG. 1D) Sequence diversity of RNA species. "Reference sequence" for each RNA species refers to a canonical, abundant sequence defining the species. Also depicted is the relation of reference sequences to Y RNA, a previously characterized sequence that can be replicated by T7 RNAP (Konarska et al. *Cell* 63, 609-618 (1990)). FIG. 1E) Length distribution of reference sequences. FIG. 1F) RNA species are constituted by sequences of both strand orientations. Plot shows fraction of reads from each reaction aligning to the canonical reference sequences (x axis) and to their reverse complements (y axis). Diagonal lines (0.5:1, 1:1 and 2:1) are shown as visual aids. FIG. 1G) Structural similarity of RNA species. Arrows denote 2-way- and 4-way-repeats. Arrows of the same length pointing in opposite directions denote complementary repeats. Five representative examples of RNA species are shown, along with 2-way- and 4-way-repeats. Prime (') denotes reverse complement of reference sequence for a species. Histograms quantify 2-way- and 4-way-repeat lengths for all RNA species. FIGS. 1C-1F follow the same color coding for RNA species.

FIG. 2A) Gel-based assay showing increased T7 RNAP reaction products after T4 RNA ligase 1 (T4Rnl1)-catalyzed addition of pAp (adenosine 3',5'-diphosphate) to the Y2 RNA G and C strands. M=marker (denatured 10 base-pair DNA ladder), nt=nucleotides, ng=nanograms. All gels were processed in parallel. Bar plot shows background-subtracted average gel intensity for duplicate reactions for each experimental condition, with the whiskers representing the range of the duplicates. FIG. 2B) "Subterminal de novo initiation" model for RNA replication by T7 RNAP. $N_{+}1$ denotes one or a few extra bases at the 3' end. Light gray=G strand with 3' extra bases, dark gray=C strand with 3' extra bases.

FIGS. 3A-3C show that replicating RNA populations consist of multiple replication-competent sequences. (FIG. 3A) Test of the hypothesis that RNAs with sequence variation compared to the reference sequence can also be replicated. Copying of RNAs with sequence variation is expected to result in complementary sequence variant profiles for the two replicating RNA strands. The degree of complementarity may be quantitatively assessed using the sample Pearson correlation coefficient. Plots in (FIG. 3B) and (FIG. 3C) show the distribution of sequence variants for two amplified RNA populations: FIG. 3B) RNA species obtained from a templated T7 RNAP reaction starting with the chemically synthesized Y2 RNA G strand with an extra 3' adenine, and FIG. 3C) RNA species 2.1 from FIG. 1. Frequencies at which sequence variants were detected are shown per position for three distinct types of variants: transitions (A→G, C→U, G→A, U→C), transversions (A→C or U, C→A or G, G→C or U, U→A or G) and single-base deletions. Symmetry between the sequence variants (complementary variation) on the two strands and values close to 1 for the sample Pearson correlation coefficient support the hypothesis that templates bearing sequence variants can be replicated by T7 RNAP. 95% confidence intervals for the sample Pearson correlation coefficient were estimated by non-parametric bootstrapping to be 0.76-0.96 for the RNA population in (FIG. 3B) and 0.96-0.999 for the population in (FIG. 3C).

FIGS. 4A-4D show that 2-way- and 4-way-repeat configurations are required for efficient replication of X and Y2 RNA. Six degenerate libraries ($X_1$-$X_4$, $Y2_1$-$Y2_2$) were constructed by randomizing the base identities at a subset of sequence positions in either X RNA or $Y_2$ RNA. G strand sequences for X and Y2 RNA are shown, with putative 2-way- (blue) and 4-way- (orange) repeats. X RNA has an imperfect 4-way repeat (vertical orange bars show sequence insertions). Positions chosen for base randomization in X RNA and Y2 RNA are listed below the degenerate library names in FIGS. 4A-4C. Degenerate libraries were used as templates in T7 RNAP reactions, and RNA populations before replication (represented by "I") and after replication (represented by "0") were sequenced. FIG. 4A) 2-way repeat requirement was tested by randomizing bases at two potentially base pairing positions in the 2-way repeat (but outside the 4-way repeat). FIG. 4B) 4-way repeat requirement was tested by randomizing bases at four potentially base pairing positions in the 4-way repeat. Post-replication, a limited diversity of FIG. 4A) 2 base- and FIG. 4B) 4 base-combinations was dominant at the randomized base positions. FIG. 4C) The X4 mutant library contained randomized bases at only two of the four potentially base pairing positions in the 4-way repeat. Post-replication, only the 2 base combination (C, G) was dominant at the randomized base positions leading to the 4 base Watson-Crick combination (G,C,G,C) in the 4-way repeat. In panels (FIGS. 4A-4C), the different Watson-Crick base combinations are shown by unique colors. An abundant non-Watson-Crick base combination (>1% relative abundance within the sequenced pool) is shown individually in gray. Infrequent non-Watson-Crick base combinations (<1% individual relative abundance within the sequenced pool) are summed together and shown in white. FIG. 4D) Shape-shifting model. The 2-way repeat requirement (panel A) evidences a long hairpin RNA secondary structure whereas the 4-way repeat requirement (FIGS. 4B and 4C) evidences an alternative RNA secondary structure which is also important over the course of replication.

FIGS. 5A-5E show that T7 RNAP can use the same template molecule processively to instruct multiple rounds of RNA synthesis. RNA dimers containing two full-length repeats of the template sequence are synthesized in T7 RNAP reactions initiated with single-copy RNA templates (RNA monomers). FIG. 5A) Two possible types of mechanisms for RNA dimer synthesis: uni-templated and bi-templated. A uni-templated mechanism involves the same monomer molecule templating synthesis of each half of the RNA dimer. A bi-templated mechanism involves two different monomer template molecules templating synthesis of each half of the dimer. FIG. 5B) Experimental scheme to assess RNA dimer synthesis. When RNA dimers are obtained using a diversity of monomer templates in the same T7 RNAP reaction, uni- and bi-templated mechanisms have distinct predictions for sequence agreement between the two halves of RNA dimers (half 1=half 2 for uni-templated synthesis; half 1=half 2 in proportion to the template concentration for bi-templated synthesis). Experiments were performed in duplicate with each of two starting diverse monomer pools, $X_1$ and $Y2_1$. Each pool contained randomized bases at a distinct set of six positions. Base identities at these six positions were used for calculating sequence agreement between the two dimer halves. FIG. 5C) Observed sequence agreement between the two dimer halves by analyzing all dimers together in bulk. FIG. 5D) Observed sequence agreement between the two dimer halves by analyzing dimers individually for the 10 most abundant RNA templates present in the sequenced pools. No mismatches were allowed in calculation of sequence agreement for panels (FIG. 5C) and (FIG. 5D). The strong sequence concordance between the dimer halves (panels (FIG. 5C) and (FIG. 5D)) supports uni-templated synthesis as the dominant mechanism for RNA dimer synthesis. FIG. 5E)

Model for uni-templated synthesis is in effect an interrupted rolling circle mechanism involving linear rather than circular templates.

Figure 6A:
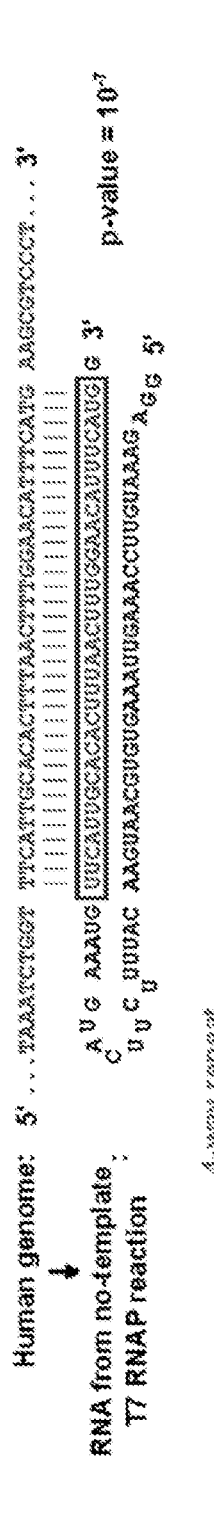
Figure 6C:
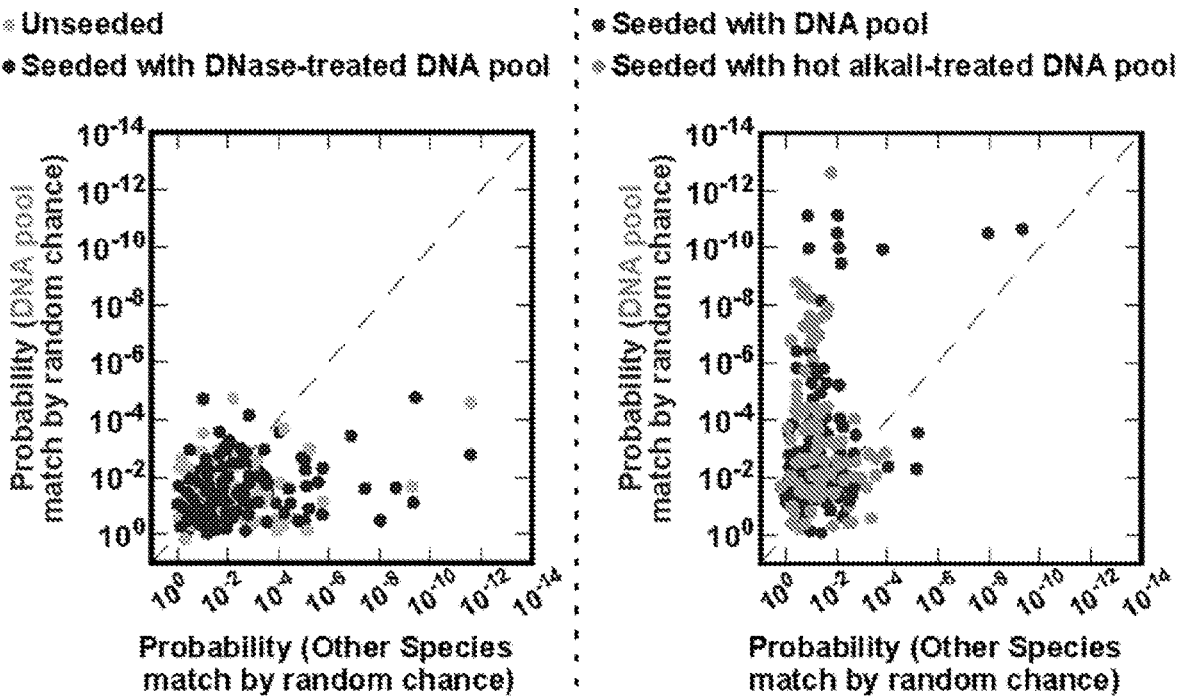
Figure 6D:
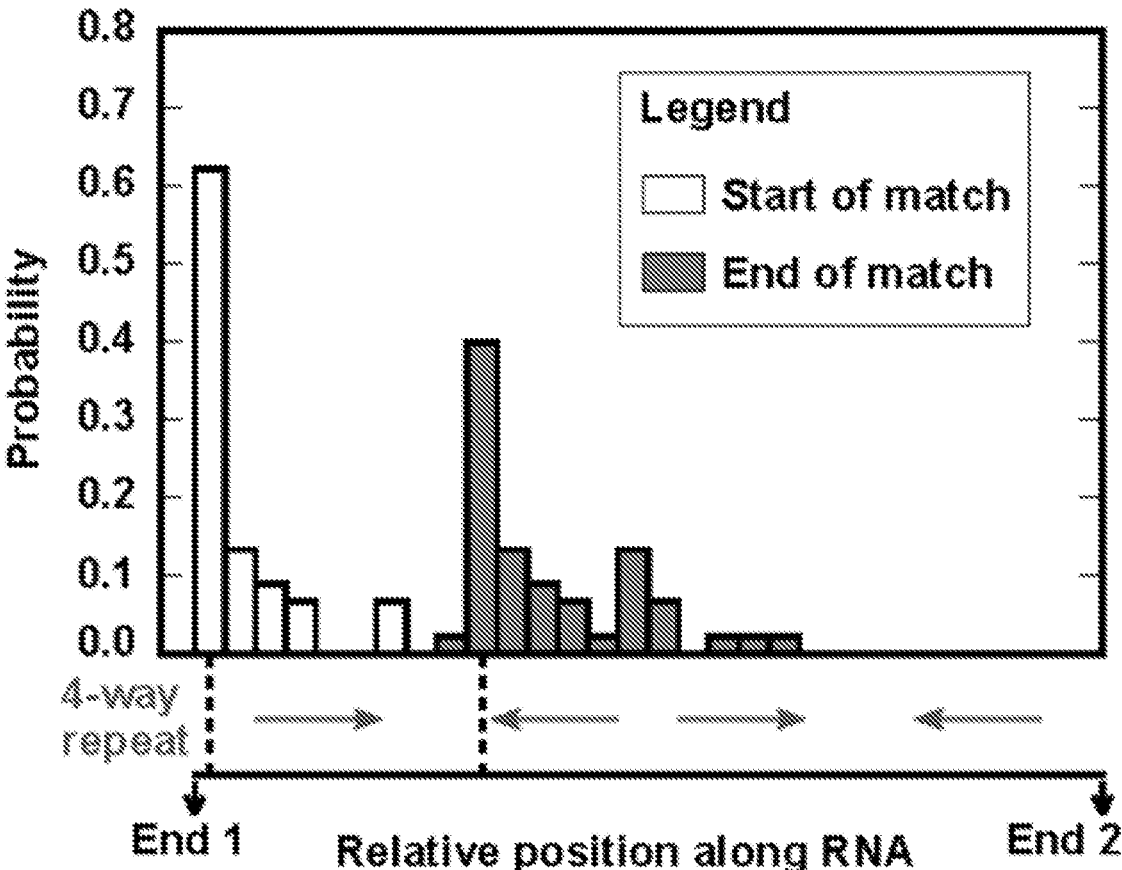
Figure 6F:
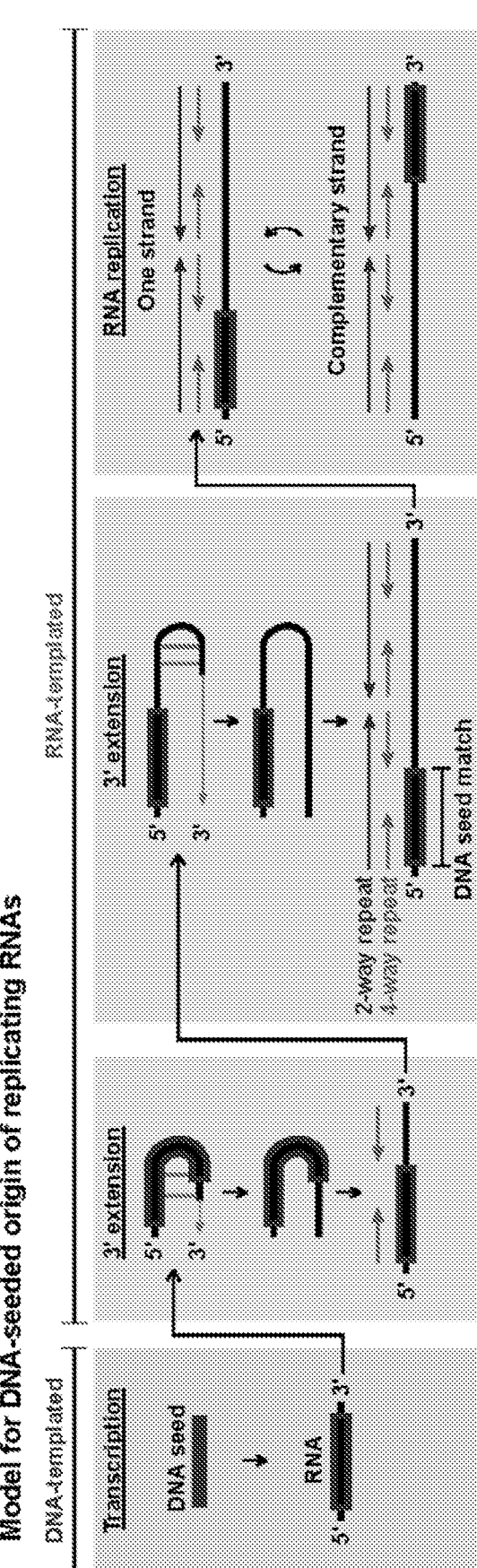

FIGS. 6A-6F show the origin of replicating RNAs via molecular evolution. FIG. 6A) Some RNA species from no-template-added T7 RNAP reactions match known genomes. An example RNA species matching the human genome is shown. p-value is based on alignment to the RefSeq genomic database. The long hairpin shown is a predicted structure. Convention for annotating RNAs: (i) Best match to a known genome is shown in a red box; (ii) 4-way repeats are shown as orange arrows, with orange asterisks indicating sequence disagreements between 4-way repeats; (iii) Long 2-way repeats, though present, are not shown for simplicity. FIG. 6B) Experimental schematic to test the hypothesis that replicating RNAs can originate through partial instruction from DNA seeds. A complex DNA pool (consisting of DNA derived from three nematode species, yeast, coliphage lambda and a plasmid) was used to seed high concentration T7 RNAP reactions. Controls performed in parallel were (i) Unseeded, (ii) Seeded with DNase-treated DNA pool, and (iii) Seeded with hot alkali-treated DNA pool. Bulk tube- and microfluidic drop-reactions were set up in parallel for each experimental condition, followed by RNA-Seq and bioinformatic analysis. FIG. 6C) Scatter plots show results of alignment of RNA species (individual points) to our designed DNA seed pool (y axis) and to all available RefSeq genome assemblies excluding those in our DNA seed pool (x axis). RNA species with strong sequence matches to input DNA seeds (upper left regions of scatter plots) were specifically observed for reactions seeded with the DNA pool or the hot alkali-treated DNA pool compared to the two negative controls (unseeded reactions and reactions seeded with DNase-treated DNA pool). 220 RNA species are shown on the left scatter plot, and 204 on the right scatter plot. For each seeded or unseeded condition, RNA species from two different aggregated drop reactions (corresponding to two time points) are shown together on scatter plots. FIG. 6D) Histogram shows relative locations of seed matches and 4-way repeats for RNA species from aggregated drop reactions seeded with the DNA pool or the hot alkali-treated DNA pool. RNA species with >=26 bases matching to our DNA pool were used for the histogram because matches in this length range were absent for RNA species from the negative controls. Seed matches start close to either 5' or 3' end of replicating RNAs and extend up to the second 4-way repeat unit that is encountered from the start of the match. FIG. 6E) Examples of RNA species that originated from different sources in our designed DNA pool. The shown RNA species were all isolated from drop reactions, either from the "Seeded with DNA pool" condition or from the "Seeded with hot alkali-treated DNA pool" condition. Annotation of RNAs as in panel (A). p-values are based on alignment to a database consisting of sequences expected to be present in our DNA seed pool. FIG. 6F) Proposed mechanism for the origin of replicating RNAs.

Figure 7:
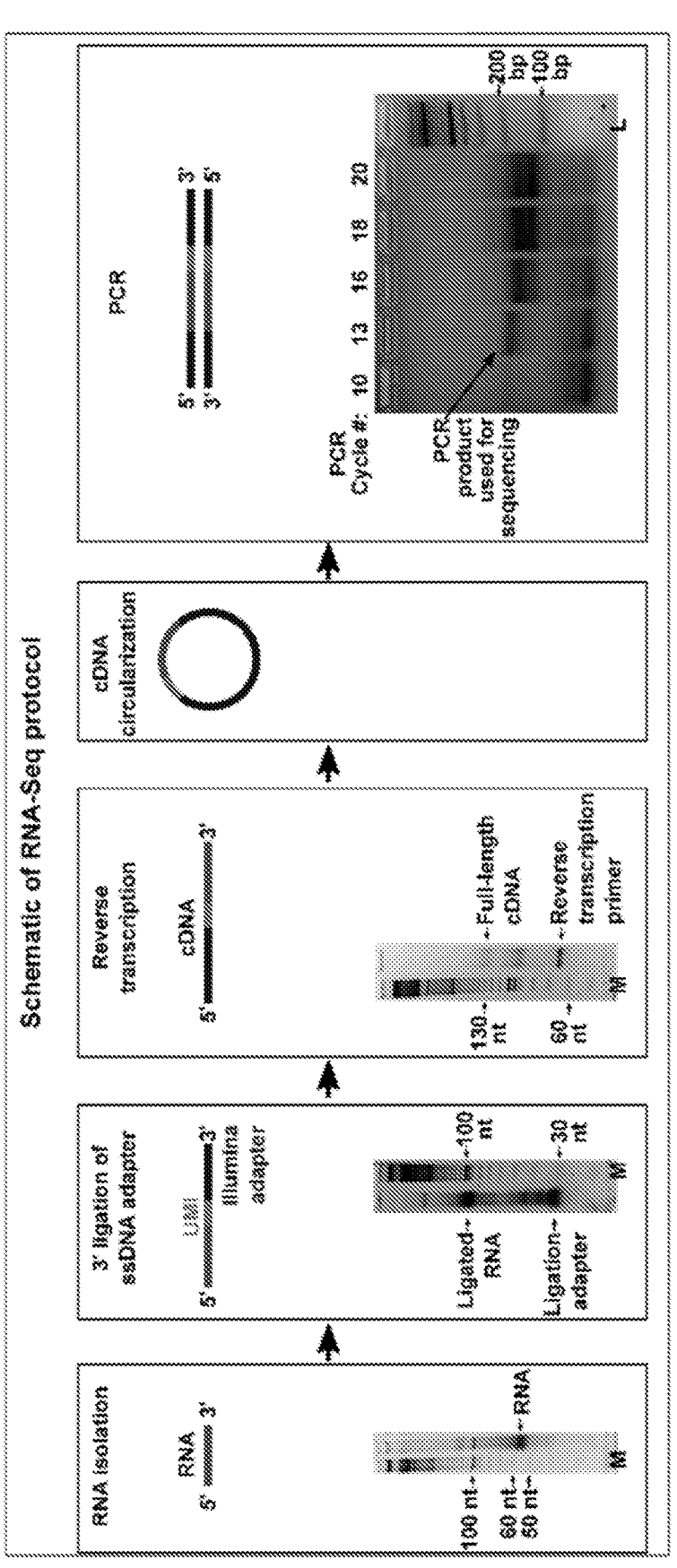

FIG. 7 shows a schematic of the RNA-Seq protocol. Representative gel images at various steps of the protocol are shown. UMI=Unique Molecular Identifier (a degenerate 6- or 8-base molecular barcode), M=marker (denatured 10 base-pair DNA ladder), L=100 base-pair ladder, bp=base-pair, nt=nucleotides.

Figure 8B:
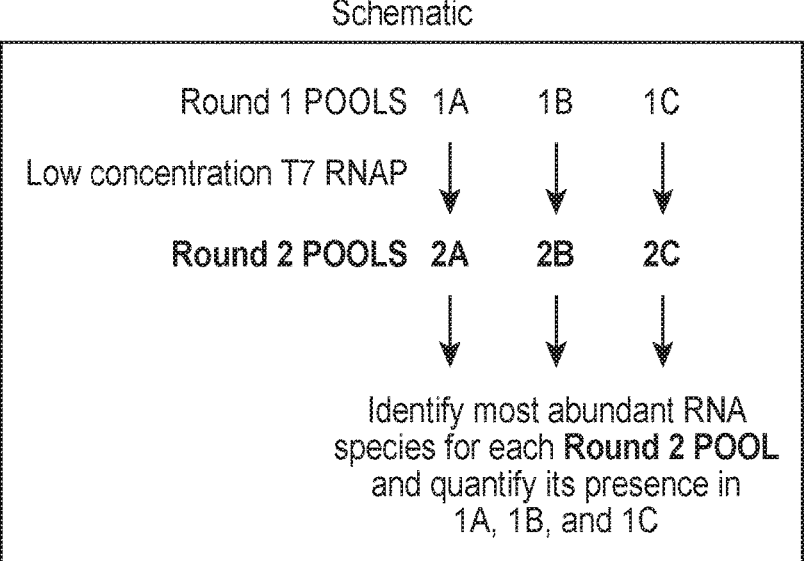

FIGS. 8A-8B show sustained and templated propagation of RNA species originally isolated from no-template-added, high concentration T7 RNAP reactions. FIG. 8A) Regeneration of RNA species upon dilution into fresh, low concentration T7 RNAP reactions. Gels for the (−) and (+) T7 RNAP reactions with the diluted Round 1 RNA pool as template were processed in parallel. nt=nucleotides. FIG. 8B) Templated growth of RNA species. Three Round 1 RNA pools (originally isolated from no-template-added reactions) were propagated in parallel. The Round 2 products from a particular reaction corresponded in sequence to the Round 1 RNA pool used as template for that reaction. Sequences for the most abundant RNA species in the three Round 2 pools are listed in Table 4.

Figure 9:
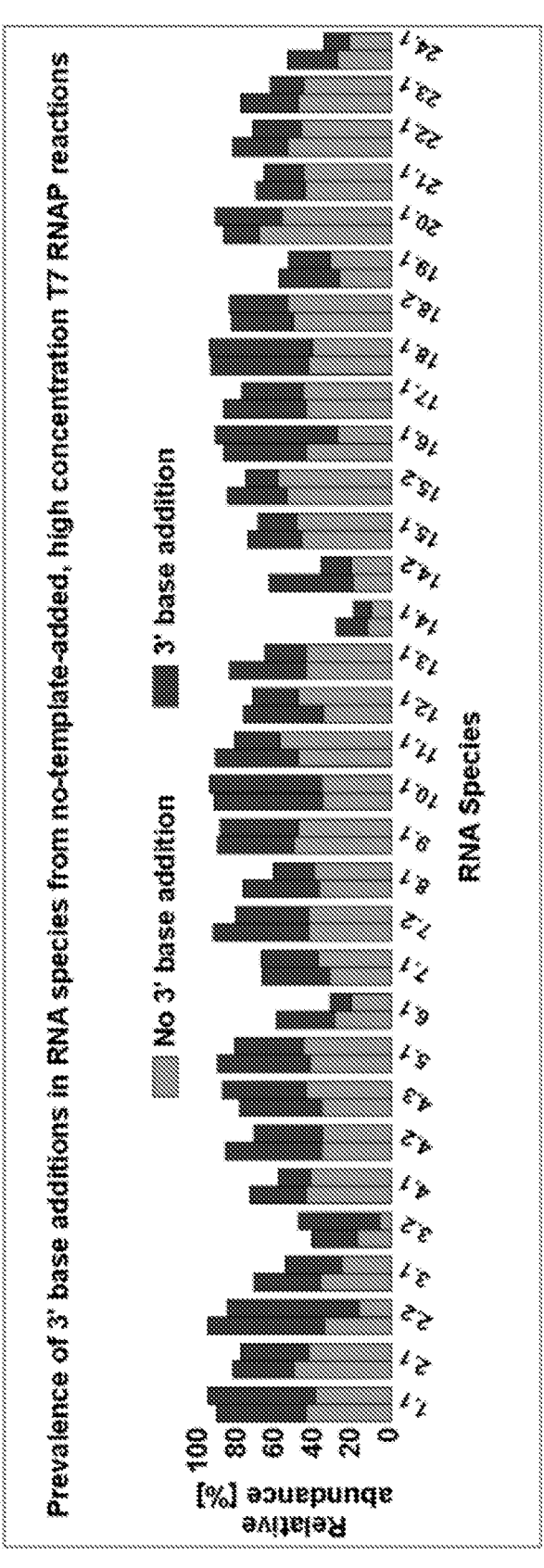

FIG. 9 shows pervasive addition of bases at the 3' end in RNA species from no-template-added reactions. RNA species from FIG. 1 further analyzed here. For each RNA reference sequence (first bar for each RNA species) and its reverse complement (second bar), the percentage of reads terminating (at positions −2, −1 and 0 from the 3' end) without further base additions ("No 3' base addition" in gray) is shown alongside the percentage of reads terminating with base additions ("3' base addition" in navy).

Figure 10A:
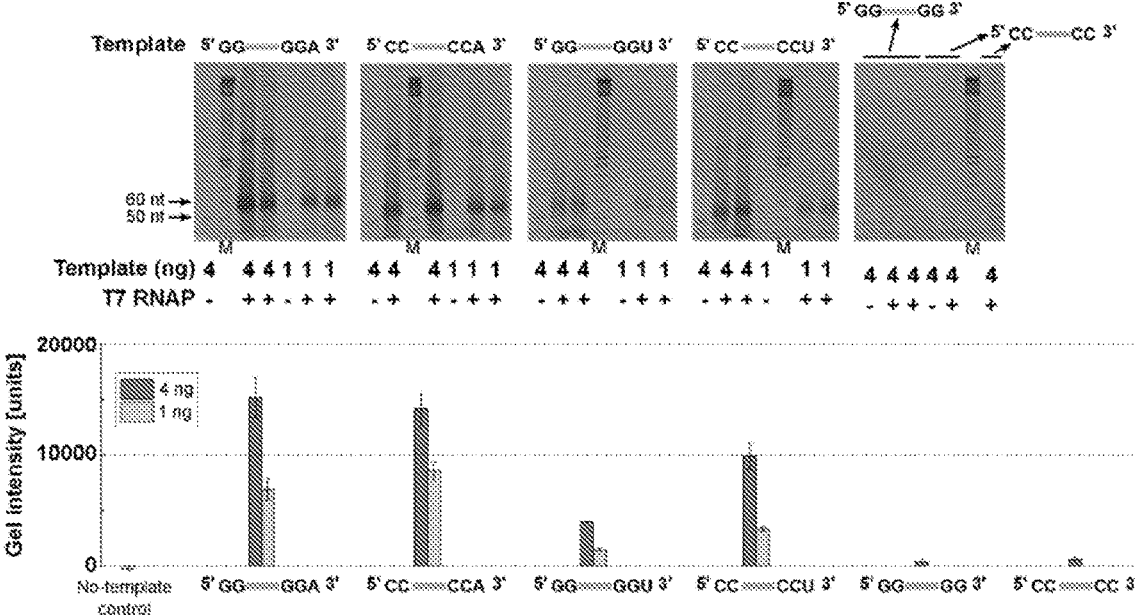
Figure 10B:
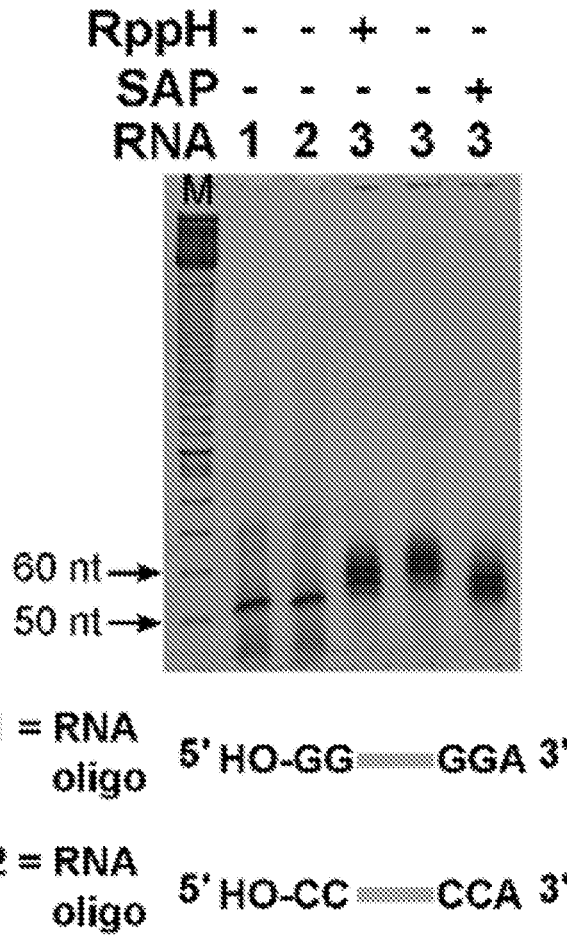
Figure 10C:
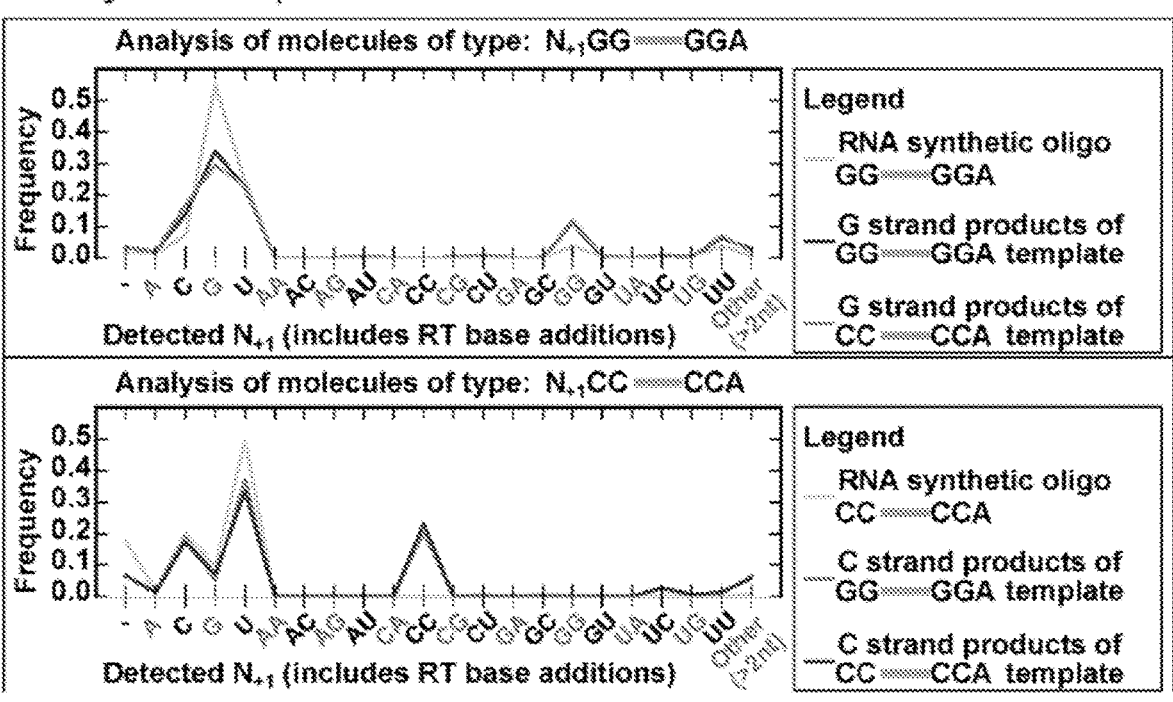

FIGS. 10A-10C show the role of 3' base additions in RNA replication by T7 RNAP. FIG. 10A) Gel-based assay showing increased T7 RNAP reaction products after chemical addition of a single adenine or uracil to the 3' ends of the Y2 RNA G and C strands. M=marker (denatured 10 base-pair DNA ladder), nt=nucleotides, ng=nanograms. All gels were processed in parallel. Bar plot shows background—subtracted average gel intensity for duplicate reactions for each experimental condition, with the whiskers representing the range of the duplicates. FIG. 10B) The RNA 5' chemical end partly accounts for differences in electrophoretic mobility between Y2 RNA replication products (5'-triphosphate) and chemically synthesized Y2 RNA oligos (5'-hydroxyl). RppH=RNA 5' Pyrophosphohydrolase, SAP=Shrimp Alkaline Phosphatase, M=marker (denatured 10 base-pair DNA ladder), nt=nucleotides, OH=hydroxyl. FIG. 10C) Sequence distributions at 5' ends of Y2 RNA synthetic oligos and Y2 RNA replication products. Complementary strand products (e.g. G strand products of CC-CCA template or C strand products of GG-GGA template) do not evidence 5' uracil above background levels observed for synthetic oligos, supporting a subterminal initiation model over terminal initiation. A background of 5' extensions in the detected sequences was expected from reverse transcriptase activity during RNA-seq library preparation. RT=reverse transcriptase.

Figure 11A:
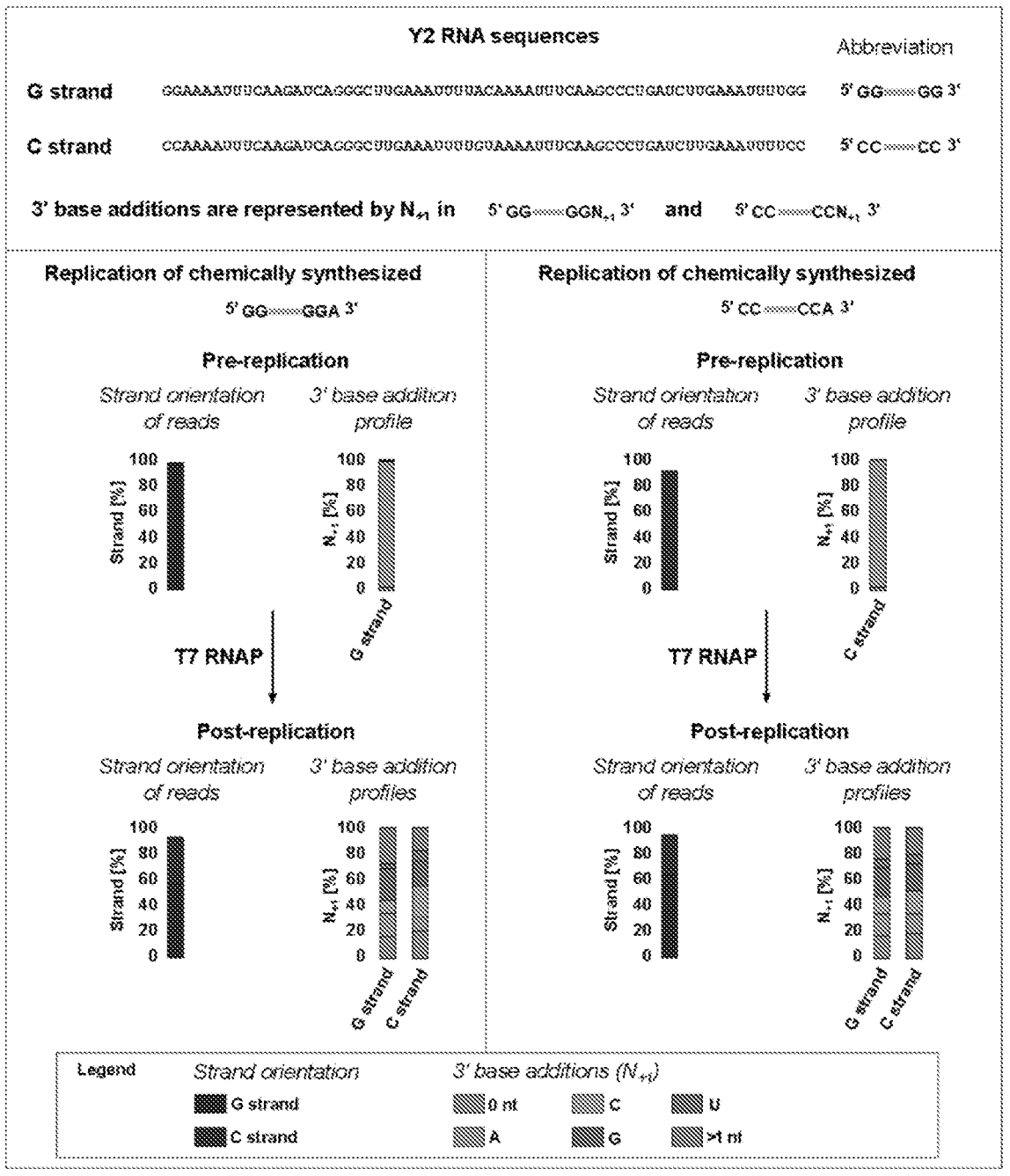
Figure 11B:
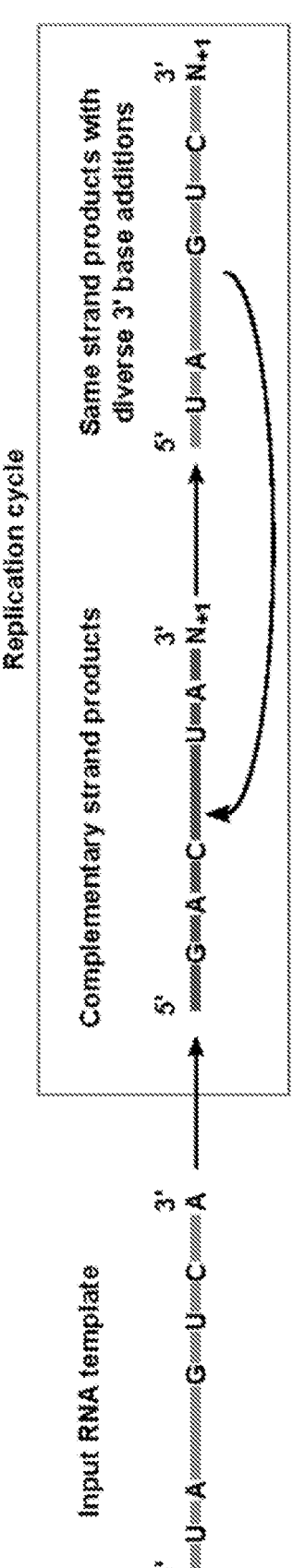

FIGS. 11A-11B show a sequencing-based readout showing a key signature of RNA replication: synthesis of RNA molecules of both strand orientations in the same reaction starting with FIG. 11A (left) chemically synthesized Y2 RNA G strand with an extra 3' adenine or FIG. 11A (right) chemically synthesized Y2 RNA C strand with an extra 3' adenine. nt=nucleotides. FIG. 11B shows a schematic to explain how newly synthesized RNA products of both strand orientations can be identified in the same T7 RNAP reaction.

Figure 12:
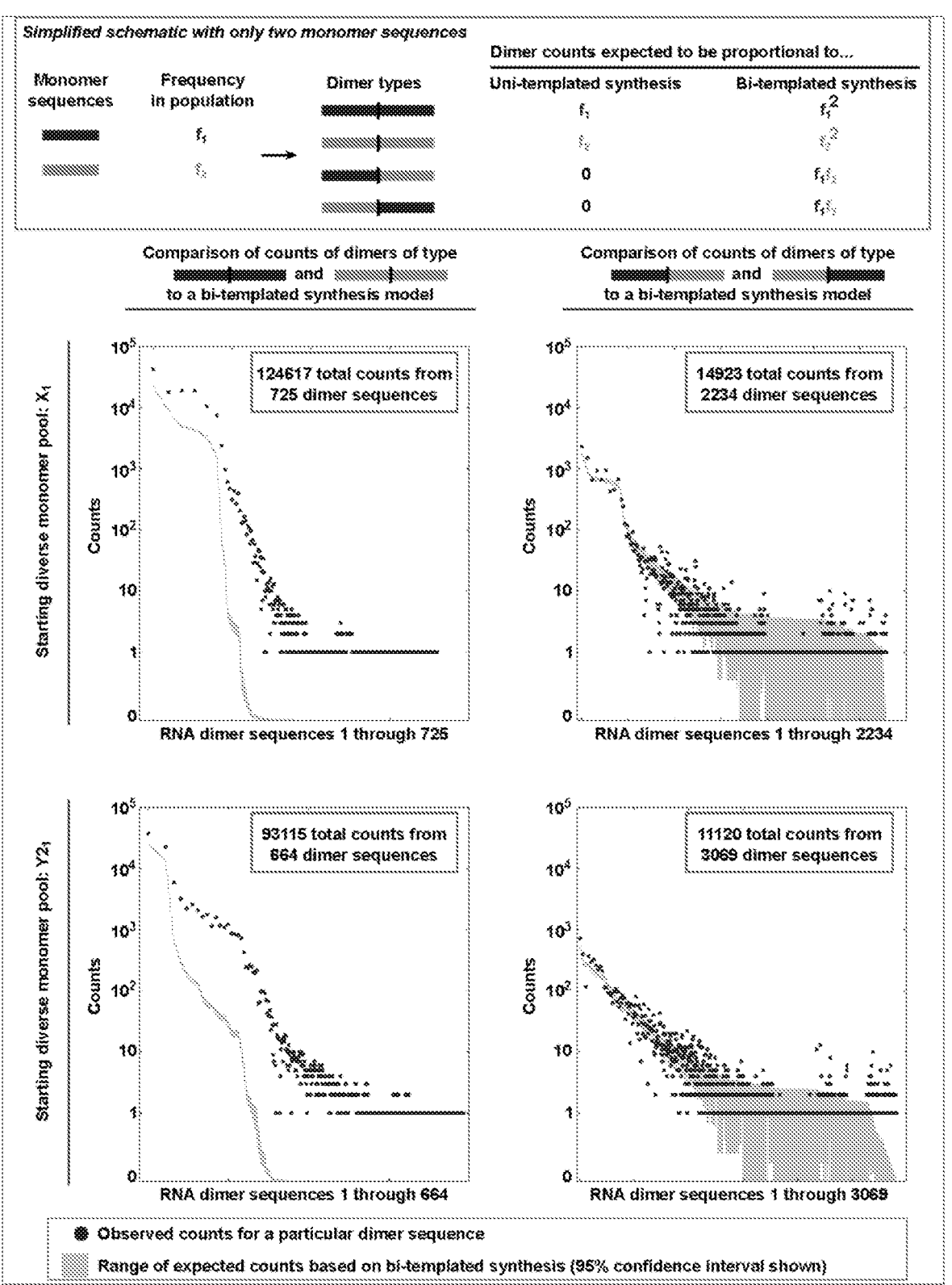

FIG. 12 shows further evidence for uni-templated synthesis being the dominant mechanism for generation of RNA dimers. In the schematic at the top, blue- and red-colored bars represent different sequences which may have one or more mismatches with respect to each other. Data shown are for dimers obtained starting with the diverse monomer template pools $X_1$ and $Y2_1$. Individual dimer sequences are plotted at different coordinates along the x axis. The vast majority of dimer sequences were concordant, i.e. had perfect sequence agreement between the first and second dimer halves. The observed counts for these concordant dimers are shown in the left plots (each blue dot represents a particular dimer sequence), along with a range of counts expected from bi-templated synthesis generating the concordant dimers (yellow area). The consistent overrepresentation of observed concordant dimer counts over expected counts, across a diversity of dimer sequences, supports a uni-templated mechanism. Conversely, such overrepresentation was not observed when analysis was performed on the small fraction of dimer sequences where there was sequence disagreement between the first and second dimer halves (plots on the right).

Figure 13A:
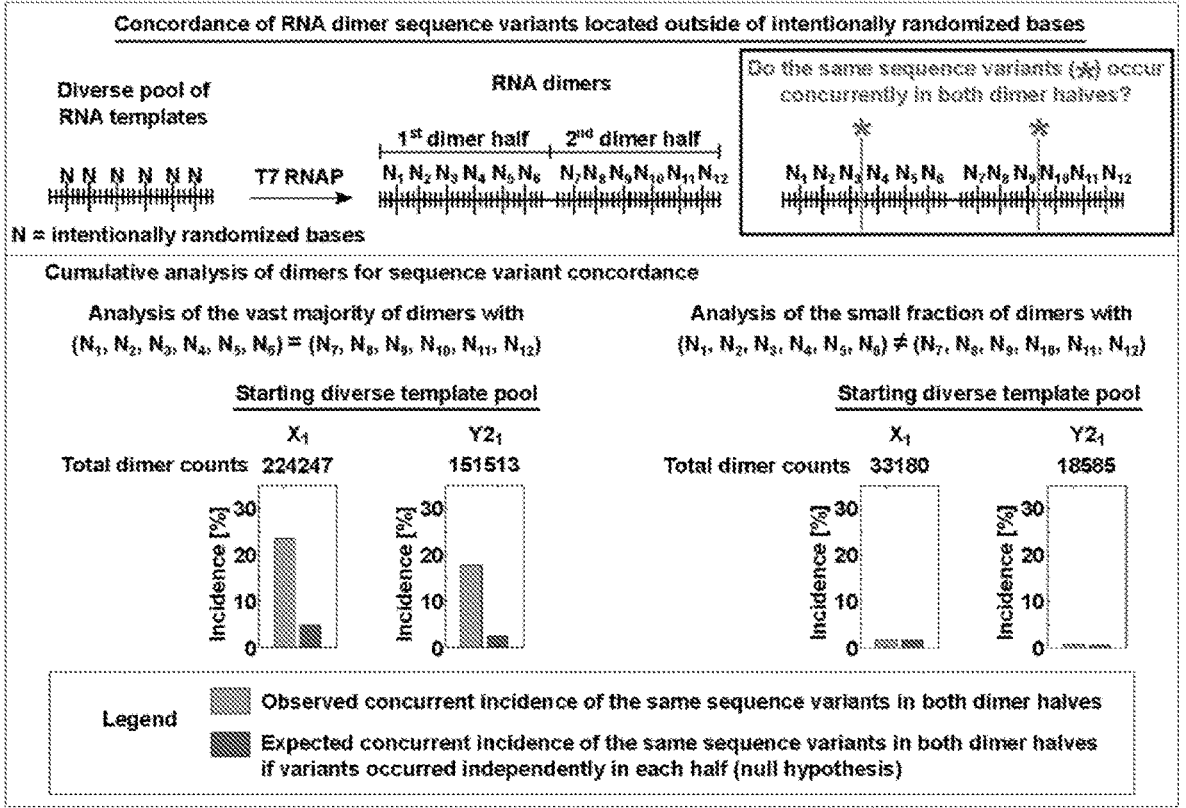
Figure 13B:
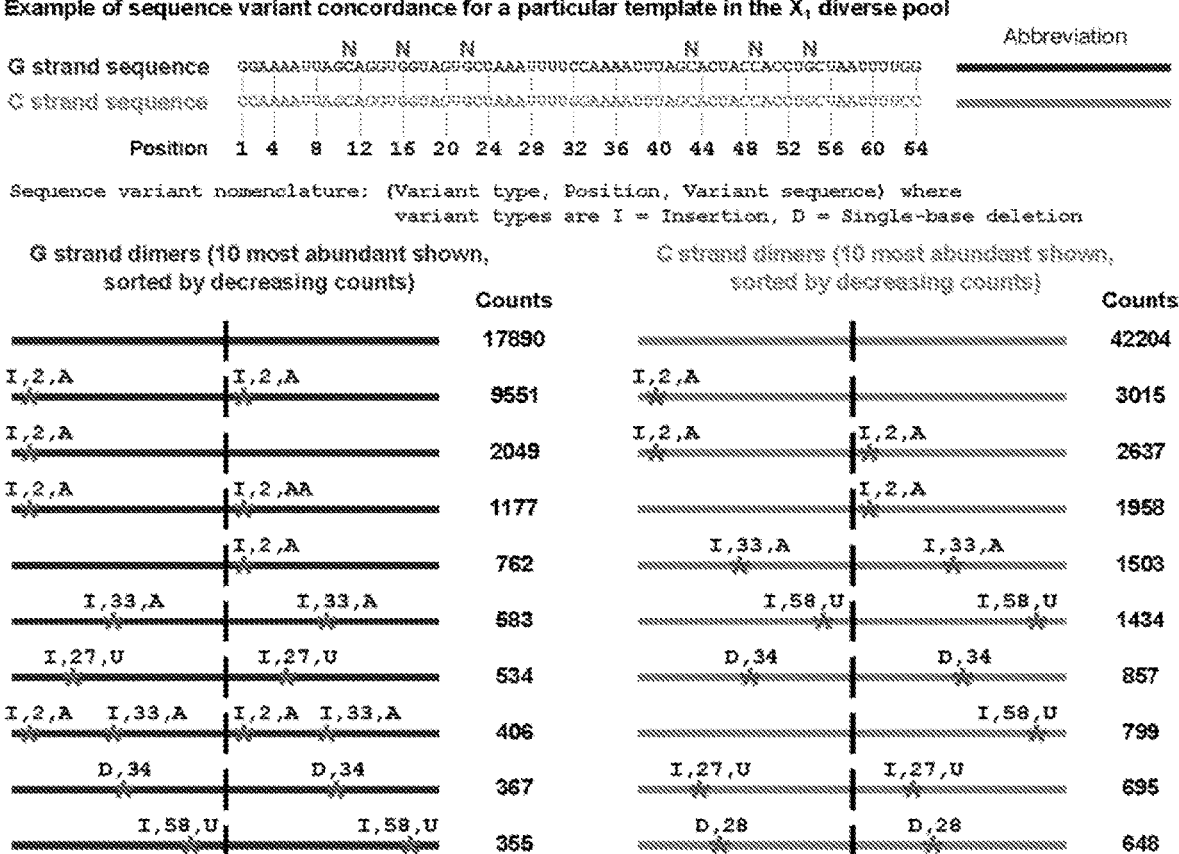

FIGS. 13A-13B show that uni-templated synthesis of RNA dimers is further supported by concordance of sequence variants between dimer halves. RNA dimers were obtained starting with the diverse monomer template pools $X_1$ and $Y2_1$; each pool contained intentionally randomized bases at a distinct set of six positions (denoted by "N"). For this figure, sequence variants refer to polymorphisms in RNA dimers located outside the intentionally randomized bases. FIG. 13A) Plots on the left show analysis for the vast majority of dimers with perfect sequence agreement between the six randomized base positions in the two dimer halves. For such dimers, the observed concurrent incidence of the same sequence variants in both dimer halves (red bars) was more frequent by 4.5 fold ($X_1$ pool) or 7 fold ($Y2_1$ pool) compared to the null hypothesis* (blue bars). Conversely, increased concurrent incidence of sequence variants compared to the null hypothesis* was not evident when analysis was performed on the small fraction of dimer sequences with sequence disagreement between the six randomized base positions in the two dimer halves (plots on the right). *=Null hypothesis was that sequence variants occur concurrently by random chance based on the frequencies of the sequence variants in the population. FIG. 13B) Concurrent incidence of sequence variants for an example RNA template from the $X_1$ pool. G strand sequence of the example template shown in blue and C strand sequence in green. The "N" in purple above the sequences shows the positions of intentionally randomized bases in the $X_1$ pool.

FIGS. 14A-14B show an analysis of the junction sequences between the two halves of the RNA dimers. FIG. 14A) Observed sequence agreement between the dimer junction and 3' end (purple bars in left plot) was close to what would be expected based on the junction sequence distribution and 3' end sequence distribution being independent of each other (mustard bars in left plot). Data shown are for dimers obtained starting from both the $X_1$ and $Y2_1$ diverse RNA monomer pools. Each pool contained intentionally randomized bases at a distinct set of six positions. Dimers used for analysis here had perfect sequence agreement between the six randomized base positions in the two dimer halves. The greater-than-expected concordance of sequence variants (located outside the intentionally randomized bases) between RNA dimer halves served as an internal positive control (based on FIG. 13 results) for our sequence agreement calculations (right plot). FIG. 14B) Dimer junction and 3' end sequences for an example RNA template from the $X_1$ pool. G strand sequence of the example template shown in dark gray and C strand sequence in light gray.

Figure 15:
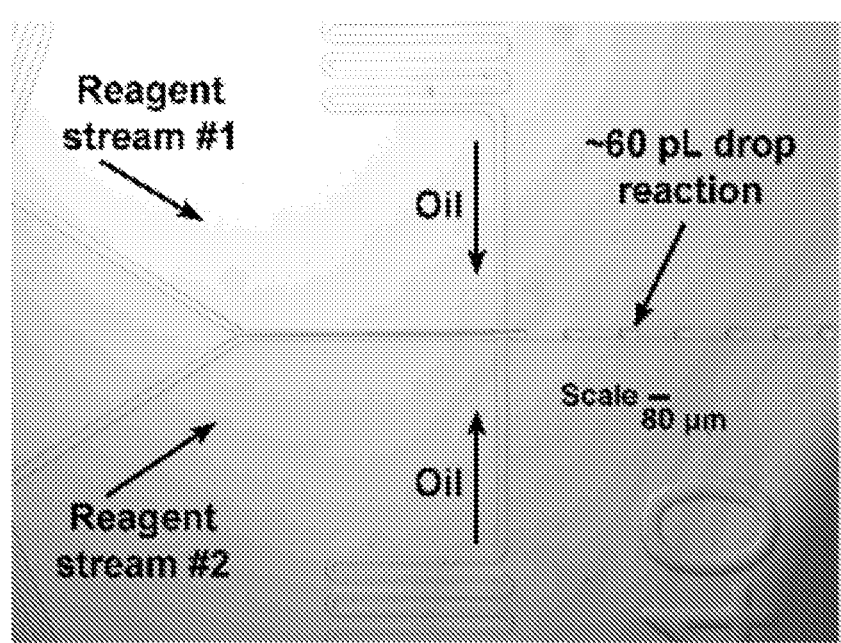

FIG. 15 shows microfluidic drop generation setup for T7 RNAP-catalyzed RNA replication reactions. One reagent stream was used to flow in nucleoside triphosphates (NTPs) and when stated, RNA or DNA templates. The other reagent stream was used to flow in T7 RNAP.

Figure 16:
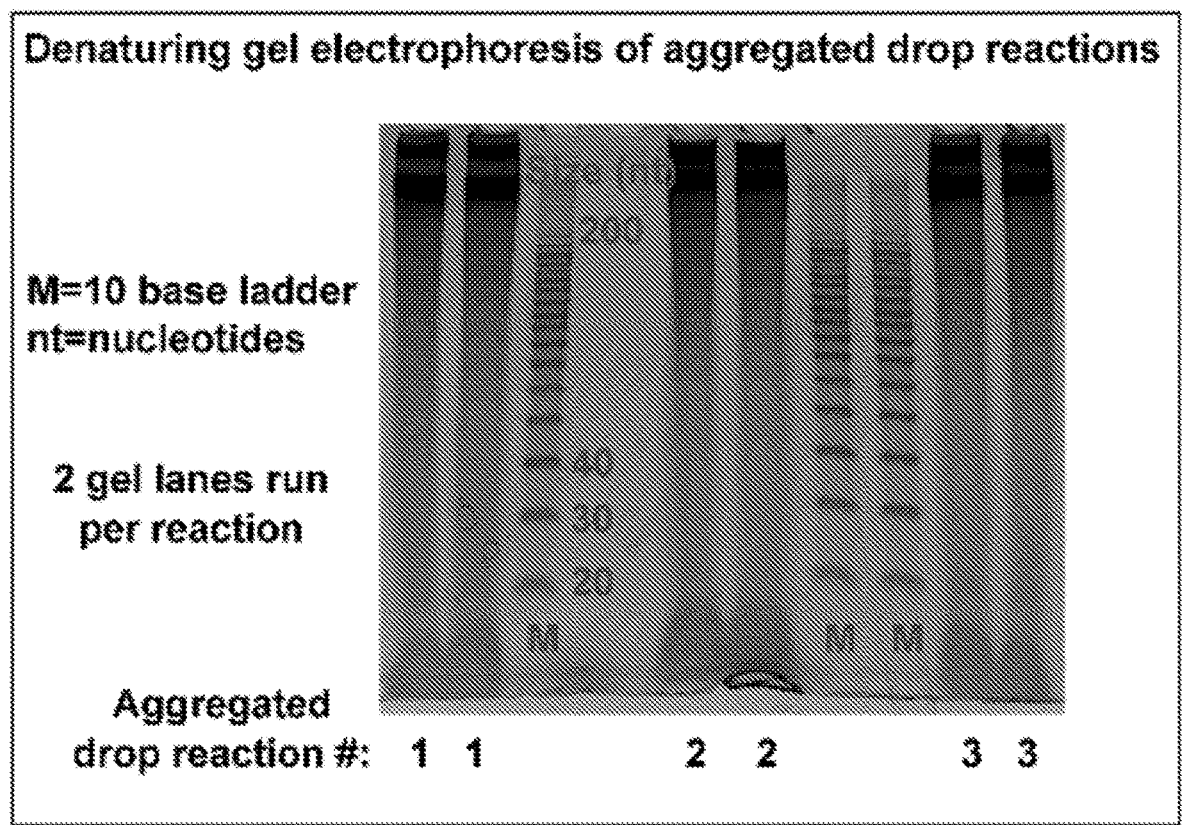

FIG. 16 shows migration of aggregated drop reactions on denaturing gels. Reactions were conducted at high concentration of T7 RNAP. Aggregated drop reactions shown correspond to: (i) no-template-added (reaction 1), (ii) seeded with a DNA pool consisting of DNA from nematodes, yeast, phage and a plasmid (reaction 2), and (iii) seeded with the DNA pool, with the DNA pool having been pre-treated with DNase (reaction 3).

FIG. 17 shows digital droplet RNA replication. Chemically synthesized G strand of Y2 RNA with an extra 3' adenine was used as template. Reactions were conducted at low concentration of T7 RNAP. Bright, fluorescent drops evidence RNA replication. % drops fluorescent reported as (Mean+/−Standard deviation). If replication could proceed starting with a single template molecule, then using the measurements obtained with the 3.31 template copies/drop condition, the % drops fluorescent predicted by Poisson statistics for the 0.39 copies/drop condition would be 5.2+/−0.6, close to the observed value of 6.6+/−1.1. In contrast, if replication could only proceed starting with two or more template molecules, the % drops fluorescent predicted for the 0.39 copies/drop condition would be 1.0+/−0.1, which deviates from observation.

Figure 18:
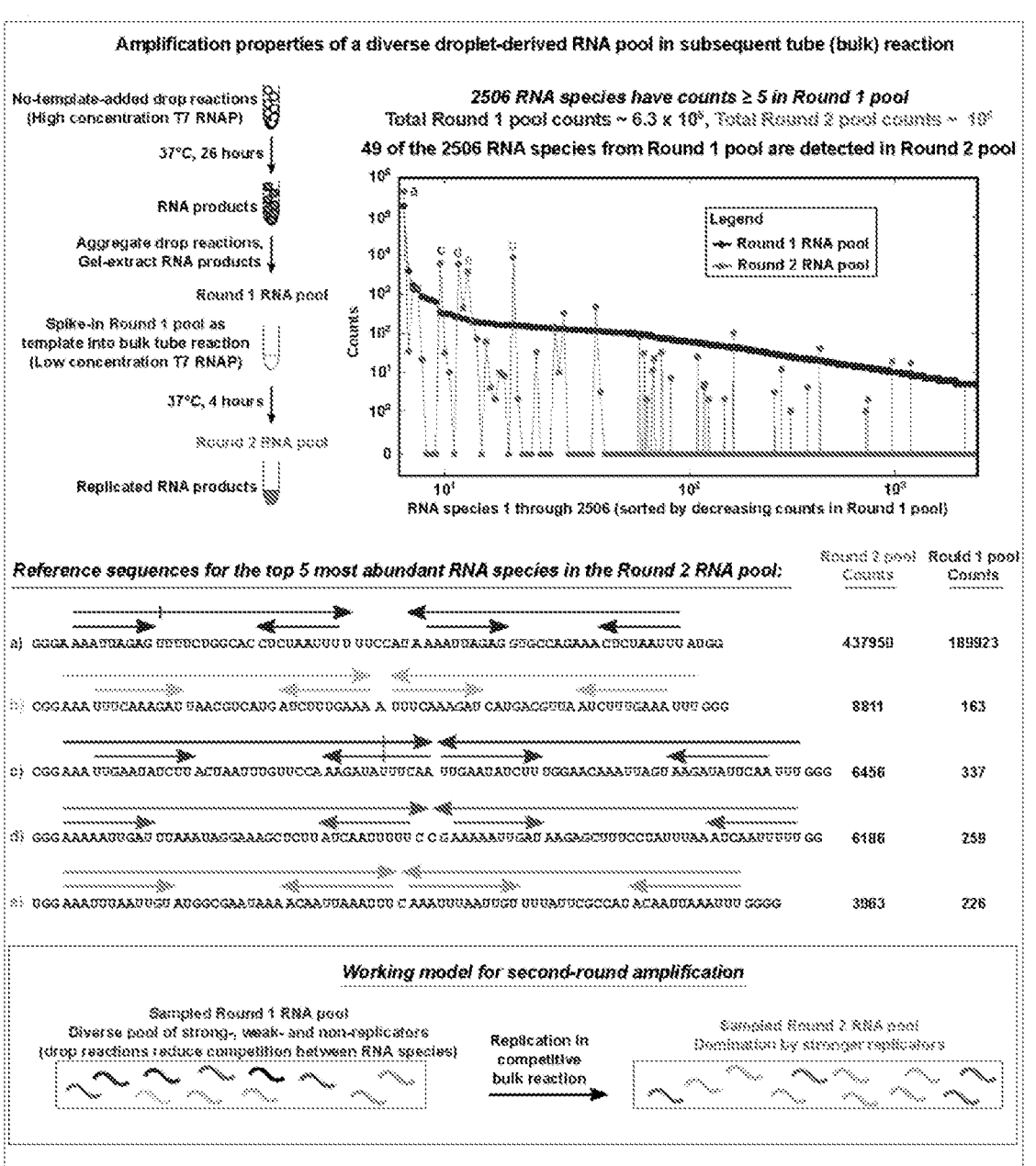

FIG. 18 shows novel replicating RNAs can be isolated from no-template-added, high concentration T7 RNAP reactions set up in microfluidic droplets. A gel-extracted sample of aggregated drop reactions (Round 1 RNA pool) was used in bulk as template in a 10 µl low concentration T7 RNAP reaction (products called Round 2 RNA pool). Both Round 1- and Round 2-RNA pools were characterized by RNA-Seq. As expected from competition between RNA species during amplification of the Round 1 pool, most RNA species from the Round 1 pool were not detected in the Round 2 pool. The predominance in the Round 2 pool of a small subset of species from the Round 1 pool demonstrates the capability of this subset of species to replicate (and to survive by out-competing other species). Furthermore, the predominant species in the Round 2 pool exhibited typical sequence and structural hallmarks of RNAs replicated by T7 RNAP (e.g. 2-way repeats and 4-way repeats). The top five most abundant RNA species in the Round 2 pool are shown as examples. Arrows above each RNA sequence represent 2-way- and 4-way-repeats, with vertical bars along the arrows indicating sequence disagreements between the repeats.

Figure 19:
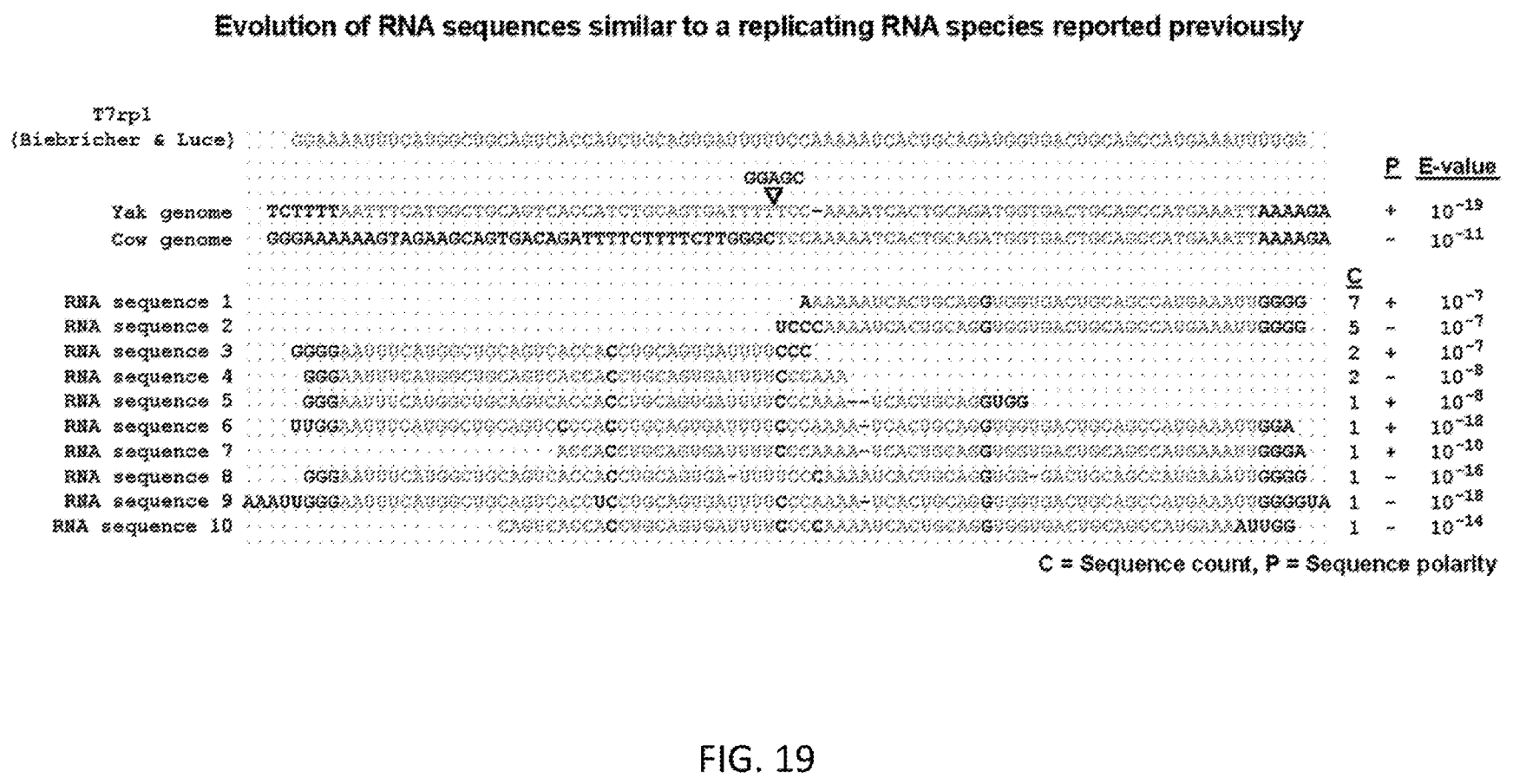

FIG. 19 shows evolution of RNA sequences similar to the T7rp1 replicating RNA reported by Biebricher and Luce (*EMBO J.* 15, 3458-3465 (1996)). Bases matching in alignments to T7rp1 are shown in red. Sequences with the same strand orientation as T7rp1 are assigned polarity ("P") of plus (+); sequences complementary to T7rp1 are assigned polarity of minus (−). T7rp1 strongly matches the cow and yak genomes. The 10 RNA sequence examples shown were isolated as follows. First, we generated no-template-added, high concentration T7 RNAP drop reactions. Bovine serum albumin (BSA) was included in the reactions during drop generation. An aggregate of drop reactions was then used in bulk as template in a 10 µl low concentration T7 RNAP tube reaction. Sequences shown were products of this second-round tube reaction.

Figure 20A:
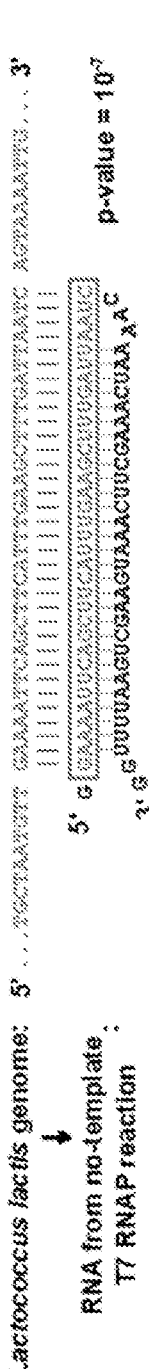
Figure 20B:
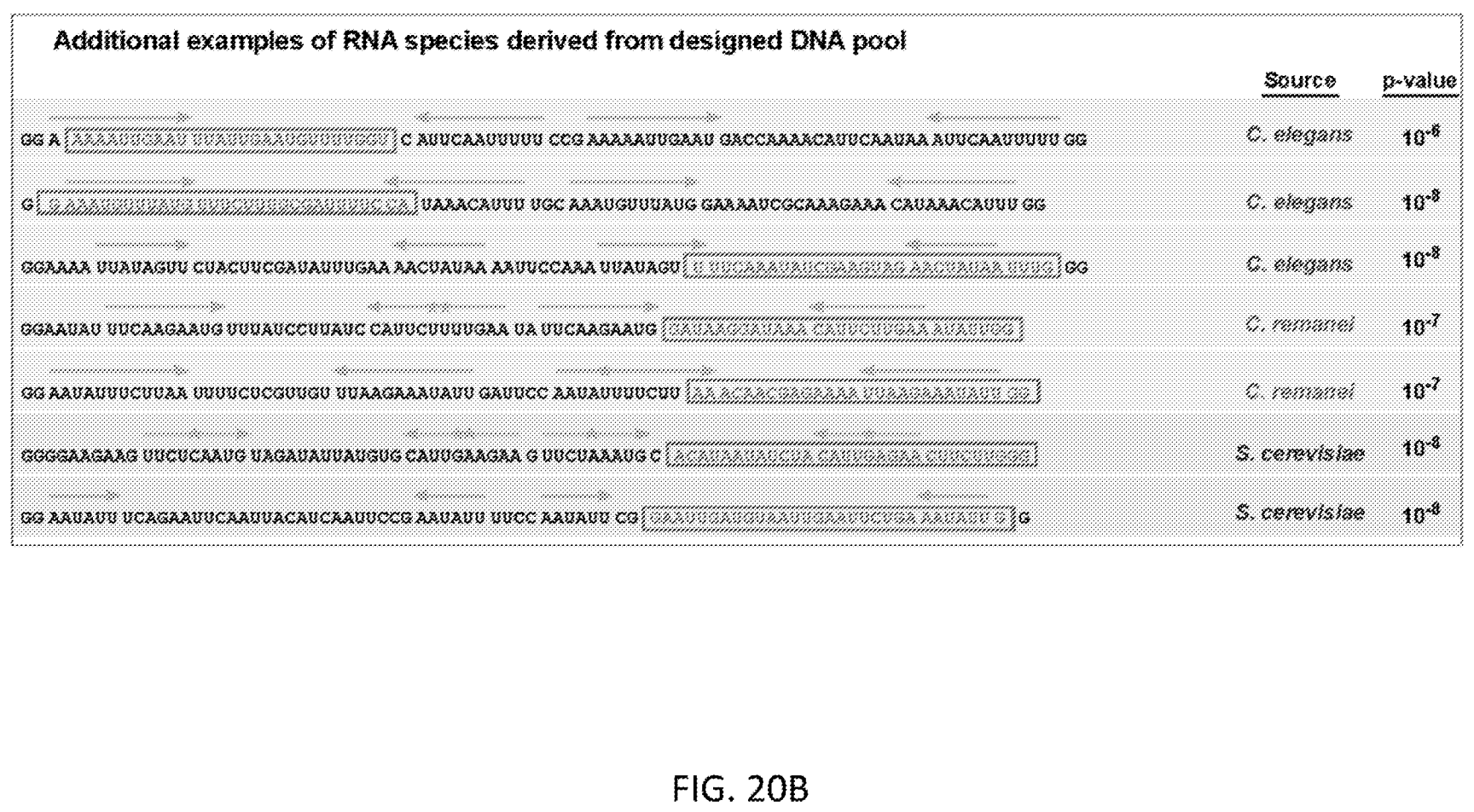

FIGS. 20A-20B show RNAs replicated by T7 RNAP can originate through partial instruction from DNA seeds. FIG. 20A) An example RNA species from a no-template-added T7 RNAP reaction matching the genome of *Lactococcus lactis* is shown. This panel supplements FIG. 6A. p-value is based on alignment to the RefSeq genomic database. The long hairpin shown is a predicted structure. FIG. 20B) More examples of RNA species that originated from different sources in our designed DNA pool. This panel supplements FIG. 6E. With the exception of the third RNA listed in this panel, the shown RNA species were all isolated from drop reactions, either from the "Seeded with DNA pool" condition or from the "Seeded with hot alkali-treated DNA pool" condition. The third RNA example was isolated from a tube reaction for the "Seeded with hot alkali-treated DNA pool" condition. Convention for annotating RNAs: (i) Best match to a source genome is shown in a red box; (ii) 4-way repeats are shown as orange arrows, with orange asterisks indicating sequence disagreements between 4-way repeats; (iii) Long 2-way repeats, though present, are not shown for simplicity. p-values are based on alignment to a database consisting of sequences expected to be present in our DNA seed pool.

DETAILED DESCRIPTION OF EMBODIMENTS

Compositions and methods for amplifying RNA by replication using transcription polymerases are disclosed. Such replicated RNAs are useful in various applications including, without limitation, RNAi therapeutics, diagnostic probes, RNA sequencing, directed evolution of RNA aptamers without intermediate conversion to DNA, and RNA vaccines.

Before the present compositions and methods are described, it is to be understood that this invention is not limited to a particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "an RNA" includes a plurality of such RNAs and reference to "the RNA" includes reference to one or more RNAs and equivalents thereof, e.g. transcripts, tRNA, rRNA, mRNA, and non-coding RNA (e.g., miRNA, siRNA, shRNA, lncRNA) known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The term "about", particularly in reference to a given quantity, is meant to encompass deviations of plus or minus five percent.

As used herein, a "biological sample" refers to a sample of cells, tissue, or fluid isolated from a prokaryotic or eukaryotic organism, including but not limited to, for example, blood, plasma, serum, fecal matter, urine, bone marrow, bile, spinal fluid, lymph fluid, sputum, ascites, bronchial lavage fluid, synovial fluid, samples of the skin, external secretions of the skin, respiratory, intestinal, and genitourinary tracts, tears, saliva, milk, organs, biopsies, and also samples of cells, including cells from bacteria, archaea, fungi, protists, plants, and animals as well as in vitro cell culture constituents, including but not limited to, conditioned media resulting from the growth of cells and tissues in culture medium, e.g., recombinant cells, and cell components, and also samples containing nucleic acids from viruses.

"Substantially purified" generally refers to isolation of a substance (compound, RNA, DNA, polynucleotide) such that the substance comprises the majority percent of the sample in which it resides. Typically in a sample, a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

By "isolated" is meant, when referring to a protein, polypeptide, or peptide, that the indicated molecule is separate and discrete from the whole organism with which the molecule is found in nature or is present in the substantial absence of other biological macro molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

The term "derived from" is used herein to identify the original source of a molecule but is not meant to limit the method by which the molecule is made which can be, for example, by chemical synthesis or recombinant means.

"Homology" refers to the percent identity between two polynucleotide or two polypeptide molecules. Two nucleic acid, or two polypeptide sequences are "substantially homologous" to each other when the sequences exhibit at least about 50% sequence identity, preferably at least about 75% sequence identity, more preferably at least about 80% 85% sequence identity, more preferably at least about 90% sequence identity, and most preferably at least about 95% 98% sequence identity over a defined length of the molecules. As used herein, substantially homologous also refers to sequences showing complete identity to the specified sequence.

In general, "identity" refers to an exact nucleotide to nucleotide or amino acid to amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in Atlas of Protein Sequence and Structure M. O. Dayhoff ed., 5 Suppl. 3:353 358, National biomedical Research Foundation, Washington, DC, which adapts the local homology algorithm of Smith and Waterman Advances in Appl. Math. 2:482 489, 1981 for peptide analysis. Programs for determining nucleotide sequence identity are available in the Wisconsin Sequence Analysis Package, Version 8 (available from Genetics Computer Group, Madison, WI) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, CA). From this suite of packages, the Smith Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs are readily available.

Alternatively, homology can be determined by hybridization of polynucleotides under conditions which form stable duplexes between homologous regions, followed by digestion with single stranded specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., *Molecular Cloning: A Laboratory Manual* (3$^{rd}$ Edition, 2001); *DNA Cloning*, Vols I & 2. (edited by D. Glover, IRL Press, Oxford, 1985); *Nucleic Acid Hybridization* (edited by S. Lukyanov, Springer, 2007).

"Recombinant" as used herein to describe a nucleic acid molecule means a polynucleotide of genomic, cDNA, viral, semisynthetic, or synthetic origin which, by virtue of its origin or manipulation, is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

"Purified polynucleotide" refers to a polynucleotide of interest or fragment thereof which is essentially free, e.g., contains less than about 50%, preferably less than about 70%, and more preferably less than about at least 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

Replicating RNA

RNA templates that can be replicated by a transcription polymerase are typically linear and comprise (i) a 2-way repeat configuration comprising a first inverted repeat, and (ii) a 4-way repeat configuration comprising a second inverted repeat that is shorter than the first inverted repeat, wherein each arm of the 2-way repeat comprises the second inverted repeat. In some embodiments, the replicating RNA further comprises one strand comprising two G bases at or close to the 5' end and two G bases at or close to the 3' end (i.e., a G RNA strand), and a complementary RNA strand comprising two C bases at or close to the 5' end and two C bases at or close to the 3' end (i.e., a C RNA strand). In certain embodiments, at least one base is added to the 3' end of the G RNA strand and/or the C RNA strand. In some embodiments, one to three bases are added to the 3' end of the G RNA strand and/or the C RNA strand. For example, 1, 2, or 3 bases can be added to either the G RNA strand or the C RNA strand or both the G RNA strand and the C RNA strand. In one embodiment, an adenine base is added to the 3' end of the G RNA strand and/or the C RNA strand.

In certain embodiments, the RNA template ranges from about 50 to about 120 nucleotides in length, including any length within this range such as 50, 55, 60, 65, 70, 75, 80, 85, 90, 95, 100, 105, 110, 115, or 120 nucleotides in length.

In certain embodiments, each repeat region within the 2-way repeat configuration ranges from about 10 to about 60 nucleotides in length, or any length within this range such as 10, 15, 20, 25, 30, 35, 40, 45, 50, 55, or 60 nucleotides in length. In certain embodiments, each repeat region within the 2-way repeat configuration ranges from about 20% to about 50% of the total length of the replicating RNA, or any length within this range such as 20%, 22%, 23%, 24%, 26%, 28%, 30%, 32%, 34%, 36%, 38%, 40%, 42%, 44%, 46%, 48%, or 50% of the total length of the replicating RNA.

In certain embodiments, each repeat region within the 4-way repeat configuration ranges from about 5 to about 25 nucleotides in length, or any length within this range such as 5, 6, 7, 8, 9, 10, 11, 12, 13, 14, 15, 16, 17, 18, 19, 20, 21, 22, 23, 24, or 25 nucleotides in length. In certain embodiments, each repeat region within the 4-way repeat configuration ranges from about 5% to about 20% of the total length of the replicating RNA, or any length within this range such as 5%, 6%, 7%, 8%, 9%, 10%, 11%, 12%, 13%, 14%, 15%, 16%, 17%, 18%, 19%, or 20% of the total length of the replicating RNA.

Exemplary replicating RNAs are listed in Tables 1, 2, and 4 (see Examples). In certain embodiments, the replicating RNA comprises a nucleotide sequence selected from Tables 1, 2, or 4, or a sequence displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto. In some embodiments, the replicating RNA comprises i) a 2-way repeat configuration comprising a first inverted repeat, and (ii) a 4-way repeat configuration comprising a second inverted repeat that is shorter than the first inverted repeat, wherein each arm of the 2-way repeat comprises the second inverted repeat.

The transcription polymerase used in RNA replication can be any RNA polymerase capable of catalyzing replication of an RNA template having this structural configuration. Transcription polymerases can be obtained, for example, from bacteria, archaea, eukaryotes, and viruses. Exemplary transcription polymerases include, without limitation, those from bacteriophages (e.g., T7, T3, and SP6), bacteria (e.g., *Escherichia coli*), and eukaryotic chloroplasts and mitochondria. In certain embodiments, the RNA polymerase is engineered to improve its capability in replicating RNA. For example, the RNA polymerase may be engineered to comprise one or more mutations that enhance its catalytic activity, improve thermal stability, enhance promoter clearance, and/or increase processivity. T7 RNA polymerases genetically engineered to increase thermal stability are commercially available, for example, from New England Biolabs (Ipswich, MA) and Toyobo U.S.A., Inc. (New York, NY).

For replication, the RNA polymerase is added to a reaction mixture containing the RNA template and a set of ribonucleoside triphosphates to catalyze polymerization and replication of RNA. The set of ribonucleoside triphosphates will usually include ATP, CTP, UTP and GTP, but may also include one or more modified ribonucleoside triphosphates or non-natural ribonucleoside triphosphate analogues, which may be incorporated into the RNA during polymerization. Alternatively or additionally, nucleotides may be modified in the RNA product after replication of the RNA is completed.

Modified nucleotides may include one or more modifications to the ribose and/or the base of the nucleoside. Such modifications may include, for example, without limitation, acyl, amino acid, aminoacyl, aminoalkyl, amino, carboxymethyl, epoxycyclopentane, glycosyl, heavy atom, hydrocarbon, hydrogen, hydroxyalkyl, methoxycarbonyl, methyl, nucleobase, nucleotide, oxo, peroxide, phosphoribose, polyamine, saccharide, seleno, sulfur, and/or thioalkyl moieties.

Modified nucleotides may include, for example, without limitation 1,2'-O-dimethyladenosine, 1,2'-O-dimethyl-guanosine, 1,2'-O-dimethylinosine, 1-methyl-3-(3-amino-3-carboxypropyl)pseudouridine, 1-methyladenosine, 1-methylguanosine, 1-methylinosine, 1-methylpseudouridine, 2,8-dimethyladenosine, msms2i6A, 2-geranylthiouridine, 2-lysidine, 2-methyladenosine, 2-methylthio cyclic N6-threonylcarbamoyladenosine, 2-methylthio-N6-(cis-hydroxyisopentenyl) adenosine, 2-methylthio-N6-hydroxynor-valylcarbamoyladenosine, 2-methylthio-N6-isopentenyladenosine, 2-methylthio-N6-methyladenosine, 2-methylthio-N6-threonylcarbamoyladenosine, 2-selenouridine, 2-thio-2'-O-methyluridine, 2-thiocytidine, 2-thiouridine, 2'-O-methyladenosine, 2'-O-methylcytidine, 2'-O-methylguanosine, 2'-O-methylinosine, 2'-O-methylpseudouridine, 2'-O-methyluridine, 2'-O- methyluridine 5-oxyacetic acid methyl ester, 2'-O-ribosylad-
enosine (phosphate), 2'-O-ribosylguanosine (phosphate),
2'3'-cyclic phosphate end, hm5Cm, 3,2'-O-dimethyluridine,
3-(3-amino-3-carboxypropyl)-5,6-dihydrouridine, 3-(3-
amino-3-carboxypropyl)pseudouridine, 3-(3-amino-3-car-
boxypropyl) uridine, 3-methylcytidine, 3-methylpseudouri-
dine, 3-methyluridine, 4-demethylwyosine, 4-thiouridine,
5,2'-O-dimethylcytidine, 5,2'-O-dimethyluridine, 5-(car-
boxyhydroxymethyl)-2'-O-methyluridine methyl ester,
5-(carboxyhydroxymethyl)uridine methyl ester, 5-(isopen-
tenylaminomethyl)-2-thiouridine, 5-(isopentenylaminom-
ethyl)-2'-O-methyluridine, 5-(isopentenylaminomethyl)uri-
dine, 5-aminomethyl-2-geranylthiouridine, 5-aminomethyl-
2-selenouridine, 5-aminomethyl-2-thiouridine,
5-aminomethyluridine, 5-carbamoylhydroxymethyluridine,
5-carbamoylmethyl-2-thiouridine, 5-carbamoylmethyl-2'-
O-methyluridine, 5-carbamoylmethyluridine, 5-carboxyhy-
droxymethyluridine, 5-carboxymethyl-2-thiouridine, 5-car-
boxymethylaminomethyl-2-geranylthiouridine,
5-carboxymethylaminomethyl-2-selenouridine, 5-car-
boxymethylaminomethyl-2-thiouridine, 5-carboxymethyl-
aminomethyl-2'-O-methyluridine, 5-carboxymethylami-
nomethyluridine, 5-carboxymethyluridine,
5-cyanomethyluridine, 5-formyl-2'-O-methylcytidine,
5-formylcytidine, 5-hydroxycytidine, 5-hydroxymethylcyti-
dine, 5-hydroxyuridine, 5-methoxycarbonylmethyl-2-thiou-
ridine, 5-methoxycarbonylmethyl-2'-O-methyluridine,
5-methoxycarbonylmethyluridine, 5-methoxyuridine,
5-methyl-2-thiouridine, 5-methylaminomethyl-2-geranylth-
iouridine, 5-methylaminomethyl-2-selenouridine, 5-methyl-
aminomethyl-2-thiouridine, 5-methylaminomethyluridine,
5-methylcytidine, 5-methyldihydrouridine, 5-methyluridine,
5-taurinomethyl-2-thiouridine, 5-taurinomethyluridine, 5'
(3'-dephospho-CoA), 5' (3'-dephosphoacetyl-CoA), 5' (3'-
dephosphomalonyl-CoA), 5' (3'-dephosphosuccinyl-CoA),
5' diphosphate end, 5' hydroxyl end, 5' monophosphate end,
5' nicotinamide adenine dinucleotide, 5' triphosphate end,
7-aminocarboxypropyl-demethylwyosine, 7-aminocarboxy-
propylwyosine, 7-am inocarboxypropylwyosine methyl
ester, 7-aminomethyl-7-deazaguanosine, 7-cyano-7-deaz-
aguanosine, 7-methylguanosine, 7-methylguanosine cap
(cap 0), 8-methyladenosine, N2,2'-O-dimethylguanosine,
N2,7,2'-O-trimethylguanosine, N2,7-dimethylguanosine,
N2,7-dimethylguanosine cap (cap DMG), N2,N2,2'-O-trim-
ethylguanosine, N2,N2,7-trimethylguanosine, N2,N2,7-
trimethylguanosine cap (cap TMG), N2,N2-dimethyl-
guanosine, N2-methylguanosine, N4,2'-O-dimethylcytidine,
N4,N4,2'-O-trimethylcytidine, N4,N4-dimethylcytidine,
N4-acetyl-2'-O-methylcytidine, N4-acetylcytidine,
N4-methylcytidine, N6,2'-O-dimethyladenosine, N6,N6,2'-
O-trimethyladenosine, N6,N6-dimethyladenosine, N6-(cis-
hydroxyisopentenyl)adenosine, N6-acetyladenosine,
N6-formyladenosine, N6-glycinylcarbamoyladenosine,
N6-hydroxymethyladenosine, N6-hydroxynorvalylcarbam-
oyladenosine, N6-isopentenyladenosine, N6-methyl-N6-
threonylcarbamoyladenosine, N6-methyladenosine,
N6-threonylcarbamoyladenosine, Qbase, agmatidine, alpha-
dimethylmonophosphate cap, alpha-methylmonophosphate
cap, archaeosine, cyclic N6-threonylcarbamoyladenosine,
dihydrouridine, epoxyqueuosine, galactosyl-queuosine,
gamma-methyltriphosphate cap, glutamyl-queuosine,
guanosine added to any nucleotide, guanylylated 5' end (cap
G), hydroxy-N6-threonylcarbamoyladenosine, hydroxywy-
butosine, inosine, isowyosine, mannosyl-queuosine, meth-
ylated undermodified hydroxywybutosine, methylwyosine,
peroxywybutosine, preQ0base, preQ1base, pseudouridine, queuosine, under modified hydroxywybutosine, uridine
5-oxyacetic acid, uridine 5-oxyacetic acid methyl ester,
wybutosine, and wyosine.

Nucleotides can be modified, for example, either syntheti-
cally or enzymatically using RNA-modifying enzymes.
RNA modifying enzymes include, but are not limited to,
methyltransferases, amidinotransferases, transglycosylases,
deaminases, dehydratases, isomerases, oxidoreductases,
methylphosphate capping enzymes, threonylcarbamoylad-
enosine synthetases, kinases, thiolases, pseudouridine syn-
thases, guanylyltransferases, triphosphatases, hydrolases,
carboxymethyltransferases, acetyltransferases, cysteine des-
ulfurases, selenotransferases, geranyltransferases, dimethyl-
allyltransferases, methyltiotransferases, sulfurtransferases,
threonylcarbamoyltransferases, alpha-amino-alpha-car-
boxypropyltransferases, agmatidine synthases, adenylyl-
transferases, and thiosulfate sulfurtransferases. For a
description of nucleotide modifications and RNA-modifying
enzymes, see, e.g., Rozenski et al. (1999). Nucl Acids Res
27: 196-197, Boccaletto et al. (2018) Nucleic Acids Res.
46(D1):D303-D307; MODOMICS database (modomics-
.genesilico.pl/), the RNA Modification Database
(RNAMDB, rna-mdb.cas.albany.edu/RNAmods/), and the
RMBase (mirlab.sysu.edu.cn/rmbase).

The RNA template can be derived from a biological
sample containing RNA. The biological sample can be any
sample of cells, tissue, or fluid isolated from a prokaryotic
or eukaryotic organism, including but not limited to, for
example, blood, plasma, serum, fecal matter, urine, bone
marrow, bile, spinal fluid, lymph fluid, sputum, ascites,
bronchial lavage fluid, synovial fluid, samples of the skin,
external secretions of the skin, respiratory, intestinal, and
genitourinary tracts, tears, saliva, milk, organs, biopsies, and
also samples of cells, including cells from bacteria, archaea,
fungi, protists, plants, and animals as well as in vitro cell
culture constituents, including but not limited to, condi-
tioned media resulting from the growth of cells and tissues
in culture medium, e.g., recombinant cells, and cell compo-
nents, and also samples containing nucleic acids from
viruses.

In certain embodiments, a DNA seed is provided instead
of an RNA template, wherein the RNA template for repli-
cation is generated by transcription of the DNA seed. In
some embodiments, the DNA seed comprises a nucleotide
sequence of interest and a 4-way repeat unit. In certain
embodiments, the DNA seed is added to the reaction mixture
such that the RNA polymerase generates a first RNA com-
prising the 4-way repeat unit by transcription of the DNA
seed. In some embodiments, the method further comprises
carrying out a first round of self-templated 3'-extension of
the first RNA to produce a second RNA comprising a second
4-way repeat unit; and carrying out a second round of
self-templated 3'-extension of the second RNA to produce
the RNA template comprising the 4-way repeat configura-
tion.

RNA can be purified before or after replication using
methods well-known in the art. For example, RNA may be
further purified by immobilization on a solid support, such
as silica, RNA adsorbent beads (e.g., oligo(dT) coated beads
or beads composed of polystyrene-latex, glass fibers, cellu-
lose or silica), magnetic beads, or by reverse phase, gel
filtration, ion-exchange, or affinity chromatography. RNA
can also be isolated from suspensions by conventional
methods, such as phenol-chloroform extraction or precipi-
tation with alcohol. Alternatively, an electric field-based
method can be used to separate the desired RNA molecule
from other molecules. Exemplary electric field-based methods include polyacrylamide gel electrophoresis, agarose gel electrophoresis, capillary electrophoresis, pulsed field electrophoresis, and isotachophoresis. See, e.g., RNA: Methods and Protocols (Methods in Molecular Biology, edited by H. Nielsen, Humana Press, 1st edition, 2010); Rio et al. RNA: A Laboratory Manual (Cold Spring Harbor Laboratory Press; 1st edition, 2010); Farrell RNA Methodologies: Laboratory Guide for Isolation and Characterization (Academic Press; 4.sup.th edition, 2009); Zahringer (2012) Lab Times (2-2012):52-63; Garcia-Schwarz et al. (2012) Journal of Visualized Experiments 61:e3890; Rogacs et al. (2012) Anal. Chem. 84(14):5858-5863; Hagan et al. (2009) Anal Chem. 81(13):5249-5256; Righetti (2005) J. Chromatogr. A10 79(1-2):24-40; Gebauer et al. (2011) Electrophoresis 32(1):83-89; herein incorporated by reference in their entireties.

RNA amplified by replication according to the methods described herein can be used for various purposes, including, but not limited to, PCR, ligation, transcriptome analysis, microarray analysis, northern analysis, cDNA library construction, RNA interference, sequencing, vaccines, and directed evolution of RNA aptamers without intermediate conversion to DNA.

Kits

Also provided are kits for amplifying RNA by replication using a transcription polymerase, as described herein. At least one RNA template capable of replication by a transcription polymerase (i.e., RNA comprising a 2-way repeat configuration and a 4-way repeat configuration) may be included in a kit. Kits may also include a transcription polymerase, a set of ribonucleoside triphosphates comprising ATP, CTP, GTP, and UTP, and optionally modified ribonucleoside triphosphates or analogues. The different components may be contained in separate compositions or in the same composition. In some embodiments, the kit further comprises a container for collecting an RNA sample. The kit may also include reagents for purifying and/or sequencing an RNA sample.

In addition, the kits may further include (in certain embodiments) instructions for practicing the subject methods. These instructions may be present in the subject kits in a variety of forms, one or more of which may be present in the kit. For example, instructions may be present as printed information on a suitable medium or substrate, e.g., a piece or pieces of paper on which the information is printed, in the packaging of the kit, in a package insert, and the like. Another form of these instructions is a computer readable medium, e.g., diskette, compact disk (CD), flash drive, and the like, on which the information has been recorded. Yet another form of these instructions that may be present is a website address which may be used via the internet to access the information at a removed site.

In certain embodiments, the kit comprises an RNA template comprising a nucleotide sequence selected from Tables 1, 2, or 4, or a sequence displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto. In some embodiments, the RNA template comprises (i) a 2-way repeat configuration comprising a first inverted repeat, and (ii) a 4-way repeat configuration comprising a second inverted repeat that is shorter than the first inverted repeat, wherein each arm of the 2-way repeat comprises the second inverted repeat. In some embodiments, the RNA template comprises a G RNA strand comprising two G bases at or close to a 5' end and two G bases at or close to a 3' end of the G RNA strand, or a C RNA strand comprising two C bases at or close to a 5' end and two C bases at or close to a 3' end of the C RNA strand.

In certain embodiments, the kit further comprises a DNA seed comprising a nucleotide sequence of interest and a 4-way repeat unit.

It will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Example 1

A Consistent RNA Structural Framework Drives the Origin and Molecular Mechanisms of RNA Replication by a Transcription Polymerase Introduction To date, five distinct RNA sequences that can be replicated by T7 RNAP have been described, two by Konarska and Sharp (X RNA and Y RNA) (4) and three by Biebricher and Luce (T7rp1, T7rp2 and T7rp3) (5). All five RNAs could form long-hairpin secondary structures. The origins of the RNAs replicated by T7 RNAP have been unclear. Konarska and Sharp speculated that replicating RNA templates could have been pre-existing RNA contaminants in their T7 RNAP preparations, whereas Biebricher and Luce proposed that replicating RNAs form as a result of molecular evolution in T7 RNAP reactions.

By combining next-generation sequencing, microfluidics and bioinformatics with classical biochemistry approaches, we address three questions: (i) How does a DNA-dependent RNA polymerase replicate RNA? We describe subterminal de novo initiation, RNA shape-shifting and interrupted rolling circle synthesis as three underlying mechanisms for RNA replication by T7 RNAP. (ii) How diverse is the family of RNAs that can be replicated by a transcription polymerase? We isolated hundreds of new RNA species replicated by T7 RNAP. (iii) What are the origins of RNAs replicated by a transcription polymerase? Sequence analysis of our large repertoire of RNA species led us to the hypothesis that replicating RNAs can originate through partial instruction from DNA seeds. In support of this hypothesis, we show that T7 RNAP can catalyze the emergence of novel replicating RNAs from a complex DNA seed pool of our own choosing.

Figure 1A:
FIGS. 1A-1G show diverse but structurally-similar RNAs isolated from no-template-added, high concentration T7 RNA polymerase (T7 RNAP) reactions set up in parallel.
Figure 1B:
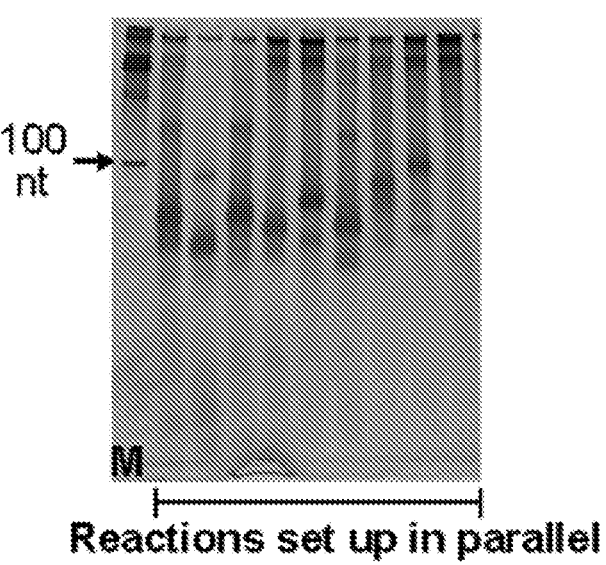

Emergence of Diverse but Structurally-Similar Replicating RNAs from No-Template-Added Reactions We set up a series of T7 RNAP reactions in parallel using aliquots of the same reagents (FIG. 1A). Each reaction contained a high concentration (2 µM) of T7 RNAP. No nucleic acid template was explicitly added to the reactions, with the reaction composition (3) otherwise typical for T7 RNAP. After incubation at 37° C. for ~24 hours, each reaction contained large amounts of synthesized RNA. The relative gel migration of synthesized RNA products varied from reaction-to-reaction (FIG. 1B), indicating distinct RNAs in each reaction. These data were consistent with the findings of Biebricher and Luce (5).

We analyzed the synthesized sequences for a set of 24 no-template-added T7 RNAP reactions conducted in parallel. Dominant reaction products were sequenced using an RNA-seq protocol that we optimized for efficient reverse transcription of structured RNAs (FIG. 7). Upon unsupervised sequence classification of the reaction products, we observed that each reaction yielded one or more clusters of RNA sequences. Each such cluster—henceforth referred to as an RNA species—was itself a heterogenous population of closely related sequences. For each RNA species, we chose a canonical, abundant sequence that could serve as a "reference" for the information content of the RNA species.

Figure 1C:
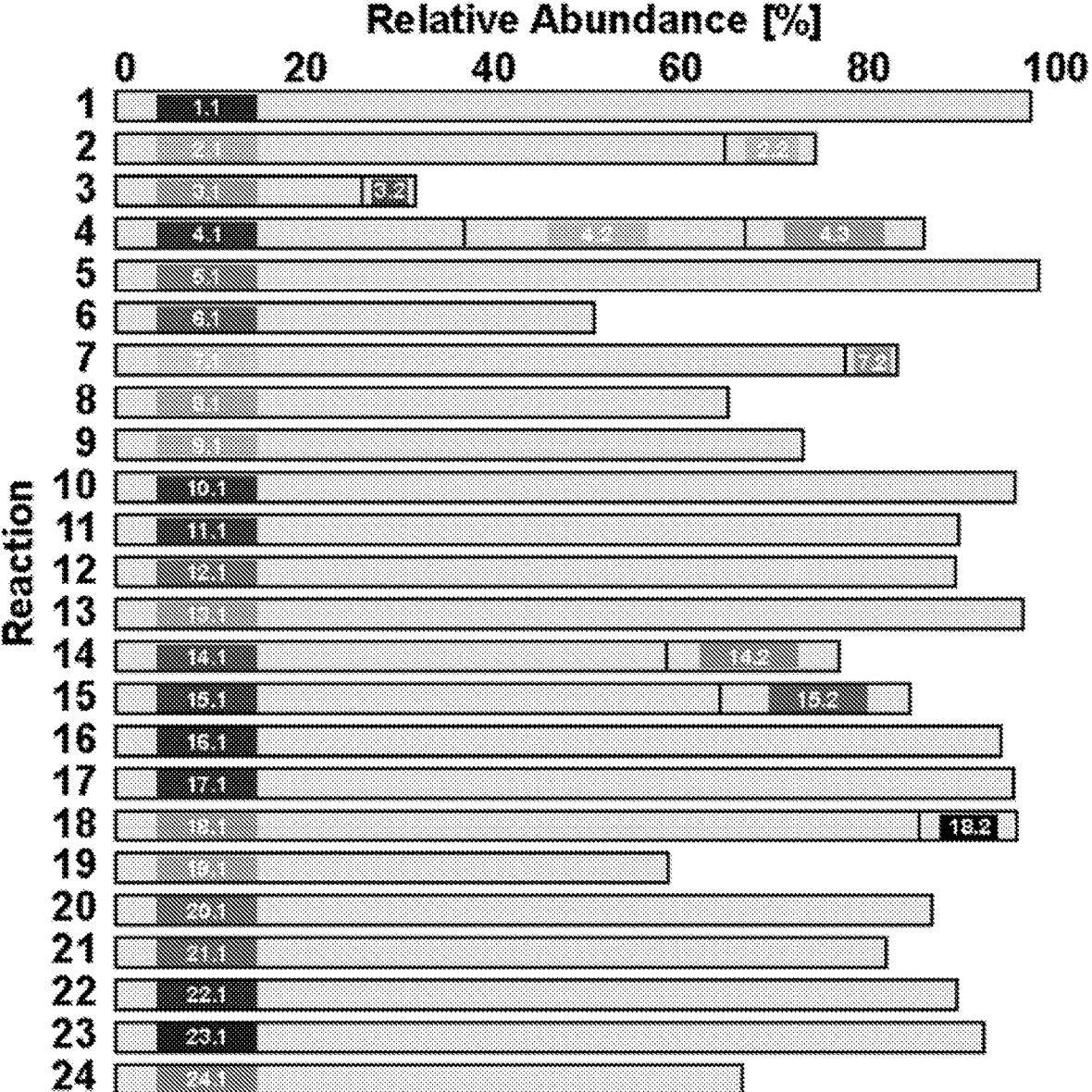
Figure 1D:
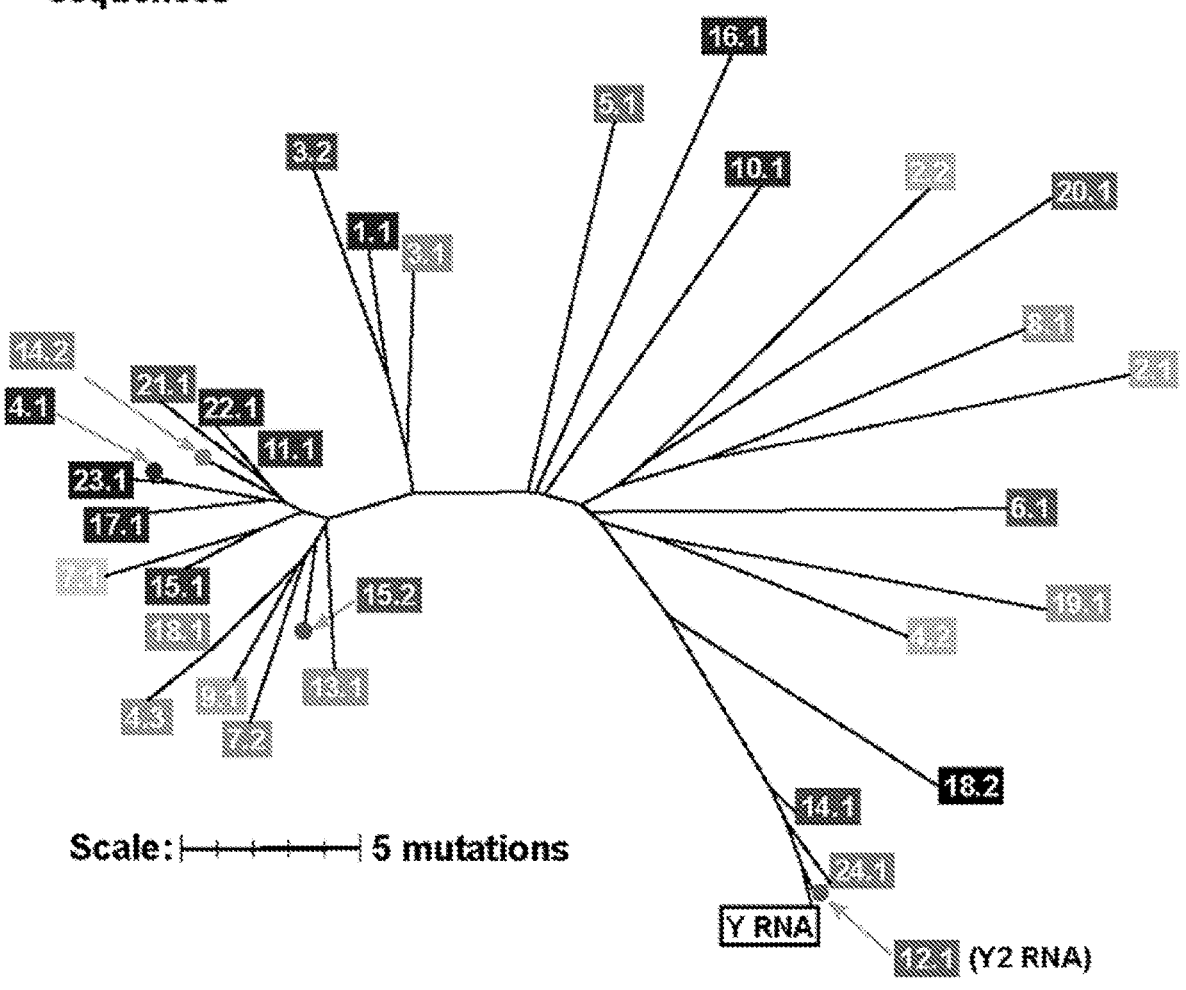
Figure 1E:
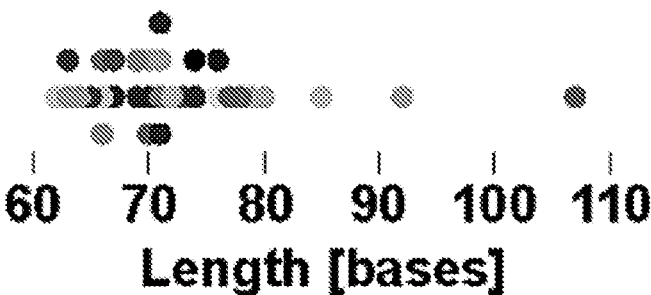

A small number (1 to 3) of RNA species were predominant in each of the 24 sequenced pools (FIG. 1C, Table 1; predominant defined here as relative abundance >5% within a sequenced pool). Reference sequences for the predominant RNA species differed between the 24 no-template reactions (FIG. 1D), although some reactions (e.g. reactions 11 and 22) yielded reference sequences that were related. Furthermore, three of the reference sequences (12.1, 14.1 and 24.1) were related to Y RNA, which was previously characterized as an RNA replicated by T7 RNAP (4).

Figure 1F:
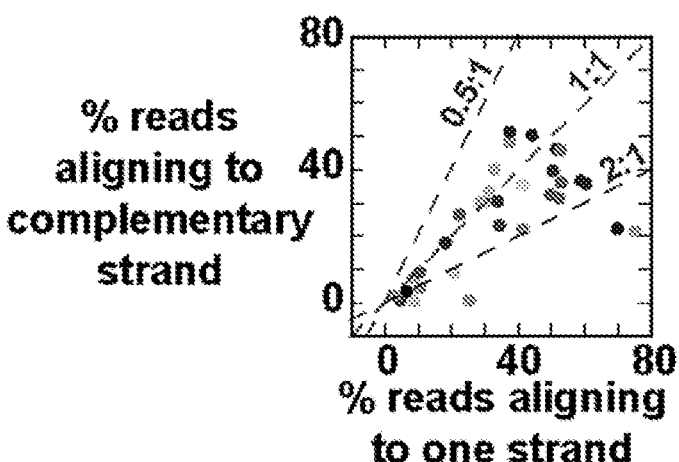
Figure 1G:
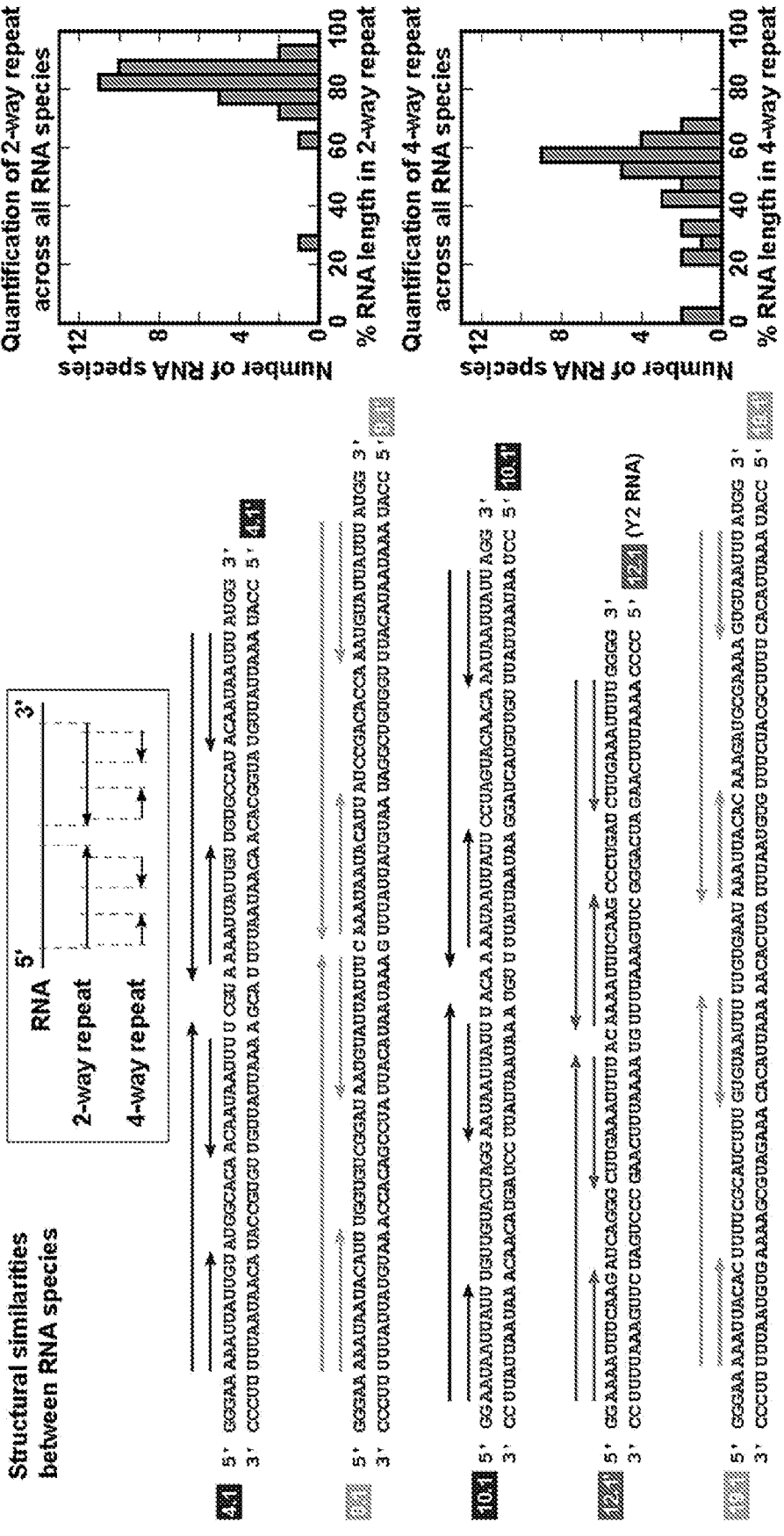

Most RNA reference sequences were between 60 to 80 bases in length (FIG. 1E), consistent with the migration patterns observed on denaturing gels. As our RNA-seq protocol is strand-specific (e.g. see sequencing of chemically synthesized RNA oligos in FIG. 11), we further analyzed the strand orientations of RNA sequences within each RNA species. Most RNA species showed comparable counts of (i) reads with the same strand orientation as the species reference sequence, and of (ii) reads with a strand orientation complementary to the species reference sequence (FIG. 1F). Of note, RNA replication would be expected to yield sequences of both strand orientations.

Though distinct in sequence content, the RNA species shared structural features (FIG. 1G): (i) A "2-way repeat" configuration characterized by an inverted repeat throughout the RNA length, suggesting possible formation of a long hairpin structure, and (ii) A "4-way repeat" configuration entailing a shorter inverted repeat embedded within each arm of the 2-way repeat. Of interest, the 2-way- and 4-way-repeat configurations were also noted for the previously described RNAs that can be replicated by T7 RNAP (4, 5).

The capability of no-template-added, high concentration T7 RNAP reactions to yield novel RNA sequences bearing the 2-way and 4-way repeat patterns was independently reproduced in our study both at Stanford and Galveston.

Our working hypothesis at this point was that the RNA species from no-template reactions can be sustainably replicated by T7 RNAP. To test this hypothesis, we assessed growth of several distinct RNA species in parallel upon dilution into fresh T7 RNAP reactions. A clear sequence correspondence was evident between the RNA species used as spike-in templates in the reactions and the resulting products (FIG. 8), suggesting that the RNAs were replicating. It is to be emphasized that to test templated RNA replication in this experiment (and also in the ensuing work), we used a low reaction concentration of T7 RNAP and checked that no-template-added controls conducted in parallel at the low T7 RNAP concentration did not yield any products detectable by gel electrophoresis. In concordance with previous reports (e.g. 5), we note that T7 RNAP reaction concentration provides a means to experimentally distinguish between (i) RNA replication starting from a defined RNA template (assayed at low T7 RNAP concentration), and (ii) an enzymatic capability to synthesize replicating RNAs unique to a reaction without added template (assayed at high T7 RNAP concentration).

3' End Sequence Requirements for RNA Replication

Figure 2A:
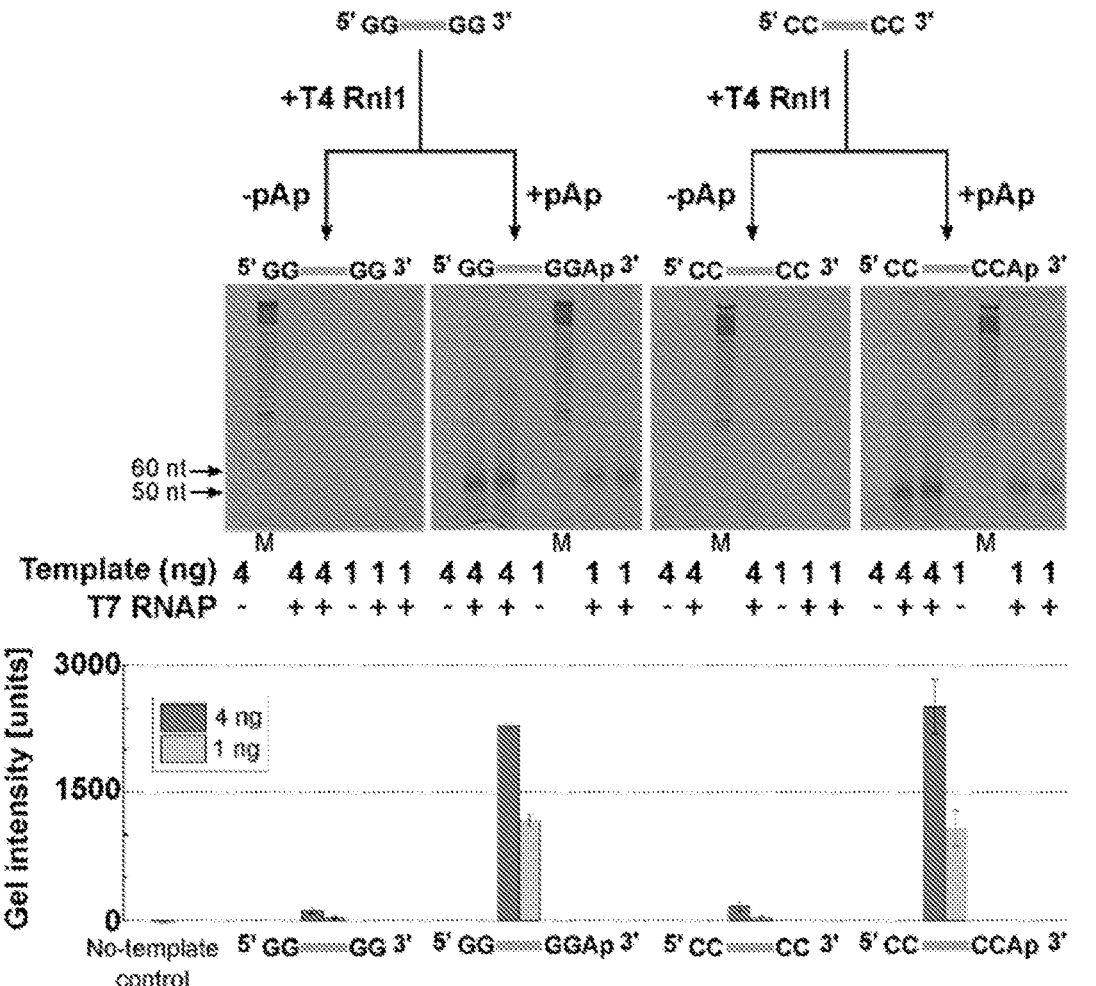
FIGS. 2A-2B show 3' base additions to the G and C strand templates are required for efficient RNA synthesis.

Although regeneration of RNA species upon dilution into fresh T7 RNAP reactions suggested an ongoing templated replication process, it remained possible that the RNA species we were analyzing were not themselves templates but rather byproducts of more complex reactions. To establish replication from defined RNA templates, we probed a series of chemically synthesized RNAs for replication by T7 RNAP. In describing the templates tested, we will use the nomenclature of Konarska and Sharp who referred to the complementary strands of replicating RNAs as the G strand and C strand. The G strand sequence has two G bases at the 5' end and two G bases at the 3' end, and the C strand, two C bases at the 5' end and two C bases at the 3' end. We initially tested replication of chemically synthesized G and C strand sequences for the RNA species 12.1 from FIG. 1 (henceforth, we will refer to this RNA species as Y2 RNA because of its sequence similarity to Y RNA; FIG. 2A). Synthetic Y2 RNA G and C strands failed to instruct efficient RNA synthesis. Mixing the two strands (to assess template activity of the RNA duplex between the G and C strands) did not increase RNA synthesis.

In considering possible features that may define active templates, we initially focused our attention on 3' end sequences. Compared to the previously proposed replicating RNA 3' end sequences ( . . . GG-3' for one strand, . . . CC-3' for complementary strand) (4, 5), the Y2 RNA species we isolated contained a diversity of 3' sequence additions ranging from one to a few bases in length. 3' base additions, a known feature of T7 RNAP activity (e.g. 9, 10), were highly frequent more generally in the RNA species obtained from the no-template, high concentration T7 RNAP reactions (FIG. 9). To mimic the 3' base additions, we added an extra base to the 3' ends of the Y2 RNA G and C strands. Upon adding a 3' extra base either enzymatically (FIG. 2A) or chemically (FIG. 10A), the amounts of T7 RNAP reaction products increased dramatically. These results demonstrate a requirement of 3' base additions to G and C strand sequences for efficient RNA replication.

We sequenced the RNA products of T7 RNAP reactions from templates with an extra 3' adenine (FIG. 11). The product sequences corresponded to the input template sequences, as expected for templated RNA replication. Importantly, RNA products of both strand orientations were detected in the same reaction initiated with a particular chemically synthesized RNA template (FIG. 11C). When a T7 RNAP reaction was initiated with the Y2 RNA G strand with an extra 3' adenine, 35% of the products aligned uniquely to the complementary C strand (FIG. 11A). Furthermore, newly synthesized products with G strand orientation could be identified distinctly from starting template molecules because T7 RNAP adds bases to the 3' ends of RNA. Indeed, a diversity of 3' end sequences was observed in the T7 RNAP reaction products that aligned uniquely to the G strand compared to a single 3' end sequence for the starting template (FIG. 11A). Analogously, newly synthesized RNA molecules of both strand orientations were detected when a T7 RNAP reaction was initiated with the Y2 RNA C strand with an extra 3' adenine (FIG. 11B).

Figure 2B:
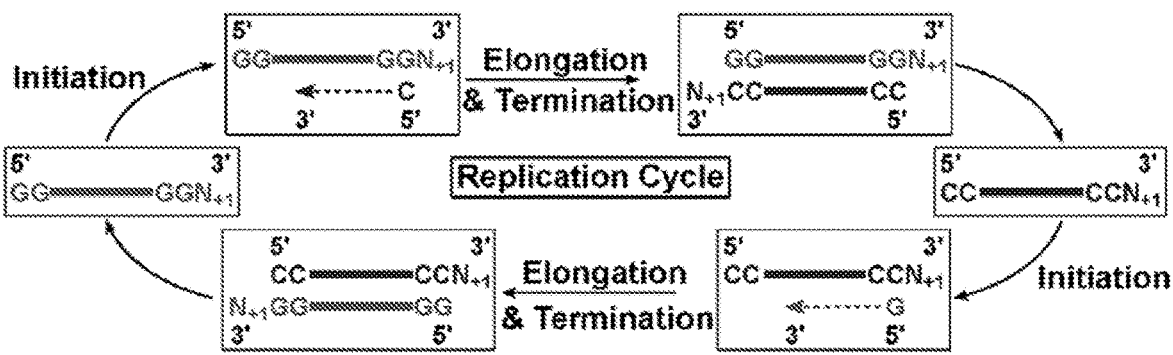

Our results, in particular the lack of copying of the added 3' base, inform a "subterminal de novo initiation" model for RNA replication by T7 RNAP (FIG. 2B). Under our model, T7 RNAP de novo initiates upstream of the 3' extra bases rather than at the 3' end. After 5'→3' copying of the RNA template, T7 RNAP adds 3' extra bases to the RNA product. In effect, the 3' base addition confers the appropriate 3' end for the RNA product to subsequently serve as an efficient template, while maintaining the chain length of the replicating RNA species.

The requirement of 3' extra bases exemplifies a hallmark of RNA replication that is shared between numerous viral RNA-dependent RNA polymerase (RdRp) systems (11) and the transcription polymerase studied here. A possible mechanism for the function of 3' extra bases is suggested by experiments with the RdRp of bacteriophage Qβ showing that a 3' extra base can provide stabilizing interactions at the polymerase active site for more efficient de novo initiation (12).

Replicating RNAs as Sequence Ensembles

Figure 3B:
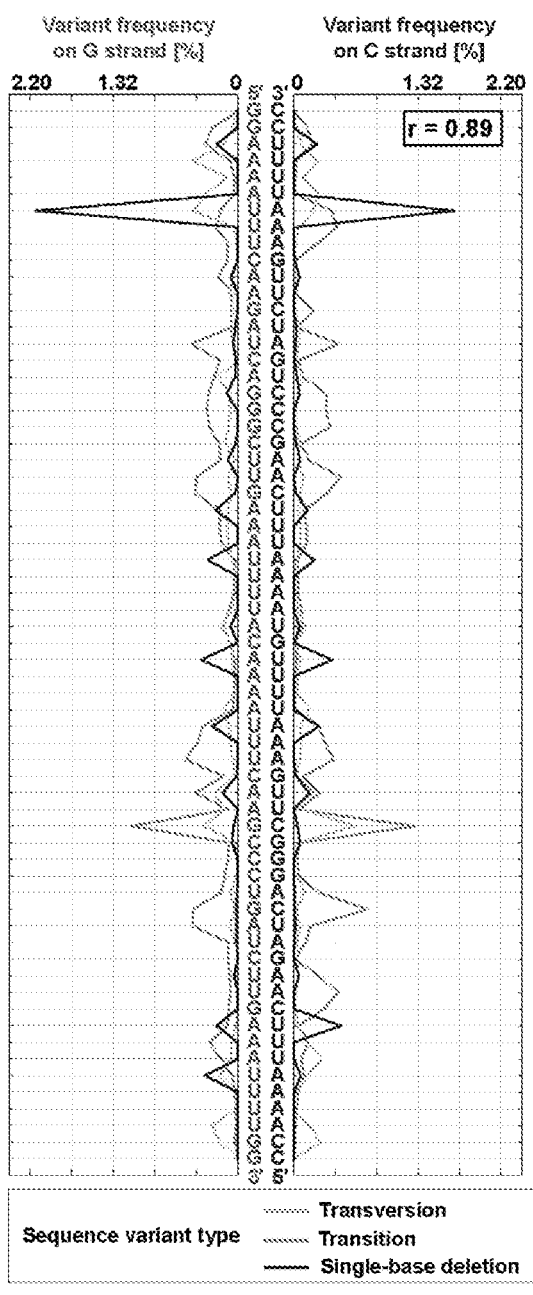
Figure 3C:
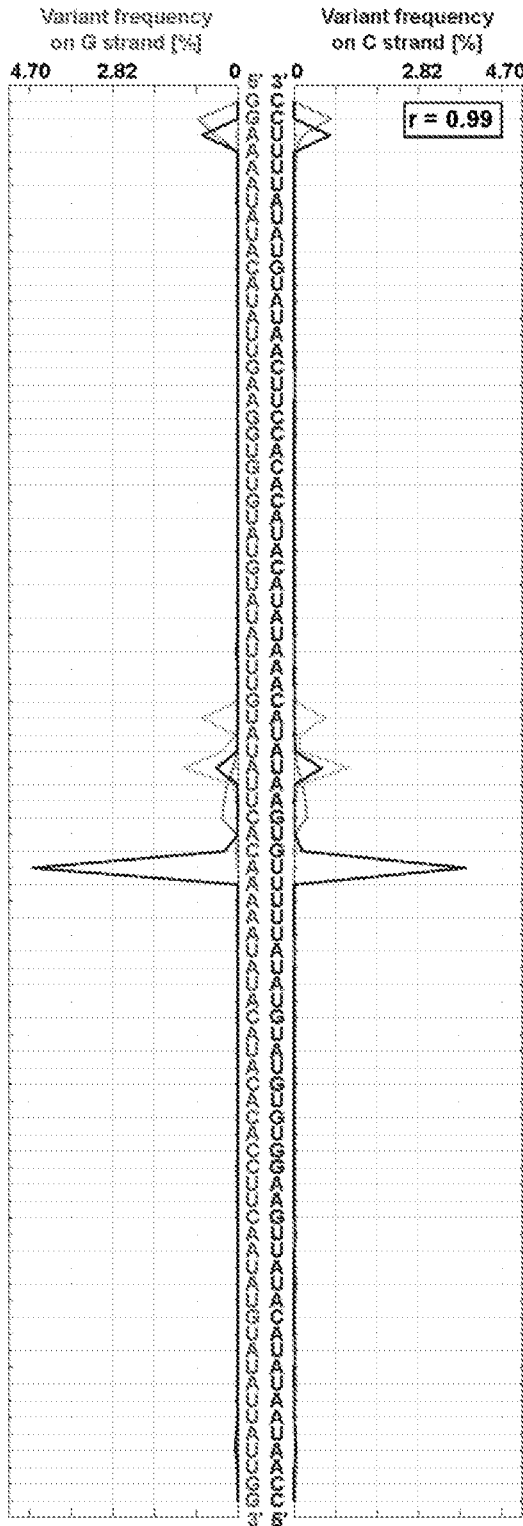

Viral replicating RNAs are heterogeneous populations consisting of multiple replication-competent sequences (e.g. 13). We assessed the population-level sequence heterogeneity of RNAs replicated by T7 RNAP. Upon examining full-length sequences from replicating RNA populations, we found that sequence variants on the two RNA strands were complementary and that complementary variants occurred at similar frequencies (FIG. 3). As an example of such complementarity, for the RNA species shown in FIG. 3B, G→A variation at position 44 (from the 5' end) on one strand occurs at a frequency of ~1.1%, while C→U variation at position 21 (from the 5' end) on the complementary strand (this is position 44 from the 3' end) occurs at a frequency of ~1.3%. As our RNA-seq protocol is strand-specific (e.g. see sequencing of chemically synthesized RNA oligos in FIG. 11), complementary variation on the two strands shows that RNA templates bearing sequence variants can be replicated. RNA species replicated by T7 RNAP thus consist of multiple replication-competent sequences, and should be conceptualized as sequence ensembles rather than as individual sequences.

Structural Requirements for RNA Replication 2-way and 4-way repeats were structural features shared by the RNA sequences obtained from the no-template-added, high concentration T7 RNAP reactions. We performed high-throughput mutagenesis of the 2-way and 4-way repeats to directly test whether these particular structural features are required for RNA replication. Specifically, we designed a series of degenerate libraries; each library was made by randomizing a subset of base identities at a distinct set of 5 or 6 positions in either X RNA (4) or Y2 RNA. Each library thus contained $4^5$-$4^6$ RNA sequence variants. To test the 4-way repeat requirement, four potentially base pairing positions in the 4-way repeat were randomized. To test the 2-way repeat requirement, two potentially base pairing positions in the 2-way repeat (but outside the 4-way repeat) were randomized. We performed T7 RNAP replication reactions with the degenerate libraries to enrich for efficiently replicating RNAs, sequenced RNA populations before and after replication, and asked whether the replicated populations showed sequence co-constraints between the positions with randomized bases (FIG. 4).

At the positions used to test the 2-way repeat requirement, the combinations represented after RNA replication were dominated by Watson-Crick base-pairs (FIG. 4A). At the positions used to test the 4-way repeat requirement, the most abundant RNA sequences had one of the four possible 4-way Watson-Crick base combinations—(A,U,A,U), (U,A,U,A), (G,C,G,C) or (C,G,C,G) (FIG. 4B).

It should be noted that not all Watson-Crick base combinations were replicated efficiently for any given degenerate library. But for each set of positions used to test the 2-way or 4-way repeat requirements, we did detect at least two abundant Watson-Crick base combinations (FIGS. 4A and 4B).

We also constructed a degenerate library where we randomized the base identities at only two of the four potentially base pairing positions in a 4-way repeat. After templated replication of this library, the most abundant RNA sequences contained a single 4-way Watson-Crick base combination that was expected given the identity of the fixed bases in the 4-way repeat (FIG. 4C). We conclude that both the 2-way and 4-way repeats are required for efficient replication of X and Y2 RNA by T7 RNAP.

Based on the function of the 2-way repeat, we suggest that a long hairpin structure is required for RNA replication by T7 RNAP. A long hairpin may thermodynamically allow for strand separation of the complementary strands, which would be needed to generate active single-stranded templates for continued replication (14).

Figure 4D:
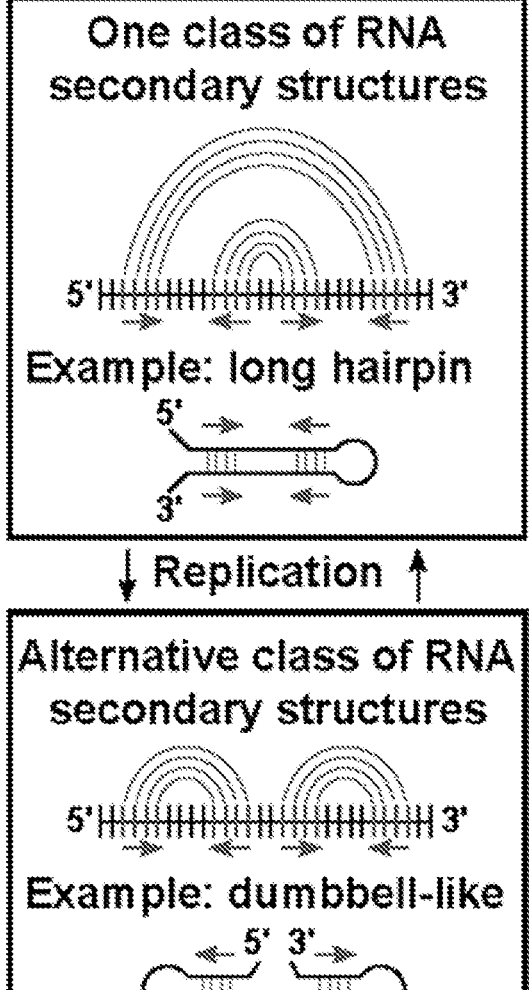

The functional role of the 4-way repeat suggests that the capability to change secondary structure ("shape-shift") is required for an RNA template to be efficiently replicated by T7 RNAP (FIG. 4D). Possible advantages conferred by shape-shifting include faster strand separation of the complementary strands (15) and more efficient unwinding of the RNA template by T7 RNAP.

Interrupted Rolling Circle Mechanism for RNA Concatemer Synthesis

RNA concatemers—RNA chains consisting of multiple, full-length repeats of template sequence—have been identified as intermediates during replication of viroids and Hepatitis delta (16, 17). A ladder of RNA concatemers (dimers, trimers, tetramers etc.) also forms during RNA replication by T7 RNAP (3). To investigate mechanisms of RNA concatemer formation, we analyzed the sequences of RNA dimers obtained from T7 RNAP reactions starting with diverse pools of chemically synthesized RNA monomer templates. For terminology, we define an "RNA monomer" as comprising a single repeat of full-length template RNA sequence and an "RNA dimer" as comprising two repeats.

Figure 5A:
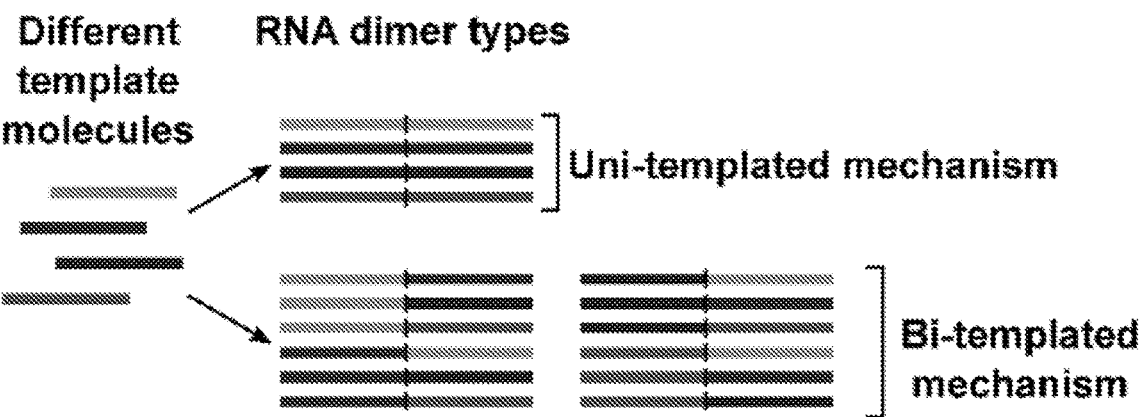

We considered two types of mechanisms for RNA dimer formation using monomer templates (FIG. 5A)—1) Uni-templated and 2) Bi-templated. In a uni-templated mechanism, the same monomer template molecule instructs synthesis twice to form the dimer. In a bi-templated mechanism, two different monomer template molecules (which may still have the same sequence) instruct synthesis of each half of the dimer.

Figure 5B:
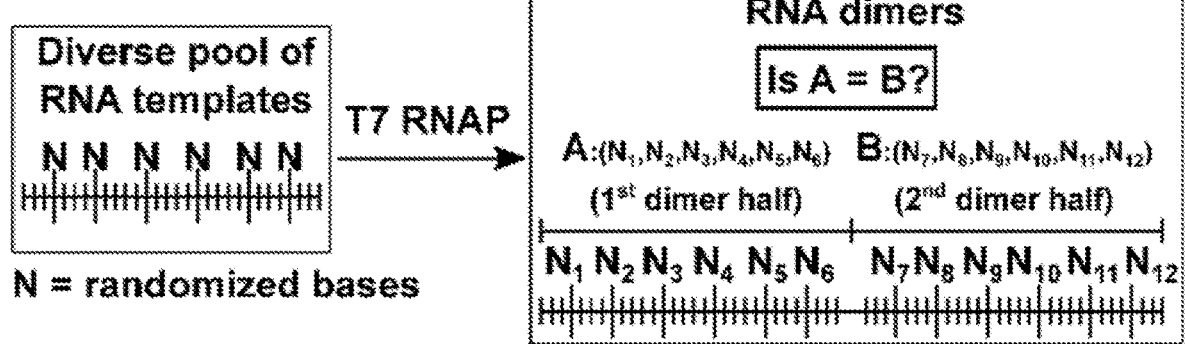

The presence of a diversity of monomer templates in the same T7 RNAP reaction was a key aspect of the experimental design to elucidate the RNA dimer formation mechanism (FIG. 5B) (18). We sequenced RNA dimers from two starting monomer template pools called $X_1$ and $Y2_1$ (these pools were also used earlier for FIG. 4 experiments, and were constructed by randomizing a subset of base identities at six positions each in the X RNA and Y2 RNA sequences, respectively). We expected that uni-templated synthesis would result in the two halves of RNA dimers containing the same six base combination at the positions with initially randomized bases. In contrast, bi-templated synthesis would be expected to lead to relatively rare agreement of the six base combination between the two dimer halves (in proportion to the concentration of the six base combination in the reaction pool).

Figure 5D:
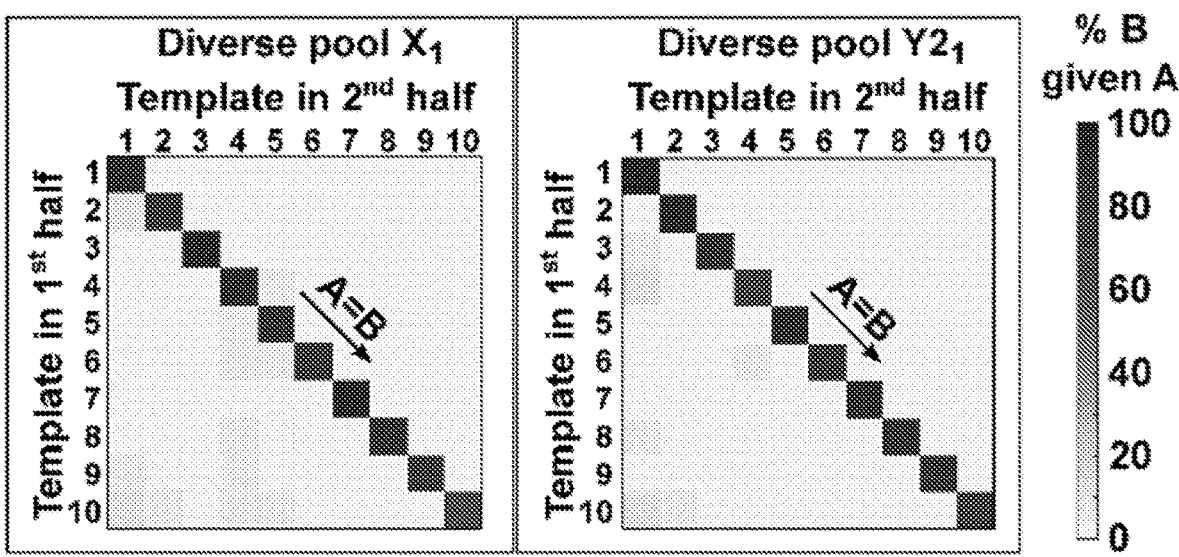

We found strong sequence agreement between the six base combinations of both dimer halves for the vast majority of dimer sequences (analysis in bulk in FIG. 5C and by individual RNA templates in FIG. 5D). These results suggest that uni-templated synthesis is the dominant mechanism for formation of RNA dimers. As predicted by a uni-templated synthesis mechanism, we also found that sequence variants located outside the intentionally randomized six bases were concordant between the dimer halves (FIG. 13). Of note, the concordance of sequence variants between RNA dimer halves provides direct and independent evidence for active replication of RNA templates bearing sequence variation compared to the reference sequence (shown earlier in FIG. 3).

Figure 5E:
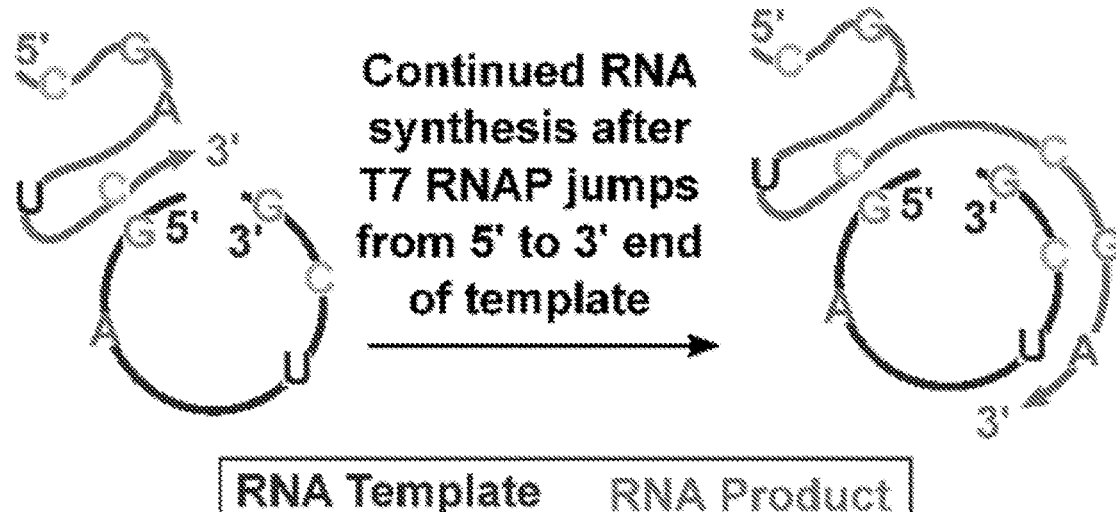

How does T7 RNAP use the same template molecule processively to instruct multiple rounds of RNA synthesis? We propose that after reaching the 5' end of a replicating RNA template during RNA synthesis, T7 RNAP can jump (19) from the 5' end to the 3' end of the template without dissociation of the RNAP-template-product complex. Continued RNA synthesis after the jump appends a new copy of the template to the existing RNA product. We refer to this mechanism as interrupted rolling circle synthesis (FIG. 5E).

We further examined the junction sequences between the two RNA dimer halves to assess whether the proposed jumping of T7 RNAP is associated with any sequence signatures. A diversity of sequences was found at the dimer junction. The junction sequences qualitatively resemble the 3' end sequences of RNA monomers (including the extra base additions) followed by the 5' end sequences of RNA monomers. Further, as would be expected for RNA dimer synthesis from a linear monomer template, the junction sequence for a particular dimer molecule did not necessarily agree with the 3' end sequence of that dimer (FIG. 14). Two other pieces of evidence also suggest that the monomer templates instructing dimer synthesis were linear rather than circular: (i) we obtained RNA dimers starting with monomer RNAs bearing ends (5'-OH and 3'-OH) that are chemically incompatible for ligation, and (ii) Konarska and Sharp found that explicitly circularized X or Y RNA were not replicated efficiently (4).

Potential Relevance of an Interrupted Rolling Circle Model for Viroids and Hepatitis Delta Current mechanistic models for replication of viroids and Hepatitis delta involve RNA concatemer intermediates produced by rolling circle synthesis using circular RNA templates. Linear RNA molecules are also detected alongside circular RNAs in populations of viroids and Hepatitis delta.

It has been proposed that the linear RNA molecules may be active as templates for instructing RNA synthesis (20, 21 and references therein) but how linear RNAs could template synthesis of RNA concatemers remained unanswered.

An interrupted rolling circle mechanism with linear RNA templates offers a plausible alternative to the use of circular templates for RNA concatemer synthesis. To assess the applicability of an interrupted rolling circle mechanism to viroid replication, we examined published data for avocado sunblotch viroid (ASBVd) (22) and peach latent mosaic viroid (PLMVd) (20). Both ASBVd and PLMVd belong to the Avsunviroidae family of viroids, and are replicated in the chloroplasts of infected plants. Interestingly, ASBVd may be replicated by a chloroplastic RNA polymerase similar to T7 RNAP (8). ASBVd and PLMVd populations contain particular 5' triphosphate-bearing, monomer-length, linear RNA sequences for both strand orientations. The following two aspects of these linear monomers are more parsimoniously explained by a linear template model rather than a circular template model: (i) Initiation of RNA synthesis (or 5' end specification): The measured 5' initiation sites for ASBVd and PLMVd are such that the 5' initiation site for the (+) strand corresponds to the 3' end of a linear (−) molecule present in the RNA population and the 5' initiation site for the (−) strand corresponds to the 3' end of a linear (+) molecule in the population. Under a circular template model, such positioning for the 5' ends of the (+) and (−) strands would be a priori considered coincidental, with an additional source of specificity such as particular structural or sequence motifs (20, 22) required to explain the initiation site positioning. Under a linear template model, the measured 5' ends of the (+) and (−) strands would be expected simply based on full-length copying. (ii) Termination of RNA synthesis (or 3' end specification): The presence of a defined set of monomer-length linear molecules in ASBVd and PLMVd populations requires an explanation for precise 3' end generation. Under a circular template model, the RNA 3' ends can be explained by positing specific termination signals for RNA synthesis or by particular RNA cleavage events in vivo. Under a linear template model, the RNA 3' ends can be explained more simply by the termination of RNA synthesis upon reaching the template end.

An implication of the linear template model may be that viroids and Hepatitis delta circularize not for their replication but to withstand other selective pressures such as degradation by exonucleases.

Origin of Replicating RNAs Via Molecular Evolution

The variability observed in the sequences of replicating RNAs between no-template-added reactions raises several fundamental questions regarding the origins of replicating RNAs. Do distinct replicating RNAs originate in each reaction or are pre-existing replicating RNAs amplified? If new replicating RNAs do originate in each reaction, are they assembled from single nucleotides or is their formation partly templated?

We conjectured that obtaining many additional sequences of replicating RNA species may provide insights towards these questions of replicating RNA origins. We thus developed a microfluidic assay to conduct no-template reactions in high-throughput (FIG. 15). By splitting our usual 10 μl reaction volume into ~170 thousand isolated drop reactions (each drop was ~60 picoliters), we expected to capture a higher diversity of replicating RNAs that would otherwise be lost because of competition in bulk. We analyzed the RNA contents of the no-template, high concentration T7 RNAP reactions in drop format by aggregating ~$10^5$ drops at a time, and found, as expected, numerous RNA species (Table 2) that had different sequences but similar structures to what was observed in the earlier tube reactions. Examples of RNA species obtained from the aggregated drop reactions are shown in FIG. 6E, FIG. 18 and FIG. 20B.

Within the large repertoire of RNA species we compiled using drop reactions, a subset of the RNAs contained sequence stretches that matched perfectly to known biological sources. Matches were commonly found to humans and to biological materials or organisms found in proximity to humans. From one no-template-added drops experiment, where we had included bovine serum albumin (BSA) in our reactions to aid drop-reaction generation, we isolated RNA sequences similar to a replicating RNA sequence T7rp1 reported previously by Biebricher and Luce (5). Interestingly, T7rp1 (and also the RNA sequences we isolated) strongly matched a sequence found in the genomes of cow and yak (FIG. 19). These results suggested that replicating RNAs could evolve from residual nucleic acids present in the high concentration T7 RNAP reactions. Of note, we never synthesized or handled any of the replicating RNA sequences reported by Biebricher and Luce.

As with drop reactions, we also found novel RNA species that matched known genomes upon sequencing more no-template-added reactions set up in tubes (e.g. FIG. 6A shows an RNA species matching humans and FIG. 20A shows an RNA species matching a bacterium commonly found in cheese (23)).

A working hypothesis at this point was that the RNAs replicated by T7 RNAP can originate through partial instruction from DNA seeds. We first focused on DNA seeds as a possibility (rather than the alternate possibility of RNA seeds) because the detected matches in replicating RNAs were represented throughout the genome rather than in specific transcribed regions.

To experimentally test the hypothesis that replicating RNAs can originate from DNA seeds, we assessed whether T7 RNAP could catalyze the emergence of new replicating RNAs from a complex DNA seed pool of our own choosing (FIG. 6B). The seed pool we used was a mixture of well-characterized model system genomes [three nematode species (*Caenorhabditis elegans, Caenorhabditis remanei* and *Caenorhabditis brenneri*), yeast (*Saccharomyces cerevisiae* strain S288C), coliphage lambda and a laboratory plasmid]. We chose these particular sources of DNA to reflect a range of genome sizes and sequence complexities. An additional consideration was that the chosen DNA sources did not significantly match any of the replicating RNAs that we had previously isolated. With the exception of lambda DNA which was isolated from purified phage, the DNA seeds were derived from cellular sources. Hence, we extensively treated the DNA seeds with RNase A and RNase I before use. After treating with RNases and combining the DNA seeds from all the chosen sources, we split the seed pool into three equal parts. One part underwent no further treatment, the second part was treated with DNase and the third part was heated with alkali (0.2 N sodium hydroxide at 70° C. for 1 hour) to further hydrolyze any possible remaining RNA (hot alkali treatment also provided an assessment of seed activity from denatured DNA).

We conducted high concentration T7 RNAP reactions in drop and tube format for four experimental conditions in parallel: (1) Unseeded, (2) Seeded with DNA pool (which we had prepared), (3) Seeded with DNase-treated DNA pool, and (4) Seeded with hot alkali-treated DNA pool. For each experimental condition, we sequenced aggregated drop and tube reactions. From comparable reaction volumes and sequencing depths, the number of replicating RNAs identified per reaction was 53+/−22 (mean+/−standard deviation) for 8 aggregated drop reactions and 7+/−5 for 6 tube reactions (Table 2). We then used BLAST (24) to align the replicating RNAs obtained from all four conditions to the expected sequences present in our designed DNA pool. As a control, we also aligned the replicating RNAs to the complete genomes of all other species that were available in the RefSeq Genomic database (25). Of the four experimental conditions examined, only the "Seeded with DNA pool" and "Seeded with hot alkali-treated DNA pool" conditions yielded replicating RNAs that were derived from our designed DNA pool (FIGS. 6C, 6E, 20B). Significant matches specific to our DNA pool were absent in two negative controls—the "Unseeded" and "Seeded with DNase-treated DNA pool" conditions (FIG. 6C). These results demonstrate that the RNAs replicated by T7 RNAP can originate from DNA seeds.

What may be the molecular mechanism for the origin of replicating RNAs from DNA seeds? A striking pattern is revealed when the location of the matching seed in a replicating RNA sequence is compared to the positions of the 4-way repeat units for that sequence. The seed match starts at an end of the replicating RNA and extends up to the second 4-way repeat unit that is encountered from the start of the match (FIG. 6D). These data are consistent with models for the formation of replicating RNAs which at minimum include the steps of (FIG. 6F): (i) T7 RNAP-catalyzed transcription of a DNA seed to RNA, (ii) One round of self-templated 3' extension of RNA to acquire a second 4-way repeat unit, and (iii) A second round of self-templated 3' extension of RNA to acquire the full 2-way and 4-way repeat configurations (26, 27). This minimal series of biochemical steps can lead to the formation of RNA molecules with 2-way and 4-way repeat configurations. Once such RNAs are formed, they have the potential to replicate efficiently (based on FIG. 4) and to become predominant in the high concentration T7 RNAP reactions because of Darwinian selection. Thus, an RNA structural framework drives the DNA-seeded emergence of replicating RNAs.

In terms of biological significance, our work provides an experimental window into how replicating RNAs such as viroids or Hepatitis delta might originate via host transcription polymerase activities. Just as new replicating RNAs originate from distinct DNA seeds in our T7 RNAP reactions, so may emergence of new RNA replicons be ongoing in nature, independent of other pre-existing RNA replicons. Of note, derivation from host nucleic acids is one of several hypotheses that have been put forth for the origins of viroids and Hepatitis delta (28-30).

Our work also provides new insights into the rich history of mysterious products emerging from in vitro no-template-added reactions for both DNA and RNA polymerases (e.g. 31, 32). A key question was whether such reactions evidence molecular evolution or are the observed products a result of amplification of pre-existing templates. Ascertaining the involvement of a pre-existing template was challenging because a replicative cycle triggered by a single template molecule (which would be below detection limits) could have resulted in the observed products. Emergence of novel RNA replicons from a complex DNA seed pool of our own choosing (FIG. 6B-E) shows that high concentration T7 RNAP reactions can witness DNA-seeded origin and evolution of replicating RNAs rather than just amplification of pre-existing templates.

Biotechnological Applications

We have shown that the sequence space of RNA templates that can be replicated by T7 RNAP is large. T7 RNAP-catalyzed RNA replication can thus serve as a valuable strategy for a myriad in vitro RNA amplification applications, including direct selection of RNA aptamers without intermediate conversion to DNA and synthesis of large amounts of RNA. In vivo applications of T7 RNAP-RNA replication may rely on transfection of cells with pools of replicating RNAs synthesized in vitro or on stable maintenance of replicating RNAs in vivo. The latter approach is facilitated by the relative simplicity of T7 RNAP as a single polypeptide chain that has already been transgenically expressed in vivo in a variety of organisms. RNAs replicated by T7 RNAP consist of long 2-way repeats and hence, may be particularly suitable for gene silencing applications utilizing hairpin RNAs.

Role of 3' Base Additions in RNA Replication

To distinguish between subterminal (FIG. 2B) and terminal initiation mechanisms, we analyzed the 5' and 3' sequence ends of RNA products from reactions initiated with templates bearing an extra 3' adenine. Under a terminal initiation model for such templates, uracil would be expected as the 5' base for complementary strand products. Further, for products with the same strand orientation as the starting template, an expectation with terminal initiation would be that a 3' consensus adenine is positioned in the sequences before the occurrence of diverse, T7 RNAP-catalyzed, 3' base additions. On the other hand, under a subterminal initiation model, both (i) 5' uracil for the complementary strand products and (ii) a 3' consensus adenine for the same strand products, would not be expected.

In our data, complementary strand products do not evidence 5' uracil above background levels (background measured using control chemically synthesized RNA oligos; a background of 5' extensions was expected from reverse transcriptase activity during RNA-seq library preparation) (FIG. 10C). An interpretation of our observed 5' sequence distributions is that guanine serves as the main 5' initiation nucleotide on one strand and cytosine on the other strand, consistent with the 5' initiation nucleotide identities experimentally determined by Konarska and Sharp using two different assays (3). Furthermore, in our data, same strand products did not contain a 3' consensus adenine (FIG. 11). 3' base additions by T7 RNAP were not positioned after a possible 3' consensus adenine; instead, diverse 3' base additions were detected prior to the expected position of a 3' consensus adenine. Thus, analysis of both the 5' and 3' sequence ends of RNA products supports a subterminal initiation model over terminal initiation.

We note that previously published chromatography data are consistent with our findings regarding the significance of 3' base additions in RNA replication by T7 RNAP. The high frequency of 3' base additions in replicating RNA populations may explain why Konarska and Sharp observed all four bases at the 3' end of X RNA using a radioactivity-based assay (FIG. 7D in (4)). Furthermore, a role of 3' extra bases could potentially have been masked in previous studies on T7 RNAP-RNA replication because the RNA templates were prepared using run-off transcription of synthetic DNA oligos, which is known to result in RNA products with 3' extra bases (e.g. 9, 10).

We further note a slight gel mobility difference between Y2 RNA replication products and chemically synthesized Y2 RNA oligos (FIG. 2A, FIG. 10A) on our denaturing gels [10% TBE-urea gel (29:1 acrylamide/bis)]. The mobility difference may be collectively accounted for by (i) the different 5' chemical ends of replication products (5'-triphosphate) and RNA oligos (5'-hydroxyl) (FIG. 10B), and (ii) 3' base additions longer than one nucleotide in replication products.

Requirement of 2-Way and 4-Way Repeats for Efficient RNA Replication 2-way and 4-way repeats confer a fitness advantage for RNA replication by T7 RNAP. However, RNA templates with distortive mutations that would disrupt perfect complementarity in the 2-way or 4-way repeats can (at least in some cases) still be replicated, as evidenced by (i) strong correlation between frequencies of distortive mutations on one strand and frequencies of their complementary mutations on the other strand (FIG. 3), and (ii) concordance of distortive mutations between the two halves of RNA dimers (FIG. 13). The capability of templates with distortive mutations to be replicated shows a lack of rigid RNA structure requirements for replication, and has implications for replicating RNA evolution: RNAs could evolve gradually through single sequence changes at a time.

Additionally, we note that for the Y21 degenerate library in FIG. 4, the second most abundant 4 base combination was not Watson-Crick but was a single sequence change away from the most abundant 4 base combination (which was a 4-way Watson-Crick base combination). The specific single sequence change in the second most abundant 4 base combination would not allow a Watson-Crick base pair but could still allow a GU wobble base pair for one of the replicating RNA strands.

Interrupted Rolling Circle Mechanism for RNA Concatemer Synthesis

We performed several quantitative analyses to assess the sequence agreement between RNA dimer halves. We found that the observed sequence agreement between dimer halves was much more frequent than would be expected based on a bi-templated synthesis model (FIG. 12). These results suggest that uni-templated synthesis is the dominant mechanism for formation of RNA dimers.

We had obtained RNA dimers starting with mixtures of monomer templates containing intentionally randomized bases at specific positions. In evaluating sequence variants located outside the intentionally randomized bases in RNA dimers, we found that the concordance of variants between the two dimer halves was more frequent by 4.5-7 fold than would be expected based on the variants occurring independently in each dimer half (FIG. 13). To give a sense of the magnitude of this concordance: for most sequence variants, concurrent incidence in both dimer halves was more frequent than incidence in either half alone. These results again support a uni-templated synthesis mechanism for RNA dimer formation.

From examining previously published data on the RNA concatemers of X RNA (3), we note that the interrupted rolling circle model quantitatively explains the RNase T1 cleavage patterns observed for these RNA concatemers. A previous report had hypothesized an apparent rolling-circle mechanism operating on single-stranded linear DNA oligos transcribed by T7 RNAP (33). But in that report, only a single template sequence was used per reaction and therefore, the data shown were also consistent with a mechanism for RNA concatemer formation involving multiple template molecules.

A structural interpretation of our interrupted rolling circle model may be that upon completion of a round of template copying, the 5' and 3' ends of a replicating RNA monomer template are close to each other in space at the active site of T7 RNAP. The proximity of the template ends in space may facilitate jumping of T7 RNAP from the 5' to 3' end.

The mechanism generating the extra bases observed at the junction between the two halves in RNA dimers is not fully known. The extra bases at dimer junctions could be a result of 3' extra base additions to RNA products by T7 RNAP as it jumps from the 5' to 3' end of the RNA template and/or a result of the copying of the extra bases present at the 3' end of the monomer template.

Origin of Replicating RNAs Through Partial Instruction from DNA Seeds

Before conducting the no-template-added, high concentration T7 RNAP reactions in drop format, we first tested whether our microfluidic assay could support replication of our characterized chemically synthesized RNA templates at low concentrations of T7 RNAP. Templated RNA replication catalyzed by T7 RNAP in drops was evident using (i) gel electrophoresis analysis, whereby RNA synthesized cumulatively in a pool of drops could be visualized, and using (ii) a fluorescence imaging-based drop-by-drop assay of RNA synthesis, with inclusion of a nucleic-acid binding dye into the drops. In the latter approach, dilution of the starting RNA template allowed us to track the percentage of drops that were fluorescent after reaction incubation as a function of the starting RNA template concentration, akin to digital droplet PCR (FIG. 17).

For the RNAs synthesized in no-template-added, high concentration T7 RNAP drop reactions, we also conducted functional tests to assess replication-competence. Specifically, aggregated drop reactions were used in bulk as templates in fresh, microliter-scale, low concentration T7 RNAP reactions and the resulting RNA pools sequenced. The numerous RNA species from the initial no-template-added drop reactions that were amplified in the bulk, low concentration T7 RNAP reactions exhibited typical sequence and structural hallmarks of replicating RNAs (FIG. 18)—(i) 2-way repeats, (ii) 4-way repeats and (iii) GG and CC end sequences outside the 2-way repeats: one strand containing two G bases at or close to both the 5' and 3' ends (and therefore, the complementary strand containing two C bases at or close to both the 5' and 3' ends). We concluded that novel replicating RNAs can be isolated from no-template-added drop reactions.

Of note, no-template-added tube and no-template-added aggregated drop reactions migrated differently on denaturing gels. The tube reactions appeared mostly as well-defined bands corresponding to particular replicating RNA species (e.g. FIG. 1B). The aggregated drop reactions appeared as smears (FIG. 16), reflecting the rich diversity of RNA products that was also evident upon high-throughput sequencing.

We performed the analyses presented in FIG. 6B-E and FIG. 20B as follows. For each sequenced pool from an aggregated drop reaction or tube reaction, we performed a global, sequence-agnostic analysis and grouped all the detected sequences into RNA species. For each of the aggregated drop reactions, a subset of species contained complementary RNA sequences with GG and CC end sequences located outside a 2-way repeat configuration. Within this subset of RNA species, two distinguishable clusters of species were observed, corresponding to species with long and short 2-way repeats. Based on previous experimental results (FIGS. 1, 4, and 18), we identified as replicating RNAs from all drop and tube reactions, RNA species that contained two sequence hallmarks: (i) long 2-way repeats, and (ii) GG and CC end sequences outside the 2-way repeats (with the molecules containing the GG and CC end sequences being complementary). These two sequence hallmarks were also found to be sufficient to identify the predominant RNA species in cases where the reaction products migrated as well-defined bands on denaturing gels (i.e. tube reactions that had been set up in parallel as part of the experiment). It should be noted that other RNA species in the aggregated drop reactions that we are currently excluding from analysis (e.g. species with short 2-way repeats or species without the GG and CC end sequences) could also be competent for replication. Our current knowledge of replicating RNA sequence features stems primarily from tube-based replication assays which are inherently competitive in nature. Compartmentalizing the volume of a tube reaction into smaller drop reactions could lead to better detection of replicating RNA species with divergent sequence features.

The chemical space of nucleic acids that can seed emergence of novel RNA replicons is not fully known. Although our experiments evidence the origin of replicating RNAs from DNA seeds, it is foreseeable that particular RNA molecules could also work as seeds in certain circumstances (34). For example, we might expect any RNA that mimics an intermediate product involved in the proposed model in FIG. 6F to serve as a seed. Furthermore, our assays do not currently allow us to gauge relative seeding efficiencies for different types of DNA molecules (single-stranded versus double-stranded, or with differing seed length, sequence identity or end configuration such as 3' overhang versus 5' overhang versus blunt ended for dsDNA seeds). As we obtained replicating RNAs matching our complex seed pool both before and after treatment of the seed pool with hot alkali, both single-stranded and double-stranded DNA molecules may be competent as seeds.

It is important to appreciate the difference between (i) a replicating RNA originating from a seed and (ii) being able to detect a replicating RNA as having originated from a seed. We can only confidently assign replicating RNAs to initiating seeds when the detected seed matches are long, and essentially mismatch- and gap-free. Such high-quality seed matches were observed for only a subset of replicating RNAs. The lack of a significant seed match to a replicating RNA could be for several reasons, including: (i) the initial seed used in generating the replicating RNA may have contributed only a short sequence, (ii) the replicating RNA may have diverged in sequence from its seed due to extensive mutation and selection, (iii) the seed sequence may be absent from our current databases, and (iv) the replicating RNA could conceivably have originated through alternative mechanisms such as de novo assembly from single nucleotides (31).

Some details of the mechanistic scheme proposed in FIG. 6F are also worth clarifying: (i) The RNA product in the first step of the model ("Transcription") contains a sequence stretch matching the DNA seed (red box in FIG. 6F) but may additionally contain novel 5' and 3' end sequences generated by T7 RNAP (black stubs flanking the red box); (ii) The first round of RNA-templated 3' extension may be primed by bases that were copied from the DNA seed and/or by extra bases added by T7 RNAP to the 3' end of the transcribed RNA product; (iii) While the two rounds of RNA-templated 3' extension are depicted as being intramolecular in FIG. 6F, the possibility of RNA-templated intermolecular 3' extension cannot be excluded; (iv) More than two rounds of RNA-templated 3' extension could also occur [e.g. sequence in the loop region of the putative long hairpin could (at least in some cases) be derived from an additional round of RNA-templated 3' extension]; and (v) RNA-templated synthesis of new RNA chains could occur at several intermediate steps before the formation of a full-length replicating RNA.

RNA Replication by the DNA-Dependent RNA Polymerase of Bacteriophage T3

We found that T3 RNA polymerase can replicate an RNA species with a reference sequence similar to Y2 RNA. The capability of T3 RNA polymerase to replicate RNA was also noted by Biebricher and Luce (5).

Materials and Methods

Key Reagents/Equipment
10% TBE-Urea gels (Bio-Rad #4566033)
TBE running buffer (prepared from National Diagnostics #EC-860)
Gel Loading Buffer II (Ambion #AM8547) (solution of 95% Formamide, 18 mM EDTA,
0.025% SDS, Xylene Cyanol and Bromophenol Blue)
SYBR Gold 10,000× Concentrate (ThermoFisher #511494)
Nucleoside triphosphates or NTPs (NEB #N0466)
PEG 8000 (Fluka #81268)
0.2 micron syringe filter (Pall Life Sciences #4192)
DTT (Gold Biotechnology #DTT10)
Spermidine (Sigma #S0266)
0.1% (v/v) Triton X-100 (Sigma #T8787)
1.5 ml siliconized tubes (Thomas Scientific #2591L12)
Glycoblue (Ambion #AM9515)
T4 RNA ligase 2, truncated, K227Q (NEB #M0351)—50% PEG 8000 and 10×T4 RNA ligase buffer (500 mM Tris-HCl, 100 mM MgCl$_2$, 10 mM DTT, pH 7.5 at 25° C.) supplied with this product are used in the 3' adapter ligation reactions
SuperScript III (Invitrogen #18080044)—5× First Strand Buffer (250 mM Tris-HCl (pH 8.3), 375 mM KCl, 15 mM MgCl$_2$) and 0.1 M DTT supplied with this product are used in the reverse transcription reactions
RNase OUT (Invitrogen #10777019)
Deoxynucleoside triphosphates dNTPs (Sigma/Roche #11969064001)
CircLigase II (Epicenter #CL9025K)—10× circLigase II buffer (0.33 M Tris-acetate (pH 7.5),
0.66 M potassium acetate and 5 mM DTT), 50 mM MnCl2 and 5M Betaine supplied with this product are used in cDNA circularization reactions
CircLigase (Epicenter #CL4115K)—10× circLigase buffer (0.5 M MOPS (pH 7.5), 0.1 M KCl, 50 mM MgCl$_2$, and 10 mM DTT), 50 mM MnCl$_2$, 5M Betaine and 1 mM ATP supplied with this product are used in cDNA circularization reactions TrackIt 10 bp DNA ladder (Invitrogen #10488019)
20/100 ladder (IDT #51-05-15-02)
2× Phusion Master Mix (Thermo Fisher #F531)
HFE-7500 containing 2% wt/wt 008-FluoroSurfactant (RAN Biotechnologies #008-FluoroSurfactant-2wtH-50G)
TURBO DNase and 10× TURBO DNase buffer from TURBO-DNase kit (Ambion #AM1907)
$^1$H,$^1$H,$^2$H,$^2$H-Perfluoro-1-octanol (PFO) (Sigma #370533)
Adenosine 3',5'-diphosphate disodium salt (pAp) (Carbosynth #NA15774)
T4 RNA ligase 1 (NEB #M0204S)—10×T4 RNA ligase reaction buffer (500 mM Tris-HCl, 100 mM MgCl$_2$, 10 mM DTT, pH 7.5 at 25° C.) supplied with this product is used for 3' base addition reactions Lambda phage DNA (NEB #N3011S)
*S. cerevisiae* genomic DNA (Sigma/EMD Millipore #69240)
*C. elegans* strain PD1074 (a wild-type N2 strain characterized extensively in the Fire lab)
*C. remanei* strain PB4641, gift from Marie-Anne Felix and Aurélien Richaud
*C. brenneri* strain JU1397, gift from Marie-Anne Felix and Aurélien Richaud
RNase A (ThermoFisher #EN0531)
RNase I (Ambion #AM2295)
Zymo Clean and Concentrator kit (Zymo Research #D4014)
ZymoPURE Plasmid Miniprep kit (Zymo Research #D4208S)
Restriction enzyme MnlI (NEB #R0163S), supplied with 10× CutSmart buffer (500 mM Potassium Acetate, 200 mM Tris-acetate, 100 mM Magnesium Acetate, 1 mg/ml BSA, pH 7.9 at 25° C.)
Restriction enzyme Hpy188III (NEB #R0622S), supplied with 10× CutSmart buffer MS2 genomic RNA (Sigma/Roche #10165948001) used for creating an internal, spike-in standard for quantification of RNA-Seq libraries
Qubit dsDNA BR (ThermoFisher #Q32850) and HS (ThermoFisher #Q32851) kits for quantification of dsDNA DNA and RNA Oligonucleotide Synthesis
Oligos were purchased from IDT, and are listed in Table 3.

Polyacrylamide Gels
Samples were loaded on denaturing gels after adding an equal volume of Gel Loading Buffer II and denaturing at 95° C. for >=2 minutes. Gels were pre-run for at least 30 minutes before sample loading. Gels were stained in a 1:5000-1:10,000 dilution of SYBR Gold stock reagent (dilution in 1×TBE) for 15-30 minutes covered with aluminum foil on a rocker. Gels were imaged using an AlphaImager HP system (ProteinSimple). Two 10 base ladders were used as markers on denaturing gels: (i) TrackIt 10 bp DNA ladder and (ii) 20/100 ladder mixed with a set of DNA ultramers to get a 10 base ladder from 20-200 bases. The ladders were also dissolved in Gel Loading Buffer II and denatured at 95° C. prior to gel loading.

For display purposes, for each of the gel images shown in FIG. 1, FIG. 8, FIG. 10 and FIG. 16, a constant gamma correction (γ=0.3) was applied uniformly across the entire image using MATLAB (Natick, MA). For display purposes in FIG. 2A, a constant gamma correction (γ=0.3) and a constant increase in brightness were applied uniformly across the entire set of gel images using MATLAB. For display purposes in FIG. 7, a constant gamma correction with γ=3.33 was applied uniformly to the denaturing gel images (first three gels from left to right) and with γ=1.0 was applied uniformly to the PCR gel image (rightmost gel) using AlphaView software (ProteinSimple). Gel images that are shown for side-by-side comparison (FIG. 2A, FIG. 8 and FIG. 10A) were all taken at the same exposure.

T7 RNAP-RNA Replication Reactions
High concentration T7 RNAP was either prepared in-house using a protocol previously used to purify crystallography-grade T7 RNAP (35), or purchased as a special order from New England Biolabs (NEB). High concentration T7 RNAP was stored at −80° C. Commercially available low concentration T7 RNAP preps (from either NEB or Agilent) were stored either at −20° C. or −80° C. Unless otherwise stated, buffer composition of T7 RNAP reactions was: 40 mM Tris-HCl (pH 8), 80 mg/ml PEG 8000, 20 mM MgCl$_2$, 5 mM DTT, 1 mM spermidine, 0.01% (v/v) Triton X-100, and 4 mM of each NTP (3). Before use, buffers were sterile-filtered using a 0.2 micron syringe filter. In experiments where several experimental conditions were tested in parallel, the same stocks of buffers, NTPs and T7 RNAP were used for all conditions. Gel filtration (GF) buffer (50 mM Tris-HCl at pH 8, 200 mM NaCl, 2 mM EDTA, 5% glycerol and 2 mM DTT) was used for storage and dilution of the in-house isolated T7 RNAP. To minimize formation of protein aggregates, we recommend diluting T7 RNAP by no more than 10-fold at a time.

It is important to place high concentration T7 RNAP reactions at 37° C. quickly after setup. We further note that while the reactions described in FIG. 1 were incubated for ~1 day, subsequent experiments showed that turbidity and substantial RNA synthesis for no-template-added, high concentration T7 RNAP reactions set up in tubes can also be observed at much earlier time points (e.g. at ~4 hours into incubation at 37° C.). We also note that high concentration T7 RNAP reactions exhibit a strong temperature dependence. Reactions (set up in bulk in tubes) that were maintained for a length of time at room temperature (~25° C.) appeared as smears on denaturing gels. We have not extensively characterized the RNA products synthesized at room temperature but some sequencing results indicate that the time spent by a reaction at room temperature is correlated with the count of homopolymeric RNA sequences (specifically, poly(rA) and poly(rU)) detected in the corresponding sequenced pool.

Gel Extraction from Polyacrylamide Gels

Excised gel fragments were transferred to autoclaved, nuclease-free 0.6 ml tubes that had small cross-shaped incisions at the bottom. The 0.6 ml tubes were contained in 1.5 ml siliconized tubes. Gel fragments were shredded by centrifugation. 300-400 µl of RNA elution buffer (300 mM sodium acetate at pH 5.3, 1 mM EDTA) or DNA elution buffer (300 mM sodium chloride, 10 mM Tris-HCl at pH 8, 1 mM EDTA) (36) was added to shredded gel pieces. The specific elution buffer used depended on the nature of nucleic acid to be extracted (e.g. RNA elution buffer was used for extracting replicating RNA populations and for extracting ligated RNA during RNA-seq library preparation; DNA elution buffer was used for extracting cDNA and for extracting DNA oligos such as the reverse transcription primer used for RNA-seq library preparation). Shredded gel with elution buffer added was briefly vortexed and frozen at −80° C. for 15 minutes, followed by rocking overnight at 4° C. (for RNA) or at room temperature (for DNA). Gel was then sedimented by centrifugation, and the supernatant transferred to a new 1.5 ml siliconized tube. To ensure maximal recovery of nucleic acids, gel was further washed in 100 µl of elution buffer and centrifuged. The resultant supernatant was combined with the supernatant obtained from the previous gel centrifugation step. After a final centrifugation of the pooled supernatants to sediment any remaining gel pieces, the recovered solution was ethanol precipitated with 2.5 volumes of 100% ethanol.

RNA-Seq Protocol (See Also FIG. 7)

The basic skeletal framework for the RNA-seq protocol used in this study is based on previous work by our lab and others (e.g. "RNA-seq protocol 1" in (37) and references therein; see also (36)). We made several optimizations for efficient capture of replicating RNAs. In particular, we optimized full-length cDNA synthesis because under standard reverse transcription conditions with commonly available enzymes, no full-length cDNAs were detectable by SYBR Gold gel staining (though bands corresponding to particular truncated cDNA fragments were clearly observed). The problem of inefficient reverse transcription of the RNAs replicated by T7 RNAP was also reported previously (5). Sequencing of chemically synthesized RNA oligos (e.g. AF-NJ-223 and AF-NJ-224) served as a positive control for our protocol.

3' ligation of ssDNA adapter to RNA: A 20 µl reaction was set up for each sample=7.6 µl RNA+2 µl 100% DMSO+6 µl 50% PEG 8000+2 µl 10×T4 RNA ligase buffer+0.4 µl 100 µM AF-NJ-269 (or AF-JA-34)+2 µl T4 RNA ligase 2, truncated, K227Q (400 units). Ligation reactions were incubated at 16° C. in a thermal cycler for 18 hours-20 hours 40 minutes. Reactions were heat-inactivated at 65° C. for 20 minutes. Ligation products were gel extracted and resuspended in 0.5×TE (pH 7.4). Note that AF-NJ-269 and AF-JA-34 have 8 and 6 degenerate bases at the 5' end, respectively, which serve as molecular identifiers (UMIs) in downstream bioinformatic analyses.

Reverse transcription: 8 µl of the ligated RNA was heated at 95° C. for 3 minutes in a thermal cycler, followed by snap cooling on ice for 3 minutes (see Table 1 in (38)). Next, added to each reaction (on ice) was 4 µl 5× First Strand Buffer, 1 µl RNase OUT (40 units), 1 µl 0.1 M DTT and 1 µl dNTPs (10 mM each), 0.64 µl 72 ng/µl gel-extracted AF-JA-126 (concentration quantified by Qubit ssDNA kit, Thermo Fisher #Q10212) and 0.36 µl water, followed by 4 µl (800 units) of SuperScript III. Of note, the 95° C. denaturation-snap cooling step and using more SuperScript III were key optimizations for increasing yield of full-length cDNAs.

Reactions were immediately placed in a thermal cycler with a pre-heated lid and incubated at 50° C. for 2 hours 30 minutes-2 hours 40 minutes. [After cDNA synthesis, RNA can be hydrolyzed by treatment with sodium hydroxide (final concentration 0.2 N) at 70° C. for 15 minutes.] cDNA products were gel extracted and resuspended in RNase-free water.

A no-template reaction was set up in parallel each time the reverse transcription protocol was performed; no products were detected for the no-template controls.

Circularization of cDNA: 5.5 µl of the cDNA was heated at 95° C. for 3 minutes in a thermal cycler, followed by snap cooling on ice for 3 minutes. Either CircLigase reaction components or CircLigase II reaction components were then added to each reaction on ice [CircLigase reaction components: 1 µl 10× circLigase buffer+0.5 µl 50 mM MnCl$_2$+2 µl 5M Betaine+0.5 µl 1 mM ATP+0.5 µl circLigase enzyme (50 units); CircLigase II reaction components: 1 µl 10× circLigase II buffer+0.5 µl 50 mM MnCl$_2$+2 µl 5M Betaine+1 µl circLigase II enzyme (100 units)]. Reactions were immediately incubated at 60° C. for 1-2 hours, followed by heat inactivation at 80° C. for 10 minutes.

PCR: Illumina TruSeq HT indices and adapter sequences were appended using PCR. We set up 30 µl PCR reactions consisting of: 15 µl 2× Phusion Master Mix+0.3 µl 100 µM Primer 1+0.3 µl 100 µM Primer 2+1 µl circularized cDNA (reaction contents from cDNA circularization step directly used)+13.4 µl nuclease-free water. For each sample, we set up several PCR reactions with differing PCR cycle numbers, and selected for sequencing the reaction with the least number of cycles that yielded the expected product band on an ethidium bromide-stained 3.5%-4% agarose gel. The PCR cycling conditions were:

98° C., 30 seconds

For n cycles, where n is variable, perform: 98° C., 10 seconds

60° C., 10 seconds

72° C., 20 seconds-60 seconds

10° C., hold

PCR amplified RNA-seq libraries were gel-extracted using the MinElute gel extraction kit (Qiagen #28604), and quantified using the Qubit dsDNA HS kit.

All samples were sequenced on the Illumina MiSeq platform.

Note that gel electrophoresis following each of the steps of 3' ligation, reverse transcription and PCR provided a visual assessment of reaction efficiencies for each sample we sequenced.

During sample loading on gels, samples were always separated by at least one gel lane (which was either left empty or contained a size marker) to minimize cross-contamination. For experiments where we compared template sequences with product sequences for a T7 RNAP RNA replication reaction, gel cuts for the template and product pools were made at similar sizes during RNA-seq library preparation.

Droplet Microfluidics

We used standard methods in soft lithography (39) to fabricate all microfluidic devices using a 10:1 base-to-curing agent ratio from the Sylgard 184 Silicone Elastomer kit (Dow Corning). Inlet and outlet holes were made using a 1 mm biopsy punch (Miltex), and the PDMS devices were plasma bonded to glass slides in a cleanroom.

We used a standard flow-focusing geometry with a Y-junction mixer to generate droplets (FIG. 15). The height of our droplet generation channels was 27 microns. Three syringe pumps (Kent Scientific) were used to inject the three fluid streams into our device at fixed flow rates. The aqueous droplet phase consisted of a mixture of two aqueous reagent streams which were combined at a Y-junction upstream of the flow-focusing nozzle. One aqueous reagent stream was used to flow in NTPs, PEG 8000 and any DNA/RNA template, and the other stream was used to flow in all other reagents. The continuous oil phase consisted of HFE-7500 containing 2% wt/wt 008-FluoroSurfactant. We used Aquapel (Pittsburgh, PA) to render the channels hydrophobic to prevent droplet wetting of the walls. Following Aquapel treatment, we carefully wrapped the droplet generation devices in aluminum foil and autoclaved on a gravity cycle. Autoclaved channels were kept wrapped in aluminum foil until use. In cases where multiple experimental conditions were tested in parallel, a separate autoclaved channel was used for each condition.

We used a flow rate of 0.1 ml/hr for each of the two aqueous drop phases (0.2 ml/hr combined flow rate) and a flow rate of 0.4 ml/hr for the continuous oil phase. We used a high-speed camera (Phantom v7.3) mounted on an inverted microscope with a 4× objective to continuously monitor droplet generation and also to record videos of the droplet formation process at 40,000 fps for measurement of droplet size. For the latter, we measured the time it took to form a single drop and calculated the droplet size based off of the combined aqueous phase flow rate of 0.2 ml/hr.

We did this for multiple drops to obtain a distribution of droplet size. Once the droplet size stabilized (after the first few minutes of drop generation), we serially collected droplets in 0.2 ml PCR tubes for assay purposes.

Bioinformatic Analysis

We have deposited all the code used in our study in a GitHub repository. A brief description of the deposited code can be found in Table 5. Other software that was additionally used for analysis included the ViennaRNA suite (40), Phylip (41), Interactive Tree of Life web interface (42), Trimmomatic (43), BWA (44) and Samtools (45). For sequence alignment of replicating RNAs, we used the classical Needleman-Wunsch (46) and Smith-Waterman algorithms (47).

FIG. 2A- and FIG. 10-Specific Protocols

To each of the RNA oligos AF-NJ-219 and AF-NJ-220, an extra adenine was added using T4 RNA ligase 1 (48) as follows: 90 µl of reaction volume containing 50 pmol of RNA oligo was denatured at 95° C. for 3 minutes followed by snap cooling on ice for 3 minutes. The reaction was removed from ice and the following reagents were quickly added: 10 µl of 100 µM pAp (in water), 15 µl of 10×T4 RNA ligase reaction buffer, 15 µl of 10 mM ATP, 15 µl of 100% DMSO and 5 µl of T4 RNA ligase 1 (50 units). Reaction incubation was at 16° C. for 22.25 hours in a thermal cycler. The reaction was stopped by addition of SDS and EDTA, followed by an extraction with 1:1 phenol-chloroform.

We used serial dilution to quantitatively compare T7 RNAP reaction yields from three template types (FIG. 2A, FIG. 10A and data not shown): (i) Y2 RNA synthetic oligos with an extra 3' adenine, (ii) Y2 RNA synthetic oligos without an extra 3' base and (iii) gel-extracted Y2 RNA monomer replication products. In these assays, RNA oligos with an extra 3' adenine were far more potent than oligos without an extra base in generating replicating populations, with yields from 16-fold dilution of extra 3' adenine containing oligos comparable to yields from undiluted oligos which did not contain an extra 3' base. The third template type—gel-extracted Y2 RNA monomer replication products—yielded roughly similar amounts of reaction products after ~16-32 fold dilution compared to undiluted RNA oligos with an extra 3' adenine. Several possibilities could account for the lower template efficiency of RNA oligos with an extra 3' adenine compared to the gel-extracted Y2 RNA monomer replication products, including (i) an uncharacterized template requirement (e.g. particular dependence on a type of RNA structure or on the 5' chemical end of the RNA (synthetic RNA oligos have 5' hydroxyl ends whereas replication products have 5' triphosphate ends)), (ii) a more efficient value for a characterized template requirement (e.g. 3' extra base combinations other than a single adenine may be more efficient for instructing RNA synthesis), and (iii) an uncharacterized growth advantage due to the complex ensemble character of the Y2 RNA replication products (see e.g. FIG. 3) versus the synthetic RNA oligos.

Quantification of gel intensities was done using the raw image data with AlphaView software (ProteinSimple). For each reaction lane, gel intensity was quantified within a bounding box made from approximately 52 to 60 nucleotides (RNA oligo input bands at ~50 nucleotides were excluded so as not to have signal from the input template). The bounding boxes did not contain any saturated pixels. The average intensity from "blank" bounding boxes on the same gel was used for background subtraction.

For treatment of Y2 RNA replication products with RppH or SAP (FIG. 10B), RNA was first denatured at 95° C. for 3 minutes followed by snap cooling on ice for 3 minutes. Buffer components and enzymes were added subsequently. Buffer compositions for the phosphatase treatments were based on manufacturer recommendations. Phosphatase reactions were incubated at 37° C. for 1 hour followed by heat inactivation at 65° C. for 20 minutes. Prior to loading on gels, RNA was isolated by addition of SDS and EDTA, 1:1 phenol-chloroform extraction and ethanol precipitation.

FIG. 4-Specific Protocols

Replication reactions and sequencing for the $X_1$ (AF-NJ-257) and $Y2_1$ (AF-NJ-258) libraries were performed in duplicate with similar results. Starting RNA oligo template concentrations for replication of the X1 and Y21 libraries were 2 ng/μl and 4 ng/μl, respectively.

The pre-replication RNA pools for the $X_2$, $X_3$, $X_4$ and $Y2_2$ libraries were prepared by T7 RNAP-catalyzed DNA transcription of DNA oligos AF-NJ-200, AF-NJ-201, AF-JTG-11 and AF-JTG-13, respectively. In these reactions, final concentrations of AF-NJ-200 and AF-NJ-201 were 25 nM, and of AF-JTG-11 and AF-JTG-13 were ~2.4 ng/μl.

Prior to RNA replication, the transcribed X2 and $X_3$ RNA pools were treated with TURBO DNase (3 μl TURBO DNase in a 50 μl reaction with 1× TURBO DNase buffer) at 37° C. for 1 hour, followed by addition of SDS and EDTA, 1:1 phenol-chloroform extraction and ethanol precipitation. FIG. 6B-E-, FIG. 16- and FIG. 20B-Specific Protocols Covaris shearing of DNA: DNA (in TE, pH 8) was sheared using a Covaris instrument to a size range of 100-300 bp as assessed by agarose gel electrophoresis. Sheared DNA was purified using the Zymo Clean and Concentrator kit. Column purification of DNA seeds using the Zymo Clean and Concentrator kit is expected to impose a lower limit size cutoff on the recovered DNA fragments.

Restriction digestion: 75 μl reactions with either MnII (7.5 μl) or Hpy188III (6 μl), DNA and 1× CutSmart buffer were incubated at 37° C. for 2 hours. Digests were monitored to reach near completion by agarose gel electrophoresis. Digested DNA fragments were purified using the Zymo Clean and Concentrator kit. To minimize denaturation of short dsDNA fragments, heat inactivation was not used for stopping the restriction enzyme reactions. Hpy188III and MnII were chosen as restriction enzymes because the two enzymes are expected to generate, on average, fragments of roughly similar size as fragments generated by Covaris shearing. Additionally, these two enzymes allow for generation of a diverse pool of DNA seeds because: (i) The recognition sequences and/or cleavage sites of the two enzymes contain degenerate bases, (ii) The two enzymes leave different kinds of overhangs (Hpy188III leaves 5' overhangs and MnII leaves 3' overhangs), and (iii) The two enzymes have different relationships between the cleavage site and recognition sequence (Hpy188III cuts at its recognition sequence whereas MnII cuts a few bases away from its recognition sequence).

Lambda DNA was Covaris sheared. The plasmid pPD122.03 was mini-prepped using the ZymoPURE Plasmid Miniprep kit, which includes an RNase A digestion step (RNase A containing buffer ZymoPURE P1 was stored at 4° C. to ensure maximal activity). The plasmid was then Covaris sheared. *S. cerevisiae* genomic DNA was restriction digested separately with MnII and with Hpy188III.

Genomic DNA was prepared from the nematode strains using a standard protocol involving SDS-Proteinase K treatment followed by phenol-chloroform extraction and ethanol precipitation. Genomic DNA preps (DNA amounts up to 7 μg/prep) were treated with 30 μg of RNase A (ThermoFisher) at pH 7.4 at 42° C. for 2 hours (no salt added for RNase A treatment), followed by Proteinase K-SDS treatment and 2 extractions with 1:1 phenol-chloroform. No gel density corresponding to RNA was visible by agarose gel electrophoresis following RNase A digestion. *C. elegans* DNA was then Covaris sheared, *C. remanei* DNA digested with MnII and *C. brenneri* DNA digested with Hpy188III.

The predefined DNA seed pool consisted of seven types of DNA seeds (percentage contribution by mass given): (i) Sheared lambda phage genomic DNA (7%), (ii) Sheared *C. elegans* genomic DNA (7%), (iii) Sheared DNA from the plasmid pPD122.03 (7%), (iv) MnII digested *C. remanei* genomic DNA (20%), (v) Hpy188III digested *C. brenneri* genomic DNA (15%), (vi) MnII digested *S. cerevisiae* genomic DNA (19%), and (vii) Hpy188III digested *S. cerevisiae* genomic DNA (25%). After pooling the seven types of DNA seeds together, the combined DNA seed pool was treated with 100 units of RNase 1 in the presence of 100 mM NaCl at pH 8 at 37° C. for 1 hour. RNase I was removed using 0.2% SDS treatment followed by 2 extractions with 1:1 phenol-chloroform6. A "No RNase I control" was used to confirm that RNase 1 treatment did not lead to loss of DNA.

The DNA seed pool was then split into three equal parts: (i) No further treatment (except for addition of TURBO DNase buffer to 1× final concentration), (ii) Treatment with 3 μl TURBO DNase (in a 50 μl reaction with 1× TURBO DNase buffer) at 37° C. for 1 hour, and (iii) Heating with sodium hydroxide (0.2 N; reaction volume was 10 μl) at 70° C. for 1 hour. For neutralization of the sodium hydroxide, 20 μl 200 mM Tris-HCl at pH 7 was added.

After the respective treatments to the three parts of the DNA seed pool, SDS and EDTA were added to each part, followed by extraction with 1:1 phenol-chloroform and ethanol precipitation.

The efficacy of TURBO DNase treatment of the DNA seed pool was assessed by measuring DNA concentrations for the 1st (no DNase treatment) and 2nd parts (+DNase treatment) of the seed pool. DNase treatment was found to reduce DNA amount by ~50 fold.

T7 RNAP reactions were set up in drop and tube format for four experimental conditions in parallel: (1) Unseeded, (2) Seeded with DNA pool, (3) Seeded with DNase-treated DNA pool and (4) Seeded with hot alkali-treated DNA pool. For the "Seeded with DNA pool" condition, the volume seeded with the 1st part of the DNA seed pool (neither DNase nor NaOH treated) gave a final DNA seed reaction concentration of ~47 femtograms per μl (estimated to correspond to ~10-15 molecules of DNA seeds per droplet); an equivalent volume of the 2nd and 3rd parts of the DNA seed pool was seeded for the "Seeded with DNase-treated DNA pool" and "Seeded with hot alkali-treated DNA pool" conditions, respectively. Each replicate of drop reactions for an experimental condition consisted of ~50 μl total volume (drops+oil) and took ~5 minutes for generation.

The MS2-spike in was created by fragmentation of bacteriophage MS2 genomic RNA in a solution of 5 mM $Na_2CO_3$, 45 mM $NaHCO_3$ and 1 mM EDTA at 95° C. for 30 minutes (49). MS2 fragments in the 70-90 nucleotides size range were gel-extracted and subsequently 3' dephosphorylated by T4 PNK treatment in 100 mM MES-NaOH (pH 5.4), 10 mM $MgCl_2$, 10 mM beta-mercaptoethanol and 300 mM NaCl, at 37° C. for 6 hours (49); this was followed by purification using the NEB Monarch RNA Cleanup kit (NEB #T2030S), and then by an extraction with 1:1 phenol-chloroform and ethanol precipitation. 60 picograms of the prepared MS2-spike in was added to the aggregated drop reaction products for sequencing, and 300 picograms to the tube reaction products.

FIG. 17-Specific Protocols

Four experimental conditions were set up in parallel: (1) +Template, −T7 RNAP; (2) −Template, +T7 RNAP; (3) +Template, +T7 RNAP; (4) +Template (diluted 10 fold), +T7 RNAP. SYBR Gold was included in reactions for all four conditions at a final concentration of 1×. AF-NJ-223 was used as template for conditions (1), (3) and (4) at a final concentration of 0.1 pM, 0.1 pM and 0.01 pM, respectively. Reactions were kept covered with aluminum foil during incubation.

Bright-field and fluorescence images of drops were acquired in 30 micron tall microfluidic wells using an epifluorescence microscope (Nikon Ti-U) equipped with an electron multiplying CCD camera (Andor). We used an excitation filter with transmission centered at 470 nm and an emission filter with transmission centered at 525 nm. An exposure time of 0.2 s was used during imaging.

Percentage drops fluorescent for a field of view was calculated by using the fluorescence and bright-field images for the field of view. Specifically, percentage drops fluorescent was calculated as the ratio of the number of drops detected in the fluorescence image to the number of drops detected in the bright-field image. Images for all four experimental conditions were processed using the same parameters. Automated detection of drops was checked by visual inspection.

Best Practices for Conducting T7 RNAP-Catalyzed RNA Replication Reactions

Best laboratory practices for minimizing cross-contamination when working with nucleic acid amplification technologies (e.g. (50)) also apply to the study and use of T7 RNAP-catalyzed RNA replication. Amplification of contaminating templates could be harder to control with T7 RNAP-catalyzed RNA replication compared to PCR because (i) no primers are required for RNA replication, and (ii) amplification proceeds continuously during RNA replication as opposed to in discrete cycles during PCR. Amplification of contaminating RNA replicons that are not part of an input template pool but are pre-existing in the laboratory can be minimized using droplet microfluidics as contaminants could be confined to a few drops. We further highlight key best practices for studying T7 RNAP-catalyzed RNA replication using bulk tube reactions below:

To prevent contamination of T7 RNAP preps with RNA replicons, we highly recommend that the polymerase preps be isolated in a facility which does not receive any shipments from the facility where experiments on RNA replication have been or are being conducted. Contamination of polymerase preps with a pre-existing replicon will lead to subsequent no-template-added, high concentration T7 RNAP reactions consistently yielding that particular replicon because templated replication occurs more efficiently than evolution of a novel replicon (see e.g. (5)).

Maintain a catalogue of which RNA replicon sequences have already been isolated in the laboratory and when these were isolated. If a no-template-added, high concentration T7 RNAP reaction yields a sequence similar to what has previously existed in a laboratory, then it cannot be ascertained whether the new reaction witnessed molecular evolution or amplified a pre-existing template.

When studying templated RNA replication, conduct reactions at low concentration of T7 RNAP and for short durations of time (~few hours). Also perform no-template-added controls in parallel and check that no products are detected for these controls.

TABLE 1

| Reference sequences for the RNA species described in FIG. 1. | |
| --- | --- |
| RNA Reference Sequence Number | Sequence |
| 1.1 (SEQ ID NO: 1) | CCAUAAUUAUUGUAUGACACU GGCCAAUAAUUAUUGUAUAU UGGCCAGUGUCAUACAAUAA UUUUCC |

TABLE 1-continued

| Reference sequences for the RNA species described in FIG. 1. | |
| --- | --- |
| RNA Reference Sequence Number | Sequence |
| 2.1 (SEQ ID NO: 2) | GGAAAAUAUACAUAUUGAAGG UGUGUAUGUAUAUUUGUAU AUUCACAAAAAUAUACAUACA CACCUUCAAUAUGUAUAUUA UUGG |
| 2.2 (SEQ ID NO: 3) | CCAUAAUGUGAAUGCGCGUCG CCUUGGCGCUGAUUUGCG UUAAUUGGGAAUUAACGCAAA UC |
| 3.1 (SEQ ID NO: 4) | CCCCAAAAUUAUUGUAUGGCA CUGGCCCCAUUCAAUAAUU GAAAAUUAUUGAAUGGGGCCA GU |
| 3.2 (SEQ ID NO: 5) | CCAAAAUUAUUGUAUGGCACU GGCCCCAUUCAAUAAUUAU UGUAUGGCACUGGCCCCAUUC AAUAAUUUUCAA |
| 4.1 (SEQ ID NO: 6) | GGGAAAAAUUAUUGUAUGGCA CAACAAUAAUUUUCGUAAAA UUAUUGUUGUGCCAUACAAUA AUUUAUGG |
| 4.2 (SEQ ID NO: 7) | GGGGAAAAAAUUAUCACUCGC CGGAUAAUUUCUCCUAGAA AUUAUCCGGCGAGUGAUAAUU UCUGG |
| 4.3 (SEQ ID NO: 8) | CCAUAAUUAUUGUAUGGCUCG UACAAUAAUUAUUAUUAUUA UUAAUAAUUAUUUAAUAAUAA AUUAUUGUACGAGCCAUACA AUAAUUUUCC |
| 5.1 (SEQ ID NO: 9) | GGUAAAUUAAUGUUCUUAACA CUACCAUUAAUUUACAAAAU UAAUGGUAGUGUUAAGAACAU UAAUUUUGG |
| 6.1 (SEQ ID NO: 10) | GGGAAAAAUUUAUUAUUUUCU UGGAAAUUUAUUAUUUUCU UGGAAAUUUAUUAAAUAAUAA AUUUCCAAGGAAAUAAUAAA UUUCCAAGAAAAUAAUAAAUU UUGGG |
| 7.1 (SEQ ID NO: 11) | CCGAAAAUUAUUGUAUGGCAC ACAACAAUAAUUUUUCGUGA AAAUUAUUGUUGUGUGCCAUA CAAUAAUUUUAUUC |
| 7.2 (SEQ ID NO: 12) | CCGAAAAUUAUUGUAUGUCGUC ACAAUAAUUUUCGACGAAAA UUAUUGUGACGACAUACAAUA AUUUUUCC |
| 8.1 (SEQ ID NO: 13) | GGGAAAAAUAAUACAUUUGGU GUCGGAUAAUGUAUUAUUU CAAAUAAUACAUUAUCCGACA CCAAAUGUAUUAUUUAUGG |
| 9.1 (SEQ ID NO: 14) | GGGAAAAAUUAUUGUAUGGCU CGUCAAUAAUUUUGUCCA AAAUUAUUGACGAGCCAUACA AUAAUUUUGGG |
| 10.1 (SEQ ID NO: 15) | GGAAUAAUUAUUUGUUGUACU AGGAAUAAUUAUUUACAAAA UAAUUAUUCCUAGUACAACAA AUAAUUAUUAGG |

TABLE 1-continued

Reference sequences for the RNA species described in FIG. 1.

| RNA Reference Sequence Number | Sequence |
|---|---|
| 11.1 (SEQ ID NO: 16) | GGGAAAAAUUAUUGUAUGGCA CACAAUAAUUUUCAUUAUU GUGUGCCAUACAAUAAUUUUG GG |
| 12.1 (SEQ ID NO: 17) | CCCCAAAAUUUCAAGAUCAGG GCUUGAAAUUUUGUAAAAUU UCAAGCCCUGAUCUUGAAAUU UUCC |
| 13.1 (SEQ ID NO: 18) | GGGAAAAAUUAUUGUAUGUCU CAACAAUAAUUUUCGUGAAA AUUAUUGUUGAGACAUACAAU AAUUUUGGG |
| 14.1 (SEQ ID NO: 19) | GGGAAAAAUUUCAAGAUCAGG GAUUGAAAUUUUACAAAAUU UCAAUCCCUGAUCUUGAAAUU UUGGG |
| 14.2 (SEQ ID NO: 20) | GGGAAAAAUUAUUGUAUGGCC ACAAUAAUUUUCGAAAAAUU AUUGUGGCCAUACAAUAAUUU UGGG |
| 15.1 (SEQ ID NO: 21) | GGGAAAAAAUUAUUGUAUGGC AAAUAAUUUUUCACGAAAAU UAUUUGCCAUACAAUAAUUUU CGG |
| 15.2 (SEQ ID NO: 22) | GGGAAAAAAUUAUUGUAUGGC UCACAAUAAUUUUCUCGAAA AUUAUUGUGAGCCAUACAAUA AUUUUCGG |
| 16.1 (SEQ ID NO: 23) | CCAAUUAUACUCUACCCAACU GAGGGUAUAAUAUGGUAAU UAUACCCUCAGUUGGGUAGAG UAUAAAUUCC |
| 17.1 (SEQ ID NO: 24) | GGGAAAAAUUAUUGUAUGGCA AACCAAUAAUUUUCGUCAAA AUUAUUGGUUUGCCAUACAAU AAUUUUGGG |

TABLE 1-continued

Reference sequences for the RNA species described in FIG. 1.

| RNA Reference Sequence Number | Sequence |
|---|---|
| 18.1 (SEQ ID NO: 25) | CCAUAAUUAUUGUAUGGCUCG UACAAUAAUGAAAAUUAUUG UACGAGCCAUACAAUAAUUUU CC |
| 18.2 (SEQ ID NO: 26) | CCAUAAAUAUUUCUCCUAGGG CAAUGAAAUAUUAUGGAUCA UAAUAUUUCAUUGCCCUAGGA GAAAUAUUAUCC |
| 19.1 (SEQ ID NO: 27) | GGGAAAAAUUACACUUUUCGC AUCUUUGUGUAAUUUUUGU GAAUAAAUUACACAAGAUGC GAAAAGUGUAAUUUAUGG |
| 20.1 (SEQ ID NO: 28) | CCAAUAAUACAAUAUUUCCU CAUCCUCAUUUGUAUUAUAA UACAAAUGAGGAUGAGGAAAU AUUUGUAUUAUAAUCC |
| 21.1 (SEQ ID NO: 29) | GGGAAAAAUUAUUGUAUGGCA CAAACAAUAAUAAUUUUCUU UAAAAAUUAUUGUUUGUGCCA UACAAUAAUUUUGGG |
| 22.1 (SEQ ID NO: 30) | GGGAAAAAUUAUUGUAUGGCA CACAAUAAUUUUUAACAAAA UUAUUGUGUGCCAUACAAUAA UUUUGGG |
| 23.1 (SEQ ID NO: 31) | GGGAAAAAUUAUUGUAUGGCA CAACAACAAUAAUUUUCGUA AAAUUAUUGUUGUUGUGCCAU ACAAUAAUUUAUGG |
| 24.1 (SEQ ID NO: 32) | GGGAAAAAUUUCAAGAUCAGG GGCUUGAAAUUUUACAAAA UUUCAAGCCCCUGAUCUUGAA AUUUUGGG |

NB: (i) Short 5' and 3' base extensions (of one or a few bases) may be present in the sequences for reasons discussed in the text.
(ii) A few sequences may not be full-length because particular truncated cDNAs or prematurely terminated 17 products were predominant in the sequenced pool. E.g. Sequence 3.1 reported for reaction 3 is unlikely to be a full-length sequence. The RNA species for reaction 3 were not efficiently reverse transcribed, which makes detection of the full-length sequences more challenging.

TABLE 2

Sequences of RNA species described in FIGS. 6B-6E and FIG. 20B.

| Sample information | RNA species number | Sequence |
|---|---|---|
| Unseeded, Aggregated Drop Reaction, 1 day time point | 1 | GGAUAAUUAUUAUCAUUGAUCAUCAAUGAUGAUG AAUUAUUAUCAUUGAUGAUCAAUGAUAAUAAUUAU GG (SEQ ID NO: 33) |
| Unseeded, Aggregated Drop Reaction, 1 day time point | 2 | GGAAAAAUAAUUAUUCUUGCUGUAGAAAUAAUUAU UCCGAAUAAUUAUUUCUACAGCAAGAAUAAUUAUU UCGG (SEQ ID NO: 34) |
| Unseeded, Aggregated Drop Reaction, 1 day time point | 3 | GGAAGAAACAUUGUCAAUUGCCUUGGCCCAAUGU UUCCUGAAACAUUGGCCAAGGCAAUUGACAAUGU UUCAUGG (SEQ ID NO: 35) |
| Unseeded, Aggregated Drop Reaction, 1 day time point | 4 | GGAUAAACUUUCUUUCAUUCUGUCUAAGAAAGUU UAAACAGAGUUUUAAACUUUCUUAGACAGAAUGAA AGAAAGUUUAAGG (SEQ ID NO: 36) |

TABLE 2-continued

Sequences of RNA species described in FIGS. 6B-6E and FIG. 20B.

| Sample information | RNA species number | Sequence |
|---|---|---|
| Unseeded, Aggregated Drop Reaction, 1 day time point | 5 | GGAAUAAUAAUAAUUCUAAGUAAGAGUUAUAUUAA UACAUAAUUUCAAAUUAUGUAUUAAUAUAACUCUU ACUUAGAAUUAUUAUUCGG (SEQ ID NO: 37) |
| Unseeded, Aggregated Drop Reaction, 1 day time point | 6 | GGAAUUUUAAAUUAUUUAAAUGGAAUUUCCAUUUA AUAUUAAUUAAAUGGAAAUUCCAUUUAAAUAAUUU AAAAAUGG (SEQ ID NO: 38) |
| Unseeded, Aggregated Drop Reaction, 1 day time point | 7 | GGAUAAUAUUUCAAUAUUCCAUUUUAUUAUUGAAA UUGUAAUAUUUCAAUAAUAAAAUGGAAUAUUGAAA UAUUUUGG (SEQ ID NO: 39) |
| Unseeded, Aggregated Drop Reaction, 1 day time point | 8 | GGAUUAAUUAAUUGAUUCAUAAUUAAUUAAUUGAA UAAUUAAUUAUGAAUCAAUUAAUUAUGG (SEQ ID NO: 40) |
| Unseeded, Aggregated Drop Reaction, 1 day time point | 9 | GGAAAAAUUAAAUAUAGUUCCAGUUUCUCCUAUAU UUAAUUAGAAAUUAAAUAUAGGAGAAACUGGAACU AUAUUUAAUUUCUGG (SEQ ID NO: 41) |
| Unseeded, Aggregated Drop Reaction, 1 day time point | 10 | GGAAAAUUUCAAGAUCAGGGCUUGAAAUUUUACA AAAUUUUCAAGCCCUGAUCUUGAAAUUUUGGGG (SEQ ID NO: 42) |
| Unseeded, Aggregated Drop Reaction, 1 day time point | 11 | GGUUAAAUAUUAUUGAAAUCUCAAAAUAAUAAAAC CAAAUAUUAUUUUGAGAUUUCAAUAAUAUAUUUGG (SEQ ID NO: 43) |
| Seeded with DNA pool, Aggregated Drop Reaction, 1 day time point | 1 | GGAAUUAUCAUUUCUUGCAGAUAAAGAUGAUAAU CCAAUUAUCAUCUUUAUCUGCAAGAAAUGAUAAUU GG (SEQ ID NO: 44) |
| Seeded with DNA pool, Aggregated Drop Reaction, 1 day time point | 2 | GGAAAAUAUUAUUUUCAAGCUAUAUCUAAUAAUAU UUUGCCAAAAUAUUAUUAGAUAUAGCUUGAAAAUA AUAUUUUGG (SEQ ID NO: 45) |
| Seeded with DNA pool, Aggregated Drop Reaction, 1 day time point | 3 | GGAAUAUUUCAUUGAUGAAAUUACAAUGAUCAAUG AAUAUUUCAUUGAUCAUUGUAAUUUCAUCAAUGAA AUAUUGG (SEQ ID NO: 46) |
| Seeded with DNA pool, Aggregated Drop Reaction, 1 day time point | 4 | GGAAAAAAUUCUUUUCAGAAAUGAAUUGAAAUUCU UUUCAAUUCAUUUCUGAAAAGAAUUUUUGG (SEQ ID NO: 47) |
| Seeded with DNA pool, Aggregated Drop Reaction, 1 day time point | 5 | GGAAAAAUUGUAUCUAUCCAAUUUUGAUACAAAAU UGUAUCAAAAUUGGAUAGAUACAAUUUUGG (SEQ ID NO: 48) |
| Seeded with DNA pool, Aggregated Drop Reaction, 1 day time point | 6 | GGAAAAUAUCAAUAAUUUCCGAUUAUUAUUGAUAA AAUAUCAAUAAUAAUCGGAAAUUAUUGAUAUUUUA UGG (SEQ ID NO: 49) |
| Seeded with DNA pool, Aggregated Drop Reaction, 1 day time point | 7 | GGAAAAAUUGAAAAGUCCAAUUCAAUUUAACCAAA AUUGAAUUGGACUUUUCAAUUUUGG (SEQ ID NO: 50) |
| Seeded with DNA pool, Aggregated Drop Reaction, 1 day time point | 8 | GGAAAUUUGGAUUUGGUAAAUUCUCCAAAAUUUC CGAAAUUUUGGAGAAUUUACCAAAUCCAAAAUUGG (SEQ ID NO: 51) |
| Seeded with DNA pool, Aggregated Drop Reaction, 1 day time point | 9 | GGAAAAUCUUGUCAUGAAUCAAUAGAUUUUCUUG UCAUGAAAUCUAUUGAUUCAUGACAAGAUUUUGG (SEQ ID NO: 52) |
| Seeded with DNA pool, Aggregated Drop Reaction, 1 day time point | 10 | GGAUAUAUAUAUAUGUGUGUGUGUGUAUAUAUAU UCCGAUGAAUAUAUAUACACACACACAUAUAUA UAUCGG (SEQ ID NO: 53) |
| Seeded with DNA pool, Aggregated Drop Reaction, 1 day time point | 11 | GGAUAAAUUAAAUAGGUUUCUGACUUUGUUAUUC CUAUUUAAUCGGGAUUAAAUAGGAAUAACAAAGUC AGAAACCUAUUUAAUUUUGG (SEQ ID NO: 54) |

TABLE 2-continued

Sequences of RNA species described in FIGS. 6B-6E and FIG. 20B.

| Sample information | RNA species number | Sequence |
|---|---|---|
| Seeded with DNA pool, Aggregated Drop Reaction, 1 day time point | 12 | GGAAAAUAUGUCAUACAUUGGUCAGAGAAAAUGU AUGUCAUACAUUUUCUCUGACCAAUGUAUGACAU AUUUAGG (SEQ ID NO: 55) |
| Seeded with DNA pool, Aggregated Drop Reaction, 1 day time point | 13 | GGAAAAAUUCAAAUCAAUUGCCGAUGAUUUGAUU UUUCAUUCAAAUCAUCGGCAAUUGAUUUGAAUUU GGGG (SEQ ID NO: 56) |
| Seeded with DNA pool, Aggregated Drop Reaction, 1 day time point | 14 | GGAUUAAAUUUCAUAUUGUUAAUAUUUAUUAAUGU AUGUACAAUAUGAAAUUUCAUAUUGUACAUACAUU AAUAAAUAUUAACAAUAUGAAAUUUCGG (SEQ ID NO: 57) |
| Seeded with DNA pool, Aggregated Drop Reaction, 1 day time point | 15 | GGAAAAAUUUAAUAGGAGUUCAGUUUAUUCUAUU AAAUUUCCGGAAAUUUAAUAGAAUAAACUAGAACUC CUAUUAAAUUUUGG (SEQ ID NO: 58) |
| Seeded with DNA pool, Aggregated Drop Reaction, 1 day time point | 16 | GGAAAUUUAUUUGAGAGUUGUUCCAAAUAAAUUU UCGGAAAAUUUAUUUGGAACAACUCUCAAAUAAAU UUUGG (SEQ ID NO: 59) |
| Seeded with DNA pool, Aggregated Drop Reaction, 1 day time point | 17 | GGAAAAAAUUUCUUCUUCGAGAAAUUUGAAUUCCA AAUUUCUCGAAGAAGAAAUUUUGGG (SEQ ID NO: 60) |
| Seeded with DNA pool, Aggregated Drop Reaction, 1 day time point | 18 | GGAAAGAAUGUUUUCAUAAGGUACAACAUUCUUU UUCUAAAGAAUGUUGUACCUUAUGAAAACAUUCUU CAGG (SEQ ID NO: 61) |
| Seeded with DNA pool, Aggregated Drop Reaction, 1 day time point | 19 | GGAAAAUUUAAAUGUGCACUCCAUAUUCUCCGCA UUUAAAUUUUCCAUAUUCAAAUGCGGAGAAUAUG GAGUGCACAUUUAAAUUUGGG (SEQ ID NO: 62) |
| Seeded with DNA pool, Aggregated Drop Reaction, 1 day time point | 20 | GGAAAUUGAAUAAGACUUUCCCUUAUUCAUUAAAA UUGAAUAAGGGAAAGUCUUAUUCAAUUUGG (SEQ ID NO: 63) |
| Seeded with DNA pool, Aggregated Drop Reaction, 1 day time point | 21 | GGAAGAAAUCAGAAUAUUCUCCUUUUUCUGAUUU UCUGAAGAAAUCAGAAAAAGGAGAAUAUUCUGAU UUCUUGGG (SEQ ID NO: 64) |
| Seeded with DNA pool, Aggregated Drop Reaction, 1 day time point | 22 | GGAAAAUGAUUUCCUCAUUAGUUGAUCAUCAAAAU GAUUUCAACUAAUGAGGAAAUCAUUUUGGG (SEQ ID NO: 65) |
| Seeded with DNA pool, Aggregated Drop Reaction, 1 day time point | 23 | GGAAAUUUAAAUGUGCCAUGAAUAUAUGGAAAUUUAA AUGUGCUUUUAAAUUUCCAUAUUCAUGGCACAUU UAAAUUUGG (SEQ ID NO: 66) |
| Seeded with DNA pool, Aggregated Drop Reaction, 1 day time point | 24 | GGAAAAAAAUUCUGAUCGUAGUAGGAUUUCAGAA UUUUCUUCCGAAAAUUCUGAAAUCCUACUACGAU CAGAAUUUCGG (SEQ ID NO: 67) |
| Seeded with DNA pool, Aggregated Drop Reaction, 1 day time point | 25 | GGAAAUAUACAAUUCUAUAUCAUUCCAUGAUAUAG AAUAUAGAAUUGUAAAUAUACAAUUCUAUAUUCUA UAUCAUGGAAUGAUAUAGAAUUGUAUAUUUGGG (SEQ ID NO: 68) |
| Seeded with DNA pool, Aggregated Drop Reaction, 1 day time point | 26 | GGAAAAUUCAAAAUUGAAUUGAAUUUGGAUUUUU CCAAAUUCAAUUCAAUUUUGAAUUUGGG (SEQ ID NO: 69) |
| Seeded with DNA pool, Aggregated Drop Reaction, 1 day time point | 27 | GGAUGAUUAUUUCAUGUGUCUCUAAUGAUCUAAA CAUUAGAUCAUUAGAGACACAUGAAAUACUGG (SEQ ID NO: 70) |
| Seeded with DNA pool, Aggregated Drop Reaction, 1 day time point | 28 | GGGAAUAUUAAUUCAAAUUCAAUAUUGGGUGUAAUA UUAAUUCAAAUUACACCAAUAUUGAAUUUGAAUUA AUAUUGG (SEQ ID NO: 71) |
| Seeded with DNA pool, Aggregated Drop Reaction, 1 day time point | 29 | GGAUGAUUUGAUACAUAUUCGUUUCUAUGUAUUU AACAAAUCAUCUUUGAUGAUUUGUUAAAUACAUAG AAACGAAUAUGUAUCAAAUCUUGG (SEQ ID NO: 72) |

TABLE 2-continued

Sequences of RNA species described in FIGS. 6B-6E and FIG. 20B.

| Sample information | RNA species number | Sequence |
|---|---|---|
| Seeded with DNA pool, Aggregated Drop Reaction, 1 day time point | 30 | GGAAAAAUCAAGUGUCACUUUCUCCCACUUGAUU UUGUCAAUCAAGUGGGAGAAAGUGACACUUGAUU UUGG (SEQ ID NO: 73) |
| Seeded with DNA pool, Aggregated Drop Reaction, 1 day time point | 31 | GGAAAAAAUUCAAGAAUCCUCUUCUUGAAUCUUGA AUUUUCAAAAUUCAAGAUUCAAGAAGAGGAUUCUU GAAUUUUGG (SEQ ID NO: 74) |
| Seeded with DNA pool, Aggregated Drop Reaction, 1 day time point | 32 | GGAAAAUAUCAACUCGAUAUUUGAUAUUUAUUCCA AAUAUCAAAUAUCGAGUUGAUAUUUUGGG (SEQ ID NO: 75) |
| Seeded with DNA pool, Aggregated Drop Reaction, 1 day time point | 33 | GGAAAAUUCAAACGAUCACCUUCGUUUUGAUUUG UCAAUUCAAACGAAGGUGAUCGUUUGAAUUUAGG (SEQ ID NO: 76) |
| Seeded with DNA pool, Aggregated Drop Reaction, 1 day time point | 34 | GGAUGAAUAUAUUUGUUUUGACUCCAUUCUACAA AUAUAUUCCGAAUAUAUUUGUAGAAUGGAGUCAAA ACAAAUAUAUUCUGG (SEQ ID NO: 77) |
| Seeded with DNA pool, Aggregated Drop Reaction, 1 day time point | 35 | GGAAAUUAAGAUUUUUUCUCCUUUCUAAAUCUUAA UUUUACAAAUUAAGAUUUAGAAAGGAGAAAAAAUC UUAAUUUGG (SEQ ID NO: 78) |
| Seeded with DNA pool, Aggregated Drop Reaction, 1 day time point | 36 | GGGAAAAUUAACAAUAUUCUUUCGAUUGUUCAAUA UUGAAAUUUUCCAAUUAACAAUAUUGAACAAUCGA AAGAAUAUUGUUAAUUUGG (SEQ ID NO: 79) |
| Seeded with DNA pool, Aggregated Drop Reaction, 1 day time point | 37 | GGAAAAAACAAUUCAAUCAAUUCGUCAUGAUUGAA ACAAUUCAAUCAUGACGAAUUGAUUGAAUUGUUU UUGG (SEQ ID NO: 80) |
| Seeded with DNA pool, Aggregated Drop Reaction, 1 day time point | 38 | GGAAAAAUUAAUUUGAAUAAUUAAUUUCUUCUUAA UUUCUUCCAAUUAAUUAAGAAGAAAUUAAUUAUUC AAAUUAAUUUUUGGG (SEQ ID NO: 81) |
| Seeded with DNA pool, Aggregated Drop Reaction, 1 day time point | 39 | GGAAAAAAUUCAUUCGGAUUUUGUGCGAAUGAAA UUCAUUCGCACAAAAUCCGAAUGAAUUUGGGGG (SEQ ID NO: 82) |
| Seeded with DNA pool, Aggregated Drop Reaction, 1 day time point | 40 | GGUUAUAUAUAUAUUUGAUCCUUGCAAUAUAUAAUU AUAUAUUGCAAGGAUCAAUAUAUAUAUUGG (SEQ ID NO: 83) |
| Seeded with DNA pool, Aggregated Drop Reaction, 1 day time point | 41 | GGAAUUCAAUGAGAAAAAAUCUCCCACUCAUUGAU UCCCAAUUCAAUGAGUGGGAGAUUUUUCUCAUUG AAUUGGG (SEQ ID NO: 84) |
| Seeded with DNA pool, Aggregated Drop Reaction, 1 day time point | 42 | GGAAAAAUUUCAGAAUUUCUUCAUCCUCUGAAAUU UUCUCAAAAUUUCAGAGGAUGAAGAAAUUCUGAAA UUUCGGG (SEQ ID NO: 85) |
| Seeded with DNA pool, Aggregated Drop Reaction, 1 day time point | 43 | GGAUAAAUACCAUAACGUUGAAUAUGAAGGUAUUA UCCAAAAUACCUUCAUAUUCAACGUUAUGGUAUUU UGG (SEQ ID NO: 86) |
| Seeded with DNA pool, Aggregated Drop Reaction, 1 day time point | 44 | GGAAAAAAUUGGAUGAGAAAGUUAAAAUUAUUCAA UUUUCCGAAAAUUGAAUAAUUUUAACUUUCUCAUC CAAUUUUCGG (SEQ ID NO: 87) |
| Seeded with DNA pool, Aggregated Drop Reaction, 1 day time point | 45 | GGAAUAUUAACAAAGAUAGGGAUAAGAAUGUAAUC UUUUGUUGAAUAUUAACAAAGAUUACAUUCUUAUC CCUAUCUUUGUUAAUAUUGG (SEQ ID NO: 88) |
| Seeded with DNA pool, Aggregated Drop Reaction, 1 day time point | 46 | GGAAAAUUCAAAUUCAAGAUUGGAUUCUCUUGAA UUUCAAAAUUCAAGAGAAUCCAAUCUUGAAUUUGA AUUUGGG (SEQ ID NO: 89) |
| Seeded with DNA pool, Aggregated Drop Reaction, 1 day time point | 47 | GGAUUGUUAUCAAUGUAUUCUUCCAAACAUUGAA CAAUGUAUCAAUGUUUGGAAGAAUACAUUGAUAAC AUGGG (SEQ ID NO: 90) |

TABLE 2-continued

Sequences of RNA species described in FIGS. 6B-6E and FIG. 20B.

| Sample information | RNA species number | Sequence |
|---|---|---|
| Seeded with DNA pool, Aggregated Drop Reaction, 1 day time point | 48 | GGAAAAUAAUUUCCAAAUCAAAAUUAUUUGAUUUC CAAAUCAAAUAAUUUUGAUUUGGAAAUUAUUUGG (SEQ ID NO: 91) |
| Seeded with DNA pool, Aggregated Drop Reaction, 1 day time point | 49 | GGAAAAAAUCAUUUCUCUAAUGCAAUUCAGAGAAU GAAUAAAUCAUUUUCUCUGAAUUGCAUUAGAGAAA UGAUUUAUUGG (SEQ ID NO: 92) |
| Seeded with DNase-treated DNA pool, Aggregated Drop Reaction, 1 day time point | 1 | GGAAGAAUUUAAUUUCAUCCUCUUAAAUUCUUUAA ACCAAGAAAUUUAAGAGGAUGAAAUUAAAUUCUUG G (SEQ ID NO: 93) |
| Seeded with DNase-treated DNA pool, Aggregated Drop Reaction, 1 day time point | 2 | GGAAAAUUAAAGUUCAAUGCAAUUUAAUUUUCCAA AAUUAAAUUGCAUUGAACUUUAAUUUUGG (SEQ ID NO: 94) |
| Seeded with DNase-treated DNA pool, Aggregated Drop Reaction, 1 day time point | 3 | GGAAUUAAUUUAGUCUAGGUGGAACUAAUUAUAC UAAUUAAUUUAGUUCCACCUAGACUAAAUUAAUUA GG (SEQ ID NO: 95) |
| Seeded with DNase-treated DNA pool, Aggregated Drop Reaction, 1 day time point | 4 | GGAGAAUUUAAAUCAUUAUCUUCUUUGAUUUAAAU UUAUGGCCAUAAAUUUAAAUCAAAGAAGAUAAUGA UUUAAAUUCUGG (SEQ ID NO: 96) |
| Seeded with DNase-treated DNA pool, Aggregated Drop Reaction, 1 day time point | 5 | GGAAAUUUCAAUUCAAUGGGUUGUAUUAAUUGAA AUUGCCCAAUUUCAAUUAAUACAACCCAUUGAAUU GAAAUUGG (SEQ ID NO: 97) |
| Seeded with DNase-treated DNA pool, Aggregated Drop Reaction, 1 day time point | 6 | GGAAAAUAUCAACUCGAUAUUUUGAUAUUUAUUCC AAAUAUCAAAUAUCGAGUUGAUAUUUUGG (SEQ ID NO: 98) |
| Seeded with DNase-treated DNA pool, Aggregated Drop Reaction, 1 day time point | 7 | GGAAUUGAAUGGAAUGGACAAAUUCCAUAUGAUU CCAAUUCAUAUGGAAUUUGUCCAUUCCAUUCAAU UGG (SEQ ID NO: 99) |
| Seeded with DNase-treated DNA pool, Aggregated Drop Reaction, 1 day time point | 8 | GGAUAAUCAUUAUCAAAUGGGAAUCUGAUAAUGA UGAUUAAUCAUUAUCAGAUUCCCAUUUGAUAAUGA UUCUGG (SEQ ID NO: 100) |
| Seeded with DNase-treated DNA pool, Aggregated Drop Reaction, 1 day time point | 9 | GGAAUCAAAUAGAAUCCAUUAUCUAUUUGAUUCAA UCAAAAUAGAUAAUGGAUUCUAUUUCGG (SEQ ID NO: 101) |
| Seeded with DNase-treated DNA pool, Aggregated Drop Reaction, 1 day time point | 10 | GGAAAAUUUCUAAAUAUUACUGAUCAUCAGUAAUC UAAAUAUUACUGAUGAUCAGUAAUAUUUAGAAAUU UGG (SEQ ID NO: 102) |
| Seeded with DNase-treated DNA pool, Aggregated Drop Reaction, 1 day time point | 11 | GGAAUGUAAUAAAUUAUUGUUAUAUUCACUCCAAU GUAAUAAAUUACAUUGGAGUGAAUAUAACAAUAAU UUAUUACAUUGG (SEQ ID NO: 103) |
| Seeded with DNase-treated DNA pool, Aggregated Drop Reaction, 1 day time point | 12 | GGAUUAUUUUAUUCAAUCUUCAUAACACCGGAAG AUUUAUUCAAUCUUCCGGUGUUAUGAAGAUUGAA UAAAAUAAUGG (SEQ ID NO: 104) |
| Seeded with DNase-treated DNA pool, Aggregated Drop Reaction, 1 day time point | 13 | GGAAUUUCAAUUUCUCAUCUUGUAUAUAAAUACAA UUUCUCAUCUUGAAAAUGUAUUUAUAUACAAGAUG AGAAUUGAAAUUGG (SEQ ID NO: 105) |
| Seeded with DNase-treated DNA pool, Aggregated Drop Reaction, 1 day time point | 14 | GGAAAAUUCAAAUUGCAGUAGAUAUUGAAUUUUU UUCCAAAAUUCAAUAUCUACUGCAAUUUGAAUUUU GGG (SEQ ID NO: 106) |
| Seeded with DNase-treated DNA pool, Aggregated Drop Reaction, 1 day time point | 15 | GGAUAAAUUGAUAGGAACAAUUAAUAGUGUCAAUU UAUCCGAUAAAUUGACACUAUUAAUUGUUCCUAUC AAUUUAGGG (SEQ ID NO: 107) |
| Seeded with DNase-treated DNA pool, Aggregated Drop Reaction, 1 day time point | 16 | GGGAAAAAUCAAGUUCUGAGUUUUGAUUUAUCCA AAAAUCAAAAAACUCAGAACUUGAUUUUUGG (SEQ ID NO: 108) |

TABLE 2-continued

Sequences of RNA species described in FIGS. 6B-6E and FIG. 20B.

| Sample information | RNA species number | Sequence |
|---|---|---|
| Seeded with DNase-treated DNA pool, Aggregated Drop Reaction, 1 day time point | 17 | GGAAGAUUGAAAAUCUUAUAAUAUCUAAGAGAUAG AUUUUCAUGAUUGAAAAAUCUAUCUCUUAGAUAUU AUAAGAUUUUCAAUCAUGG (SEQ ID NO: 109) |
| Seeded with DNase-treated DNA pool, Aggregated Drop Reaction, 1 day time point | 18 | GGAAAAAUUAUUACAAUGCACCCAUAUCAUUGUAA UUUGAAAUUAUUACAAUGAUAUGGGUGCAUUGUA AUAAUUUCGG (SEQ ID NO: 110) |
| Seeded with DNase-treated DNA pool, Aggregated Drop Reaction, 1 day time point | 19 | GGAAGAUGAAUAUGUUAAUUAGCUUAAUCAU UCC AUAUUCAUCCGAUGAAUAUGGAAUGAUUAAGCUAA UUAACAUAUUCAUCAUGG (SEQ ID NO: 111) |
| Seeded with DNase-treated DNA pool, Aggregated Drop Reaction, 1 day time point | 20 | GGAAAAUUAUCUGUUCAAAUUCAAAUGAUGAUUUU CCAAAUUAUCAUUUGAAUUUGAACAGAUAAUUUGG (SEQ ID NO: 112) |
| Seeded with DNase-treated DNA pool, Aggregated Drop Reaction, 1 day time point | 21 | GGAAAUCAUUCCAUUCAAUGAUGUUCAAUGAAACA UCAUUUGAAUGGAAUUGAUUGG (SEQ ID NO: 113) |
| Seeded with DNase-treated DNA pool, Aggregated Drop Reaction, 1 day time point | 22 | GGAAAAAUAAUGGGAUACUUCAAACAUUAUUUUUC CGAAAAAUAAUGUUUGAAGUAUCCCAUUAUUUUUU GG (SEQ ID NO: 114) |
| Seeded with DNase-treated DNA pool, Aggregated Drop Reaction, 1 day time point | 23 | GGGAAAAUCAAUUCCAGUCCUUUCCCUGGAUUUG AAAAUCAAUUCCAGGGAAAGGACUGGAAUUGAUU UUGG (SEQ ID NO: 115) |
| Seeded with DNase-treated DNA pool, Aggregated Drop Reaction, 1 day time point | 24 | GGAAGAAAAUCAAAUAAUAUAUCUGGAUACAUUAU UUGAUUUUCAAAUAAUGUAUCCAGAUAUAUUAUUU GAUUUUCUUGG (SEQ ID NO: 116) |
| Seeded with DNase-treated DNA pool, Aggregated Drop Reaction, 1 day time point | 25 | GGAAAAUUUGAUACUAGCUAUCCAAAGUAUCAAAU UUCAUGAUACUUUGGAUAGCUAGUAUCAAAUUUG GG (SEQ ID NO: 117) |
| Seeded with DNase-treated DNA pool, Aggregated Drop Reaction, 1 day time point | 26 | GGAAAUAAAAUCAUCAUUAUUAUUUGAUGAAAUAA AAUCAUCAAAUAAUAAUGAUGAUUUUAUUUGG (SEQ ID NO: 118) |
| Seeded with DNase-treated DNA pool, Aggregated Drop Reaction, 1 day time point | 27 | GGAAAAUUAAAUUGCAUUGAACUUUAAUUUUCCCC CCAAAAUUAAAGUUCAAUGCAAUUUAAUUUUGG (SEQ ID NO: 119) |
| Seeded with DNase-treated DNA pool, Aggregated Drop Reaction, 1 day time point | 28 | GGAAGAUGUUUUUGAUACCGAGCUGGUCUCAGCA UAUAUUCCAUAAAUAUAUGCUGAGACCAGCUCG GUAUCAAAACAUCUAUGG (SEQ ID NO: 120) |
| Seeded with DNase-treated DNA pool, Aggregated Drop Reaction, 1 day time point | 29 | GGAUGAAAUUGGAAACCAUCAUUCUCCCCAAAUU UCAUCCAAUGAAAUUGGGAGAAUGAUGGUUUCCA AUUUCUUGG (SEQ ID NO: 121) |
| Seeded with DNase-treated DNA pool, Aggregated Drop Reaction, 1 day time point | 30 | GGAAAAUUAUAAUAGAAAUUAUCCCUAUUAUAAUU AUAAUAGGGAUAAUUUCUAUUAUAAUUUUGG (SEQ ID NO: 122) |
| Seeded with DNase-treated DNA pool, Aggregated Drop Reaction, 1 day time point | 31 | GGAUGAAAUCAAAAAGCUAGUCCUUUUGAUGAAA AUCAAAAGGACUAGCUUUUGAUUUCAUGG (SEQ ID NO: 123) |
| Seeded with DNase-treated DNA pool, Aggregated Drop Reaction, 1 day time point | 32 | GGAAUUAAACAAAUAUAUACUUCCACAAUAUUUGU UUGAAAACAAAUAUUGUGGAAGUAUAUAUUUGUU UUCGG (SEQ ID NO: 124) |
| Seeded with DNase-treated DNA pool, Aggregated Drop Reaction, 1 day time point | 33 | GGAUUUUUGAUUUCAUUCGAUGCUUCUGAAAAUC AAUAAUUCCCAUUUGAUUUUCAGAAGCAUCGAAU GAAAUCAAAUGG (SEQ ID NO: 125) |
| Seeded with DNase-treated DNA pool, Aggregated Drop Reaction, 1 day time point | 34 | GGAUAAAAUUCUAGUCUAUAUGGCUACUAGAAUA CUAAAUUCUAGUAGCCAUAUAGACUAGAAUUUAUG G (SEQ ID NO: 126) |

TABLE 2-continued

Sequences of RNA species described in FIGS. 6B-6E and FIG. 20B.

| Sample information | RNA species number | Sequence |
|---|---|---|
| Seeded with DNase-treated DNA pool, Aggregated Drop Reaction, 1 day time point | 35 | GGAAUUGAAAUUCAUCUUCUGUCUCUUGUGAAUU UCAUUUUAAUUGAUUGAAAUUCACAAGAGACAGAA GAUGAAUUUCAAUCAUGG (SEQ ID NO: 127) |
| Seeded with DNase-treated DNA pool, Aggregated Drop Reaction, 1 day time point | 36 | GGAAAUUUCAUAUUUCAGAAAUAGGUAAAUUUCU GAAAUAAAAUAAAUUUUUUAUUUCAGAAAUUUACC UAUUUCUGAAAUAUGAAAUUUGG (SEQ ID NO: 128) |
| Seeded with DNase-treated DNA pool, Aggregated Drop Reaction, 1 day time point | 37 | GGAAUUAUGAUCAAAAUUGAAUGGAAAUUGAAUGA UCAAAUUGAAUUAUGAUCAUUCAAUUUCCAUUCAA UUUUGAUCAUAAUUGG (SEQ ID NO: 129) |
| Seeded with DNase-treated DNA pool, Aggregated Drop Reaction, 1 day time point | 38 | GGAAGAAAAUGUUAUCUACACCGAGACAUAACAUU UUCUGACAGAAAUGUUAUGUCUCGGUGUAGAUAA CAUUUCUUGG (SEQ ID NO: 130) |
| Seeded with DNase-treated DNA pool, Aggregated Drop Reaction, 1 day time point | 39 | GGAUUAAAUUUCAAAUUAUUCCCUAAUAAUUUGAA AAUUUCAAAUUAUUAGGGAAUAAUUUGAAAUUUUG G (SEQ ID NO: 131) |
| Seeded with DNase-treated DNA pool, Aggregated Drop Reaction, 1 day time point | 40 | GGAAUGUUUAUUCUUUAUUCAAAUAAGGUUUUAA AGAAUAAACUGAAUAAAAUUUAUUCUUUAUUCAGU UUAUUCUUUAAAACCUUAUUUGAAUAAAGAAUAAA CUGG (SEQ ID NO: 132) |
| Seeded with DNase-treated DNA pool, Aggregated Drop Reaction, 1 day time point | 41 | GGGGGAAAAUUUCAAGAUCAGGGCUUGAAAUUUU UACAAAAUUUCAAGCCCUGAUCUUGAAAUUUUGG G (SEQ ID NO: 133) |
| Seeded with DNase-treated DNA pool, Aggregated Drop Reaction, 1 day time point | 42 | GGAUAAAAUAUCGUAUUUUUCCUCUAAUGUGGAU AUUUUAUGGCCAUAAAAUAUCCACAUUAGAGGAAA AAUACGAUAUUUUAUGG (SEQ ID NO: 134) |
| Seeded with DNase-treated DNA pool, Aggregated Drop Reaction, 1 day time point | 43 | GGAAUUAAUUAAUAUCUCUAAAUUAUUAAUUCGAG AAUUAAUAAUUUAGAGAUAUUAAUUCGG (SEQ ID NO: 135) |
| Seeded with DNase-treated DNA pool, Aggregated Drop Reaction, 1 day time point | 44 | GGGGAAAUUUUCAAGUUAUUUCUUUACUUGAAAU UUUCAAGUAAAGAAAUAACUUGAAAAUUUGG (SEQ ID NO: 136) |
| Seeded with DNase-treated DNA pool, Aggregated Drop Reaction, 1 day time point | 45 | GGAUUAUGAAAUUUACAUUGCUUCAAUUCAUAAUC UCCAUUAUGAAUUGAAGCAAUGUAAAUUUCAUAAU GGG (SEQ ID NO: 137) |
| Seeded with DNase-treated DNA pool, Aggregated Drop Reaction, 1 day time point | 46 | GGGAAUUUUAAUUUCAUAUUAUCGAUGAAUGAAA UUAUUGAAUUUAAUUUCAUUCAUCGAUAAUAUGAA AUUAAAUUGG (SEQ ID NO: 138) |
| Seeded with DNase-treated DNA pool, Aggregated Drop Reaction, 1 day time point | 47 | GGAAAAUCUUGUCAUGAAUCAAUAGAUUUUCUUG UCAUGAAAUCUAUUGAUUCAUGACAAGAUUUUGG (SEQ ID NO: 139) |
| Seeded with DNase-treated DNA pool, Aggregated Drop Reaction, 1 day time point | 48 | GGAAAAACAAUCUACAAAUUCAAUGCCGAAUUGAA UUUGUUGAUCUACAAAUUUAAUUCGGCAUUGAAU UUGUAGAUUGUUUUUUGGG (SEQ ID NO: 140) |
| Seeded with DNase-treated DNA pool, Aggregated Drop Reaction, 1 day time point | 49 | GGAAAAUCAAGAUAAUAAAUACUCCAUUAUUAUCU CAGAUAAUAAUGAUGGAGUAUUUAUUAUCUUGAU UUGG (SEQ ID NO: 141) |
| Seeded with DNase-treated DNA pool, Aggregated Drop Reaction, 1 day time point | 50 | GGAAAAUUUCUAAAUUGAAAGAUAAAAUUUAAUUU UCUAAAUUUUAUCUUUCAAUUUUAGAAAUUUUGG (SEQ ID NO: 142) |
| Seeded with DNase-treated DNA pool, Aggregated Drop Reaction, 1 day time point | 51 | GGGAAAAAAUAUUUUCUAAAUGGGUGAGAAAUAUUU UCCGAAAAUAUUUCUCACCAUUUAGAAAAUAUUUC GG (SEQ ID NO: 143) |
| Seeded with DNase-treated DNA pool, Aggregated Drop Reaction, 1 day time point | 52 | GGAAUUAUUUUCAUUUGUGUACUCAGUACACGAA UUUAAUUAUUUUCCAAAAUUCGUGUACUGAGUAC ACAAAUGAAAAUAAUUGG (SEQ ID NO: 144) |

TABLE 2-continued

Sequences of RNA species described in FIGS. 6B-6E and FIG. 20B.

| Sample information | RNA species number | Sequence |
|---|---|---|
| Seeded with DNase-treated DNA pool, Aggregated Drop Reaction, 1 day time point | 53 | GGAUAAUUAUCAAUAAUUCGAAUAAUUAUCAAUAA UUAUUCGAAUUAUUGAUAAUUAUGGG (SEQ ID NO: 145) |
| Seeded with DNase-treated DNA pool, Aggregated Drop Reaction, 1 day time point | 54 | GGAUAAUUUCAUUUAUAAUGAAGUUAUUCAUUUAU AAUGAAUAACUUCAUUAUAAAUGAAAUUCGGGG (SEQ ID NO: 146) |
| Seeded with hot alkali-treated DNA pool, Aggregated Drop Reaction, 1 day time point | 1 | GGAAAUAAUCAUAUUCUCAUAAUGAGAUUAUUAAA UUUCCAUUAAUAAUCUCAUUAUGAGAAUAUGAUUA AUGG (SEQ ID NO: 147) |
| Seeded with hot alkali-treated DNA pool, Aggregated Drop Reaction, 1 day time point | 2 | GGAUAAAUUUGUGUCUUCUAUUCUUAACAAAUUU GUUUUCCAUAAUUUGUUAAGAAUAGAAGACACAAA UUAUGG (SEQ ID NO: 148) |
| Seeded with hot alkali-treated DNA pool, Aggregated Drop Reaction, 1 day time point | 3 | GGAAUAAUUCAAUUAUUAUUGAUAAUAAUUCAAUU AUUAUCAAUAAUAAUUGAAUUAUUGG (SEQ ID NO: 149) |
| Seeded with hot alkali-treated DNA pool, Aggregated Drop Reaction, 1 day time point | 4 | GGAAUAUAUUAUAUGAAAUCUCUUCGUCUCAUAUA AUAUAUAUAUGGAGACGAAGAGAUUUCAUAUAAUA UAUAUGG (SEQ ID NO: 150) |
| Seeded with hot alkali-treated DNA pool, Aggregated Drop Reaction, 1 day time point | 5 | GGAAAUUUGAAUCAAUUCCUCCAAAUUGGUUCAAA UCUCAAUUUGAUGAAUUGAUUCAUCAAAUUGAUU UGAAUCAAUUUGGAGGAAUUGAUUCAAAUUUGG (SEQ ID NO: 151) |
| Seeded with hot alkali-treated DNA pool, Aggregated Drop Reaction, 1 day time point | 6 | GGAAAAAUUGUUCUCUAAUUGAUUCAUUCCGAAC AAUUUUGAUCCAAAAUUGUUCGGAAUGAAUCAAUU AGAGAACAAUUUUGG (SEQ ID NO: 152) |
| Seeded with hot alkali-treated DNA pool, Aggregated Drop Reaction, 1 day time point | 7 | GGGAAUAUUCUAUUCUUGCUCUUCUAGAGAGAGA AUAUUCUACUCUCUCUCUAGAAGAGAGCAAGAAUAGA AUAUUGG (SEQ ID NO: 153) |
| Seeded with hot alkali-treated DNA pool, Aggregated Drop Reaction, 1 day time point | 8 | GGAUAAUUAAUUAUUACUCUCAUUGGAUGUUGGG UAAAAAAUUAAUUAUUACCCAACAUCCAAUGAGAG UAAUAAUUAAUUUGG (SEQ ID NO: 154) |
| Seeded with hot alkali-treated DNA pool, Aggregated Drop Reaction, 1 day time point | 9 | GGAAAAAUCAACAGAUACAAAUUGAUUGAUUUUCC AAAUCCAAAAAUCAAUCAAUUUGUAUCUGUUGAUU UUGGG (SEQ ID NO: 155) |
| Seeded with hot alkali-treated DNA pool, Aggregated Drop Reaction, 1 day time point | 10 | GGAAUAUUUCAAUAUUUCAAAGAAAGGAAAAUAUU GAUAUUUCAAUAUUUUCCUUUCUUUGAAAUAUUG AAAUAUUGG (SEQ ID NO: 156) |
| Seeded with hot alkali-treated DNA pool, Aggregated Drop Reaction, 1 day time point | 11 | GGAAAAAAAUUCAUUCGAAGUACUUUGAAUUUUU GUUUUCCAAAAUUCAAAGUACUUCGAAUGAAUUUU GG (SEQ ID NO: 157) |
| Seeded with hot alkali-treated DNA pool, Aggregated Drop Reaction, 1 day time point | 12 | GGAAUAAUAUUCUAUCCUUCGAGAAUAUAUUAGUCU AUAAUAUUCUCGAAGGAUAGAAUAUAUUAUAGGGG (SEQ ID NO: 158) |
| Seeded with hot alkali-treated DNA pool, Aggregated Drop Reaction, 1 day time point | 13 | GGAUUUAAUCUUCAUAGAAAUAGUAUAAGAUUAAU CACAUUAAUCUUAUACUAUUUCUAUGAAGAUUAAU GG (SEQ ID NO: 159) |

TABLE 2-continued

Sequences of RNA species described in FIGS. 6B-6E and FIG. 20B.

| Sample information | RNA species number | Sequence |
|---|---|---|
| Seeded with hot alkali-treated DNA pool, Aggregated Drop Reaction, 1 day time point | 14 | GGAGAAUUUCUAAAUAGAUUACAUUUCAUUGUAAU GUAAUCUACAAUUUCAUUGUAGAUUACAUUACAAU GAAAUGUAAUCUAUUUAGAAAUUCUGG (SEQ ID NO: 160) |
| Seeded with hot alkali-treated DNA pool, Aggregated Drop Reaction, 1 day time point | 15 | GGAAAAUUUGUAAUUCAAAUUGGUAACAAAUUUGU AAUUCAAAUUUGUUACCAAUUUGAAUUACAAAUUU UGGG (SEQ ID NO: 161) |
| Seeded with hot alkali-treated DNA pool, Aggregated Drop Reaction, 1 day time point | 16 | GGAAAAUUUCAAUAACAAAAAAUCCCGUUAUUGAA AAAUUUUCAAUAACGGGAUUUUUGUUAUUGAAAU UUUGG (SEQ ID NO: 162) |
| Seeded with hot alkali-treated DNA pool, Aggregated Drop Reaction, 1 day time point | 17 | GGAAAAUUCAAUUGCUGGAAAAAUUGAAUUGUUC CAAAUUCAAUUUCCAGCAAUUGAAUUUUGGG (SEQ ID NO: 163) |
| Seeded with hot alkali-treated DNA pool, Aggregated Drop Reaction, 1 day time point | 18 | GGGGAAGAAGUUCUCAAUGUAGAUAUUAUGUGCA UUGAAGAAGUUCUAAAUGCACAUAAUAUCUACAUU GAGAACUUCUUGGG (SEQ ID NO: 164) |
| Seeded with hot alkali-treated DNA pool, Aggregated Drop Reaction, 1 day time point | 19 | GGAAAAAUAUCAAAAUACACCCUUAUUUUGAUAUA AAAUAUCAAAAAUAAGGGUGUAUUUUGAUAUUUUA UGG (SEQ ID NO: 165) |
| Seeded with hot alkali-treated DNA pool, Aggregated Drop Reaction, 1 day time point | 20 | GGAAAAAUUGAAUUUAUUGAAUGUUUUGGUCAUU CAAUUUUUCCGAAAAAUUUGAAUGACCAAAACAUUC AAUAAAUUCAAUUUUUGG (SEQ ID NO: 166) |
| Seeded with hot alkali-treated DNA pool, Aggregated Drop Reaction, 1 day time point | 21 | GGGAUUUUUCAAUCAAAUGACGAGAGAUUGAAAU UGCCAAUUUCAAUCUCUCGUCAUUUGAUUGAAAU UGG (SEQ ID NO: 167) |
| Seeded with hot alkali-treated DNA pool, Aggregated Drop Reaction, 1 day time point | 22 | GGAUUUAUAAUCAUCGAUCAUAAUAUUAUAAUCGA UCAAUUAUAAUAUUAUGAUCGAUGAUUAUAAUUGG (SEQ ID NO: 168) |
| Seeded with hot alkali-treated DNA pool, Aggregated Drop Reaction, 1 day time point | 23 | GGAAAAUAUUUUACAUCUGGAAUUAAAAUAUUUUU CUCCAAAUAUUUUAAUUCCAGAUGUAAAAUAUUUG G (SEQ ID NO: 169) |
| Seeded with hot alkali-treated DNA pool, Aggregated Drop Reaction, 1 day time point | 24 | GGGAAAAAAAUCUAAUUGAUCAGAGACAAUUAGAU UAGAAAAUCUAAUUGUCUCUGAUCAAUUAGAUUUU UGG (SEQ ID NO: 170) |
| Seeded with hot alkali-treated DNA pool, Aggregated Drop Reaction, 1 day time point | 25 | GGAUUAUUAUUAUUUGAAUCAAUUCCCAAAUAAUA AUCAAAUUAUUAUUUGGGAAUUGAUUCAAAUAAUA AUUGG (SEQ ID NO: 171) |
| Seeded with hot alkali-treated DNA pool, Aggregated Drop Reaction, 1 day time point | 26 | GGAAAAAAUUUCAUAUUUUCAAUUCCAAUAUGAAA AUUUCAUAUUGGAAUUGAAAAUAUGAAAUUUUCG G (SEQ ID NO: 172) |
| Seeded with hot alkali-treated DNA pool, Aggregated Drop Reaction, 1 day time point | 27 | GGAUAAAAUCUUAUAUCUUUCAUCUAGAGAUAUGA UGAUUUAUAUCUUUCAUCAUAUCUCUAGAUGAAA GAUAUAAGAUUUUUUUGG (SEQ ID NO: 173) |
| Seeded with hot alkali-treated DNA pool, Aggregated Drop Reaction, 1 day time point | 28 | GGAAAAAUAAAUUUGUUCCAUUUCACAAAUUUAUU CCGAAUAAAUUUGUGAAAUGGAACAAAUUUAUUUU GGG (SEQ ID NO: 174) |

TABLE 2-continued

Sequences of RNA species described in FIGS. 6B-6E and FIG. 20B.

| Sample information | RNA species number | Sequence |
|---|---|---|
| Seeded with hot alkali-treated DNA pool, Aggregated Drop Reaction, 1 day time point | 29 | GGUUUAAUUUUAACAUUUUGGGUGUGUUAAUUUU AACACACCCAAAAUGUUAAAAUUAAUGG (SEQ ID NO: 175) |
| Seeded with hot alkali-treated DNA pool, Aggregated Drop Reaction, 1 day time point | 30 | GGAAAUAUAAUAUAAGUUUGGUAUUCCUUAUAUUA UAUAUUUAUAUAAUAUAAGUGAAUACCAAACUUAU AUUUAUAUUGGG (SEQ ID NO: 176) |
| Seeded with hot alkali-treated DNA pool, Aggregated Drop Reaction, 1 day time point | 31 | GGAUUAUUUCAAUGUUUCACUAAUUCAUUGAAUU AUUUCAAUGAAUUAGUGAAACAUUGAAAUAAUGGG GGG (SEQ ID NO: 177) |
| Seeded with hot alkali-treated DNA pool, Aggregated Drop Reaction, 1 day time point | 32 | GGAAUAAUUGAAUAAUUAGACUUAUCCAAUUUUCC AAAAUUGGAAAAUUGGAUAAGUCUAAUUAUUCAAU UUUGG (SEQ ID NO: 178) |
| Seeded with hot alkali-treated DNA pool, Aggregated Drop Reaction, 1 day time point | 33 | GGAUAAUUAAUCAAAUGAAUACAUGAUUAAUUAAA AUGAUUUAAUUAAUCAUGUAUUCAUUUGAUUAAUU AAUGG (SEQ ID NO: 179) |
| Seeded with hot alkali-treated DNA pool, Aggregated Drop Reaction, 1 day time point | 34 | GGAAAUUUUCAAUUUCACAUCAUGAUCCGUGUUU UGAAUUUUCAAUUUCACACGGAUCAUGAUGUGAA AUUGAAAAUUUAGG (SEQ ID NO: 180) |
| Seeded with hot alkali-treated DNA pool, Aggregated Drop Reaction, 1 day time point | 35 | GGAAAAAUCAAUUCAUUUGAAGAGUUCCAAAAUCA AUUCUCUUCAAAUUCAUUGAAGAGAAUUGAUUUU UUGGAACUCUUCAAAUGAAUUGAUUUUGGG (SEQ ID NO: 181) |
| Seeded with hot alkali-treated DNA pool, Aggregated Drop Reaction, 1 day time point | 36 | GGAAAAUUAUAUCAAGUAACACAACCAGAUAUAUU UUUUUCUAUAUCUGGUUGUGUUACUUGAUAUAAU UUUGGG (SEQ ID NO: 182) |
| Seeded with hot alkali-treated DNA pool, Aggregated Drop Reaction, 1 day time point | 37 | GGAAUGAAAAUUGUUUGAUAAGAAAGGAUAAGCAA CAAUUUUCUGAAAAUUGUUGCUUAUCCUUUCUUA UCAAACAAUUUUCUUGG (SEQ ID NO: 183) |
| Seeded with hot alkali-treated DNA pool, Aggregated Drop Reaction, 1 day time point | 38 | GGAAAAUUGAAAUGAAAAAAUUCCAUUUCAUUUCA UUUCAAAAAAUUGAAAUGAAAUGAAAUGGAAUUUU UCAUUUCAAUUUUGG (SEQ ID NO: 184) |
| Seeded with hot alkali-treated DNA pool, Aggregated Drop Reaction, 1 day time point | 39 | GGAAAUAUACAAUUCUAUAUCAUUCAGAUAUAGAA UGAAAUUGCCAAAUUUCCUUCUAUAUCUGAAUGA UAUAGAAUUGUAUAUUUGG (SEQ ID NO: 185) |
| Seeded with hot alkali-treated DNA pool, Aggregated Drop Reaction, 1 day time point | 40 | GGAAAUUAAUUCAAUUAUCAUCAAUUAAUUUGGAU GAUUCCAAAUUAAUUGAUGAUAAUUGAAUUAAUUU GG (SEQ ID NO: 186) |
| Seeded with hot alkali-treated DNA pool, Aggregated Drop Reaction, 1 day time point | 41 | GGAAAAUUUCAAUCAAUUCCAUUCCUGAUUGAAAA UUUCAAUCAGGAAUGGAAUUGAUUGAAAUUUUGG GGGGG (SEQ ID NO: 187) |
| Seeded with hot alkali-treated DNA pool, Aggregated Drop Reaction, 1 day time point | 42 | GGAAAAAAAUAUAAUAUGUCAUUUCCAUAUUAUAU AUAAUAAUAUGGAAAUGACAUAUUAUAUUUUGGG (SEQ ID NO: 188) |
| Unseeded, Aggregated Drop Reaction, 5 day time point | 1 | GGAUUAAUCAAAUCCUCAAUAUUUUGAUUAAUUAA UAUUGAAUUAAUUAAUCAAAAUAUUGAGGAUUUGA UUAAUUAAUUCGG (SEQ ID NO: 189) |

TABLE 2-continued

Sequences of RNA species described in FIGS. 6B-6E and FIG. 20B.

| Sample information | RNA species number | Sequence |
|---|---|---|
| Unseeded, Aggregated Drop Reaction, 5 day time point | 2 | GGAAAUUAGAAUCAAACGUCUCAAUUCUAAUUCCG AAAUUAGAAUUGAGACGUUUGAUUCUAAUUUGGG (SEQ ID NO: 190) |
| Unseeded, Aggregated Drop Reaction, 5 day time point | 3 | GGAUUAUUAGAAGACAAUUAAACUAAUAAUAAUCC CUUUAUUAUUAGUUUAAUUGUCUUCUAAUAAAGG (SEQ ID NO: 191) |
| Unseeded, Aggregated Drop Reaction, 5 day time point | 4 | GGAAAAUAUUUGAAUUGCAAUUCCCAAAUAUUUG GCCAAAUAUUUGGGAAUUGCAAUUCAAAUAUUUG G (SEQ ID NO: 192) |
| Unseeded, Aggregated Drop Reaction, 5 day time point | 5 | GGAAUUUAAAUCAAAGUUCUUAUUAAAUUGCUUU GAAUUUAAAUCAAAGCAAUUUAAUAAGAACUUUGA UUUAAAUUGG (SEQ ID NO: 193) |
| Unseeded, Aggregated Drop Reaction, 5 day time point | 6 | GGAUAUUUAUCAUCGAGGUGUUGAGAGAUAAAAU CCAUUAUUUAUCUCUCAACACCUCGAUGAUAAAUA AUGG (SEQ ID NO: 194) |
| Unseeded, Aggregated Drop Reaction, 5 day time point | 7 | GGAAUAUUCAAUUAAUAUUGAAACAAAAUUAAUUG AUUUAAUUCAAUUAAUUUUGUUUCAAUAUUUAAUUG AAUAUGG (SEQ ID NO: 195) |
| Unseeded, Aggregated Drop Reaction, 5 day time point | 8 | GGAUAUAUUUCAAUAUAUGGUAGAUAUAUUUCAAU AUAUCUACCAUAUAUUGAAAUAUAGG (SEQ ID NO: 196) |
| Unseeded, Aggregated Drop Reaction, 5 day time point | 9 | GGAAGAAUUUGUUAUUUUGCUUCUUAACACAAAU UCUUCCGAAGAAUUUGUGUUAAGAAGCAAAAUAAC AAAUUCUUGG (SEQ ID NO: 197) |
| Unseeded, Aggregated Drop Reaction, 5 day time point | 10 | GGAUGAAUUAGAGUCUACCUGUUAACCUCCUCUA AUUCUACUGAAUUAGAGGUUAACAGGUAGACUCU AAUUCAGG (SEQ ID NO: 198) |
| Unseeded, Aggregated Drop Reaction, 5 day time point | 11 | GGAAAAUUUCAAAUUUCUUCACAUUUGAAAUUUCA AAUUUCAAAUGUGAAGAAAUUUGAAAUUUGGG (SEQ ID NO: 199) |
| Unseeded, Aggregated Drop Reaction, 5 day time point | 12 | GGAUUUCAUAAACAAAUUCGAAUGUUUAUGAAAUC UAAGAAAUAGAUUUCAUAAACAUUCGAAUUUGUUU AUUCUGG (SEQ ID NO: 200) |
| Unseeded, Aggregated Drop Reaction, 5 day time point | 13 | GGAUGAAUUUGAUUUAGAUUUGGCAUUUAUCAAA UUCAUCCGAUGAAUUUGAUAAAUGCCAAAUCUAAA UCAAAUUCAUGG (SEQ ID NO: 201) |
| Unseeded, Aggregated Drop Reaction, 5 day time point | 14 | GGAAACAUUGAUUAAUAAUACGUUCAAUUUAUCAA AUGUUUUCCGAAAAACAUUGAUAAAUUGAACGUAU UAUUAAUCAAUGUUUGG (SEQ ID NO: 202) |
| Unseeded, Aggregated Drop Reaction, 5 day time point | 15 | GGAUAAAAAGAAUUGUUCCUUUCUCUUCUUUUUA UGUUCCAUAAAAGAAGAGAAAGGAACAAUUCUUUU AUGG (SEQ ID NO: 203) |
| Unseeded, Aggregated Drop Reaction, 5 day time point | 16 | GGAAAAAUACAAGUUUCCUAUAUUCAUUGUAUUUU CUCCAAAAUACAAUGAAUAUAGGAAACUUGUAUUU UGG (SEQ ID NO: 204) |
| Unseeded, Aggregated Drop Reaction, 5 day time point | 17 | GGAAAAUAUUGAAUCUACCGAUGUCUCAAUAUUU CCGAAAUAUUGAGACAUCGGUAGAUUCAAUAUUU UGG (SEQ ID NO: 205) |
| Unseeded, Aggregated Drop Reaction, 5 day time point | 18 | GGAAGAAACAAUAAUUUUUCCCUGUUCUUUAUUG UUUCCCGAAACAAUAAAGAACAGGGAAAAUUAUUG UUUCUUGG (SEQ ID NO: 206) |
| Unseeded, Aggregated Drop Reaction, 5 day time point | 19 | GGAAAAUUGAAAUUUCGGAAAUUUUCAAUUUUGG ACCAAAAUUGAAAAUUUCCGAAAUUUCAAUUUUGG (SEQ ID NO: 207) |

TABLE 2-continued

Sequences of RNA species described in FIGS. 6B-6E and FIG. 20B.

| Sample information | RNA species number | Sequence |
|---|---|---|
| Unseeded, Aggregated Drop Reaction, 5 day time point | 20 | GGAAUAUUGAAUAUGAAUAUCCAUAUUCAUGAUUC AUGAAUAUGGAUAUUCAUAUUCAAUAUGGG (SEQ ID NO: 208) |
| Unseeded, Aggregated Drop Reaction, 5 day time point | 21 | GGAAAUUAUCAAUGUGUGGUAUGGAUCAACAUUG AAAUUAUCAAUGUUGAUCCAUACCACACAUUGAUA AUUUGG (SEQ ID NO: 209) |
| Unseeded, Aggregated Drop Reaction, 5 day time point | 22 | GGAAUUUUGGAAUUUGACAACUGGUAUCCAAAAU UCCGAAUUUUGGAUACCAGUUGUCAAAUUCCAAA AUUGG (SEQ ID NO: 210) |
| Unseeded, Aggregated Drop Reaction, 5 day time point | 23 | GGAAAAAUUGCUAAUAUCAUCUUGAAAGCAAUUUU CCCAAAUUGCUUUCAAGAUGAUAUUAGCAAUUUU GG (SEQ ID NO: 211) |
| Unseeded, Aggregated Drop Reaction, 5 day time point | 24 | GGAUAAUAAUCAUUAUUAUUCCCUAUAAAAUAAUG AUUUAUGAAAUAAUCAUUAUUUUAUAGGGAAUAAU AAUGAUUAUUCGG (SEQ ID NO: 212) |
| Unseeded, Aggregated Drop Reaction, 5 day time point | 25 | GGAAAAAUUGCAAUUAUUUCCUUCCAUUGCAAUUA UUUCCAAAUUGCAAUGGAAGGAAAUAAUUGCAAUU UUGG (SEQ ID NO: 213) |
| Unseeded, Aggregated Drop Reaction, 5 day time point | 26 | GGAAAUACAUUUUCAUCCAAAAAAUGUAUUUUUCA UCCAAAAAUACAUUUUUUGGAUGAAAAUGUAUUUG G (SEQ ID NO: 214) |
| Unseeded, Aggregated Drop Reaction, 5 day time point | 27 | GGAAAAUUAUUCAAAUAAAUAAUUGGAAUUAUUCA AAUUAUUCCAAUUAUUUAUUUGAAUAAUUUGG (SEQ ID NO: 215) |
| Unseeded, Aggregated Drop Reaction, 5 day time point | 28 | GGAAAUAAUUCAAUUAUUUAUUUAAUUGAAUAAUU CAAUUAAAUAAAUAAUUGAAUUAUUUGG (SEQ ID NO: 216) |
| Unseeded, Aggregated Drop Reaction, 5 day time point | 29 | GGAAUAAUUAAUCAACAUCAUGAUUAUUAAUUAAU CCAAUAAUUAAUAAUCAUGAUGUUGAUUAAUUAUU GG (SEQ ID NO: 217) |
| Unseeded, Aggregated Drop Reaction, 5 day time point | 30 | GGAUAAUCAUUUAUUUAUGUCUUCCCCAAUAAAAU AAAUGAUUAUCCAAUCAUUUAUUUUAUUGGGGAA GACAUAAAUAAAUGAUAUGG (SEQ ID NO: 218) |
| Unseeded, Aggregated Drop Reaction, 5 day time point | 31 | GGAAAAUUAAUAAUCCUAAAAUUCCAGGGGAUUAUU UUAGAAAUUAAUAAUCCCCUGGAAUUUAGGAUUAU UAAUUUCGG (SEQ ID NO: 219) |
| Unseeded, Aggregated Drop Reaction, 5 day time point | 32 | GGAAAAAAAUCAAAGAGAGCUUUUCUUUGAAUCAA AGAAUCAAAGAAAGCUCUCUUUUGAUUUGG (SEQ ID NO: 220) |
| Unseeded, Aggregated Drop Reaction, 5 day time point | 33 | GGAAAAUUCAACAAAUUCUUCAAUUUCAAAUGUUG AAUUUCAACAAAUUCAACAUUUGAAAUUGAAGAAU UUGUUGAAUUUUGG (SEQ ID NO: 221) |
| Unseeded, Aggregated Drop Reaction, 5 day time point | 34 | GGAAAAAUAAAGAUGUAGCUAAACGCUAUAUAUUC CCAAUAUAUAGCGUUUAGCUACAUCUUUAUUUUU GG (SEQ ID NO: 222) |
| Unseeded, Aggregated Drop Reaction, 5 day time point | 35 | GGAAUAAUAAUCAUUGAACGGAAUCCUCAAUGAUU AUUUCAUUUAAUCAUUGAGGAUUCCGUUCAAUGA UUAUUCGG (SEQ ID NO: 223) |
| Unseeded, Aggregated Drop Reaction, 5 day time point | 36 | GGAAAUAAUUUCUAUUAAAUUAUUUGAUAGAAAU AAUUUCUAUCAAAUAAUUUAAUAGAAAUUAUUUUG G (SEQ ID NO: 224) |
| Unseeded, Aggregated Drop Reaction, 5 day time point | 37 | GGAUAAUAUUUCUAAUUAACUACCCAUAAUUAGAA AUAUUUCUAAUUAUGGGUAGUUAAUUAGAAAUAUU CGG (SEQ ID NO: 225) |

TABLE 2-continued

Sequences of RNA species described in FIGS. 6B-6E and FIG. 20B.

| Sample information | RNA species number | Sequence |
|---|---|---|
| Unseeded, Aggregated Drop Reaction, 5 day time point | 38 | GGAAAAAUUCAAUAAUCUCUAUUAUUAUUGAAAAA UUCAAUAAUAAUAGAGAUUAUUGAAUUUUUGG (SEQ ID NO: 226) |
| Unseeded, Aggregated Drop Reaction, 5 day time point | 39 | GGAAAAAUUCAAAAUUGUUGUCUGAAUUGAAUUAU UUUCCCAAAAUUCAAUUCAGACAACAAUUUUGAAU UUUGGG (SEQ ID NO: 227) |
| Unseeded, Aggregated Drop Reaction, 5 day time point | 40 | GGAUGAUCAAUGUGUCCUGCAAUUCACACACAUU GACAUGAUCAAUGUGUGAAUUGCAGGACACAUUG AUCUUGG (SEQ ID NO: 228) |
| Unseeded, Aggregated Drop Reaction, 5 day time point | 41 | GGAAAUAUUAUAAAUACAUAUGGGAGAAGUUGUA UUUAUAAAUACAACUUCUCCCAUAUGUAUUUAUAAU AUUUGG (SEQ ID NO: 229) |
| Unseeded, Aggregated Drop Reaction, 5 day time point | 42 | GGAAAAAUUGGAUUCAUAACUUCGCCUAUCCAAU UUUCCCGAAAAUUGGAUAGGCGAAGUUAUGAAUC CAAUUUUGGG (SEQ ID NO: 230) |
| Unseeded, Aggregated Drop Reaction, 5 day time point | 43 | GGAAAAAAAUUCAUUCGAAUGAAAUUGAUUUCAUU CGAAUGAAAUCAAUUUCAUUCGAAUGAAUUUUUUU GG (SEQ ID NO: 231) |
| Unseeded, Aggregated Drop Reaction, 5 day time point | 44 | GGAAAAUCAAAUACUUGGUCUAUUUUAUUUGAUU UUCUCAAAAUAAAAUAGACCAAGUAUUUGAUUUUG G (SEQ ID NO: 232) |
| Unseeded, Aggregated Drop Reaction, 5 day time point | 45 | GGAAUAAUUUCAAACAUCAUUGUCCUUUGUUUGA AUAAUUUCAAACAAAGGACAAUGAUGUUUGAAAUU AUUGG (SEQ ID NO: 233) |
| Unseeded, Aggregated Drop Reaction, 5 day time point | 46 | GGAAUUUAUUCAAUUCAUCUGCAAUUGAAUUAAUU UAUUCAAUUGCAGAUGAAUUGAAUAAAUUAGG (SEQ ID NO: 234) |
| Unseeded, Aggregated Drop Reaction, 5 day time point | 47 | GGAUUCAAUUAGGUAUUCAAUCUUCCCCUAAUUG AAUCUCAAUUAGGGGAAGAUUGAAUACCUAAUUU CUGG (SEQ ID NO: 235) |
| Unseeded, Aggregated Drop Reaction, 5 day time point | 48 | GGAAUAUCAAAUUUCCAAUAUGUUUUGAUUUCCAA AUAUCAAAAACAUAUUGGAAAUUUGAUAUUGG (SEQ ID NO: 236) |
| Unseeded, Aggregated Drop Reaction, 5 day time point | 49 | GGAAAAUUCCAAUUUUGGUCGAUGGAAACAAAAU UGGAAUUCCAAUUUUGUUUCCAUCGACCAAAAUU GGAAUUUGGG (SEQ ID NO: 237) |
| Unseeded, Aggregated Drop Reaction, 5 day time point | 50 | GGAAAAUAUUUCUCAUAUUGGGCGAUAUUUCUCA AUAUCGCCCAAUAUGAGAAAUAUUUUGGG (SEQ ID NO: 238) |
| Unseeded, Aggregated Drop Reaction, 5 day time point | 51 | GGAAAAAAAUUAUCAUUGGUGUGGGAUGAUAAUU UCUCGAAAUUAUCAUCCCACACCAAUGAUAAUUUU CGG (SEQ ID NO: 239) |
| Unseeded, Aggregated Drop Reaction, 5 day time point | 52 | GGAAAAAUUCAAAUUCAAUCGAGAAUAAUUUGAAU CAAAAUUCAAAUUAUUCUCGAUUGAAUUUGAAUUU UGG (SEQ ID NO: 240) |
| Unseeded, Aggregated Drop Reaction, 5 day time point | 53 | GGAUUAUUGAUUUCCAUCAACAUCAAUAAUCGCUA UUAUUGAUGUUGAUGGAAAUCAAUAAUAGGG (SEQ ID NO: 241) |
| Unseeded, Aggregated Drop Reaction, 5 day time point | 54 | GGAUUAAUAAUCAUUUCGAAAUGAUUUCCAAUAAA CGAAAUGAUUAUUGGAAAUCAUUUCGAAAUGAUUA UUGG (SEQ ID NO: 242) |
| Unseeded, Aggregated Drop Reaction, 5 day time point | 55 | GGAAUUGAAUUCAAAAUCUCAAUUGAUUUCAUUCC AAUUGAAAAUCAAUUGAGAUUUUGAAUUCAAUUGG (SEQ ID NO: 243) |

TABLE 2-continued

Sequences of RNA species described in FIGS. 6B-6E and FIG. 20B.

| Sample information | RNA species number | Sequence |
|---|---|---|
| Unseeded, Aggregated Drop Reaction, 5 day time point | 56 | GGGAAAAUUCAAAAGUUUCCUGAACUUUUUUGAA AAUUCAAAAGUUCAGGAAACUUUUGAAUUUUGGG (SEQ ID NO: 244) |
| Unseeded, Aggregated Drop Reaction, 5 day time point | 57 | GGAUCAUUAAUAUCAUUACUACAGUCUAGUAAUGA UAUCAUUACUAGACUGUAGUAAUGAUAUUAAUCU GG (SEQ ID NO: 245) |
| Unseeded, Aggregated Drop Reaction, 5 day time point | 58 | GGAAAAUAAUUCUAAUAUUUGCAUUUAUUUUAGAA AAUAAUUCUAAUAUUUUCUAAAAUAAAUGCAAAUA UUAGAAUUAUUUGG (SEQ ID NO: 246) |
| Unseeded, Aggregated Drop Reaction, 5 day time point | 59 | GGAUGAAAUCUUCAUAAUAUUAUCGUAUAUAUAUU UCAUAAUAUAUAUACGAUAAUAUUAUGAAGAUUGG G (SEQ ID NO: 247) |
| Unseeded, Aggregated Drop Reaction, 5 day time point | 60 | GGGAAUAAUUAAUUGAUUAUUUGAAUUAAUCGAU UAAUUCAAAUAAUCAAUUAAUUAUUGG (SEQ ID NO: 248) |
| Unseeded, Aggregated Drop Reaction, 5 day time point | 61 | GGAAAAUUUCAAAGUACUAUCAACUUUGAAUCAAG UUCAAAGUUGAUAGUACUUUGAAUUUUGG (SEQ ID NO: 249) |
| Unseeded, Aggregated Drop Reaction, 5 day time point | 62 | GGAUGAUCAAUGUGUCCUGCAAUUCACAUUGAUU CGAUCAAUGUGAAUUGCAGGACACAUUGAUCUUG GGG (SEQ ID NO: 250) |
| Unseeded, Aggregated Drop Reaction, 5 day time point | 63 | GGAAUAUUUAUCAAGCAUUCGAAAAUAUAUCCAAU AUUUUCGAAUGCUUGAUAAAUAUUGG (SEQ ID NO: 251) |
| Unseeded, Aggregated Drop Reaction, 5 day time point | 64 | GGAAAGAAAUAUUUCUAAUUAACUACCUAGAUUUG AAAUAUUUCUAAUAUUUCUAAUCUAGGUAGUUAAU UAGAAAUAUUUCUUUGGG (SEQ ID NO: 252) |
| Unseeded, Aggregated Drop Reaction, 5 day time point | 65 | GGUUUAAUUUAUCUGCAUCAAAUUCUGAUAAAUUA AUUCCUUUAAUUUAUCAGAAUUUGAUGCAGAUAAA UUAAAGGG (SEQ ID NO: 253) |
| Unseeded, Aggregated Drop Reaction, 5 day time point | 66 | GGAUGAUCAAUGUGUCCUGCAAUUCACAUUCCGU GAAUUCACAUUGAAUUCACGAUCAAUGUGAAUUG CAGGACACAUUGAUCUUGG (SEQ ID NO: 254) |
| Unseeded, Aggregated Drop Reaction, 5 day time point | 67 | GGAAAAUAUUUGAAUUGCAAUUCCCAAAUAUUUG GGAAUUGCAAUUCAAAUAUUUGG (SEQ ID NO: 255) |
| Unseeded, Aggregated Drop Reaction, 5 day time point | 68 | GGAAAAAAUAAUAUGCAGGUGGGGCAUAUUAUUU AAUUAAAAUAAUAUGCCCCACCUGCAUAUUAUUUU UGGG (SEQ ID NO: 256) |
| Unseeded, Aggregated Drop Reaction, 5 day time point | 69 | GGAUUUUAUCUCUCAACACCUCGAUGAUAAAUAU CCCCAUUAUUUAUCAUCGAGGUGUUGAGAGAUAA AUAAUGG (SEQ ID NO: 257) |
| Unseeded, Aggregated Drop Reaction, 5 day time point | 70 | GGAAAUUUCAAAGAUUUAGUAACCACUUUGAAAAU UUCAAAGUGGUUACUAAAUCUUUGAAAUUUGG (SEQ ID NO: 258) |
| Unseeded, Aggregated Drop Reaction, 5 day time point | 71 | GGAAAAUUCAAAGUCCAGUGCACUUUGAAUUUCA AAAGAAAUUCAAAGUGCACUGGACUUUGAAUUCG GG (SEQ ID NO: 259) |
| Seeded with DNA pool, Aggregated Drop Reaction, 5 day time point | 1 | GGAAUAUUUAUAUUCAAACUCGGAAUAUAAUAUAU AUUUAUAUUCCGAGUUUGAAUAUAAUAUUGG (SEQ ID NO: 260) |
| Seeded with DNA pool, Aggregated Drop Reaction, 5 day time point | 2 | GGAAAUUUGAUUUCUCAAAUUCAAAUUUAGAAUUC CAAAUUUGAAUUUGAGAAAUCAAAUUUGG (SEQ ID NO: 261) |

TABLE 2-continued

Sequences of RNA species described in FIGS. 6B-6E and FIG. 20B.

| Sample information | RNA species number | Sequence |
|---|---|---|
| Seeded with DNA pool, Aggregated Drop Reaction, 5 day time point | 3 | GGAAUAUUUCUUAAUUUUCUCGUUGUUUAAGAAA UAUUGAUUCCAAUAUUUUCUUAAACAACGAGAAAA UUAAGAAAUAUUGG (SEQ ID NO: 262) |
| Seeded with DNA pool, Aggregated Drop Reaction, 5 day time point | 4 | GGAAUGAUGAAUUCAUUCAACAUCAUUGAAUGAAU GAUGAAUUCAUUCAAUUCAUUCAAUGAUGUUGAA UGAAUUCAUCAUUGGG (SEQ ID NO: 263) |
| Seeded with DNA pool, Aggregated Drop Reaction, 5 day time point | 5 | GGAAUAAUUUCAAUCUAAAUCUCCAGAUUGAAUAA UUUCAAUCUGGAGAUUUAGAUUGAAAUUAUUGGG (SEQ ID NO: 264) |
| Seeded with DNA pool, Aggregated Drop Reaction, 5 day time point | 6 | GGAAUAAAAUUCAAUAUUUUCCUUAUAUAUUGAAU AAAAUUCAAUAUAUAAGGAAAAAUAUUGAAUUUUAU UGG (SEQ ID NO: 265) |
| Seeded with DNA pool, Aggregated Drop Reaction, 5 day time point | 7 | GGAAAAUUAAUCAAAUCUACCUGAUUUUGAUUUGA AAUUAAUCAAAUCAAAAUCAGGUAGAUUUGAUUAA UUUUGG (SEQ ID NO: 266) |
| Seeded with DNA pool, Aggregated Drop Reaction, 5 day time point | 8 | GGAAAUAAAGAAUUUCGAUUCCUAUAUUCUUAUUU GGAAUUUCCAAAUAAAGAAUAUAGGAAUCGAAAUU CUUUAUUUGGG (SEQ ID NO: 267) |
| Seeded with DNA pool, Aggregated Drop Reaction, 5 day time point | 9 | GGAAAAUUUCAAUUCAAAUUUGCCGAAAUUGAAAU UUCAAUUCAAUUCGGCAAAUUUGAAUUGAAAUUUU GGG (SEQ ID NO: 268) |
| Seeded with DNA pool, Aggregated Drop Reaction, 5 day time point | 10 | GGAAAAAUAUUCUUCAAACUCAAUAUUGAAUAUUU UUCCAAAAAUAUUCAAUAUUGAGUUUGAAGAAUAU UUUUGG (SEQ ID NO: 269) |
| Seeded with DNA pool, Aggregated Drop Reaction, 5 day time point | 11 | GGAAUAAAUAUCUGUUCAAUUAGUUCCCUAAUUU GUUCAAUUAGGGAACUAAUUGAACAGAUAUUUAU UGG (SEQ ID NO: 270) |
| Seeded with DNA pool, Aggregated Drop Reaction, 5 day time point | 12 | GGAAAAUUCAAAGUCAACAAUUUGAAUUUCUCCAA AAAUUCAAAUUGUUGACUUUGAAUUUUGGGG (SEQ ID NO: 271) |
| Seeded with DNA pool, Aggregated Drop Reaction, 5 day time point | 13 | GGAAAAUUUAUCUUAUCUACCCAACCUGAGAUAAA UUUUGGAAUUUCAAAUUUAUCUCAGGUUGGGUAG AUAAGAUAAAUUUGG (SEQ ID NO: 272) |
| Seeded with DNA pool, Aggregated Drop Reaction, 5 day time point | 14 | GGGAAAAAUUGUUUCAAAUGCAGCAAACAAUUUU GGCCAAAAUUGUUUGCUGCAUUUGAAACAAUUUU GG (SEQ ID NO: 273) |
| Seeded with DNA pool, Aggregated Drop Reaction, 5 day time point | 15 | GGAAAAACUAUUCAUUUGUCUCUAAUCAGAAUAGA UUUUCCAAAAAACUAUUCUGAUUAGAGACAAAUGA AUAGUUUUUGG (SEQ ID NO: 274) |
| Seeded with DNA pool, Aggregated Drop Reaction, 5 day time point | 16 | GGAAAAUUAUCAAAAGUCGAUGAUAAAUUUUGACCA AAUUAUCAUCGACUUUUUGAUAAUUUUGG (SEQ ID NO: 275) |
| Seeded with DNA pool, Aggregated Drop Reaction, 5 day time point | 17 | GGAAAAUUCAAAAUAUUUGGUGAUAUUUUGAAUU CAAAUAUCACCAAAUAUUUUGAAUUUGGG (SEQ ID NO: 276) |
| Seeded with DNA pool, Aggregated Drop Reaction, 5 day time point | 18 | GGAAAUACUAUUUCAUCAUUCUCCUGAUGAUGAU GAAAGAUGAAUACUAUUUCAUCUUUCAUCAUCAUC AGGAGAAUGAUGAAAUAGUAUUGG (SEQ ID NO: 277) |
| Seeded with DNA pool, Aggregated Drop Reaction, 5 day time point | 19 | GGGAAAAUUAUCAUUUGAAAGUGGUCAAAUGAAAA UUAUCAUUUGACCACUUUCAAAUGAUAAUUUUGG (SEQ ID NO: 278) |
| Seeded with DNA pool, Aggregated Drop Reaction, 5 day time point | 20 | GGAAAAUUAAACUUUCACAAUCCUCCGUGAAAGU GAUUAAACUUUCACGGAGGAUUGUGAAAGUUUAA UUUUGG (SEQ ID NO: 279) |

TABLE 2-continued

Sequences of RNA species described in FIGS. 6B-6E and FIG. 20B.

| Sample information | RNA species number | Sequence |
|---|---|---|
| Seeded with DNA pool, Aggregated Drop Reaction, 5 day time point | 21 | GGAAAUAAAACUUUUCAUAUUCAUAUUGAUGAAGU UUUAUCCAAUAAAACUUCAUCAAUAUGAAUAUGAA AAGUUUUAUUUGG (SEQ ID NO: 280) |
| Seeded with DNA pool, Aggregated Drop Reaction, 5 day time point | 22 | GGAAAAAUUCAUCAAUGGAGAAUGUAUGAAUUUU GUCCUAAAAUUCAUACAUUCUCCAUUGAUGAAUUU UGG (SEQ ID NO: 281) |
| Seeded with DNA pool, Aggregated Drop Reaction, 5 day time point | 23 | GGGGAAAAUUGAUCAUAGUAGUUCAUCAAUUUUU CUUGCAAAAUUGAUGAACUACUAUGAUCAAUUUU GG (SEQ ID NO: 282) |
| Seeded with DNA pool, Aggregated Drop Reaction, 5 day time point | 24 | GGAAAAUUUGAUGGACUUAUGCAUACUUCAAAUU UUCCCGAAAAUUUGAAGUAUGCAUAAGUCCAUCAA AUUUUGGG (SEQ ID NO: 283) |
| Seeded with DNA pool, Aggregated Drop Reaction, 5 day time point | 25 | GGAAAAUUAAUUUGGUACCAUACUUCACCCAAAUU AAUUUUUGAAAUUUGAAUUUGGUGAAGUAUGGUA CCAAAUUAAUUUUGG (SEQ ID NO: 284) |
| Seeded with DNA pool, Aggregated Drop Reaction, 5 day time point | 26 | GGAAUUAGUUCAAUGUAUUUUUGACAAUGAAUUA GUUCAAUGUCAAAAAUACAUUGAACUAAUUGG (SEQ ID NO: 285) |
| Seeded with DNA pool, Aggregated Drop Reaction, 5 day time point | 27 | GGAAAAUUUCAUAUUGUUAAUUACACAAUAUGAAC AAUAUGAAAUUUCAUAUUGUUCAUAUUGUGUAAUU AACAAUAUGAAAUUUCGG (SEQ ID NO: 286) |
| Seeded with DNA pool, Aggregated Drop Reaction, 5 day time point | 28 | GGAAAGUUAAAUAAAUAAAUUCAAAUUCAAAUUCU AUUUAUCUUUUCCAAAGUUAAAUAGAAUUUGAAUU UGAAUUUAUUUAUUUAACUUUGG (SEQ ID NO: 287) |
| Seeded with DNA pool, Aggregated Drop Reaction, 5 day time point | 29 | GGAAAUAUUUCCUAUUUGGGUAGUUAGGAAAUAU UUUACCCAAAUAUUUCCCUAACUACCCAAAUAGGA AAUAUUUGGG (SEQ ID NO: 288) |
| Seeded with DNA pool, Aggregated Drop Reaction, 5 day time point | 30 | GGAAAAAUUAGAUUCUGCUAUCAAUCUAAUUUUCC UAAAUUAGAUUGAUAGCAGAAUCUAAUUUUAGG (SEQ ID NO: 289) |
| Seeded with DNA pool, Aggregated Drop Reaction, 5 day time point | 31 | GGAAUAUCAAAAUCUAAUUAGGAGGCUAGAUUUG AAAUAUCAAAUCUAGCCUCCUAAUUAGAUUUGAUA UUGG (SEQ ID NO: 290) |
| Seeded with DNA pool, Aggregated Drop Reaction, 5 day time point | 32 | GGAAAUUCAAUCUGAUGACUUUGAAUUUCAAUCU GAAAAAUUCAAAGUCAUCAGAUUGAAUUUGG (SEQ ID NO: 291) |
| Seeded with DNA pool, Aggregated Drop Reaction, 5 day time point | 33 | GGAAUAUUCAAAUGCGUUGGAUUUGAAUAUUCAA UGCAAUAUUCAAAUCCAACGCAUUGAAUAUUGG (SEQ ID NO: 292) |
| Seeded with DNA pool, Aggregated Drop Reaction, 5 day time point | 34 | GGAAAUUUGAAAGAAGAUUUGCUAAAAUUCAAAUU UCCAAAUUGAAAUUUGAAUUUUUAGCAAAUCUUCU UUCAAAUUGG (SEQ ID NO: 293) |
| Seeded with DNA pool, Aggregated Drop Reaction, 5 day time point | 35 | GGAUAUUUUCAAUUUGUAUAGCAAGUCAAUACAAA ACAAAAUUGACAUAUUUUCAAUUUGUUUUUUGUAUU GACUUGCUAUACAAAUUGAAAAUAUGGG (SEQ ID NO: 294) |
| Seeded with DNA pool, Aggregated Drop Reaction, 5 day time point | 36 | GGAUGAUGAAUACUUCUAACAUUGUGAUCCCAGU AUUCAUCGGAUGAAUACUGGGAUCACAAUGUUAG AAGUAUUCAUCUUGGG (SEQ ID NO: 295) |
| Seeded with DNA pool, Aggregated Drop Reaction, 5 day time point | 37 | GGGAAAACAAAUUGAAAAUUGUGGCAUUCACAAUU UGUUUCCCAAAAACAAAUUGUGAAUGCCACAAUUU UCAAUUUGUUUUGGG (SEQ ID NO: 296) |
| Seeded with DNA pool, Aggregated Drop Reaction, 5 day time point | 38 | GGAAAAUAUUCAAAUUUUGAAUGAAUUCAAAUUUU GAAUUCAUUCAAAAUUUGAAUAUUUUGGGG (SEQ ID NO: 297) |

TABLE 2-continued

| Sample information | RNA species number | Sequence |
|---|---|---|
| Seeded with DNA pool, Aggregated Drop Reaction, 5 day time point | 39 | GGAAUAAAAUGUGUUUAUUUGGUUAUUUUUCACA UUUUUAUUCCCUAAAAAUGUGAAAAAUAACCAAAU AAACACAUUUUAGGG (SEQ ID NO: 298) |
| Seeded with DNA pool, Aggregated Drop Reaction, 5 day time point | 40 | GGAAAAAUUCAUAUUAUAGAAAUGAAUAAUAUGAA AAAUUCAUAUUAUUCAUUUCUAUAAUAUGAAUUUU GG (SEQ ID NO: 299) |
| Seeded with DNA pool, Aggregated Drop Reaction, 5 day time point | 41 | GGAAGAAUCAAAUGAAUACUGUGAUGAACAGUGU UUUAGUUCUUCCGAAGAACUAAAAAACACUGUUCA UCACAGUAUUCAUUUGAUUCUUGGG (SEQ ID NO: 300) |
| Seeded with DNA pool, Aggregated Drop Reaction, 5 day time point | 42 | GGAAUAUUCUUCAAUCUUCUACCUAGAUUGAUUG GAUUGAUUGCAAUAUUCUUCAAUCCAAUCAAUCUA GGUAGAAGAUUGAAGAAUAUUGG (SEQ ID NO: 301) |
| Seeded with DNA pool, Aggregated Drop Reaction, 5 day time point | 43 | GGAAAUAUUUCAUAUUAUGUAUGGAAUCAUAAUUU UAAUAUGAUGAAUAUUUCAUAUUAAAAAAAAAUUAU GAUUCCAUACAUAAUAUGAAAUAUUUGG (SEQ ID NO: 302) |
| Seeded with DNA pool, Aggregated Drop Reaction, 5 day time point | 44 | GGAAAUUGCAAAUAUACAAUUCUAUAUCAUUCGAU AUAGAAUUGUAUAUUGAAUUUUUUGG (SEQ ID NO: 303) |
| Seeded with DNA pool, Aggregated Drop Reaction, 5 day time point | 45 | GGAAAAAUCAAUAAUAUCUUUCCAAUCUGGAAAGA UAUUAUUGGGAUAUUAUUUCCAAUAAUAUCUUUC CAGAUUGGAAAGAUAUUAUUGAUUUUUGG (SEQ ID NO: 304) |
| Seeded with DNase-treated DNA pool, Aggregated Drop Reaction, 5 day time point | 1 | GGAAAUUUUCAAUAAUUAAUUCCCAAAUUAUUGAA AUUUUCAAUAAUUUGGGAAUUAAUUAUUGAAAAUU UGG (SEQ ID NO: 305) |
| Seeded with DNase-treated DNA pool, Aggregated Drop Reaction, 5 day time point | 2 | GGAAUAAUAUGAAAUGGAAUGGAUUCCUAUUAUU CCGAAUAAUAUGAAUCCAUUCCAUUUCAUAUUAUU GG (SEQ ID NO: 306) |
| Seeded with DNase-treated DNA pool, Aggregated Drop Reaction, 5 day time point | 3 | GGAAUAAAUCAUUAAAUAUCAUUAUCGAUGAUUUA UCCAUAAAUCAUCGAUAAUGAUAUUUAAUGAUUUA UGG (SEQ ID NO: 307) |
| Seeded with DNase-treated DNA pool, Aggregated Drop Reaction, 5 day time point | 4 | GGAAUAUUCAUUCAAUAUUCAUCUAUUGAAUAUAU UCAUUCAAUAUUCAAUAGAUGAAUAUUGAAUGAAU AUUGG (SEQ ID NO: 308) |
| Seeded with DNase-treated DNA pool, Aggregated Drop Reaction, 5 day time point | 5 | GGAAAUUAUAUUGAGCUUCCAAUCCUCAAUAUAAU UUUAUAUUGAGGAUUGGAAGCUCAAUAUAAUUUG G (SEQ ID NO: 309) |
| Seeded with DNase-treated DNA pool, Aggregated Drop Reaction, 5 day time point | 6 | GGAAAUUAUUUCUAUGUACCAUUUUGAAAUAAUUU CCCAAAUUAUUUCAAAAUGGUACAUAGAAAUAAUU UGG (SEQ ID NO: 310) |
| Seeded with DNase-treated DNA pool, Aggregated Drop Reaction, 5 day time point | 7 | GGAAUAUUAUCACAAUAAUUUCCAUUUUGUGAAUA UUAUCACAAAAUGGAAAUUAUUGUGAUAAUAUUGG (SEQ ID NO: 311) |
| Seeded with DNase-treated DNA pool, Aggregated Drop Reaction, 5 day time point | 8 | GGAAUAAUUAAUUAAGAAGAUUAAUUAUUACCUA AUAAUUAAUCUUCUUAAUUAAUUAUUUGG (SEQ ID NO: 312) |
| Seeded with DNase-treated DNA pool, Aggregated Drop Reaction, 5 day time point | 9 | GGAAAUAUUCAAAUGAGAAAAUAUCAUUUGAAAUA UUCAAAUGAUAUUUCUCAUUUGAAUAUUUGG (SEQ ID NO: 313) |
| Seeded with DNase-treated DNA pool, Aggregated Drop Reaction, 5 day time point | 10 | GGAAAUUAAUCAAAUUAAUUAAUUGAUUUGAUUUC AAAUUAAUCAAAUCAAUUAAUUAAUUUGAUUAAUU GG (SEQ ID NO: 314) |

TABLE 2-continued

Sequences of RNA species described in FIGS. 6B-6E and FIG. 20B.

| Sample information | RNA species number | Sequence |
|---|---|---|
| Seeded with DNase-treated DNA pool, Aggregated Drop Reaction, 5 day time point | 11 | GGAAAAUUUCAUGUUGAAUUCCAAUCCCAACAACA UGAAAAUUUCAUGUUGGGAUUGGAAUUCAACAUG AAAUUUGG (SEQ ID NO: 315) |
| Seeded with DNase-treated DNA pool, Aggregated Drop Reaction, 5 day time point | 12 | GGGAAAAUUCAAUUGAAAUCAAUUGGAAUCAAUUA AAAUUCAAUUGAUUCCAAUUGAUUUCAAUUGAAUU UUGG (SEQ ID NO: 316) |
| Seeded with DNase-treated DNA pool, Aggregated Drop Reaction, 5 day time point | 13 | GGAAUGAAUCAAAUAAUUCAUUCAAUGAAUCAAAU AAUUCGAUGAAUUAUUUGAUUCAUUAUUGAAUGAA UUAUUUUGAAUGG (SEQ ID NO: 317) |
| Seeded with DNase-treated DNA pool, Aggregated Drop Reaction, 5 day time point | 14 | GGAAAAAUAGAAUUCAAGUUAAACUAUUUUCUAUU UUUCCAAAAUAGAAAAUAGUUUUAACUUGAAUUCUA UUUUGG (SEQ ID NO: 318) |
| Seeded with DNase-treated DNA pool, Aggregated Drop Reaction, 5 day time point | 15 | GGAAAAUUAUAAUUGGAUUUGGAUAGACAAUUAUA AUUUGCAAAAUUAUAAUUGUCUAUCCAAAUCCAAU UAUAAUUUGGG (SEQ ID NO: 319) |
| Seeded with DNase-treated DNA pool, Aggregated Drop Reaction, 5 day time point | 16 | GGAAAAUUAUCUAUACAUCUCCGAUAAUUUUCUUU CCAAAUUAUCGGAGAUGUAUAGAUAAUUUGGG (SEQ ID NO: 320) |
| Seeded with DNase-treated DNA pool, Aggregated Drop Reaction, 5 day time point | 17 | GGAAAUUGAAUCAAUUAGAUGAUUUAAUUGAAAUU GAAUCAAUUAAAUCAUCUAAUUGAUUCAAUUUGG (SEQ ID NO: 321) |
| Seeded with DNase-treated DNA pool, Aggregated Drop Reaction, 5 day time point | 18 | GGGAAUUUCAUAAGUUCAUCGUUUGCUUAUGAAA CAAUUUCAUAAGCAAACGAUGAACUUAUGAAAUUG G (SEQ ID NO: 322) |
| Seeded with DNase-treated DNA pool, Aggregated Drop Reaction, 5 day time point | 19 | GGGAAGAUAUAUCAAAGAAAUAUAUUUUUCCCAAA AAUAUAUUUCUUUGAUAUAUCUUGG (SEQ ID NO: 323) |
| Seeded with DNase-treated DNA pool, Aggregated Drop Reaction, 5 day time point | 20 | GGAAAAUUUAUCUUUGGUAAAUUUGAUAAAUUUUA AUCCAAAUUUAUCAAAUUUACCAAAGAUAAAUUUG G (SEQ ID NO: 324) |
| Seeded with DNase-treated DNA pool, Aggregated Drop Reaction, 5 day time point | 21 | GGAAAUUUCAAUUUCAAUUGGAAUUAAUUGAAAUU UCAAUUUCAAUUAAUUCCAAUUGAAAUUGAAAUUU GG (SEQ ID NO: 325) |
| Seeded with DNase-treated DNA pool, Aggregated Drop Reaction, 5 day time point | 22 | GGAAAAUUUGUUAUGUAUGCAUUGGACAAAUUUU CCCAAUUUGUCCAAUGCAUACAUAACAAAUUGGG (SEQ ID NO: 326) |
| Seeded with DNase-treated DNA pool, Aggregated Drop Reaction, 5 day time point | 23 | GGAAAUUCAAUUUCAAUUACAAUUGAGUUGUAAUU GAAUUUGGUUAUCCAAAUUCAAUUACAACUCAAUU GUAAUUGAAAUUGAAUUUGG (SEQ ID NO: 327) |
| Seeded with DNase-treated DNA pool, Aggregated Drop Reaction, 5 day time point | 24 | GGAAUAAUAUCUAUUUAUUAUUAUUGAUAGAUAUU AUUUAAUAAUAUCUAUCAAUAAUAAUAAAUAGAUA UUAUUGG (SEQ ID NO: 328) |
| Seeded with DNase-treated DNA pool, Aggregated Drop Reaction, 5 day time point | 25 | GGAAUUAAUUUCAAUUCUAUUCAGUAAUUGAUUAA UUUCAAUUACUGAAUAGAAUUGAAAUUAAUGG (SEQ ID NO: 329) |
| Seeded with DNase-treated DNA pool, Aggregated Drop Reaction, 5 day time point | 26 | GGAAAUUUAUCAUAUUCAUGGGGUAGAUCAUAUA UGAUGAAUUUAUCAUAUAUGAUCUACCCCAUGAAU AUGAUAAAUUUGG (SEQ ID NO: 330) |
| Seeded with DNase-treated DNA pool, Aggregated Drop Reaction, 5 day time point | 27 | GGAUUUAAUCUUUGCCUCUAAAAAGAUUAAUCCAU UUAAUCUUUUUUAGAGGCAAAGAUUUAAAUGG (SEQ ID NO: 331) |
| Seeded with DNase-treated DNA pool, Aggregated Drop Reaction, 5 day time point | 28 | GGGAUAUUAUCAUAUAUGUUUGAUGACAUAUAUC AUAUAUGUCAUCAAACAUAUAUGAUAAUAAGG (SEQ ID NO: 332) |

TABLE 2-continued

Sequences of RNA species described in FIGS. 6B-6E and FIG. 20B.

| Sample information | RNA species number | Sequence |
|---|---|---|
| Seeded with DNase-treated DNA pool, Aggregated Drop Reaction, 5 day time point | 29 | GGAAAAUUAUUUUCAAAUAAAGGUCUCUAUUAAUU AUUUUCAAAUAAUAGAGACCUUUAUUUGAAAAUAA UUUUGG (SEQ ID NO: 333) |
| Seeded with DNase-treated DNA pool, Aggregated Drop Reaction, 5 day time point | 30 | GGAAAAUUUCAAAUUGAAAAUCAAAUUUGAAAAUU UCAAAUUUGAUUUUCAAUUUGAAAUUUUGG (SEQ ID NO: 334) |
| Seeded with DNase-treated DNA pool, Aggregated Drop Reaction, 5 day time point | 31 | GGAAAAAUUAUCAUGUACUCUAAUCCAUGAUAAAA UUAUCAUGGAUUAGAGUACAUGAUAAUUUUGG (SEQ ID NO: 335) |
| Seeded with DNase-treated DNA pool, Aggregated Drop Reaction, 5 day time point | 32 | GGAAAAAUUAGAAAGAAAACCUAAUUUUUCCAAAA AUUAGGUUUUCUUUCUAAUUUUUGG (SEQ ID NO: 336) |
| Seeded with DNase-treated DNA pool, Aggregated Drop Reaction, 5 day time point | 33 | GGGAAAUUUGGAUUCUCUUCUCUUCCUAAUCCAA AUUUCCCAAAUUUGGAUUAGGAAGAGAAGAGAAU CCAAAUUUGG (SEQ ID NO: 337) |
| Seeded with DNase-treated DNA pool, Aggregated Drop Reaction, 5 day time point | 34 | GGAAAUUUGAUUAAUUCAUUUGGAAAUUUGAUUA AUUUCCAAAUGAAUUAAUCAAAUUUGG (SEQ ID NO: 338) |
| Seeded with DNase-treated DNA pool, Aggregated Drop Reaction, 5 day time point | 35 | GGGAAAUUUCUUUCAACAGAGAUAGUUUGUUGAA UUUCUUUCAACAAACUAUCUCUGUUGAAAGAAAUU UGG (SEQ ID NO: 339) |
| Seeded with DNase-treated DNA pool, Aggregated Drop Reaction, 5 day time point | 36 | GGAAAUUUCAUCUUGAAUUGUAAUCCCGAGAUUA AAUUUCAUCUCGGGAUUACAAUUCAAGAUGAAAUU UGGG (SEQ ID NO: 340) |
| Seeded with DNase-treated DNA pool, Aggregated Drop Reaction, 5 day time point | 37 | GGAAAUUAUCUUAAUUAUCUUAUCAAAUUAGAUAA GAUAAGAUAAUUAUCUAUCUUAUCUUAUCUAAUUU GAUAAGAUAAUUAAGAUAAUUUGGG (SEQ ID NO: 341) |
| Seeded with DNase-treated DNA pool, Aggregated Drop Reaction, 5 day time point | 38 | GGAUAAUAAUGGAUUAUUGGUGAUGUUCCAUUAU UAUCCGAUAAUAAUGGAACAUCACCAAUAAUCCAU UAUUAGG (SEQ ID NO: 342) |
| Seeded with DNase-treated DNA pool, Aggregated Drop Reaction, 5 day time point | 39 | GGAUUUGAAUCAAAUCAAAUCAAAUCAAAUCAUUU GAUUUGAUUUGAUUUGCUAAUCAAAUGG (SEQ ID NO: 343) |
| Seeded with DNase-treated DNA pool, Aggregated Drop Reaction, 5 day time point | 40 | GGAAAUGAAAUAAUAUCCAUCAUUCUAUUAUUUUU UCCAAAUGAAAUAAUAGAAUGAUGGAUAUUAUUUC AUUUGG (SEQ ID NO: 344) |
| Seeded with DNase-treated DNA pool, Aggregated Drop Reaction, 5 day time point | 41 | GGAAAAUUACAAAGUUCCAGUGUAAUUUUGUAAU UUCCAAUUACAAAAUUACACUGGAACUUUGUAAUU UGG (SEQ ID NO: 345) |
| Seeded with DNase-treated DNA pool, Aggregated Drop Reaction, 5 day time point | 42 | GGAAAAUAAUGGAUCAAAUAACUGUAUCAUUCAUU AUUUUCCAAAAUAAUGAAUGAUACAGUUAUUUGAU CCAUUAUUUUGG (SEQ ID NO: 346) |
| Seeded with DNase-treated DNA pool, Aggregated Drop Reaction, 5 day time point | 43 | GGAAUGAAUAUACAGGAUAAAUUAUUCACUUCAUG UAUAUUCAUUCCCAUGAAGUGAAUAAUUUAUCCU GUAUAUUCAUGG (SEQ ID NO: 347) |
| Seeded with DNase-treated DNA pool, Aggregated Drop Reaction, 5 day time point | 44 | GGAAAUAAAUUAGUCUUUCCUAAAUAAUUAGACUA AAUUAAAUAAAUUAGUCUAAUUAUUUAGGAAAGAC UAAUUUAUUUGG (SEQ ID NO: 348) |
| Seeded with DNase-treated DNA pool, Aggregated Drop Reaction, 5 day time point | 45 | GGAAAUAUAUAUUUGGUUUUUCAUCCCCAAAUAUA UAUUUAUAUUUGGGGAUGAAAACCAAAUAUAUAUU UGGG (SEQ ID NO: 349) |
| Seeded with DNase-treated DNA pool, Aggregated Drop Reaction, 5 day time point | 46 | GGAAAAUUUAGGAGUGCUUGUAAGUUUCCAUCCU AAUUUUCCCAAUUUAGGAUGGAAACUUACAAGCAC UCCUAAAUUUGG (SEQ ID NO: 350) |

TABLE 2-continued

Sequences of RNA species described in FIGS. 6B-6E and FIG. 20B.

| Sample information | RNA species number | Sequence |
|---|---|---|
| Seeded with DNase-treated DNA pool, Aggregated Drop Reaction, 5 day time point | 47 | GGAAAUAUUCAAAAGAUUUCAUCCUUUUGAAUAUU UUCUUUGAAAUAUUCAAAAGAAAAUAUUCAAAAGG AUGAAAUCUUUUGAAUAUUUGG (SEQ ID NO: 351) |
| Seeded with DNase-treated DNA pool, Aggregated Drop Reaction, 5 day time point | 48 | GGAGAAAUAAAUUUGGUAUACUGCACAUUUCAAU UUAUUUCUCGAGAAAUAAAUUGAAAUGUGCAGUA UACCAAAUUUAUUUCUGGG (SEQ ID NO: 352) |
| Seeded with DNase-treated DNA pool, Aggregated Drop Reaction, 5 day time point | 49 | GGAAAAUUUGAUUCAAAUACUUCAUAUUUGAUUCA AAUAUGAAGUAUUUGAAUCAAAUUUUGG (SEQ ID NO: 353) |
| Seeded with DNase-treated DNA pool, Aggregated Drop Reaction, 5 day time point | 50 | GGGAAAAUUCAUUUCAUUUGCAAAUGAAUUCAUU UCAAUUCAUUUGCAAAUGAAAUGAAUUUGG (SEQ ID NO: 354) |
| Seeded with DNase-treated DNA pool, Aggregated Drop Reaction, 5 day time point | 51 | GGAAAUCAAAUUAUCUUCAUCCCCAUUUCAGAUAA UUUGAGAAUCAAAUUAUCUGAAAUGGGGAUGAAG AUAAUUUGAUUGG (SEQ ID NO: 355) |
| Seeded with DNase-treated DNA pool, Aggregated Drop Reaction, 5 day time point | 52 | GGAAUAUUGGUUUUGGUAUUUGCACUUUCCAAUA UUCCCCAAUAUUGGAAAGUGCAAAUACCAAAACCA AUAUUGG (SEQ ID NO: 356) |
| Seeded with DNase-treated DNA pool, Aggregated Drop Reaction, 5 day time point | 53 | GGAAAUUGCAAUGUUAGAUUCUUUCCUCAAAUUG CAAUUUCAGUUUUUUCCAAUUUGAGGAAAGAAUC UAACAUUGCAAUUUGG (SEQ ID NO: 357) |
| Seeded with DNase-treated DNA pool, Aggregated Drop Reaction, 5 day time point | 54 | GGGAAAUUAUUCAUAGUUCUGCCUAUGAAAAUUA UUCAUAGGCAGAACUAUGAAUAAUUUAGG (SEQ ID NO: 358) |
| Seeded with DNase-treated DNA pool, Aggregated Drop Reaction, 5 day time point | 55 | GGAUAUUCAAAUCAUUAGCAAAUCCUAAUGAUGAU UUGAAAUCCAUAUUCAAAUCAUCAUUAGGAUU UGC UAAUGAUUUGAAUAUGG (SEQ ID NO: 359) |
| Seeded with DNase-treated DNA pool, Aggregated Drop Reaction, 5 day time point | 56 | GGAAAUUUUGGAAAUUGAAUGGAAUCCAAAAUUU UCCGAAAUUUUGGAUUCCAUUCAAUUUCCAAAAUU UGGG (SEQ ID NO: 360) |
| Seeded with DNase-treated DNA pool, Aggregated Drop Reaction, 5 day time point | 57 | GGGAAAAUGGAAUUGAAUGGAAAUUUCCAUUUUC CAAAUGGAAAAUGAUGAAAUUUCCAUUCAAUUCCA UUUGG (SEQ ID NO: 361) |
| Seeded with DNase-treated DNA pool, Aggregated Drop Reaction, 5 day time point | 58 | GGAAAAUUCAAAUAAUUAGAGAUUGCAUAUUAUUU GAAUUGAUUGCAUAUAAAUUCAAAUAAUAUGCAAU CUCUAAUUAUUUGAAUUUUGG (SEQ ID NO: 362) |
| Seeded with DNase-treated DNA pool, Aggregated Drop Reaction, 5 day time point | 59 | GGAAAAUUCAAAAUUCGAAUUUGAAUUUGGAAAAU UUCCAAAUUCAAAUUCGAAUUUUGAAUUUGG (SEQ ID NO: 363) |
| Seeded with DNase-treated DNA pool, Aggregated Drop Reaction, 5 day time point | 60 | GGAAAUUUCAAAAUUUCAAUCAUCGAAAUUUCAAAU UUCGAUGAUUGAAAUUUGAAAUUUGGGG (SEQ ID NO: 364) |
| Seeded with DNase-treated DNA pool, Aggregated Drop Reaction, 5 day time point | 61 | GGAUAAAUUCAUUAUCUUCAAUUCUCCAGAUAAUG AAUUUUGAUUAUCAAAAAUUCAUUAUCUGGAGAAU UGAAGAUAAUGAAUUUCGG (SEQ ID NO: 365) |
| Seeded with DNase-treated DNA pool, Aggregated Drop Reaction, 5 day time point | 62 | GGAAAUAUUCAAUAUUUCACAGGUCACUGUGAAA UAUUUGGAAUAUUGUCCAAAUUCCAAAUAUUUCAC AGUGACCUGUGAAAUAUUGAAUAUUUGGG (SEQ ID NO: 366) |
| Seeded with DNase-treated DNA pool, Aggregated Drop Reaction, 5 day time point | 63 | GGAAAAUUGAAUACUUCAUUGCAUUCCAUUCAAUU UUCCCAAAAUUGAAUGGAAUGCAAUGAAGUAUUCA AUUUUGGG (SEQ ID NO: 367) |
| Seeded with DNase-treated DNA pool, Aggregated Drop Reaction, 5 day time point | 64 | GGAAAUUAAUCAAUAAAUUUAGUGCAAUUCAUUAA UCAAUAAAUAAUGAAUUGCACUAAAAUUUAUUGAUU AAUUUGG (SEQ ID NO: 368) |

TABLE 2-continued

Sequences of RNA species described in FIGS. 6B-6E and FIG. 20B.

| Sample information | RNA species number | Sequence |
|---|---|---|
| Seeded with DNase-treated DNA pool, Aggregated Drop Reaction, 5 day time point | 65 | GGAAAUUUGGUCUCUUGUCACAUCAUCCAAAUUU CCCCCAAAUUUGGAUGAUGUGACAAGAGACCAAA UUUGG (SEQ ID NO: 369) |
| Seeded with DNase-treated DNA pool, Aggregated Drop Reaction, 5 day time point | 66 | GGAAAUUUGAAAUUUCAAAAUCAAAUGAUUUUGAA AUUUCAAAAUCAUUUGAUUUUGAAAUUUCAAAUUC GG (SEQ ID NO: 370) |
| Seeded with DNase-treated DNA pool, Aggregated Drop Reaction, 5 day time point | 67 | GGAAAUAUUUUCUUUUCUAGCAUAUCUAGAAAUAU UGAAAAAUAUUUUCUUUUUUCCCAAUAUUUCUAGA UAUGCUAGAAAAGAAAAUAUUGG (SEQ ID NO: 371) |
| Seeded with DNase-treated DNA pool, Aggregated Drop Reaction, 5 day time point | 68 | GGAAUAUUGAAUUAAUGUAAUCCACCCACAUUAAU UCACAUUGAAUUAAUGUGGUGGAUUACAUUAAUU CAAUAUUGG (SEQ ID NO: 372) |
| Seeded with DNase-treated DNA pool, Aggregated Drop Reaction, 5 day time point | 69 | GGAAAUUUAAAUACAAUUCCAAGUGCCUUGAAUU GUAUUUAAAUACAAUUCAAGGCACUUGGAAUUGU AUUUAAAUUUGG (SEQ ID NO: 373) |
| Seeded with DNase-treated DNA pool, Aggregated Drop Reaction, 5 day time point | 70 | GGAAAUUUCUCAAAAUUUGACUUGAAAUUUCUCAA AAUUCAAGUCAAAUUUUGAGAAAUUUGG (SEQ ID NO: 374) |
| Seeded with DNase-treated DNA pool, Aggregated Drop Reaction, 5 day time point | 71 | GGAAAAUAUUCUUCAACAUUAUAUUUGGUUCAUUA CAAGUUGAAAUAAUAUUCUUCAACAUUAUUUCAAC UUGUAAUGAACCAAAUAUAAUGUUGAAGAAUAUUU UGGG (SEQ ID NO: 375) |
| Seeded with DNase-treated DNA pool, Aggregated Drop Reaction, 5 day time point | 72 | GGAAUUAUUGGAAUUUGGCUAUCUUAUUAAUCCA AUAAUUUGGCAAUUAUUGGAUUAAUAAGAUAGCCA AAUUCCAAUAAUUGGG (SEQ ID NO: 376) |
| Seeded with DNase-treated DNA pool, Aggregated Drop Reaction, 5 day time point | 73 | GGAAAUAUCAAUCAAAGCCUUAUAUUUGAUUUUUC CAAAUAUCAAAUAUAAGGCUUUGAUUGAUAUUUG G (SEQ ID NO: 377) |
| Seeded with DNase-treated DNA pool, Aggregated Drop Reaction, 5 day time point | 74 | GGAAUAUUUGCUUUCUUUGAUUAUAUUCUUUGCA AAUAUUCCCAAAUAUUUGCAAAGAAUAUAAUCAAA GAAAGCAAAUAUUGGG (SEQ ID NO: 378) |
| Seeded with DNase-treated DNA pool, Aggregated Drop Reaction, 5 day time point | 75 | GGAAAUAAACUUCCAUAUAAUAUUGGAAUAUAUUA UAUAUGGAAUAAACUUCCAUAUAUAAUAUAU UCCA AUAUUAUAUGGAAGUUUAUUGGG (SEQ ID NO: 379) |
| Seeded with DNase-treated DNA pool, Aggregated Drop Reaction, 5 day time point | 76 | GGAAAAAUUGGAUAUUGCUGACUCGUUCCCAAUU UUUCCCGGAAAAUUGGAACGAGUCAGCAAUAUCC AAUUUUGG (SEQ ID NO: 380) |
| Seeded with DNase-treated DNA pool, Aggregated Drop Reaction, 5 day time point | 77 | GGGAAAUUUGAAUCUCUGCUCCAUUCAAAUUUCC AAAUUUGAAUGGAGCAGAGAUUCAAAUUUGGG (SEQ ID NO: 381) |
| Seeded with DNase-treated DNA pool, Aggregated Drop Reaction, 5 day time point | 78 | GGAAAUAAUCAAUAGUUUUACCAACCCUACUAUUG AUUAAUAAUCAAUAGUAGGGUUGGUAAACUAUUG AUUAUUGG (SEQ ID NO: 382) |
| Seeded with DNase-treated DNA pool, Aggregated Drop Reaction, 5 day time point | 79 | GGAAAAUUAGGAAUUUUGUAGCAUUUCCAUUUCC UAAUUUUCUACAAAAUUAGGAAAUGGAAAUGCUAC AAAAUUCCUAAUUUUGGG (SEQ ID NO: 383) |
| Seeded with DNase-treated DNA pool, Aggregated Drop Reaction, 5 day time point | 80 | GGAAAUAAAGAAGUAUUUCUCUUUUCCUUAUUUC UCUUUUCUAAAUAAAGAAAUAAGGAAAAAGAGAAAU ACUUCUUUAUUUGG (SEQ ID NO: 384) |
| Seeded with DNase-treated DNA pool, Aggregated Drop Reaction, 5 day time point | 81 | GGAAUAAUUCUAUUCGAUUCCUAGAAUUUUCAUU CCAUAAUUCUAGGAAUCGAAUAGAAUUAUGG (SEQ ID NO: 385) |
| Seeded with DNase-treated DNA pool, Aggregated Drop Reaction, 5 day time point | 82 | GGAUUGAUUAAAUCAAUAAGGAAUGGCUUCUUCA UUUAUUGAAGAAGCCAUUCCUUCCUUAUUGAUUU CAAGG (SEQ ID NO: 386) |

TABLE 2-continued

Sequences of RNA species described in FIGS. 6B-6E and FIG. 20B.

| Sample information | RNA species number | Sequence |
|---|---|---|
| Seeded with DNase-treated DNA pool, Aggregated Drop Reaction, 5 day time point | 83 | GGAAAAGAACUAUUUCAAUUCCAUUCUUUUGGAA UGAAAUAGAUUCUUUCUAUUUCAUUCCAAAAGAAU GGAAUUGAAAUAGUUCUUUUGG (SEQ ID NO: 387) |
| Seeded with DNase-treated DNA pool, Aggregated Drop Reaction, 5 day time point | 84 | GGAAAAUUGGAAAUCAUCAUUCUCAUCCAAUUUUC CAAAAUUGGAUGAGAAUGAUGAUUUCCAAUUUUG GG (SEQ ID NO: 388) |
| Seeded with hot alkali-treated DNA pool, Aggregated Drop Reaction, 5 day time point | 1 | GGAAUAAAUUGGACUACUUAAUACACAAUUUAUUC CAAUAAAUUGUGUAUUAAGUAGUCCAAUUUAUUG G (SEQ ID NO: 389) |
| Seeded with hot alkali-treated DNA pool, Aggregated Drop Reaction, 5 day time point | 2 | GGAAAUAACAUUUUCAUCUCACAUCAGAAAUGUUA AUUCCAAAUAACAUUUCUGAUGUGAGAUGAAAAUG UUAUUUGGG (SEQ ID NO: 390) |
| Seeded with hot alkali-treated DNA pool, Aggregated Drop Reaction, 5 day time point | 3 | GGAAUAAUUCAAUAAUUCCUAUAUUAUUGAAAUAA UUCAAUAAUAUAGGAAUUAUUGAAUUAUUGG (SEQ ID NO: 391) |
| Seeded with hot alkali-treated DNA pool, Aggregated Drop Reaction, 5 day time point | 4 | GGAAUAUUUCAGAAUUCAAUUACAUCAAUUCCGAA UAUUUUCCAAUAUUCGGAAUUGAUGUAAUUGAAU UCUGAAAUAUUGG (SEQ ID NO: 392) |
| Seeded with hot alkali-treated DNA pool, Aggregated Drop Reaction, 5 day time point | 5 | GGAAAUUUCAAUGUUAUCAUUACACAUUGAAAAUU UCAAUGUGUAAUGAUAACAUUGAAAUUUGG (SEQ ID NO: 393) |
| Seeded with hot alkali-treated DNA pool, Aggregated Drop Reaction, 5 day time point | 6 | GGAUAUUACAUUAUCAAUCCUUGCGAUGUAAUUG AUCCUAUUACAUCGCAAGGAUUGAUAAUGUAAUA GG (SEQ ID NO: 394) |
| Seeded with hot alkali-treated DNA pool, Aggregated Drop Reaction, 5 day time point | 7 | GGAAAUUAUCAUUUCUGAUCAAAGAUAUGAUUCAA UUAUCAUAUCUUUGAUCAGAAAUGAUAAUUUGG (SEQ ID NO: 395) |
| Seeded with hot alkali-treated DNA pool, Aggregated Drop Reaction, 5 day time point | 8 | GGAAAAUUUCAAAUUAUUGUGGCUGAAAUUUGAA AUUUCCAAAUUUCAAAUUUCAGCCACAAUAAUUUG AAAUUUUGGG (SEQ ID NO: 396) |
| Seeded with hot alkali-treated DNA pool, Aggregated Drop Reaction, 5 day time point | 9 | GGAAAAUUUCAAAUAAUGCCGAUUAUUUGAAAAUU UCAAAUAAUCGGCAUUAUUUGAAAUUUUGG (SEQ ID NO: 397) |
| Seeded with hot alkali-treated DNA pool, Aggregated Drop Reaction, 5 day time point | 10 | GGAAAUUUCAAACAAAUUUGUUGUGUGUUGUUUG AAUUUCAAACAAAUUUCAAAACAACACACAACAAAU UUGUUUGAAAUUUGG (SEQ ID NO: 398) |
| Seeded with hot alkali-treated DNA pool, Aggregated Drop Reaction, 5 day time point | 11 | GGAAAUUUACCAAUUCAUGGGGUGGUGAAUUUAC CAAUUUACCACCCCAUGAAUUGGUAAAUUGGG (SEQ ID NO: 399) |
| Seeded with hot alkali-treated DNA pool, Aggregated Drop Reaction, 5 day time point | 12 | GGGGAAUUUCAUUCAAUUACCCGAUUGAUGAAAU UUCAUUCAAUCGGGUAAUUGAAUGAAAUUGG (SEQ ID NO: 400) |
| Seeded with hot alkali-treated DNA pool, Aggregated Drop Reaction, 5 day time point | 13 | GGAAUAAUUGAUAUAAUGCGUCAAUCAAUUCAAUU AUUCCAUAAUUGAAUUGAUUGACGCAUUAUAUCAA UUAUGGG (SEQ ID NO: 401) |

TABLE 2-continued

Sequences of RNA species described in FIGS. 6B-6E and FIG. 20B.

| Sample information | RNA species number | Sequence |
|---|---|---|
| Seeded with hot alkali-treated DNA pool, Aggregated Drop Reaction, 5 day time point | 14 | GGAAUAUUUCAAGAAUGUUUAUCCUUAUCCAUUC UUUUGAAUAUUCAAGAAUGGAUAAGGAUAAACAUU CUUGAAAUAUUGG (SEQ ID NO: 402) |
| Seeded with hot alkali-treated DNA pool, Aggregated Drop Reaction, 5 day time point | 15 | GGAAAAUUUCGAAAUUUCCGAAAUAUCGAAAUAUC CAAAUUUCGAUAUUUCGGAAAUUUCGAAAUUUUG G (SEQ ID NO: 403) |
| Seeded with hot alkali-treated DNA pool, Aggregated Drop Reaction, 5 day time point | 16 | GGAAAAUUAUCAAUUGCACUCUUGCAAAUUGAAAU UAUCAAUUUGCAAGAGUGCAAUUGAUAAUUUUGG G (SEQ ID NO: 404) |
| Seeded with hot alkali-treated DNA pool, Aggregated Drop Reaction, 5 day time point | 17 | GGAAAUGUUUAUGUUUCUUUGCGAUUUUCCAUAA ACAUUUUGCAAAUGUUUAUGGAAAAUCGCAAAGAA ACAUAAACAUUUGG (SEQ ID NO: 405) |
| Seeded with hot alkali-treated DNA pool, Aggregated Drop Reaction, 5 day time point | 18 | GGAAAAUUCAAAUCAUUUAGAGUUCGGAUUUAAAU UUUCCAAAUUCAAAUCCGAACUCUAAAUGAUUUGA AUUUUGG (SEQ ID NO: 406) |
| Seeded with hot alkali-treated DNA pool, Aggregated Drop Reaction, 5 day time point | 19 | GGAAAUUGAAAUGCAUUUCAAAUUCAAUUUUCCAA AUUGAAAAUUGAAUUGAAAUGCAUUUCAAUUUGG G (SEQ ID NO: 407) |
| Seeded with hot alkali-treated DNA pool, Aggregated Drop Reaction, 5 day time point | 20 | GGAAAAUAAUCAAUUCCGGAUUAUUGAUUAUUAUU UCCAAUAAUCAAUAAUCCGGAAUUGAUUAUUUGG (SEQ ID NO: 408) |
| Seeded with hot alkali-treated DNA pool, Aggregated Drop Reaction, 5 day time point | 21 | GGAAAAAUUGAUUCGAUCAUUUCAAUUUUUUCCG AAAAAUUGAAAUGAUCGAAUCAAUUUUUGG (SEQ ID NO: 409) |
| Seeded with hot alkali-treated DNA pool, Aggregated Drop Reaction, 5 day time point | 22 | GGAAUAUUAAAUACUUUAUUCUCCCAAUAUUAAAU ACUUUAUUCGGAAUAAAGUAUUUAAUAUUGGGAG AAUAAAGUAUUUAAUAUUGG (SEQ ID NO: 410) |
| Seeded with hot alkali-treated DNA pool, Aggregated Drop Reaction, 5 day time point | 23 | GGAAAAUAUUUGGCAUAUAAUAUGUAUAAUAUUUU CCCAAAUAUUAUACAUAUUAUAUGCCAAAUAUUUG GG (SEQ ID NO: 411) |
| Seeded with hot alkali-treated DNA pool, Aggregated Drop Reaction, 5 day time point | 24 | GGAAAAUUAAUUAUCAAAAAGCUGUUCCUUUAAUU AUCAAAAAGGAACAGCUUUUUGAUAAUUAAUUUUG G (SEQ ID NO: 412) |
| Seeded with hot alkali-treated DNA pool, Aggregated Drop Reaction, 5 day time point | 25 | GGAAAUUAUCAUUUCUGAUCAACCCGGAAAUGAA UUAUCAUUUCCGGGUUGAUCAGAAAUGAUAAUUU GG (SEQ ID NO: 413) |
| Seeded with hot alkali-treated DNA pool, Aggregated Drop Reaction, 5 day time point | 26 | GGAAUUUUUCAAACUUUGGAUCCAGUUUGAAUUU UCAAACUGGAUCCAAAGUUUGAAAAUUGG (SEQ ID NO: 414) |
| Seeded with hot alkali-treated DNA pool, Aggregated Drop Reaction, 5 day time point | 27 | GGAAAAUUUCAAUGAUCGAUGGGAGCAUUGAAAU UUCAAUGCUCCCAUCGAUCAUUGAAAUUUUUGGG (SEQ ID NO: 415) |
| Seeded with hot alkali-treated DNA pool, Aggregated Drop Reaction, 5 day time point | 28 | GGAAUAUUUGAAAAGUUUGGACUUCUUUUCAAAU AUUGAAAGAAGUCCAAACUUUUCAAAUAUUGG (SEQ ID NO: 416) |

TABLE 2-continued

Sequences of RNA species described in FIGS. 6B-6E and FIG. 20B.

| Sample information | RNA species number | Sequence |
|---|---|---|
| Seeded with hot alkali-treated DNA pool, Aggregated Drop Reaction, 5 day time point | 29 | GGAAAUAUUCAAAAUCUACCCUUGAAUAUUUUUCC AAAUAUUCAAGGGUAGAUUUUGAAUAUUUGG (SEQ ID NO: 417) |
| Seeded with hot alkali-treated DNA pool, Aggregated Drop Reaction, 5 day time point | 30 | GGAAUAUAUCUGAUUGUCUAUUUAGAUAUUUUCC AAUAUAUCUAAAUAGACAAUCAGAUAUAUUGG (SEQ ID NO: 418) |
| Seeded with hot alkali-treated DNA pool, Aggregated Drop Reaction, 5 day time point | 31 | GGAAAAUUGGAUAUUCGUAGUUGCUUCCAAUUUU CCCGAAAAAUUGGAAGCAACUACGAAUAUCCAAUU UUGG (SEQ ID NO: 419) |
| Seeded with hot alkali-treated DNA pool, Aggregated Drop Reaction, 5 day time point | 32 | GGAACUUUUCAUAAAUCUCCUCAACAGUGCGAUG AACUUUUCAUAAAUCGCACUGUUGAGGAGAUUUA UGAAAAGUUGG (SEQ ID NO: 420) |
| Seeded with hot alkali-treated DNA pool, Aggregated Drop Reaction, 5 day time point | 33 | GGAUUUUUAGUCAUUUUCAAAACGCGUCUGACUA AAAAAGCCAUUUUUAGUCAGACGCGUUUUUGAAAA UGACUAAAAAUGG (SEQ ID NO: 421) |
| Seeded with hot alkali-treated DNA pool, Aggregated Drop Reaction, 5 day time point | 34 | GGAAAAAUUCAACUUUUUGUGCGUUGAGUUGAAU UUUCCAAAAAUUCAACUCAACGCACAAAAAGUUGA AUUUUGG (SEQ ID NO: 422) |
| Seeded with hot alkali-treated DNA pool, Aggregated Drop Reaction, 5 day time point | 35 | GGAAAAUUUCAUGAUCUUUUCUCUUGGGAAAUUU CAUAAUUUUUCCCAAGAGAAAAGAUCAUGAAAUUU GG (SEQ ID NO: 423) |
| Seeded with hot alkali-treated DNA pool, Aggregated Drop Reaction, 5 day time point | 36 | GGAAUUAAUCAAACUCAUCUUUUUCUAUUGUUUGA AUUAAUCAAACAAUAGAAAAGAUGAGUUUGAUUAA UUGGG (SEQ ID NO: 424) |
| Seeded with hot alkali-treated DNA pool, Aggregated Drop Reaction, 5 day time point | 37 | GGAAAUUCUCUUUCAAUAUUCAAGAAUUUGAGAAU UUCUUUCCAAAUUCUCAAAUUCUUGAAUAUUGAAA GAGAAUUUGGG (SEQ ID NO: 425) |
| Seeded with hot alkali-treated DNA pool, Aggregated Drop Reaction, 5 day time point | 38 | GGAAAAAUUCUAAUAAGUAUCAACUUUCUGAAUUA UUCCAAAAUUCAGAAAGUUGAUACUUAUUAGAAUU UUGG (SEQ ID NO: 426) |
| Seeded with hot alkali-treated DNA pool, Aggregated Drop Reaction, 5 day time point | 39 | GGGAAAUCAAUUGGAAUAAGCCCAAAAUUGAUUU CAAAUCAAUUUGGGCUUAUUCCAAUUGAUUUGGGG G (SEQ ID NO: 427) |
| Seeded with hot alkali-treated DNA pool, Aggregated Drop Reaction, 5 day time point | 40 | GGGGGAAAUUUGUAUUUCAUCAAAUGAUGAUUUC AUCAAAUGAUGAAAUCAUCAUUUGAUGAAAUACAA AUUUGG (SEQ ID NO: 428) |
| Seeded with hot alkali-treated DNA pool, Aggregated Drop Reaction, 5 day time point | 41 | GGAAAUUCAAUCUAUAACAGUCAUAUAGUUUGAAA AAUUCAAUCUAUAUGACUGUUAUAGAUUGAAUUU GG (SEQ ID NO: 429) |
| Seeded with hot alkali-treated DNA pool, Aggregated Drop Reaction, 5 day time point | 42 | GGGAAAUAUUGUUGUGUAUUGGAUGUUGAGUUCG UAACAAUAUUCCGAAUAUUGUUACGAACUCAACAU CCAAUACACAACAAUAUUUGG (SEQ ID NO: 430) |
| Seeded with hot alkali-treated DNA pool, Aggregated Drop Reaction, 5 day time point | 43 | GGAAAUUGGAAUAAAUGGUUUAUUACAAUUUCCAA AUUGGAAAUUGUAAUAAACCAUUUAUUCCAAUUUG GG (SEQ ID NO: 431) |

TABLE 2-continued

Sequences of RNA species described in FIGS. 6B-6E and FIG. 20B.

| Sample information | RNA species number | Sequence |
|---|---|---|
| Seeded with hot alkali-treated DNA pool, Aggregated Drop Reaction, 5 day time point | 44 | GGAAAAUUGGAAAUUGAGCAACUGUACCAAUUUU CCCGAAAAUUGGUACAGUUGCUCAAUUUCCAAUU UUGGG (SEQ ID NO: 432) |
| Seeded with hot alkali-treated DNA pool, Aggregated Drop Reaction, 5 day time point | 45 | GGAAUAAUUGAAUUACAACUUCAAAUCAAUUAUUC AGCAAUAAUUGAUUUGAAGUUGUAAUUCAAUUAUU GGG (SEQ ID NO: 433) |
| Seeded with hot alkali-treated DNA pool, Aggregated Drop Reaction, 5 day time point | 46 | GGAAUAAUUUGAAAUUGGCAGUUAUUGUUCAAAU UAUUCUCCCAAAUUUGAACAAUAACUGCCAAUUUC AAAUUUGGG (SEQ ID NO: 434) |
| Seeded with hot alkali-treated DNA pool, Aggregated Drop Reaction, 5 day time point | 47 | GGAAAAUUCAAAACUUUUCCGAAAAGUUUUUGAAA AUUCAAAACUUUUCGGAAAAGUUUUGAAUUUUGG (SEQ ID NO: 435) |
| Seeded with hot alkali-treated DNA pool, Aggregated Drop Reaction, 5 day time point | 48 | GGAAUAUUAAAUACUUUAUUCUCCCAAUAUAAAGU AUUAAAUACUUUAUAUUGGGAGAAUAAAGUAUUUA AUAUUGGG (SEQ ID NO: 436) |
| Seeded with hot alkali-treated DNA pool, Aggregated Drop Reaction, 5 day time point | 49 | GGAAAUAUUGGUAUUUAAUUUUUACUGUUUUUCU ACCAAUAUUUCCCAAAAAUUGGUAGAAAAACAGUA AAAAUUAAAUACCAAUAUUUGGG (SEQ ID NO: 437) |
| Seeded with hot alkali-treated DNA pool, Aggregated Drop Reaction, 5 day time point | 50 | GGAAAAAUAAAUGAUAUGUUUCCAUCAUUUAUCAU UUAUUUUCCUUAAAAAUAAAUGAUAAAUGAUGGAA ACAUAUCAUUUAUUUUUGG (SEQ ID NO: 438) |
| Seeded with hot alkali-treated DNA pool, Aggregated Drop Reaction, 5 day time point | 51 | GGAAAUUUCAAAGUUACAAGUCUCCGACUUUGAU UUUGACAAAUUUCAAAGUCGGAGACUUGUAACUU UGAAAUUUGG (SEQ ID NO: 439) |
| Seeded with hot alkali-treated DNA pool, Aggregated Drop Reaction, 5 day time point | 52 | GGAAGAAUUUUGGUAGUGAAAGAUGCUACAAAUU CUUCGAAGAAUUUUUGUAGCAUCUUUCACUACCA AAAUUCUUGGG (SEQ ID NO: 440) |
| Seeded with hot alkali-treated DNA pool, Aggregated Drop Reaction, 5 day time point | 53 | GGAAUAAAUCUUCAAUAAAUCCGAAGAUUUUAUUU UUCAAUAAAAUCUUCGGAUUUAUUGAAGAUUUAUU GG (SEQ ID NO: 441) |
| Seeded with hot alkali-treated DNA pool, Aggregated Drop Reaction, 5 day time point | 54 | GGGAAAAUCAUCAAUCGGUUCCUCUGAUGAUUUU CCAAAUCAUCAGAGGAACCGAUUGAUGAUUUGGG (SEQ ID NO: 442) |
| Seeded with hot alkali-treated DNA pool, Aggregated Drop Reaction, 5 day time point | 55 | GGGAAAAUUGGAAUCGAUACUCCUAUAUCCAAUU UUCCCCAAAAUUGGAUAUAGGAGUAUCGAUUCCA AUUUUGG (SEQ ID NO: 443) |
| Seeded with hot alkali-treated DNA pool, Aggregated Drop Reaction, 5 day time point | 56 | GGAAAAUAUGAAUAUCAAUCCCCAUUCAUAUUUCA AAAAUAUGAAUGGGGAUUGAUAUUCAUAUUUUGG (SEQ ID NO: 444) |
| Seeded with hot alkali-treated DNA pool, Aggregated Drop Reaction, 5 day time point | 57 | GGAUUAAUUCAAAUUAAUUAAUGGAAUUAAUUCAA AUUAAUUCCAUUAAUUAAUUUGAAUUAAUGG (SEQ ID NO: 445) |

TABLE 2-continued

Sequences of RNA species described in FIGS. 6B-6E and FIG. 20B.

| Sample information | RNA species number | Sequence |
|---|---|---|
| Seeded with hot alkali-treated DNA pool, Aggregated Drop Reaction, 5 day time point | 58 | GGAAAAAUUCAAAUCAAGUAUCGAUUUGAAAUUCA AAUCGAUACUUGAUUUGAAUUUUGG (SEQ ID NO: 446) |
| Seeded with hot alkali-treated DNA pool, Aggregated Drop Reaction, 5 day time point | 59 | GGAAAUUUGAAUUGCAACCAACGAUUCAAAUUCUC CCAAUUUGAAUCGUUGGUUGCAAUUCAAAUUGGG (SEQ ID NO: 447) |
| Seeded with hot alkali-treated DNA pool, Aggregated Drop Reaction, 5 day time point | 60 | GGGAGGAGAUUCAAAUUUCAGAAGGACGAUUUGA AUUUCAGAUUCAAAUCGUCCUUCUGAAAUUUGAA UCUGG (SEQ ID NO: 448) |
| Seeded with hot alkali-treated DNA pool, Aggregated Drop Reaction, 5 day time point | 61 | GGAAAAAAGUUCUAUUCAGUCCUAGACUUUUUUC UUCCAAAAGUCUAGGACUGAAUAGAACUUUUGGG (SEQ ID NO: 449) |
| Seeded with hot alkali-treated DNA pool, Aggregated Drop Reaction, 5 day time point | 62 | GGAUUAUUUCUAGAUUAUUGAAAUAAUGAAAUAAC CCAUUAUUUCAUUAUUUCAAUAAUCUAGAAAUAAU GGG (SEQ ID NO: 450) |
| Seeded with hot alkali-treated DNA pool, Aggregated Drop Reaction, 5 day time point | 63 | GGAGAAAUAUUCAUUCUCAUAUUCAAUAGCAUUG CAAUAUGAGAAUGAAUAUUGG (SEQ ID NO: 451) |
| Seeded with hot alkali-treated DNA pool, Aggregated Drop Reaction, 5 day time point | 64 | GGAAAAUUUCUAAUAAUUCUAGAAAUUUCUAAUAA AUUUCUAGAAUUAUUAGAAAUUUUGG (SEQ ID NO: 452) |
| Seeded with hot alkali-treated DNA pool, Aggregated Drop Reaction, 5 day time point | 65 | GGAAAUCAUUGGAAUUUUGUUGGCUUUCCAAUGA UUCCUCAUCAUCAUUGGAAAGCCAACAAAAUUCCA AUGAUUUGG (SEQ ID NO: 453) |
| Seeded with hot alkali-treated DNA pool, Aggregated Drop Reaction, 5 day time point | 66 | GGAAUAAUUCAAAAUAAUUCUAUCUCAUUUUGAAA UAAUUCAAAAUGAGAUAGAAUUAUUUUGAAUUAUU GG (SEQ ID NO: 454) |
| Seeded with hot alkali-treated DNA pool, Aggregated Drop Reaction, 5 day time point | 67 | GGAAUUCAAUUCAAAAGUUUCCUUUUGACUUUUG AAUUCAAUUCAAAAGUCAAAAGGAAACUUUUGAAU UGAAUUGGG (SEQ ID NO: 455) |
| Seeded with hot alkali-treated DNA pool, Aggregated Drop Reaction, 5 day time point | 68 | GGAAAAUUUCAAACUACCAUUCCCUGUUUGAAAAU UUCAAACAGGGAAUGGUAGUUUGAAAUUUGGG (SEQ ID NO: 456) |
| Unseeded, Tube Reaction, 1 day time point | 1 | GGAACAUAAUGUUUGUUUCCACAUAAUGUUACAU GUGUGGAAACAUUAUUACACAUAAUGUUUCCACA CAUGUAACAUUAUGUGGAAACAAACAUUAUGUUG GG (SEQ ID NO: 457) |
| Unseeded, Tube Reaction, 1 day time point | 2 | GGAAAAAUAUAAAUAUAAGAGAGUAUUUAUAUUUA GAAAAUAUAAAUACUCUCUUAUAUUUAUAUUUUGG (SEQ ID NO: 458) |
| Unseeded, Tube Reaction, 1 day time point | 3 | GGAUUGAAUUCAAUUUCACUGAAUUCAGUGAAAU UCGAAUUUUGGAUUGAAUUCAAUUUCACUGAAUU CAGUGAAAUUCGAAUUUUGG (SEQ ID NO: 459) |
| Seeded with DNA pool, Tube Reaction, 1 day time point | 1 | GGAAAAUUCAAUUCUAUCUAUUCAACAAUAGAAAA UUCAAUUCUAUCUAUUGUUGAAUAGAUAGAAUUG AAUUUGG (SEQ ID NO: 460) |

TABLE 2-continued

Sequences of RNA species described in FIGS. 6B-6E and FIG. 20B.

| Sample information | RNA species number | Sequence |
|---|---|---|
| Seeded with DNA pool, Tube Reaction, 1 day time point | 2 | GGAAUUUUCAGAUAUUUAUUGCCUCUAUAUCUGA UAAAUUUCAGAUAUAGAGGCAAUAAAUAUCUGAAA UUUGG (SEQ ID NO: 461) |
| Seeded with DNA pool, Tube Reaction, 1 day time point | 3 | GGGAAAAAUUCAAUUGAUAAUACAAUGUUUCCAUU GAAUUUCAAAAAUUCAAUGGAAACAUUGUAUUAUC AAUUGAAUUUUUGG (SEQ ID NO: 462) |
| Seeded with DNA pool, Tube Reaction, 1 day time point | 4 | GGAAAAAUUCAAUGAUGCUUCGUUUCAUUGAAUU CAAAAUUCAAGGAAACGAAGCAUCAUUGAAUUUUG GGG (SEQ ID NO: 463) |
| Seeded with DNA pool, Tube Reaction, 1 day time point | 5 | GGGGAAAAUUGAUAUUGCAGACUUUUUUUUCAAU AUCAAAUUGAUAUUGAAAAAAAGUCUGCAAUAUCA AUUUGG (SEQ ID NO: 464) |
| Seeded with DNA pool, Tube Reaction, 1 day time point | 6 | GGGGAUGAAAUUCAAUUCGAGACGAAUUUCAUUU CAAUGAAAUUCGUCUCGAAUUGAAUUUCAUUGGG G (SEQ ID NO: 465) |
| Seeded with DNA pool, Tube Reaction, 1 day time point | 7 | GGAAAAAAUCAAUUCAAUUCAAUUGAUUUUUGAAU CAAUCCCAAAAAUCAAUUGAAUUGAAUUGAUUUUU GGG (SEQ ID NO: 466) |
| Seeded with DNase-treated DNA pool, Tube Reaction, 1 day time point | 1 | GGAUUAAAAUCAAAUGAUCCUAUUCUCCAUCAUUU GAAUUAAAAUCAAAUGAUGGAGAAUAGGAUCAUUU GAUUUUCGG (SEQ ID NO: 467) |
| Seeded with DNase-treated DNA pool, Tube Reaction, 1 day time point | 2 | GGGGAAAAUUGAUUUUCAAUUCAAUUUCGAAAUU GAUUUCUUUCAAUUUCGAAAUUGAAUUGAAAAUCA AUUUUGGG (SEQ ID NO: 468) |
| Seeded with DNase-treated DNA pool, Tube Reaction, 1 day time point | 3 | GGGGAAUAUUUCAUUUCUUAUAUCCAAUAUUUCC GAAAUAUUUCCCAAUAUUUCGGAAAUAUUUGGAUAU AAGAAAUGAAAUAUUGGGG (SEQ ID NO: 469) |
| Seeded with hot alkali-treated DNA pool, Tube Reaction, 1 day time point | 1 | GGAAUAAUAAAGGAUUCAAAUAUCAUUAUUAUACC AAUAAUAAUGAUAUUUGAAUCCUUUAUUAUUGG (SEQ ID NO: 470) |
| Seeded with hot alkali-treated DNA pool, Tube Reaction, 1 day time point | 2 | GGUAUAAUAAUGAUAUUUGAAUCCUUUAUUAUUC CCAAUAAUAAAGGAUUCAAAUAUCAUUAUUAUUG G (SEQ ID NO: 471) |
| Seeded with hot alkali-treated DNA pool, Tube Reaction, 1 day time point | 3 | GGAAUAAUAAAGGAUUCAAAUAUCAUUAUUAUACC AAUAAUAAUGAUAUUUAAUGAUAUUUGAAUCCUUU AUUAUUGG (SEQ ID NO: 472) |
| Seeded with hot alkali-treated DNA pool, Tube Reaction, 1 day time point | 4 | GGAAUAAUAAAGGAUUCAAAUAUCAUUAUUAUAAU GAUAUUUGAAUCCUUUAUUAUUGG (SEQ ID NO: 473) |
| Unseeded, Tube Reaction, 5 day time point | 1 | GGAUGAAAUCUUUCAGACGUUUUCUCUGAUUUUU UGUCCAAGAAAUCAGAGAAAACGUCUGAAAGAUUU CUUGG (SEQ ID NO: 474) |
| Unseeded, Tube Reaction, 5 day time point | 2 | GGAUGAAAUCUUUCAGACGUUUUCUCUGAUUUUU UUUUCAGAGAAAACGUCUGAAAGAUUUCUUGG (SEQ ID NO: 475) |
| Unseeded, Tube Reaction, 5 day time point | 3 | GGAAAAUUUCUAUAUCACAUUACAUAUGUAAUUUU CUAUAUUACAUAUGUAAUGUGAUAUAGAAAUUUUG G (SEQ ID NO: 476) |
| Unseeded, Tube Reaction, 5 day time point | 4 | GGAAAAAUAAAUCUUUAUCAUUUUACCUGAAGAUU UAUGAAUAAAUCUUCAGGUAAAAUGAUAAAGAUU UAUUUUGG (SEQ ID NO: 477) |
| Unseeded, Tube Reaction, 5 day time point | 5 | GGAAGAAUUAAUGGUAUUUCUAUUAUAAUUUGCA AAUUAUAAUAGAAAUACCAUUAAUUCUUGG (SEQ ID NO: 478) |

TABLE 2-continued

Sequences of RNA species described in FIGS. 6B-6E and FIG. 20B.

| Sample information | RNA species number | Sequence |
|---|---|---|
| Unseeded, Tube Reaction, 5 day time point | 6 | GGAAAAAUUCAAUGAAGCGCUUCCUUGAAUUUGA AAGUGAAGAAAUUCAAUGAAGCGCUUCAUUGAAU UUUGG (SEQ ID NO: 479) |
| Unseeded, Tube Reaction, 5 day time point | 7 | GGACAAAAAAUCAGAGAAAACGUCUGAAAGAUUUC AUCCCCAAGAAAUCUUUCAGACGUUUUUCUCUGA UUUCUUGGG (SEQ ID NO: 480) |
| Unseeded, Tube Reaction, 5 day time point | 8 | GGAAGAAUUAAUGGUAUUUCUAUUAUAAUUUGCG GAUAAAAAAUUGUGCAAAUUAUAAUAGAAAUACCA UUAAUUCUUGG (SEQ ID NO: 481) |
| Unseeded, Tube Reaction, 5 day time point | 9 | GGAUGAAAUCUUUCAGACGUUUUCUCUGAUUUUU UUGUCCAAGAAAUCAGAGAAAAAAUCAGAGAAAA CGUCUGAAAGAUUUCUUGG (SEQ ID NO: 482) |
| Unseeded, Tube Reaction, 5 day time point | 10 | GGAUGAAAUCUUUCAGACGUUUUCUCUGAUUAAA UCAGAGAAAAAACGUCUGAAAGAUUUCUUGG (SEQ ID NO: 483) |
| Unseeded, Tube Reaction, 5 day time point | 11 | GGAAGAAUUAAUGGUAUUUCUAUUAUAAUAGAAAU ACCAUUAAUUCAUGG (SEQ ID NO: 484) |
| Seeded with hot alkali-treated DNA pool, Tube Reaction, 5 day time point | 1 | GGAAUAUUUCUUCAAUUCAACAUGAAAUAAUAUUC CAAUAUUUCAUGUUGAAUUGAAGAAAUAUUGG (SEQ ID NO: 485) |
| Seeded with hot alkali-treated DNA pool, Tube Reaction, 5 day time point | 2 | GGAUAAUAAUAAUUGAAUUCCAUUUUCCAAUUAUU AUCCAAAUAUAAUAAUUGGAAAAUGGAAUUCAAUU AUUAUUUUGG (SEQ ID NO: 486) |
| Seeded with hot alkali-treated DNA pool, Tube Reaction, 5 day time point | 3 | GGAUAAUUCUAAUAGUCAAUUCUCCCUAUUUAGAA UUAUAAUAUAUAUUAUAUAUAAUUCUAAUAGGGGA GAAUUGACUAUUAGAAUUAUGG (SEQ ID NO: 487) |
| Seeded with hot alkali-treated DNA pool, Tube Reaction, 5 day time point | 4 | GGAAAAUUAUAGUUCUACUUCGAUAUUUGAAAACU AUAAAAUUCCAAAUUAUAGUUUUCAAAUAUCGAAG UAGAACUAUAAUUUGGG (SEQ ID NO: 488) |
| Seeded with hot alkali-treated DNA pool, Tube Reaction, 5 day time point | 5 | GGAAAUUUCAAUAUGAAUAUUUUGUUUCGUAUUU GAUUUUAAAUUUCAAUACGAAACAAAAUAUUCAUA UUGAAAUUUGG (SEQ ID NO: 489) |
| Seeded with hot alkali-treated DNA pool, Tube Reaction, 5 day time point | 6 | GGGAGAUUAUACUCAUUCGAACCCAGAGUAUAUG AUUAUACUCUGGGUUCGAAUGAGUAUAAUCAUGG (SEQ ID NO: 490) |
| Seeded with hot alkali-treated DNA pool, Tube Reaction, 5 day time point | 7 | GGAAAAUUUCAAAUUCAAGCCUGAAUGAAAUUUUU CAAAUUCAUUCAGGCUUGAAUUUGAAAUUUUGG (SEQ ID NO: 491) |
| Seeded with hot alkali-treated DNA pool, Tube Reaction, 5 day time point | 8 | GGAAUAUUUCUUCAAUUCAAUGUUGAAUUGAAGA AAUAUUGG (SEQ ID NO: 492) |
| Seeded with hot alkali-treated DNA pool, Tube Reaction, 5 day time point | 9 | GGAAAAUAUAAUUCAUAUUGGAAGACAGAAUUAUU UAUACAAAUAUAAUUCUGUCUUCCAAUAUGAAUUA UAUUUGG (SEQ ID NO: 493) |
| Seeded with hot alkali-treated DNA pool, Tube Reaction, 5 day time point | 10 | GGAAAAAUUAAACAAAAAUGCUUUGUAUGUUUAAU UUUCAUCCAAAAUUAAACAUACAAAGCAUUUUUGU UUAAUUUUGGG (SEQ ID NO: 494) |
| Seeded with hot alkali-treated DNA pool, Tube Reaction, 5 day time point | 11 | GGAAAAAUAAUCGAAAUAUUUUGAUCGAUUAUUUU GAUUAAGUUCAAAAAUAAUCGAUCAAAAUAUUUCG AUUAUUUUGGG (SEQ ID NO: 495) |
| Seeded with hot alkali-treated DNA pool, Tube Reaction, 5 day time point | 12 | GGGAAAAUAUUUGUUUCAGAUCUCCAAAUAUUUG CCAAAUAUUUUGGAGAUCUGAAACAAAUAUUUGG (SEQ ID NO: 496) |
| Seeded with hot alkali-treated DNA pool, Tube Reaction, 5 day time point | 13 | GGAAAAUUUGAAUUCAAUUCUCUGAAGAAUUCAAA UUUUGAAUUCUUCAGAGAAUUGAAUUCAAAUUUG GGGG (SEQ ID NO: 497) |

TABLE 2-continued

| Sequences of RNA species described in FIGS. 6B-6E and FIG. 20B. | | |
| --- | --- | --- |
| Sample information | RNA species number | Sequence |
| Seeded with hot alkali-treated DNA pool, Tube Reaction, 5 day time point | 14 | GGAAUUAAUAUUAUUCAUAUUCAAUUGAUGAAUUA AUAUUAUUCAUCAAUUGAAUAUGAAUAAUAUUAAU UGG (SEQ ID NO: 498) |
| Seeded with hot alkali-treated DNA pool, Tube Reaction, 5 day time point | 15 | GGAUAUAAUAGUACAUCUUCAAUUCCUACUAUUAA UAUCCAAUAAUAGUAGGAAUUGAAGAUGUACUAUU AUUGG (SEQ ID NO: 499) |

NB: Short 5' and 3' base extensions (of one or a few bases) may be present in the sequences for reasons discussed in the text.

TABLE 3

| Oligonucleotide sequences used in our study. | | |
| --- | --- | --- |
| Oligo name | Sequence | Notes |
| AF-NJ-269 | /5rApp/NNNNNNNNAGATCGGAAGAGCACACGICT /3ddC/ (SEQ ID NO: 500) | RNase-free HPLC purified, /5rApp/ is the IDT code for 5' Adenylation, Ns are machine mixed, /3ddC/ is the IDT code for 3' Dideoxycytidine |
| AF-NJ-200 | CCAAAATTNGTANGTAGTAGTACNAAATTTTGGAA AATTTNGTACTACTACNTACNAATTTTCCTATAGT GAGTCGTATTANNNNTAATACGACTCACTATA (SEQ ID NO: 501) | Standard desalting, ordered as DNA ultramer, Ns are machine mixed |
| AF-NJ-201 | CCAAAATTANTAGNTAGTAGTANTAAATTTTGGAA AATTTANTACTACTANCTANTAATTTTCCTATAGTG AGTCGTATTANNNNTAATACGACTCACTATA (SEQ ID NO: 502) | Standard desalting, ordered as DNA ultramer, Ns are machine mixed |
| AF-JTG-11 | CCAAAATTAGTAGGTANTAGTANTAAATTTTGNAA AATTTANTACTANTACCTACTAATTTTCCTATAGTG AGTCGTATTANNNNTAATACGACTCACTATA (SEQ ID NO: 503) | Standard desalting, ordered as DNA ultramer |
| AF-JTG-13 | CCAAAATTTNAAGATCAGGGCTTNAAATTTTGNAA AATTTNAAGCCCTGATCTTNAAATTTTCCTATAGT GAGTCGTATTANNNNTAATACGACTCACTATA (SEQ ID NO: 504) | Standard desalting, ordered as DNA ultramer |
| AF-KLA-67 | AATGATACGGCGACCACCGAGATCTACACTATAG CCTACACTCTTTCCCTACACGACGCTCTTCCGAT CT (SEQ ID NO: 505) | |
| AF-KLA-68 | AATGATACGGCGACCACCGAGATCTACACATAGA GGCACACTCTTTCCCTACACGACGCTCTTCCGAT CT (SEQ ID NO: 506) | |
| AF-KLA-69 | AATGATACGGCGACCACCGAGATCTACACCCTAT CCTACACTCTTTCCCTACACGACGCTCTTCCGAT CT (SEQ ID NO: 507) | |
| AF-KLA-70 | AATGATACGGCGACCACCGAGATCTACACGGCTC TGAACACTCTTTCCCTACACGACGCTCTTCCGAT CT (SEQ ID NO: 508) | |
| AF-KLA-71 | AATGATACGGCGACCACCGAGATCTACACAGGC GAAGACACTCTTTCCCTACACGACGCTCTTCCGA TCT (SEQ ID NO: 509) | |
| AF-KLA-72 | AATGATACGGCGACCACCGAGATCTACACTAATC TTAACACTCTTTCCCTACACGACGCTCTTCCGATC T (SEQ ID NO: 510) | |

TABLE 3-continued

Oligonucleotide sequences used in our study.

| Oligo name | Sequence | Notes |
|---|---|---|
| AF-KLA-73 | AATGATACGGCGACCACCGAGATCTACACCAGG ACGTACACTCTTTCCCTACACGACGCTCTTCCGA TCT (SEQ ID NO: 511) | |
| AF-KLA-74 | AATGATACGGCGACCACCGAGATCTACACGTACT GACACACTCTTTCCCTACACGACGCTCTTCCGAT CT (SEQ ID NO: 512) | |
| AF-ZF-838 | CAAGCAGAAGACGGCATACGAGATCGAGTAATGT GACTGGAGTTCAGACGTGTGCTCTTCCGATCT (SEQ ID NO: 513) | |
| AF-ZF-839 | CAAGCAGAAGACGGCATACGAGATTCTCCGGAG TGACTGGAGTTCAGACGTGTGCTCTTCCGATCT (SEQ ID NO: 514) | |
| AF-ZF-840 | CAAGCAGAAGACGGCATACGAGATAATGAGCGG TGACTGGAGTTCAGACGTGTGCTCTTCCGATCT (SEQ ID NO: 515) | |
| AF-ZF-841 | CAAGCAGAAGACGGCATACGAGATGGAATCTCG TGACTGGAGTTCAGACGTGTGCTCTTCCGATCT (SEQ ID NO: 516) | |
| AF-ZF-842 | CAAGCAGAAGACGGCATACGAGATTTCTGAATGT GACTGGAGTTCAGACGTGTGCTCTTCCGATCT (SEQ ID NO: 517) | |
| AF-ZF-843 | CAAGCAGAAGACGGCATACGAGATACGAATTCGT GACTGGAGTTCAGACGTGTGCTCTTCCGATCT (SEQ ID NO: 518) | |

TABLE 4

Sequences of RNA species described in FIG. 8.

| Round 2 RNA pool | Reference sequence for most abundant RNA species |
|---|---|
| 2A | GGAAAAUUUCAAACAUUAUGUUGUAAUUUGUUUGAAAAUUUCAAACAAAUUACAA CAUAAUGUUUGAAAUUUUGGGGGGAAAAU (SEQ ID NO: 519) |
| 2B | CCCAAUAUCAUCAAUUGCUGACGAAGAUGAUAUUGAUAAUAUCAUCUUCGUCAG CAAUUGAUGAUAUU (SEQ ID NO: 520) |
| 2C | GGAAAAUCAAUGACUGGUCAAUCUCAUUGAUUUUUGAAAUCAAUGAGAUUGACC AGUCAUUGAUUUU (SEQ ID NO: 521) |

NB: (i) Short 5' and 3' base extensions (of one or a few bases) may be present
in the sequences for reasons discussed in the text. (ii) Sequences may not
be full-length because particular truncated cDNAs or prematurely terminated
T7 products were predominant in the sequenced pool.

TABLE 5

Brief description of the functionality of the code deposited on GitHub.

| Code Name | Functionality (brief description) | Notes |
|---|---|---|
| trimmer_20180216.py analyzer.py | Adapter trimming Obtaining a list of unique sequences (with associated counts) from paired-end read data | (i) Checks that for each retained sequence, both paired-end reads perfectly match to minimize effects from sequencing errors, (ii) Stores two counts for each sequence (1. Non-redundant UMI count: # unique molecular identifiers associated with sequence, 2. Possibly redundant UMI count: total # counts of sequence) |

TABLE 5-continued

Brief description of the functionality of the code deposited on GitHub.

| Code Name | Functionality (brief description) | Notes |
| --- | --- | --- |
| denovoClustering_ver10_20180228.py | Unsupervised classification of sequences | (i) Groups sequences into clusters such that no sequence stretch of 20 nucleotides is shared between clusters, (ii) Within each cluster, sequences are further grouped into subclusters. Reference sequences for subclusters have more than 1 sequence variant every 20 bases (on average) with respect to each other. (iii) Definition of reference sequences for subclusters: Sequences are parsed in decreasing order of counts in the code. A subcluster is thus initially defined by a reference sequence which is the most abundant sequence representing the information content of the subcluster. |
| smithWaterman_collapser_20180301.py | Aligning reference sequences for all subclusters (across all clusters) with respect to each other | (i) Results in a list of unique reference sequences defining the RNA species for a sequenced pool, (ii) Unique reference sequences have more than 1 sequence variant every 10 bases (on average) with respect to each other. |
| collapsingEndHeterogeneityAlignments_20180301.py | Pruning potential 5' and 3' extra bases from reference sequences | |
| alignmentQuantification_ver2_20180305.py | Quantifying relative abundance of RNA species in a sequenced pool using reference sequences for alignment | |
| finalQuantification_phylipFitch_ver2_20180315.py | Creating a distance tree between reference sequences based on number of sequence variants between the references | (i) Used for FIG. 1D |
| 2dPlots_Final_ver4_20190503.py | Calculating various metrics for RNA species; automated detection of 2-way and 4-way repeats in reference sequences | (i) Used for FIG. 1E-G |

*Notes regarding the sequences reported in FIG. 1 and Table 1: (i) Short 5' and 3' base extensions (of one or a few bases) may be present in the sequences for reasons discussed in the text. (ii) A few sequences may not be full-length because particular truncated cDNAs or prematurely terminated T7 products were predominant in the sequenced pool.

REFERENCES AND NOTES

1. C. K. Biebricher, L. E. Orgel, An RNA that Multiplies Indefinitely with DNA-Dependent RNA Polymerase: Selection from a Random Copolymer. *Proc. Natl. Acad. Sci.* 70, 934-938 (1973).

2. A. Wettich, C. K. Biebricher, RNA Species that Replicate with DNA-Dependent RNA Polymerase from *Escherichia coli. Biochemistry.* 40, 3308-3315 (2001).

3. M. M. Konarska, P. A. Sharp, Replication of RNA by the DNA-dependent RNA polymerase of phage T7. *Cell.* 57, 423-431 (1989).

4. M. M. Konarska, P. A. Sharp, Structure of RNAs replicated by the DNA-dependent T7 RNA polymerase. *Cell* 63, 609-618 (1990).

5. C. K. Biebricher, R. Luce, Template-free generation of RNA species that replicate with bacteriophage T7 RNA 15 polymerase. *EMBO J.* 15, 3458-3465 (1996).

6. Y. Kakimoto, A. Fujinuma, S. Fujita, Y. Kikuchi, S. Umekage, Abnormal rapid non-linear RNA production induced by T7 RNA polymerase in the absence of an exogenous DNA template. *AIP Conf. Proc.* 1649, 113-115 (2015).

7. T. A. Steitz, The structural basis of the transition from initiation to elongation phases of transcription, as well as translocation and strand separation, by T7 RNA polymerase. *Curr. Opin. Struct. Biol.* 14, 4-9 (2004).

8. J.-A. Navarro, A. Vera, R. Flores, A Chloroplastic RNA Polymerase Resistant to Tagetitoxin Is Involved in Replication of Avocado Sunblotch Viroid. *Virology.* 268, 218-225 (2000).

9. Y. Gholamalipour, A. Karunanayake Mudiyanselage, C. T. Martin, 3' end additions by T7 RNA polymerase are RNA self-templated, distributive and diverse in character—RNA-Seq analyses. *Nucleic Acids Res.* 46, 9253-9263 (2018).

10. S. N. Sarcar, D. L. Miller, A specific, promoter-independent activity of T7 RNA polymerase suggests a general model for DNA/RNA editing in single subunit RNA Polymerases. *Sci. Rep.* 8 (2018), doi:10.1038/s41598-018-32231-6.

11. C. C. Kao, P. Singh, D. J. Ecker, De Novo Initiation of Viral RNA-Dependent RNA Synthesis. *Virology.* 287, 251-260 (2001).

12. D. Takeshita, K. Tomita, Molecular basis for RNA polymerization by Qβ replicase. *Nat. Struct. Mol. Biol.* 19, 229-237 (2012).

13. E. Domingo, D. Sabo, T. Taniguchi, C. Weissmann, Nucleotide sequence heterogeneity of an RNA phage population. *Cell.* 13, 735-744 (1978).

14. C. Priano, F. R. Kramer, D. R. Mills, Evolution of the RNA Coliphages: The Role of Secondary Structures during RNA Replication. *Cold Spring Harb. Symp. Quant. Biol.* 52, 321-330 (1987).

15. D. Bartel, 5 Re-creating an RNA Replicase. *Cold Spring Harb. Monogr. Arch.* 37 (1999) (available at cshmonographs.org/index.php/monographs/article/view/5108/4205).

16. R. Flores et al., Viroid Replication: Rolling-Circles, Enzymes and Ribozymes. *Viruses.* 1, 317-334 (2009).

17. M. M. C. Lai, RNA Replication without RNA-Dependent RNA Polymerase: Surprises from Hepatitis Delta Virus. *J. Virol.* 79, 7951-7958 (2005).

18. A. Fire, S. Q. Xu, Rolling replication of short DNA circles. *Proc. Natl. Acad. Sci. U.S.A.* 92, 4641-4645 (1995).

19. W. Zhou, D. Reines, P. W. Doetsch, T7 RNA polymerase bypass of large gaps on the template strand reveals a critical role of the nontemplate strand in elongation. *Cell.* 82, 577-585 (1995).

20. S. Delgado, Á. E. M. de Alba, C. Hernandez, R. Flores, A Short Double-Stranded RNA Motif of Peach Latent Mosaic Viroid Contains the Initiation and the Self-Cleavage Sites of Both Polarity Strands. *J. Virol.* 79, 12934-12943 (2005).

21. S. O. Gudima, J. Chang, J. M. Taylor, Restoration in vivo of defective hepatitis delta virus RNA genomes. *RNA N. Y. N.* 12, 1061-1073 (2006).

22. J.-A. Navarro, R. Flores, Characterization of the initiation sites of both polarity strands of a viroid RNA reveals a motif conserved in sequence and structure. *EMBO J.* 19, 2662-2670 (2000).

23. C. Ginzburg, *Il formaggio e i vermi. Il cosmo di un mugnaio del '500* (Turin: Einaudi, 1976).

24. S. F. Altschul, W. Gish, W. Miller, E. W. Myers, D. J. Lipman, Basic local alignment search tool. *J. Mol. Biol.* 215, 403-410 (1990).

25. K. Pruitt, G. Brown, T. Tatusova, D. Maglott, *The Reference Sequence (RefSeq) Database* (National Center for Biotechnology Information (US), 2012; ncbi.nlm.nih.gov/books/NBK21091/).

26. C. Cazenave, O. C. Uhlenbeck, RNA template-directed RNA synthesis by T7 RNA polymerase. *Proc. Natl. Acad. Sci. U.S.A.* 91, 6972-6976 (1994).

27. H. S. Zaher, P. J. Unrau, T7 RNA Polymerase Mediates Fast Promoter-Independent Extension of Unstable Nucleic Acid Complexes. *Biochemistry.* 43, 7873-7880 (2004).

28. R. Brazas, D. Ganem, A Cellular Homolog of Hepatitis Delta Antigen: Implications for Viral Replication and Evolution. *Science.* 274, 90-94 (1996).

29. T. O. Diener, Viroids: "living fossils" of primordial RNAs? *Biol. Direct.* 11, 15 (2016).

30. K. Salehi-Ashtiani, A. Luptak, A. Litovchick, J. W. Szostak, A genomewide search for ribozymes reveals an HDV-like sequence in the human CPEB3 gene. *Science.* 313, 1788-1792 (2006).

31. M. Sumper, R. Luce, Evidence for de novo production of self-replicating and environmentally adapted RNA structures by bacteriophage Qbeta replicase. *Proc. Natl. Acad. Sci.* 72, 162-166 (1975).

32. N. V. Zyrina, V. N. Antipova, L. A. Zheleznaya, Ab initio synthesis by DNA polymerases. *FEMS Microbiol. Lett.* 351, 1-6 (2014).

33. G. Krupp, Unusual promoter-independent transcription reactions with bacteriophage RNA polymerases. *Nucleic Acids Res.* 17, 3023-3036 (1989).

34. M. D. Moody et al., Evolution of Host Cell RNA into Efficient Template RNA by Q.beta. Replicase: The Origin of RNA in Untemplated Reactions. *Biochemistry.* 33, 13836-13847 (1994).

35. Y. W. Yin, T. A. Steitz, The Structural Mechanism of Translocation and Helicase Activity in T7 RNA Polymerase. *Cell.* 116, 393-404 (2004).

36. N. T. Ingolia, S. Ghaemmaghami, J. R. S. Newman, J. S. Weissman, Genome-Wide Analysis in Vivo of Translation with Nucleotide Resolution Using Ribosome Profiling. *Science.* 324, 218-223 (2009).

37. J. A. Arribere et al., Translation readthrough mitigation. *Nature.* 534, 719-723 (2016).

38. K. A. Wilkinson, E. J. Merino, K. M. Weeks, Selective 2'-hydroxyl acylation analyzed by primer extension (SHAPE): quantitative RNA structure analysis at single nucleotide resolution. *Nat. Protoc.* 1, 1610 (2006).

39. Y. Xia, G. M. Whitesides, Soft Lithography. *Annu. Rev. Mater. Sci.* 28, 153-184 (1998).

40. R. Lorenz et al., ViennaRNA Package 2.0. *Algorithms Mol. Biol.* 6, 26 (2011).

41. J. Felsenstein, PHYLIP—Phylogeny Inference Package (Version 3.2). *Cladistics.* 5, 164-166 (1989).

42. I. Letunic, P. Bork, Interactive Tree Of Life (iTOL) v4: recent updates and new developments. *Nucleic Acids Res.*, doi:10.1093/nar/gkz239.

43. A. M. Bolger, M. Lohse, B. Usadel, Trimmomatic: a flexible trimmer for Illumina sequence data. *Bioinformatics.* 30, 2114-2120 (2014).

44. H. Li, R. Durbin, Fast and accurate short read alignment with Burrows-Wheeler transform. *Bioinformatics.* 25, 1754-1760 (2009).

45. H. Li et al., The Sequence Alignment/Map format and SAMtools. *Bioinforma. Oxf. Engl.* 25, 2078-2079 (2009).

46. S. B. Needleman, C. D. Wunsch, A general method applicable to the search for similarities in the amino acid sequence of two proteins. *J. Mol. Biol.* 48, 443-453 (1970).

47. T. F. Smith, M. S. Waterman, Identification of common molecular subsequences. *J. Mol. Biol.* 147, 195-197 (1981).

48. T. E. England, O. C. Uhlenbeck, 3'-Terminal labelling of RNA with T4 RNA ligase. *Nature.* 275, 560 (1978).

49. H. Guo, N. T. Ingolia, J. S. Weissman, D. P. Bartel, Mammalian microRNAs predominantly act to decrease target mRNA levels. *Nature.* 466, 835-840 (2010).

50. S. J. Furrows, G. L. Ridgway, 'Good laboratory practice' in diagnostic laboratories using nucleic acid amplification methods. *Clin. Microbiol. Infect.* 7, 227-229 (2001).

What is claimed is:

1. A method of amplifying RNA comprising:

constructing an RNA template for said amplifying the RNA, the RNA template comprising (i) a 2-way repeat configuration comprising a first inverted repeat, (ii) a 4-way repeat configuration comprising a second inverted repeat that is shorter than the first inverted repeat, wherein each arm of the 2-way repeat comprises the second inverted repeat, (iii) a 3' end sequence comprising GG or CC and one or more additional nucleotides following the GG or the CC, and (iv) a nucleotide sequence of interest; and replicating the RNA in a reaction mixture comprising:

an RNA polymerase;

a set of ribonucleoside triphosphates comprising ATP, CTP, GTP, and UTP, or analogues or derivatives thereof; and the RNA template.

2. The method of claim 1, wherein the RNA polymerase is a bacteriophage transcription polymerase.

3. The method of claim 2, wherein the bacteriophage transcription polymerase is a T7 bacteriophage RNA polymerase.

4. The method of claim 1, wherein the reaction mixture contains no DNA.

5. The method of claim 1, wherein the RNA template ranges from 50 to 120 nucleotides in length.

6. The method of claim 1, wherein each repeat region within the 2-way repeat configuration ranges from 10 to 60 nucleotides in length or about 20% to about 50% of the total length of the replicating RNA.

7. The method of claim 1, wherein each repeat region within the 4-way repeat configuration ranges from 5 to 25 nucleotides in length or about 5% to about 20% of the total length of the replicating RNA.

8. The method of claim 1, wherein the replicating RNA in the reaction comprises a G RNA strand comprising two G bases at or close to a 5' end and two G bases at or close to a 3' end, and a complementary C RNA strand comprising two C bases at or close to a 5' end and two C bases at or close to a 3' end.

9. The method of claim 8, further comprising adding at least one base to the 3' end of the G RNA strand or the C RNA strand.

10. The method of claim 1, wherein the RNA template is linear.

11. The method of claim 1, wherein said constructing the RNA template comprises transcription of a DNA seed, wherein the DNA seed consists of a portion of a full-length sequence of an RNA replication product produced by said replicating.

12. The method of claim 11, wherein the DNA seed comprises the nucleotide sequence of interest and a 4-way repeat unit.

13. The method of claim 12, wherein the DNA seed is added to the reaction mixture such that the RNA polymerase generates a first RNA comprising the 4-way repeat unit by transcription of the DNA seed.

14. The method of claim 13, further comprising carrying out a first round of 3'-extension of the first RNA to produce a second RNA comprising a second 4-way repeat unit; and carrying out a second round of 3'-extension of the second RNA to produce the RNA template comprising the 4-way repeat configuration.

15. The method of claim 1, wherein a single RNA or a plurality of RNAs are replicated in the reaction mixture.

16. The method of claim 15, wherein the plurality of RNAs are RNA variants.

17. The method of claim 15, wherein the method is performed in a microfluidic device comprising a droplet generator and further comprises partitioning the plurality of RNAs into a plurality of droplets and replicating the RNA using digital droplet RNA replication.

18. The method of claim 1, further comprising using the amplified RNA for RNA interference, sequencing, expression profiling, a vaccine, or directed evolution of RNA aptamers without intermediate conversion to DNA.

\* \* \* \* \*

SEQUENCE LISTING

<160> NUMBER OF SEQ ID NOS: 521

<210> SEQ ID NO 1
<211> LENGTH: 67
<212> TYPE: RNA

<213> ORGANISM: Artificial Sequence
<220> FEATURE:
<223> OTHER INFORMATION: RNA Reference Sequence Number 1.1

<400> SEQUENCE: 1
ccauaauuau uguaugacac uggccaauaa uuauuguaua uuggccagug ucauacaaua     60
auuuucc                                                               67

<210> SEQ ID NO 2
<211> LENGTH: 85
<212> TYPE: RNA
<213> ORGANISM: Artificial Sequence
<220> FEATURE:
<223> OTHER INFORMATION: RNA Reference Sequence Number 2.1

<400> SEQUENCE: 2
ggaaaauaua cauauugaag guguguaugu auauuuguau auucacaaaa auauacauac     60
acaccuucaa uauguauauu auugg                                          85

<210> SEQ ID NO 3
<211> LENGTH: 62
<212> TYPE: RNA
<213> ORGANISM: Artificial Sequence
<220> FEATURE:
<223> OTHER INFORMATION: RNA Reference Sequence Number 2.2

<400> SEQUENCE: 3
ccauaaugug aaugcgcguc gccuuggcgc ugauuugcgu uaauugggaa uuaacgcaaa     60
uc                                                                   62

<210> SEQ ID NO 4
<211> LENGTH: 63
<212> TYPE: RNA
<213> ORGANISM: Artificial Sequence
<220> FEATURE:
<223> OTHER INFORMATION: RNA Reference Sequence Number 3.1

<400> SEQUENCE: 4
ccccaaaauu auuguauggc acuggcccca uucaauaauu gaaaauuauu gaaugggggcc    60 agu                                                                  63

<210> SEQ ID NO 5
<211> LENGTH: 73
<212> TYPE: RNA
<213> ORGANISM: Artificial Sequence
<220> FEATURE:
<223> OTHER INFORMATION: RNA Reference Sequence Number 3.2

<400> SEQUENCE: 5
ccaaaauuau uguauggcac uggccccauu caauaauuau uguauggcac uggccccauu     60
caauaauuuu caa                                                       73

<210> SEQ ID NO 6
<211> LENGTH: 70
<212> TYPE: RNA
<213> ORGANISM: Artificial Sequence
<220> FEATURE:
<223> OTHER INFORMATION: RNA Reference Sequence Number 4.1

<400> SEQUENCE: 6
gggaaaaauu auuguauggc acaacaauaa uuuucguaaa auuauuguug ugccauacaa     60
uaauuuaugg                                                           70

```
<210> SEQ ID NO 7
<211> LENGTH: 66
<212> TYPE: RNA
<213> ORGANISM: Artificial Sequence
<220> FEATURE:
<223> OTHER INFORMATION: RNA Reference Sequence Number 4.2

<400> SEQUENCE: 7
ggggaaaaaa uuaucacucg ccggauaauu ucuccuagaa auuauccggc gagugauaau      60
uucugg                                                                 66

<210> SEQ ID NO 8
<211> LENGTH: 92
<212> TYPE: RNA
<213> ORGANISM: Artificial Sequence
<220> FEATURE:
<223> OTHER INFORMATION: RNA Reference Sequence Number 4.3

<400> SEQUENCE: 8
ccauaauuau uguauggcuc guacaauaau uauuauuauu auuaauaauu auuuaauaau      60
aaauuauugu acgagccaua caauaauuuu cc                                    92

<210> SEQ ID NO 9
<211> LENGTH: 71
<212> TYPE: RNA
<213> ORGANISM: Artificial Sequence
<220> FEATURE:
<223> OTHER INFORMATION: RNA Reference Sequence Number 5.1

<400> SEQUENCE: 9
gguaaauuaa uguucuuaac acuaccauua auuuacaaaa uuaaugguag uguuaagaac      60
auuaauuuug g                                                           71

<210> SEQ ID NO 10
<211> LENGTH: 107
<212> TYPE: RNA
<213> ORGANISM: Artificial Sequence
<220> FEATURE:
<223> OTHER INFORMATION: RNA Reference Sequence Number 6.1

<400> SEQUENCE: 10
gggaaaaauu uauuauuuuc uuggaaauuu auuauuuucu uggaaauuua uuaaauaaua      60
aauuuccaag gaaauaauaa auuuccaaga aaauaauaaa uuuuggg                   107

<210> SEQ ID NO 11
<211> LENGTH: 76
<212> TYPE: RNA
<213> ORGANISM: Artificial Sequence
<220> FEATURE:
<223> OTHER INFORMATION: RNA Reference Sequence Number 7.1

<400> SEQUENCE: 11
ccgaaaauua uuguauggca cacaacaaua auuuuucgug aaaauuauug uugugugcca      60
uacaauaauu uuauuc                                                      76

<210> SEQ ID NO 12
<211> LENGTH: 70
<212> TYPE: RNA
<213> ORGANISM: Artificial Sequence
<220> FEATURE:
<223> OTHER INFORMATION: RNA Reference Sequence Number 7.2
```

-continued

```
<400> SEQUENCE: 12
ccgaaauuau uguaugucgu cacaauaauu uucgacgaaa auuauuguga cgacauacaa      60
uaauuuuucc                                                            70

<210> SEQ ID NO 13
<211> LENGTH: 80
<212> TYPE: RNA
<213> ORGANISM: Artificial Sequence
<220> FEATURE:
<223> OTHER INFORMATION: RNA Reference Sequence Number 8.1

<400> SEQUENCE: 13
gggaaaaaua auacauuugg ugucggauaa uguauuauuu caaauaauac auuauccgac      60
accaaaugua uuauuuaugg                                                 80

<210> SEQ ID NO 14
<211> LENGTH: 72
<212> TYPE: RNA
<213> ORGANISM: Artificial Sequence
<220> FEATURE:
<223> OTHER INFORMATION: RNA Reference Sequence Number 9.1

<400> SEQUENCE: 14
gggaaaaauu auuguauggc ucgucaauaa uuuuugucca aaauuauuga cgagccauac      60
aauaauuuug gg                                                         72

<210> SEQ ID NO 15
<211> LENGTH: 74
<212> TYPE: RNA
<213> ORGANISM: Artificial Sequence
<220> FEATURE:
<223> OTHER INFORMATION: RNA Reference Sequence Number 10.1

<400> SEQUENCE: 15
ggaauaauua uuuguuguac uaggaauaau uauuuacaaa auaauuauuc cuaguacaac      60
aaauaauuau uagg                                                       74

<210> SEQ ID NO 16
<211> LENGTH: 63
<212> TYPE: RNA
<213> ORGANISM: Artificial Sequence
<220> FEATURE:
<223> OTHER INFORMATION: RNA Reference Sequence Number 11.1

<400> SEQUENCE: 16
gggaaaaauu auuguauggc acacaauaau uuucauuauu gugugccaua caauaauuuu      60
ggg                                                                  63

<210> SEQ ID NO 17
<211> LENGTH: 66
<212> TYPE: RNA
<213> ORGANISM: Artificial Sequence
<220> FEATURE:
<223> OTHER INFORMATION: RNA Reference Sequence Number 12.1

<400> SEQUENCE: 17
ccccaaaauu ucaagaucag ggcuugaaau uuuguaaaau uucaagcccu gaucuugaaa      60
uuuucc                                                               66

<210> SEQ ID NO 18
<211> LENGTH: 71
```

-continued

```
<212> TYPE: RNA
<213> ORGANISM: Artificial Sequence
<220> FEATURE:
<223> OTHER INFORMATION: RNA Reference Sequence Number 13.1

<400> SEQUENCE: 18
gggaaaaauu auuguauguc ucaacaauaa uuuucgugaa aauuauuguu gagacauaca        60
auaauuuugg g                                                            71

<210> SEQ ID NO 19
<211> LENGTH: 67
<212> TYPE: RNA
<213> ORGANISM: Artificial Sequence
<220> FEATURE:
<223> OTHER INFORMATION: RNA Reference Sequence Number 14.1

<400> SEQUENCE: 19
gggaaaaauu ucaagaucag ggauugaaau uuuacaaaau uucaaucccu gaucuugaaa        60
uuuuggg                                                                 67

<210> SEQ ID NO 20
<211> LENGTH: 66
<212> TYPE: RNA
<213> ORGANISM: Artificial Sequence
<220> FEATURE:
<223> OTHER INFORMATION: RNA Reference Sequence Number 14.2

<400> SEQUENCE: 20
gggaaaaauu auuguauggc cacaauaauu uucgaaaaau uauuguggcc auacaauaau        60
uuuggg                                                                  66

<210> SEQ ID NO 21
<211> LENGTH: 65
<212> TYPE: RNA
<213> ORGANISM: Artificial Sequence
<220> FEATURE:
<223> OTHER INFORMATION: RNA Reference Sequence Number 15.1

<400> SEQUENCE: 21
gggaaaaaau uauuguaugg caaauaauuu uucacgaaaa uuauuugcca uacaauaauu        60
uucgg                                                                   65

<210> SEQ ID NO 22
<211> LENGTH: 70
<212> TYPE: RNA
<213> ORGANISM: Artificial Sequence
<220> FEATURE:
<223> OTHER INFORMATION: RNA Reference Sequence Number 15.2

<400> SEQUENCE: 22
gggaaaaaau uauuguaugg cucacaauaa uuuucucgaa aauuauugug agccauacaa        60
uaauuuucgg                                                              70

<210> SEQ ID NO 23
<211> LENGTH: 71
<212> TYPE: RNA
<213> ORGANISM: Artificial Sequence
<220> FEATURE:
<223> OTHER INFORMATION: RNA Reference Sequence Number 16.1

<400> SEQUENCE: 23
ccaauuauac ucuacccaac ugaggguaua auaugguaau uauacccuca guuggguaga        60
```

-continued guauaaauuc c                                                                71

<210> SEQ ID NO 24
<211> LENGTH: 71
<212> TYPE: RNA
<213> ORGANISM: Artificial Sequence
<220> FEATURE:
<223> OTHER INFORMATION: RNA Reference Sequence Number 17.1

<400> SEQUENCE: 24
gggaaaaauu auuguauggc aaaccaauaa uuuucgucaa aauuauuggu uugccauaca     60
auaauuuugg g                                                         71

<210> SEQ ID NO 25
<211> LENGTH: 64
<212> TYPE: RNA
<213> ORGANISM: Artificial Sequence
<220> FEATURE:
<223> OTHER INFORMATION: RNA Reference Sequence Number 18.1

<400> SEQUENCE: 25
ccauaauuau uguauggcuc guacaauaau gaaaauuauu guacgagcca uacaauaauu     60
uucc                                                                 64

<210> SEQ ID NO 26
<211> LENGTH: 74
<212> TYPE: RNA
<213> ORGANISM: Artificial Sequence
<220> FEATURE:
<223> OTHER INFORMATION: RNA Reference Sequence Number 18.2

<400> SEQUENCE: 26
ccauaaauau uucuccuagg gcaaugaaau auuauggauc auaauauuuc auugcccuag     60
gagaaauauu aucc                                                      74

<210> SEQ ID NO 27
<211> LENGTH: 79
<212> TYPE: RNA
<213> ORGANISM: Artificial Sequence
<220> FEATURE:
<223> OTHER INFORMATION: RNA Reference Sequence Number 19.1

<400> SEQUENCE: 27
gggaaaaauu acacuuuucg caucuuugug uaauuuuugu gaauaaauua cacaaagaug     60 cgaaagugu aauuuaugg                                                  79

<210> SEQ ID NO 28
<211> LENGTH: 78
<212> TYPE: RNA
<213> ORGANISM: Artificial Sequence
<220> FEATURE:
<223> OTHER INFORMATION: RNA Reference Sequence Number 20.1

<400> SEQUENCE: 28 ccauaauac aaauauuucc ucauccucau uuguauuaua auacaaauga ggaugaggaa     60
auauuuguau uauaaucc                                                  78

<210> SEQ ID NO 29
<211> LENGTH: 77
<212> TYPE: RNA
<213> ORGANISM: Artificial Sequence
<220> FEATURE:
<223> OTHER INFORMATION: RNA Reference Sequence Number 21.1

-continued

<400> SEQUENCE: 29
gggaaaaauu auuguauggc acaaacaaua auaauuuucu uuaaaaauua uuguuugugc      60
cauacaauaa uuuuggg                                                    77

<210> SEQ ID NO 30
<211> LENGTH: 69
<212> TYPE: RNA
<213> ORGANISM: Artificial Sequence
<220> FEATURE:
<223> OTHER INFORMATION: RNA Reference Sequence Number 22.1

<400> SEQUENCE: 30
gggaaaaauu auuguauggc acacaauaau uuuuaacaaa auuauugugu gccauacaau      60
aauuuuggg                                                             69

<210> SEQ ID NO 31
<211> LENGTH: 76
<212> TYPE: RNA
<213> ORGANISM: Artificial Sequence
<220> FEATURE:
<223> OTHER INFORMATION: RNA Reference Sequence Number 23.1

<400> SEQUENCE: 31
gggaaaaauu auuguauggc acaacaacaa uaauuuucgu aaaauuauug uuguugugcc      60
auacaauaau uuaugg                                                     76

<210> SEQ ID NO 32
<211> LENGTH: 69
<212> TYPE: RNA
<213> ORGANISM: Artificial Sequence
<220> FEATURE:
<223> OTHER INFORMATION: RNA Reference Sequence Number 24.1

<400> SEQUENCE: 32
gggaaaaauu ucaagaucag gggcuugaaa uuuuacaaaa uuucaagccc cugaucuuga      60
aauuuuggg                                                             69

<210> SEQ ID NO 33
<211> LENGTH: 71
<212> TYPE: RNA
<213> ORGANISM: Artificial Sequence
<220> FEATURE:
<223> OTHER INFORMATION: replicating RNA species

<400> SEQUENCE: 33
ggauaauuau uaucauugau caucaaugau gaugaauuau uaucauugau gaucaaugau      60
aauaauuaug g                                                          71

<210> SEQ ID NO 34
<211> LENGTH: 74
<212> TYPE: RNA
<213> ORGANISM: Artificial Sequence
<220> FEATURE:
<223> OTHER INFORMATION: replicating RNA species

<400> SEQUENCE: 34
ggaaaaauaa uuauucuugc uguagaauua auuauuccga auaauuauuu cuacagcaag      60
aauaauuauu ucgg                                                       74

<210> SEQ ID NO 35

```
<211> LENGTH: 75
<212> TYPE: RNA
<213> ORGANISM: Artificial Sequence
<220> FEATURE:
<223> OTHER INFORMATION: replicating RNA species

<400> SEQUENCE: 35
ggaagaaaca uugucaauug ccuuggccca auguuccug aaacauuggc caaggcaauu     60
gacaauguuu caugg                                                     75

<210> SEQ ID NO 36
<211> LENGTH: 82
<212> TYPE: RNA
<213> ORGANISM: Artificial Sequence
<220> FEATURE:
<223> OTHER INFORMATION: replicating RNA species

<400> SEQUENCE: 36
ggauaaacuu ucuuucauuc ugucuaagaa aguuuaaaca gaguuuuaaa cuuucuuaga     60
cagaaugaaa gaaaguuuaa gg                                              82

<210> SEQ ID NO 37
<211> LENGTH: 89
<212> TYPE: RNA
<213> ORGANISM: Artificial Sequence
<220> FEATURE:
<223> OTHER INFORMATION: replicating RNA species

<400> SEQUENCE: 37
ggaauaauaa uaauucuaag uaagaguuau auuaauacau aauuucaaau uauguauuaa     60
uauaacucuu acuuagaauu auuauucgg                                      89

<210> SEQ ID NO 38
<211> LENGTH: 78
<212> TYPE: RNA
<213> ORGANISM: Artificial Sequence
<220> FEATURE:
<223> OTHER INFORMATION: replicating RNA species

<400> SEQUENCE: 38
ggaauuuuaa auuauuuaaa uggaauuucc auuuaauauu aauuaaaugg aaauuccauu     60
uaaauaauuu aaaaaugg                                                  78

<210> SEQ ID NO 39
<211> LENGTH: 78
<212> TYPE: RNA
<213> ORGANISM: Artificial Sequence
<220> FEATURE:
<223> OTHER INFORMATION: replicating RNA species

<400> SEQUENCE: 39
ggauaauauu ucaauauucc auuuuauuau ugaaauugua auauuucaau aauaaaaugg     60
aauauugaaa uauuuugg                                                  78

<210> SEQ ID NO 40
<211> LENGTH: 63
<212> TYPE: RNA
<213> ORGANISM: Artificial Sequence
<220> FEATURE:
<223> OTHER INFORMATION: replicating RNA species

<400> SEQUENCE: 40
ggauuaauua auugauucau aauuaauuaa uugaauaauu aauuaugaau caauuaauua     60
```

```
ugg                                                                           63

<210> SEQ ID NO 41
<211> LENGTH: 85
<212> TYPE: RNA
<213> ORGANISM: Artificial Sequence
<220> FEATURE:
<223> OTHER INFORMATION: replicating RNA species

<400> SEQUENCE: 41
ggaaaaauua aauauaguuc caguuucucc uauauuuaau uagaaauuaa auauaggaga     60
aacuggaacu auauuuaauu ucugg                                          85

<210> SEQ ID NO 42
<211> LENGTH: 67
<212> TYPE: RNA
<213> ORGANISM: Artificial Sequence
<220> FEATURE:
<223> OTHER INFORMATION: replicating RNA species

<400> SEQUENCE: 42
ggaaaauuuc aagaucaggg cuugaaauuu uacaaaauuu ucaagcccug aucuugaaau     60
uuugggg                                                             67

<210> SEQ ID NO 43
<211> LENGTH: 68
<212> TYPE: RNA
<213> ORGANISM: Artificial Sequence
<220> FEATURE:
<223> OTHER INFORMATION: replicating RNA species

<400> SEQUENCE: 43
gguuaaauau uauugaaauc ucaaaauaau aaaaccaaau auuauuuuga gauuucaaua     60
auauuugg                                                            68

<210> SEQ ID NO 44
<211> LENGTH: 71
<212> TYPE: RNA
<213> ORGANISM: Artificial Sequence
<220> FEATURE:
<223> OTHER INFORMATION: replicating RNA species

<400> SEQUENCE: 44
ggaauuauca uuucuugcag auaaagauga uaauccaauu aucaucuuua ucugcaagaa     60
augauaauug g                                                        71

<210> SEQ ID NO 45
<211> LENGTH: 79
<212> TYPE: RNA
<213> ORGANISM: Artificial Sequence
<220> FEATURE:
<223> OTHER INFORMATION: replicating RNA species

<400> SEQUENCE: 45
ggaaaauauu auuuucaagc uauaucuaau aauauuuugc caaaauauua uuagauauag     60
cuugaaaaua auauuuugg                                                79

<210> SEQ ID NO 46
<211> LENGTH: 77
<212> TYPE: RNA
<213> ORGANISM: Artificial Sequence
<220> FEATURE:
```

<223> OTHER INFORMATION: replicating RNA species

<400> SEQUENCE: 46
ggaauauuuc auugaugaaa uuacaaugau caaugaauau uucauugauc auuguaauuu      60
caucaaugaa auauugg                                                     77

<210> SEQ ID NO 47
<211> LENGTH: 65
<212> TYPE: RNA
<213> ORGANISM: Artificial Sequence
<220> FEATURE:
<223> OTHER INFORMATION: replicating RNA species

<400> SEQUENCE: 47
ggaaaaaauu cuuuucagaa augaauugaa auucuuuuca auucauuucu gaaaagaauu      60
uuugg                                                                  65

<210> SEQ ID NO 48
<211> LENGTH: 65
<212> TYPE: RNA
<213> ORGANISM: Artificial Sequence
<220> FEATURE:
<223> OTHER INFORMATION: replicating RNA species

<400> SEQUENCE: 48
ggaaaaauug uaucuaucca auuuugauac aaaauuguau caaaauugga uagauacaau      60
uuugg                                                                  65

<210> SEQ ID NO 49
<211> LENGTH: 73
<212> TYPE: RNA
<213> ORGANISM: Artificial Sequence
<220> FEATURE:
<223> OTHER INFORMATION: replicating RNA species

<400> SEQUENCE: 49
ggaaaauauc aauaauuucc gauuauuauu gauaaaauau caauaauaau cggaaauuau      60
ugauauuuua ugg                                                         73

<210> SEQ ID NO 50
<211> LENGTH: 60
<212> TYPE: RNA
<213> ORGANISM: Artificial Sequence
<220> FEATURE:
<223> OTHER INFORMATION: replicating RNA species

<400> SEQUENCE: 50
ggaaaaauug aaaaguccaa uucaauuuaa ccaaaauuga auuggacuuu ucaauuuugg      60

<210> SEQ ID NO 51
<211> LENGTH: 69
<212> TYPE: RNA
<213> ORGANISM: Artificial Sequence
<220> FEATURE:
<223> OTHER INFORMATION: replicating RNA species

<400> SEQUENCE: 51
ggaaauuugg auuugguaaa uucuccaaaa uuuccgaaau uuuggagaau uuaccaaauc      60
caaaauugg                                                              69

<210> SEQ ID NO 52
<211> LENGTH: 68

-continued

```
<212> TYPE: RNA
<213> ORGANISM: Artificial Sequence
<220> FEATURE:
<223> OTHER INFORMATION: replicating RNA species

<400> SEQUENCE: 52
ggaaaaucuu gucaugaauc aauagauuuu cuugucauga aaucuauuga uucaugacaa      60
gauuuugg                                                              68

<210> SEQ ID NO 53
<211> LENGTH: 75
<212> TYPE: RNA
<213> ORGANISM: Artificial Sequence
<220> FEATURE:
<223> OTHER INFORMATION: replicating RNA species

<400> SEQUENCE: 53
ggauauauau auaugugugu guguguauau auauuccgau gaauauauau acacacacac      60
acauauauau aucgg                                                      75

<210> SEQ ID NO 54
<211> LENGTH: 89
<212> TYPE: RNA
<213> ORGANISM: Artificial Sequence
<220> FEATURE:
<223> OTHER INFORMATION: replicating RNA species

<400> SEQUENCE: 54
ggauaaauua aauagguuuc ugacuuuguu auuccuauuu aaucgggauu aaauaggaau      60
aacaaaguca gaaaccuauu uaauuuugg                                       89

<210> SEQ ID NO 55
<211> LENGTH: 75
<212> TYPE: RNA
<213> ORGANISM: Artificial Sequence
<220> FEATURE:
<223> OTHER INFORMATION: replicating RNA species

<400> SEQUENCE: 55
ggaaaauaug ucauacauug gucagagaaa auguauguca uacauuuucu cugaccaaug      60
uaugacauau uuagg                                                      75

<210> SEQ ID NO 56
<211> LENGTH: 72
<212> TYPE: RNA
<213> ORGANISM: Artificial Sequence
<220> FEATURE:
<223> OTHER INFORMATION: replicating RNA species

<400> SEQUENCE: 56
ggaaaaauuc aaaucaauug ccgaugauuu gauuuuucau ucaaaucauc ggcaauugau      60
uugaauuugg gg                                                         72

<210> SEQ ID NO 57
<211> LENGTH: 98
<212> TYPE: RNA
<213> ORGANISM: Artificial Sequence
<220> FEATURE:
<223> OTHER INFORMATION: replicating RNA species

<400> SEQUENCE: 57
ggauuaaauu ucauauuguu aauauuuauu aauguaugua caauaugaaa uuucauauug      60
```

-continued uacauacauu aauaaauauu aacaauauga aauuucgg                                98

<210> SEQ ID NO 58
<211> LENGTH: 83
<212> TYPE: RNA
<213> ORGANISM: Artificial Sequence
<220> FEATURE:
<223> OTHER INFORMATION: replicating RNA species

<400> SEQUENCE: 58
ggaaaaauuu aauaggaguu caguuuauuc uauuaaauuu ccggaaauuu aauagaauaa      60
acugaacucc uauuaaauuu ugg                                               83

<210> SEQ ID NO 59
<211> LENGTH: 74
<212> TYPE: RNA
<213> ORGANISM: Artificial Sequence
<220> FEATURE:
<223> OTHER INFORMATION: replicating RNA species

<400> SEQUENCE: 59
ggaaauuuau uugagaguug uuccaaauaa auuuucggaa aauuuauuug gaacaacucu      60
caaauaaauu uugg                                                         74

<210> SEQ ID NO 60
<211> LENGTH: 60
<212> TYPE: RNA
<213> ORGANISM: Artificial Sequence
<220> FEATURE:
<223> OTHER INFORMATION: replicating RNA species

<400> SEQUENCE: 60
ggaaaaaauu ucuucuucga gaaauuugaa uuccaaauuu cucgaagaag aaauuuuggg      60

<210> SEQ ID NO 61
<211> LENGTH: 73
<212> TYPE: RNA
<213> ORGANISM: Artificial Sequence
<220> FEATURE:
<223> OTHER INFORMATION: replicating RNA species

<400> SEQUENCE: 61
ggaaagaaug uuuucauaag guacaacauu cuuuuucuaa agaauguugu accuuaugaa      60
aacauucuuc agg                                                          73

<210> SEQ ID NO 62
<211> LENGTH: 89
<212> TYPE: RNA
<213> ORGANISM: Artificial Sequence
<220> FEATURE:
<223> OTHER INFORMATION: replicating RNA species

<400> SEQUENCE: 62
ggaaaauuua aaugugcacu ccauauucuc cgcauuuaaa uuuuccauau ucaaaugcgg      60
agaauaugga gugcacauuu aaauuuggg                                         89

<210> SEQ ID NO 63
<211> LENGTH: 65
<212> TYPE: RNA
<213> ORGANISM: Artificial Sequence
<220> FEATURE:
<223> OTHER INFORMATION: replicating RNA species

<400> SEQUENCE: 63
ggaaauugaa uaagacuuuc ccuuauucau uaaaauugaa uaagggaaag ucuuauucaa        60
uuugg                                                                   65

<210> SEQ ID NO 64
<211> LENGTH: 77
<212> TYPE: RNA
<213> ORGANISM: Artificial Sequence
<220> FEATURE:
<223> OTHER INFORMATION: replicating RNA species

<400> SEQUENCE: 64
ggaagaaauc agaauauucu ccuuuuucug auuuucugaa gaaaaucaga aaaaggagaa        60
uauucugauu ucuuggg                                                      77

<210> SEQ ID NO 65
<211> LENGTH: 65
<212> TYPE: RNA
<213> ORGANISM: Artificial Sequence
<220> FEATURE:
<223> OTHER INFORMATION: replicating RNA species

<400> SEQUENCE: 65
ggaaaaugau uuccucauua guugaucauc aaaaugauuu caacuaauga ggaaaucauu        60
uuggg                                                                   65

<210> SEQ ID NO 66
<211> LENGTH: 78
<212> TYPE: RNA
<213> ORGANISM: Artificial Sequence
<220> FEATURE:
<223> OTHER INFORMATION: replicating RNA species

<400> SEQUENCE: 66
ggaaauuuaa augugccaug aauauggaaa uuuaaaugug cuuuuaaauu uccauauuca        60
uggcacauuu aaauuugg                                                     78

<210> SEQ ID NO 67
<211> LENGTH: 79
<212> TYPE: RNA
<213> ORGANISM: Artificial Sequence
<220> FEATURE:
<223> OTHER INFORMATION: replicating RNA species

<400> SEQUENCE: 67
ggaaaaaaau ucgaucgua guaggauuuc agaauuuucu uccgaaaauu cugaaauccu        60
acuacgauca gaauuucgg                                                    79

<210> SEQ ID NO 68
<211> LENGTH: 103
<212> TYPE: RNA
<213> ORGANISM: Artificial Sequence
<220> FEATURE:
<223> OTHER INFORMATION: replicating RNA species

<400> SEQUENCE: 68
ggaaauauac aauucuauau cauuccauga uauagaauau agaauuguaa auauacaauu        60
cuauauucua uaucauggaa ugauauagaa uuguauauuu ggg                         103

<210> SEQ ID NO 69
<211> LENGTH: 62
<212> TYPE: RNA

<213> ORGANISM: Artificial Sequence
<220> FEATURE:
<223> OTHER INFORMATION: replicating RNA species

<400> SEQUENCE: 69 ggaaaaauuca aaauugaauu gaauuuggau uuuuccaaau ucaauucaau uuugaauuug      60
gg                                                                     62

<210> SEQ ID NO 70
<211> LENGTH: 66
<212> TYPE: RNA
<213> ORGANISM: Artificial Sequence
<220> FEATURE:
<223> OTHER INFORMATION: replicating RNA species

<400> SEQUENCE: 70
ggaugauuau uucauguguc ucuaaugauc uaaacauuag aucauuagag acacaugaaa      60
uacugg                                                                 66

<210> SEQ ID NO 71
<211> LENGTH: 77
<212> TYPE: RNA
<213> ORGANISM: Artificial Sequence
<220> FEATURE:
<223> OTHER INFORMATION: replicating RNA species

<400> SEQUENCE: 71
gggaauauua auucaaauuc aauauuggug uaauauuaau ucaaauuaca ccaauauuga      60
auuugaauua auauugg                                                     77

<210> SEQ ID NO 72
<211> LENGTH: 93
<212> TYPE: RNA
<213> ORGANISM: Artificial Sequence
<220> FEATURE:
<223> OTHER INFORMATION: replicating RNA species

<400> SEQUENCE: 72
ggaugauuug auacauauuc guuucuaugu auuuaacaaa ucaucuuuga ugauuuguua      60
aauacauaga aacgaauaug uaucaaaucu ugg                                   93

<210> SEQ ID NO 73
<211> LENGTH: 72
<212> TYPE: RNA
<213> ORGANISM: Artificial Sequence
<220> FEATURE:
<223> OTHER INFORMATION: replicating RNA species

<400> SEQUENCE: 73
ggaaaaauca agugucacuu ucucccacuu gauuuuguca aucaaguggg agaaagugac      60
acuugauuuu gg                                                          72

<210> SEQ ID NO 74
<211> LENGTH: 79
<212> TYPE: RNA
<213> ORGANISM: Artificial Sequence
<220> FEATURE:
<223> OTHER INFORMATION: replicating RNA species

<400> SEQUENCE: 74
ggaaaaaauu caagaauccu cuucuugaau cuugaauuuu caaaauucaa gauucaagaa      60
gaggauucuu gaauuuugg                                                   79

```
<210> SEQ ID NO 75
<211> LENGTH: 64
<212> TYPE: RNA
<213> ORGANISM: Artificial Sequence
<220> FEATURE:
<223> OTHER INFORMATION: replicating RNA species

<400> SEQUENCE: 75
ggaaaauauc aacucgauau uugauauuua uuccaaauau caaauaucga guugauauuu      60
uggg                                                                   64

<210> SEQ ID NO 76
<211> LENGTH: 68
<212> TYPE: RNA
<213> ORGANISM: Artificial Sequence
<220> FEATURE:
<223> OTHER INFORMATION: replicating RNA species

<400> SEQUENCE: 76
ggaaaauuca aacgaucacc uucguuuuga uuugucaauu caaacgaagg ugaucguuug      60
aauuuagg                                                               68

<210> SEQ ID NO 77
<211> LENGTH: 84
<212> TYPE: RNA
<213> ORGANISM: Artificial Sequence
<220> FEATURE:
<223> OTHER INFORMATION: replicating RNA species

<400> SEQUENCE: 77
ggaugaauau auuuguuuug acuccauucu acaaauauau uccgaauaua uuuguagaau      60
ggagucaaaa caaauauauu cugg                                            84

<210> SEQ ID NO 78
<211> LENGTH: 79
<212> TYPE: RNA
<213> ORGANISM: Artificial Sequence
<220> FEATURE:
<223> OTHER INFORMATION: replicating RNA species

<400> SEQUENCE: 78
ggaaauuaag auuuuuucuc cuuucuaaau cuuaauuuua caaauuaaga uuuagaaagg      60
agaaaaaauc uuaauuugg                                                   79

<210> SEQ ID NO 79
<211> LENGTH: 89
<212> TYPE: RNA
<213> ORGANISM: Artificial Sequence
<220> FEATURE:
<223> OTHER INFORMATION: replicating RNA species

<400> SEQUENCE: 79
gggaaaauua acaauauucu uucgauuguu caauauugaa auuuuccaau uaacaauauu      60
gaacaaucga aagaauauug uuaauuugg                                        89

<210> SEQ ID NO 80
<211> LENGTH: 73
<212> TYPE: RNA
<213> ORGANISM: Artificial Sequence
<220> FEATURE:
<223> OTHER INFORMATION: replicating RNA species
```

```
<400> SEQUENCE: 80
ggaaaaaaca auucaaucaa uucgucauga uugaaacaau ucaaucauga cgaauugauu      60
gaauuguuuu ugg                                                          73

<210> SEQ ID NO 81
<211> LENGTH: 85
<212> TYPE: RNA
<213> ORGANISM: Artificial Sequence
<220> FEATURE:
<223> OTHER INFORMATION: replicating RNA species

<400> SEQUENCE: 81
ggaaaaauua auuugaauaa uuaauuucuu cuuaauuucu uccaauuaau uaagaagaaa      60
uuaauuauuc aaauuaauuu uuggg                                            85

<210> SEQ ID NO 82
<211> LENGTH: 67
<212> TYPE: RNA
<213> ORGANISM: Artificial Sequence
<220> FEATURE:
<223> OTHER INFORMATION: replicating RNA species

<400> SEQUENCE: 82
ggaaaaaauu cauucggauu uugugcgaau gaaauucauu cgcacaaaau ccgaaugaau      60
uuggggg                                                                67

<210> SEQ ID NO 83
<211> LENGTH: 65
<212> TYPE: RNA
<213> ORGANISM: Artificial Sequence
<220> FEATURE:
<223> OTHER INFORMATION: replicating RNA species

<400> SEQUENCE: 83
gguuauauau auauugaucc uugcaauaua uaauuauaua uugcaaggau caauauauau      60
auugg                                                                  65

<210> SEQ ID NO 84
<211> LENGTH: 76
<212> TYPE: RNA
<213> ORGANISM: Artificial Sequence
<220> FEATURE:
<223> OTHER INFORMATION: replicating RNA species

<400> SEQUENCE: 84
ggaauucaau gagaaaaaau cucccacuca uugauuccca auucaaugag ugggagauuu      60
uucucauuga auuggg                                                      76

<210> SEQ ID NO 85
<211> LENGTH: 77
<212> TYPE: RNA
<213> ORGANISM: Artificial Sequence
<220> FEATURE:
<223> OTHER INFORMATION: replicating RNA species

<400> SEQUENCE: 85
ggaaaaauuu cagaauuucu ucauccucug aaauuuucuc aaaauuucag aggaugaaga      60
aauucugaaa uuucggg                                                     77

<210> SEQ ID NO 86
<211> LENGTH: 73
```

```
<212> TYPE: RNA
<213> ORGANISM: Artificial Sequence
<220> FEATURE:
<223> OTHER INFORMATION: replicating RNA species

<400> SEQUENCE: 86
ggauaaauac cauaacguug aauaugaagg uauuauccaa aauaccuuca uauucaacgu      60
uaugguauuu ugg                                                       73

<210> SEQ ID NO 87
<211> LENGTH: 80
<212> TYPE: RNA
<213> ORGANISM: Artificial Sequence
<220> FEATURE:
<223> OTHER INFORMATION: replicating RNA species

<400> SEQUENCE: 87
ggaaaaaauu ggaugagaaa guuaaaauua uucaauuuuc cgaaaauuga auaauuuuaa      60
cuuucucauc caauuuucgg                                                 80

<210> SEQ ID NO 88
<211> LENGTH: 90
<212> TYPE: RNA
<213> ORGANISM: Artificial Sequence
<220> FEATURE:
<223> OTHER INFORMATION: replicating RNA species

<400> SEQUENCE: 88
ggaauauuaa caaagauagg gauaagaaug uaaucuuuug uugaauauua acaaagauua      60
cauucuuauc ccuaucuuug uuaauauugg                                      90

<210> SEQ ID NO 89
<211> LENGTH: 76
<212> TYPE: RNA
<213> ORGANISM: Artificial Sequence
<220> FEATURE:
<223> OTHER INFORMATION: replicating RNA species

<400> SEQUENCE: 89
ggaaaauuca aauucaagau uggauucucu ugaauuucaa aauucaagag aauccaaucu      60
ugaauuugaa uuuggg                                                     76

<210> SEQ ID NO 90
<211> LENGTH: 74
<212> TYPE: RNA
<213> ORGANISM: Artificial Sequence
<220> FEATURE:
<223> OTHER INFORMATION: replicating RNA species

<400> SEQUENCE: 90
ggauuguuau caauguauuc uuccaaacau ugaacaaugu aucaauguuu ggaagaauac      60
auugauaaca uggg                                                       74

<210> SEQ ID NO 91
<211> LENGTH: 69
<212> TYPE: RNA
<213> ORGANISM: Artificial Sequence
<220> FEATURE:
<223> OTHER INFORMATION: replicating RNA species

<400> SEQUENCE: 91
ggaaaauaau uuccaaauca aaauuauuug auuuccaaau caaauaauuu ugauuuggaa      60
``` auuauuugg                                                                      69

<210> SEQ ID NO 92
<211> LENGTH: 81
<212> TYPE: RNA
<213> ORGANISM: Artificial Sequence
<220> FEATURE:
<223> OTHER INFORMATION: replicating RNA species

<400> SEQUENCE: 92
ggaaaaaauc auuucucuaa ugcaauucag agaaugaaua aaucauuuuc ucugaauugc      60
auuagagaaa ugauuuauug g                                                        81

<210> SEQ ID NO 93
<211> LENGTH: 71
<212> TYPE: RNA
<213> ORGANISM: Artificial Sequence
<220> FEATURE:
<223> OTHER INFORMATION: replicating RNA species

<400> SEQUENCE: 93
ggaagaauuu aauuucaucc ucuuaaauuc uuuaaaccaa gaaauuuaag aggaugaaau      60
uaaauucuug g                                                                   71

<210> SEQ ID NO 94
<211> LENGTH: 64
<212> TYPE: RNA
<213> ORGANISM: Artificial Sequence
<220> FEATURE:
<223> OTHER INFORMATION: replicating RNA species

<400> SEQUENCE: 94
ggaaaauuaa aguucaaugc aauuuaauuu uccaaaauua aauugcauug aacuuuaauu      60
uugg                                                                           64

<210> SEQ ID NO 95
<211> LENGTH: 71
<212> TYPE: RNA
<213> ORGANISM: Artificial Sequence
<220> FEATURE:
<223> OTHER INFORMATION: replicating RNA species

<400> SEQUENCE: 95
ggaauuaauu uagucuaggu ggaacuaauu auacuaauua auuuaguucc accuagacua      60
aauuaauuag g                                                                   71

<210> SEQ ID NO 96
<211> LENGTH: 82
<212> TYPE: RNA
<213> ORGANISM: Artificial Sequence
<220> FEATURE:
<223> OTHER INFORMATION: replicating RNA species

<400> SEQUENCE: 96
ggagaauuua aaucauuauc uucuuugauu uaaauuuaug gccauaaauu uaaaucaaag      60
aagauaauga uuuaaaauucu gg                                                      82

<210> SEQ ID NO 97
<211> LENGTH: 77
<212> TYPE: RNA
<213> ORGANISM: Artificial Sequence
<220> FEATURE:
<223> OTHER INFORMATION: replicating RNA species -continued

<400> SEQUENCE: 97
ggaaauuuca auucaauggg uuguauuaau ugaaauugcc caauuucaau uaauacaacc      60
cauugaauug aaauugg                                                       77

<210> SEQ ID NO 98
<211> LENGTH: 64
<212> TYPE: RNA
<213> ORGANISM: Artificial Sequence
<220> FEATURE:
<223> OTHER INFORMATION: replicating RNA species

<400> SEQUENCE: 98
ggaaaauauc aacucgauau uuugauauuu auuccaaaua ucaaauaucg aguugauauu      60
uugg                                                                     64

<210> SEQ ID NO 99
<211> LENGTH: 71
<212> TYPE: RNA
<213> ORGANISM: Artificial Sequence
<220> FEATURE:
<223> OTHER INFORMATION: replicating RNA species

<400> SEQUENCE: 99
ggaauugaau ggaauggaca aauuccauau gauuccaauu cauauggaau uuguccauuc      60
cauucaauug g                                                             71

<210> SEQ ID NO 100
<211> LENGTH: 75
<212> TYPE: RNA
<213> ORGANISM: Artificial Sequence
<220> FEATURE:
<223> OTHER INFORMATION: replicating RNA species

<400> SEQUENCE: 100
ggauaaucau uaucaaaugg gaaucugaua augaugauua aucauuauca gauucccauu      60
ugauaaugau ucugg                                                         75

<210> SEQ ID NO 101
<211> LENGTH: 63
<212> TYPE: RNA
<213> ORGANISM: Artificial Sequence
<220> FEATURE:
<223> OTHER INFORMATION: replicating RNA species

<400> SEQUENCE: 101
ggaaucaaau agaauccauu aucuauuuga uucaaucaaa auagauaaug gauucuauuu      60
cgg                                                                      63

<210> SEQ ID NO 102
<211> LENGTH: 73
<212> TYPE: RNA
<213> ORGANISM: Artificial Sequence
<220> FEATURE:
<223> OTHER INFORMATION: replicating RNA species

<400> SEQUENCE: 102
ggaaaauuuc uaaauauuac ugaucaucag uaaucuaaau auuacugaug aucaguaaua      60
uuuagaaauu ugg                                                           73

<210> SEQ ID NO 103

-continued

```
<211> LENGTH: 82
<212> TYPE: RNA
<213> ORGANISM: Artificial Sequence
<220> FEATURE:
<223> OTHER INFORMATION: replicating RNA species

<400> SEQUENCE: 103
ggaauguaau aaauuauugu uauauucacu ccaauguaau aaauuacauu ggagugaaua      60
uaacaauaau uuauuacauu gg                                              82

<210> SEQ ID NO 104
<211> LENGTH: 79
<212> TYPE: RNA
<213> ORGANISM: Artificial Sequence
<220> FEATURE:
<223> OTHER INFORMATION: replicating RNA species

<400> SEQUENCE: 104
ggauuauuuu auucaaucuu cauaacaccg gaagauuuau ucaaucuucc gguguuauga      60
agauugaaua aaauaaugg                                                  79

<210> SEQ ID NO 105
<211> LENGTH: 85
<212> TYPE: RNA
<213> ORGANISM: Artificial Sequence
<220> FEATURE:
<223> OTHER INFORMATION: replicating RNA species

<400> SEQUENCE: 105
ggaauuucaa uuucucaucu uguauauaaa uacaauuucu caucuugaaa auguauuuau      60
auacaagaug agaaauugaa auugg                                           85

<210> SEQ ID NO 106
<211> LENGTH: 72
<212> TYPE: RNA
<213> ORGANISM: Artificial Sequence
<220> FEATURE:
<223> OTHER INFORMATION: replicating RNA species

<400> SEQUENCE: 106
ggaaaauuca aauugcagua gauauugaau uuuuuuccaa aauucaauau cuacugcaau      60
uugaauuuug gg                                                         72

<210> SEQ ID NO 107
<211> LENGTH: 79
<212> TYPE: RNA
<213> ORGANISM: Artificial Sequence
<220> FEATURE:
<223> OTHER INFORMATION: replicating RNA species

<400> SEQUENCE: 107
ggauaaauug auaggaacaa uuaauagugu caauuuaucc gauaaauuga cacuauuaau      60
uguuccuauc aauuuaggg                                                  79

<210> SEQ ID NO 108
<211> LENGTH: 65
<212> TYPE: RNA
<213> ORGANISM: Artificial Sequence
<220> FEATURE:
<223> OTHER INFORMATION: replicating RNA species

<400> SEQUENCE: 108
gggaaaaauc aaguucugag uuuugauuua uccaaaaauc aaaaaacuca gaacuugauu      60
```

-continued

```
uuugg                                                                 65

<210> SEQ ID NO 109
<211> LENGTH: 89
<212> TYPE: RNA
<213> ORGANISM: Artificial Sequence
<220> FEATURE:
<223> OTHER INFORMATION: replicating RNA species

<400> SEQUENCE: 109
ggaagauuga aaaucuuaua auaucuaaga gauagauuuu caugauugaa aaaucuaucu     60
cuuagauauu auaagauuuu caaucaugg                                       89

<210> SEQ ID NO 110
<211> LENGTH: 79
<212> TYPE: RNA
<213> ORGANISM: Artificial Sequence
<220> FEATURE:
<223> OTHER INFORMATION: replicating RNA species

<400> SEQUENCE: 110
ggaaaaauua uuacaaugca cccauaucau uguaauuuga aauuauuaca augauauggg     60
ugcauuguaa uaauuucgg                                                  79

<210> SEQ ID NO 111
<211> LENGTH: 87
<212> TYPE: RNA
<213> ORGANISM: Artificial Sequence
<220> FEATURE:
<223> OTHER INFORMATION: replicating RNA species

<400> SEQUENCE: 111
ggaagaugaa uauguuaauu agcuuaauca uuccauauuc auccgaugaa uauggaauga     60
uuaagcuaau uaacauauuc aucaugg                                         87

<210> SEQ ID NO 112
<211> LENGTH: 70
<212> TYPE: RNA
<213> ORGANISM: Artificial Sequence
<220> FEATURE:
<223> OTHER INFORMATION: replicating RNA species

<400> SEQUENCE: 112
ggaaaauuau cuguucaaau ucaaaugaug auuuuccaaa uuaucauuug aauuugaaca     60
gauaauuugg                                                           70

<210> SEQ ID NO 113
<211> LENGTH: 57
<212> TYPE: RNA
<213> ORGANISM: Artificial Sequence
<220> FEATURE:
<223> OTHER INFORMATION: replicating RNA species

<400> SEQUENCE: 113
ggaaaucauu ccauucaaug auguucaaug aaacaucauu ugaauggaau ugauugg        57

<210> SEQ ID NO 114
<211> LENGTH: 71
<212> TYPE: RNA
<213> ORGANISM: Artificial Sequence
<220> FEATURE:
<223> OTHER INFORMATION: replicating RNA species
```

<400> SEQUENCE: 114
ggaaaaauaa ugggauacuu caaacauuau uuuuccgaaa aauaauguuu gaaguauccc        60
auuauuuuug g                                                            71

<210> SEQ ID NO 115
<211> LENGTH: 72
<212> TYPE: RNA
<213> ORGANISM: Artificial Sequence
<220> FEATURE:
<223> OTHER INFORMATION: replicating RNA species

<400> SEQUENCE: 115
gggaaaauca auuccagucc uuucccugga uuugaaaauc aauuccaggg aaaggacugg        60
aauugauuuu gg                                                           72

<210> SEQ ID NO 116
<211> LENGTH: 81
<212> TYPE: RNA
<213> ORGANISM: Artificial Sequence
<220> FEATURE:
<223> OTHER INFORMATION: replicating RNA species

<400> SEQUENCE: 116
ggaagaaaau caaauaauau aucuggauac auuauuugau uuucaaauaa uguauccaga        60
uauauuauuu gauuuucuug g                                                  81

<210> SEQ ID NO 117
<211> LENGTH: 71
<212> TYPE: RNA
<213> ORGANISM: Artificial Sequence
<220> FEATURE:
<223> OTHER INFORMATION: replicating RNA species

<400> SEQUENCE: 117
ggaaaauuug auacuagcua uccaaaguau caaauuucau gauacuuugg auagcuagua        60
ucaaauuugg g                                                            71

<210> SEQ ID NO 118
<211> LENGTH: 67
<212> TYPE: RNA
<213> ORGANISM: Artificial Sequence
<220> FEATURE:
<223> OTHER INFORMATION: replicating RNA species

<400> SEQUENCE: 118
ggaaauaaaa ucaucauuau uauuugauga aauaaaauca ucaaauaaua augaugauuu        60
uauuugg                                                                 67

<210> SEQ ID NO 119
<211> LENGTH: 68
<212> TYPE: RNA
<213> ORGANISM: Artificial Sequence
<220> FEATURE:
<223> OTHER INFORMATION: replicating RNA species

<400> SEQUENCE: 119
ggaaaauuaa auugcauuga acuuuaauuu uccccccaaa auuaaaguuc aaugcaauuu        60
aauuuugg                                                                68

<210> SEQ ID NO 120
<211> LENGTH: 86

```
<212> TYPE: RNA
<213> ORGANISM: Artificial Sequence
<220> FEATURE:
<223> OTHER INFORMATION: replicating RNA species

<400> SEQUENCE: 120
ggaagauguu uuugauaccg agcuggucuc agcauauauu uccauaaaua uaugcugaga      60
ccagcucggu aucaaaacau cuaugg                                           86

<210> SEQ ID NO 121
<211> LENGTH: 77
<212> TYPE: RNA
<213> ORGANISM: Artificial Sequence
<220> FEATURE:
<223> OTHER INFORMATION: replicating RNA species

<400> SEQUENCE: 121
ggaugaaauu ggaaccauc auucucccca aauuucaucc aaugaaauug ggagaaugau       60
gguuuccaau uucuugg                                                     77

<210> SEQ ID NO 122
<211> LENGTH: 66
<212> TYPE: RNA
<213> ORGANISM: Artificial Sequence
<220> FEATURE:
<223> OTHER INFORMATION: replicating RNA species

<400> SEQUENCE: 122
ggaaaauuau aauagaaauu aucccuauua uaauuauaau agggauaauu ucuauuauaa      60
uuuugg                                                                 66

<210> SEQ ID NO 123
<211> LENGTH: 64
<212> TYPE: RNA
<213> ORGANISM: Artificial Sequence
<220> FEATURE:
<223> OTHER INFORMATION: replicating RNA species

<400> SEQUENCE: 123
ggaugaaauc aaaaaagcua guccuuuuga ugaaaaucaa aaggacuagc uuuugauuuc      60
augg                                                                   64

<210> SEQ ID NO 124
<211> LENGTH: 74
<212> TYPE: RNA
<213> ORGANISM: Artificial Sequence
<220> FEATURE:
<223> OTHER INFORMATION: replicating RNA species

<400> SEQUENCE: 124
ggaauuaaac aaauauauac uuccacaaua uuuguuugaa aacaaauauu guggaaguau      60
auauuuguuu ucgg                                                        74

<210> SEQ ID NO 125
<211> LENGTH: 80
<212> TYPE: RNA
<213> ORGANISM: Artificial Sequence
<220> FEATURE:
<223> OTHER INFORMATION: replicating RNA species

<400> SEQUENCE: 125
ggauuuuuga uuucauucga ugcuucugaa aaucaauaau ucccauuuga uuuucagaag      60
```

-continued

```
caucgaauga aaucaaaugg                                              80

<210> SEQ ID NO 126
<211> LENGTH: 70
<212> TYPE: RNA
<213> ORGANISM: Artificial Sequence
<220> FEATURE:
<223> OTHER INFORMATION: replicating RNA species

<400> SEQUENCE: 126
ggauaaaauu cuagucuaua uggcuacuag aauacuaaau ucuaguagcc auauagacua    60
gaauuuaugg                                                          70

<210> SEQ ID NO 127
<211> LENGTH: 87
<212> TYPE: RNA
<213> ORGANISM: Artificial Sequence
<220> FEATURE:
<223> OTHER INFORMATION: replicating RNA species

<400> SEQUENCE: 127
ggaauugaaa uucaucuucu gucucuugug aauuucauuu uaauugauug aaauucacaa    60
gagacagaag augaauuuca aucaugg                                       87

<210> SEQ ID NO 128
<211> LENGTH: 92
<212> TYPE: RNA
<213> ORGANISM: Artificial Sequence
<220> FEATURE:
<223> OTHER INFORMATION: replicating RNA species

<400> SEQUENCE: 128
ggaaauuuca uauuucagaa auagguaaau uucugaaaua aaauaaauuu uuuauuucag    60
aaauuuaccu auuucugaaa uaugaaauuu gg                                 92

<210> SEQ ID NO 129
<211> LENGTH: 86
<212> TYPE: RNA
<213> ORGANISM: Artificial Sequence
<220> FEATURE:
<223> OTHER INFORMATION: replicating RNA species

<400> SEQUENCE: 129
ggaauuauga ucaaaauuga auggaaauug aaugaucaaa uugaauuaug aucauucaau    60
uuccauucaa uuuugaucau aauugg                                        86

<210> SEQ ID NO 130
<211> LENGTH: 79
<212> TYPE: RNA
<213> ORGANISM: Artificial Sequence
<220> FEATURE:
<223> OTHER INFORMATION: replicating RNA species

<400> SEQUENCE: 130
ggaagaaaau guuaucuaca ccgagacaua acauuuucug acagaaaugu uaugucucgg    60
uguagauaac auuucuugg                                                79

<210> SEQ ID NO 131
<211> LENGTH: 71
<212> TYPE: RNA
<213> ORGANISM: Artificial Sequence
<220> FEATURE:
<223> OTHER INFORMATION: replicating RNA species
```

-continued

<400> SEQUENCE: 131
ggauuaaauu ucaaauuauu cccuaauaau uugaaaauuu caaauuauua gggaauaauu      60
ugaaauuuug g                                                          71

<210> SEQ ID NO 132
<211> LENGTH: 108
<212> TYPE: RNA
<213> ORGANISM: Artificial Sequence
<220> FEATURE:
<223> OTHER INFORMATION: replicating RNA species

<400> SEQUENCE: 132
ggaauguuua uucuuuauuc aaauaagguu uuaaagaaua aacugaauaa aauuuauucu      60
uuauucaguu uauucuuuaa aaccuuauuu gaauaaagaa uaaacugg                 108

<210> SEQ ID NO 133
<211> LENGTH: 69
<212> TYPE: RNA
<213> ORGANISM: Artificial Sequence
<220> FEATURE:
<223> OTHER INFORMATION: replicating RNA species

<400> SEQUENCE: 133 ggggaaaau uucaagauca gggcuugaaa uuuuuacaaa auuucaagcc cugaucuuga      60
aauuuuggg                                                            69

<210> SEQ ID NO 134
<211> LENGTH: 86
<212> TYPE: RNA
<213> ORGANISM: Artificial Sequence
<220> FEATURE:
<223> OTHER INFORMATION: replicating RNA species

<400> SEQUENCE: 134
ggauaaaaua ucguauuuuu ccucuaaugu ggauauuuua uggccauaaa auauccacau      60
uagaggaaaa auacgauauu uuaugg                                          86

<210> SEQ ID NO 135
<211> LENGTH: 63
<212> TYPE: RNA
<213> ORGANISM: Artificial Sequence
<220> FEATURE:
<223> OTHER INFORMATION: replicating RNA species

<400> SEQUENCE: 135
ggaauuaauu aauaucucua aauuauuaau ucgagaauua auaauuuaga gauauuaauu      60
cgg                                                                  63

<210> SEQ ID NO 136
<211> LENGTH: 65
<212> TYPE: RNA
<213> ORGANISM: Artificial Sequence
<220> FEATURE:
<223> OTHER INFORMATION: replicating RNA species

<400> SEQUENCE: 136
ggggaaauuu ucaaguuauu ucuuuacuug aaauuuucaa guaaagaaau aacuugaaaa      60
uuugg                                                                65

<210> SEQ ID NO 137

-continued

```
<211> LENGTH: 73
<212> TYPE: RNA
<213> ORGANISM: Artificial Sequence
<220> FEATURE:
<223> OTHER INFORMATION: replicating RNA species

<400> SEQUENCE: 137
ggauuaugaa auuuacauug cuucaauuca uaaucuccau uaugaauuga agcaauguaa        60
auuucauaau ggg                                                          73

<210> SEQ ID NO 138
<211> LENGTH: 79
<212> TYPE: RNA
<213> ORGANISM: Artificial Sequence
<220> FEATURE:
<223> OTHER INFORMATION: replicating RNA species

<400> SEQUENCE: 138
gggaauuuua auuucauauu aucgaugaau gaaauuauug aauuuaauuu cauucaucga        60
uaauaugaaa uuaaauugg                                                    79

<210> SEQ ID NO 139
<211> LENGTH: 68
<212> TYPE: RNA
<213> ORGANISM: Artificial Sequence
<220> FEATURE:
<223> OTHER INFORMATION: replicating RNA species

<400> SEQUENCE: 139
ggaaaaucuu gucaugaauc aauagauuuu cuugucauga aaucuauuga uucaugacaa        60
gauuuugg                                                                68

<210> SEQ ID NO 140
<211> LENGTH: 88
<212> TYPE: RNA
<213> ORGANISM: Artificial Sequence
<220> FEATURE:
<223> OTHER INFORMATION: replicating RNA species

<400> SEQUENCE: 140
ggaaaaacaa ucuacaaauu caaugccgaa uugaauuugu ugaucuacaa auuuaauucg        60
gcauugaauu uguagauugu uuuuuggg                                          88

<210> SEQ ID NO 141
<211> LENGTH: 73
<212> TYPE: RNA
<213> ORGANISM: Artificial Sequence
<220> FEATURE:
<223> OTHER INFORMATION: replicating RNA species

<400> SEQUENCE: 141
ggaaaaucaa gauaauaaau acuccauuau uaucucagau aauaaugaug gaguauuuau        60
uaucuugauu ugg                                                          73

<210> SEQ ID NO 142
<211> LENGTH: 68
<212> TYPE: RNA
<213> ORGANISM: Artificial Sequence
<220> FEATURE:
<223> OTHER INFORMATION: replicating RNA species

<400> SEQUENCE: 142
ggaaaauuuc uaaauugaaa gauaaaauuu aauuuucuaa auuuuaucuu ucaauuuaga        60
```

-continued

```
aauuuugg                                                                  68

<210> SEQ ID NO 143
<211> LENGTH: 72
<212> TYPE: RNA
<213> ORGANISM: Artificial Sequence
<220> FEATURE:
<223> OTHER INFORMATION: replicating RNA species

<400> SEQUENCE: 143
gggaaaaaau auuuucuaaa uggugagaaa uauuuuccga aaauauuucu caccauuuag      60
aaaauauuuc gg                                                             72

<210> SEQ ID NO 144
<211> LENGTH: 86
<212> TYPE: RNA
<213> ORGANISM: Artificial Sequence
<220> FEATURE:
<223> OTHER INFORMATION: replicating RNA species

<400> SEQUENCE: 144
ggaauuauuu ucauuugugu acucaguaca cgaauuuaau uauuuuccaa aauucgugua      60
cugaguacac aaaugaaaau aauugg                                              86

<210> SEQ ID NO 145
<211> LENGTH: 61
<212> TYPE: RNA
<213> ORGANISM: Artificial Sequence
<220> FEATURE:
<223> OTHER INFORMATION: replicating RNA species

<400> SEQUENCE: 145
ggauaauuau caauaauucg aauaauuauc aauaauuauu cgaauuauug auaauuaugg      60
g                                                                         61

<210> SEQ ID NO 146
<211> LENGTH: 68
<212> TYPE: RNA
<213> ORGANISM: Artificial Sequence
<220> FEATURE:
<223> OTHER INFORMATION: replicating RNA species

<400> SEQUENCE: 146
ggauaauuuc auuuauaaug aaguuauuca uuuauaauga auaacuucau uauaaaugaa      60
auucgggg                                                                  68

<210> SEQ ID NO 147
<211> LENGTH: 74
<212> TYPE: RNA
<213> ORGANISM: Artificial Sequence
<220> FEATURE:
<223> OTHER INFORMATION: replicating RNA species

<400> SEQUENCE: 147
ggaaauaauc auauucucau aaugagauua uuaaauuucc auuaauaauc ucauuaugag      60
aauaugauua augg                                                           74

<210> SEQ ID NO 148
<211> LENGTH: 75
<212> TYPE: RNA
<213> ORGANISM: Artificial Sequence
<220> FEATURE:
```

-continued

```
<223> OTHER INFORMATION: replicating RNA species

<400> SEQUENCE: 148
ggauaaauuu gugucuucua uucuuaacaa auuuguuuuc cauaauuugu uaagaauaga      60
agacacaaau uaugg                                                       75

<210> SEQ ID NO 149
<211> LENGTH: 61
<212> TYPE: RNA
<213> ORGANISM: Artificial Sequence
<220> FEATURE:
<223> OTHER INFORMATION: replicating RNA species

<400> SEQUENCE: 149
ggaauaauuc aauuauuauu gauaauaauu caauuauuau caauaauaau ugaauuauug      60
g                                                                      61

<210> SEQ ID NO 150
<211> LENGTH: 77
<212> TYPE: RNA
<213> ORGANISM: Artificial Sequence
<220> FEATURE:
<223> OTHER INFORMATION: replicating RNA species

<400> SEQUENCE: 150
ggaauauauu auaugaaauc ucuucgucuc auauaauaua uauauggaga cgaagagauu      60
ucauauaaua uauaugg                                                     77

<210> SEQ ID NO 151
<211> LENGTH: 102
<212> TYPE: RNA
<213> ORGANISM: Artificial Sequence
<220> FEATURE:
<223> OTHER INFORMATION: replicating RNA species

<400> SEQUENCE: 151
ggaaauuuga aucaauuccu ccaaauuggu ucaaaucuca auuugaugaa uugauucauc      60
aaauugauuu gaaucaauuu ggaggaauug auucaaauuu gg                        102

<210> SEQ ID NO 152
<211> LENGTH: 84
<212> TYPE: RNA
<213> ORGANISM: Artificial Sequence
<220> FEATURE:
<223> OTHER INFORMATION: replicating RNA species

<400> SEQUENCE: 152
ggaaaaauug uucucuaauu gauucauucc gaacaauuuu gauccaaaau uguucggaau      60
gaaucaauua gagaacaauu uugg                                             84

<210> SEQ ID NO 153
<211> LENGTH: 76
<212> TYPE: RNA
<213> ORGANISM: Artificial Sequence
<220> FEATURE:
<223> OTHER INFORMATION: replicating RNA species

<400> SEQUENCE: 153
gggaauauuc uauucuugcu cuucuagaga gagaauauuc uacucucucu cuagaagagc      60
aagaauagaa uauugg                                                      76
```

-continued

```
<210> SEQ ID NO 154
<211> LENGTH: 84
<212> TYPE: RNA
<213> ORGANISM: Artificial Sequence
<220> FEATURE:
<223> OTHER INFORMATION: replicating RNA species

<400> SEQUENCE: 154
ggauaauuaa uuauuacucu cauuggaugu uggguaaaaa auuaauuauu acccaacauc      60
caaugagagu aauaauuaau uugg                                            84

<210> SEQ ID NO 155
<211> LENGTH: 75
<212> TYPE: RNA
<213> ORGANISM: Artificial Sequence
<220> FEATURE:
<223> OTHER INFORMATION: replicating RNA species

<400> SEQUENCE: 155
ggaaaaauca acagauacaa auugauugau uuuccaaauc caaaaaucaa ucaauuugua      60
ucuguugauu uuggg                                                      75

<210> SEQ ID NO 156
<211> LENGTH: 78
<212> TYPE: RNA
<213> ORGANISM: Artificial Sequence
<220> FEATURE:
<223> OTHER INFORMATION: replicating RNA species

<400> SEQUENCE: 156
ggaauauuuc aauauuucaa agaaaggaaa auauugauau uucaauauuu uccuuucuuu      60
gaaauauuga aauauugg                                                   78

<210> SEQ ID NO 157
<211> LENGTH: 71
<212> TYPE: RNA
<213> ORGANISM: Artificial Sequence
<220> FEATURE:
<223> OTHER INFORMATION: replicating RNA species

<400> SEQUENCE: 157
ggaaaaaaau ucauucgaag uacuuugaau uuuuguuuuc caaaauucaa aguacuucga      60
augaauuuug g                                                          71

<210> SEQ ID NO 158
<211> LENGTH: 67
<212> TYPE: RNA
<213> ORGANISM: Artificial Sequence
<220> FEATURE:
<223> OTHER INFORMATION: replicating RNA species

<400> SEQUENCE: 158
ggaauaauau ucuauccuuc gagaauauua gucuauaaua uucucgaagg auagaauauu      60
auagggg                                                              67

<210> SEQ ID NO 159
<211> LENGTH: 72
<212> TYPE: RNA
<213> ORGANISM: Artificial Sequence
<220> FEATURE:
<223> OTHER INFORMATION: replicating RNA species

<400> SEQUENCE: 159
```

-continued

```
ggauuuaauc uucauagaaa uaguauaaga uuaaucacau uaaucuuaua cuauuucuau       60
gaagauuaau gg                                                            72

<210> SEQ ID NO 160
<211> LENGTH: 97
<212> TYPE: RNA
<213> ORGANISM: Artificial Sequence
<220> FEATURE:
<223> OTHER INFORMATION: replicating RNA species

<400> SEQUENCE: 160
ggagaauuuc uaaauagauu acauuucauu guaauguaau cuacaauuuc auuguagauu       60
acauuacaau gaaauguaau cuauuuagaa auucugg                                97

<210> SEQ ID NO 161
<211> LENGTH: 74
<212> TYPE: RNA
<213> ORGANISM: Artificial Sequence
<220> FEATURE:
<223> OTHER INFORMATION: replicating RNA species

<400> SEQUENCE: 161
ggaaaauuug uaauucaaau ugguaacaaa uuuguaauuc aaauuuguua ccaauuugaa       60
uuacaaauuu uggg                                                         74

<210> SEQ ID NO 162
<211> LENGTH: 74
<212> TYPE: RNA
<213> ORGANISM: Artificial Sequence
<220> FEATURE:
<223> OTHER INFORMATION: replicating RNA species

<400> SEQUENCE: 162
ggaaaauuuc aauaacaaaa aaucccguua uugaaaaauu uucaauaacg ggauuuuugu       60
uauugaaauu uugg                                                         74

<210> SEQ ID NO 163
<211> LENGTH: 65
<212> TYPE: RNA
<213> ORGANISM: Artificial Sequence
<220> FEATURE:
<223> OTHER INFORMATION: replicating RNA species

<400> SEQUENCE: 163
ggaaaauuca auugcuggaa aaauugaauu guuccaaauu caauuuccag caauugaauu       60
uuggg                                                                   65

<210> SEQ ID NO 164
<211> LENGTH: 83
<212> TYPE: RNA
<213> ORGANISM: Artificial Sequence
<220> FEATURE:
<223> OTHER INFORMATION: replicating RNA species

<400> SEQUENCE: 164
ggggaagaag uucucaaugu agauauuaug ugcauugaag aaguucuaaa ugcacauaau       60
aucuacauug agaacuucuu ggg                                               83

<210> SEQ ID NO 165
<211> LENGTH: 73
<212> TYPE: RNA
<213> ORGANISM: Artificial Sequence
```

-continued

```
<220> FEATURE:
<223> OTHER INFORMATION: replicating RNA species

<400> SEQUENCE: 165
ggaaaaauau caaaauacac ccuuauuuug auauaaaaua ucaaaaauaa gggguauuu      60 ugauauuuua ugg                                                       73

<210> SEQ ID NO 166
<211> LENGTH: 87
<212> TYPE: RNA
<213> ORGANISM: Artificial Sequence
<220> FEATURE:
<223> OTHER INFORMATION: replicating RNA species

<400> SEQUENCE: 166
ggaaaaauug aauuuauuga auguuuuggu cauucaauuu uuccgaaaaa uugaaugacc      60
aaaacauuca auaaauucaa uuuuugg                                         87

<210> SEQ ID NO 167
<211> LENGTH: 71
<212> TYPE: RNA
<213> ORGANISM: Artificial Sequence
<220> FEATURE:
<223> OTHER INFORMATION: replicating RNA species

<400> SEQUENCE: 167
gggauuuuuc aaucaaauga cgagagauug aaauugccaa uuucaaucuc ucgucauuug      60
auugaaauug g                                                          71

<210> SEQ ID NO 168
<211> LENGTH: 70
<212> TYPE: RNA
<213> ORGANISM: Artificial Sequence
<220> FEATURE:
<223> OTHER INFORMATION: replicating RNA species

<400> SEQUENCE: 168
ggauuuauaa ucaucgauca uaauauuaua aucgaucaau uauaauauua ugaucgauga      60
uuauaauugg                                                           70

<210> SEQ ID NO 169
<211> LENGTH: 71
<212> TYPE: RNA
<213> ORGANISM: Artificial Sequence
<220> FEATURE:
<223> OTHER INFORMATION: replicating RNA species

<400> SEQUENCE: 169 ggaaauauu uuacaucugg aauuaaaaua uuuuucucca auauuuuaa uuccgaugu      60 aaaauauuug g                                                         71

<210> SEQ ID NO 170
<211> LENGTH: 73
<212> TYPE: RNA
<213> ORGANISM: Artificial Sequence
<220> FEATURE:
<223> OTHER INFORMATION: replicating RNA species

<400> SEQUENCE: 170
gggaaaaaaa ucuaauugau cagagacaau uagauuagaa aaucuaauug ucucugauca      60
auuagauuuu ugg                                                        73
```

-continued

```
<210> SEQ ID NO 171
<211> LENGTH: 75
<212> TYPE: RNA
<213> ORGANISM: Artificial Sequence
<220> FEATURE:
<223> OTHER INFORMATION: replicating RNA species

<400> SEQUENCE: 171
ggauuauuau uauuugaauc aauucccaaa uaauaaucaa auuauuauuu gggaauugau      60
ucaaauaaua auugg                                                      75

<210> SEQ ID NO 172
<211> LENGTH: 70
<212> TYPE: RNA
<213> ORGANISM: Artificial Sequence
<220> FEATURE:
<223> OTHER INFORMATION: replicating RNA species

<400> SEQUENCE: 172
ggaaaaaauu ucauauuuuc aauuccaaua ugaaaauuuc auauuggaau ugaaaauaug      60
aaauuuucgg                                                            70

<210> SEQ ID NO 173
<211> LENGTH: 87
<212> TYPE: RNA
<213> ORGANISM: Artificial Sequence
<220> FEATURE:
<223> OTHER INFORMATION: replicating RNA species

<400> SEQUENCE: 173
ggauaaaauc uuauaucuuu caucuagaga uaugaugauu uauaucuuuc aucauaucuc      60
uagaugaaag auauaagauu uuuuugg                                          87

<210> SEQ ID NO 174
<211> LENGTH: 73
<212> TYPE: RNA
<213> ORGANISM: Artificial Sequence
<220> FEATURE:
<223> OTHER INFORMATION: replicating RNA species

<400> SEQUENCE: 174
ggaaaaauaa auuuguucca uuucacaaau uuauuccgaa uaaauuugug aaauggaaca      60
aauuuauuuu ggg                                                        73

<210> SEQ ID NO 175
<211> LENGTH: 62
<212> TYPE: RNA
<213> ORGANISM: Artificial Sequence
<220> FEATURE:
<223> OTHER INFORMATION: replicating RNA species

<400> SEQUENCE: 175
gguuuaauuu uaacauuuug ggugugguuaa uuuuaacaca cccaaaaugu uaaaauuaau     60
gg                                                                    62

<210> SEQ ID NO 176
<211> LENGTH: 81
<212> TYPE: RNA
<213> ORGANISM: Artificial Sequence
<220> FEATURE:
<223> OTHER INFORMATION: replicating RNA species

<400> SEQUENCE: 176
```

-continued

```
ggaaauauaa uauaaguuug guauuccuua uauuauauau uuauauaaua uaagugaaua      60
ccaaacuuau auuauauugg g                                               81

<210> SEQ ID NO 177
<211> LENGTH: 72
<212> TYPE: RNA
<213> ORGANISM: Artificial Sequence
<220> FEATURE:
<223> OTHER INFORMATION: replicating RNA species

<400> SEQUENCE: 177
ggauuauuuc aauguuucac uaauucauug aauuauuuca augaauuagu gaaacauuga      60
aauaaugggg gg                                                        72

<210> SEQ ID NO 178
<211> LENGTH: 75
<212> TYPE: RNA
<213> ORGANISM: Artificial Sequence
<220> FEATURE:
<223> OTHER INFORMATION: replicating RNA species

<400> SEQUENCE: 178
ggaauaauug aauaauuaga cuuauccaau uuuccaaaau uggaaaauug gauaagucua      60
auuauucaau uuugg                                                     75

<210> SEQ ID NO 179
<211> LENGTH: 75
<212> TYPE: RNA
<213> ORGANISM: Artificial Sequence
<220> FEATURE:
<223> OTHER INFORMATION: replicating RNA species

<400> SEQUENCE: 179
ggauaauuaa ucaaaugaau acaugauuaa uuaaaaugau uuaauuaauc auguauucau      60
uugauuaauu aaugg                                                     75

<210> SEQ ID NO 180
<211> LENGTH: 82
<212> TYPE: RNA
<213> ORGANISM: Artificial Sequence
<220> FEATURE:
<223> OTHER INFORMATION: replicating RNA species

<400> SEQUENCE: 180
ggaaauuuuc aauuucacau caugauccgu guuuugaauu uucaauuuca cacggaucau      60
gaugugaaau ugaaaauuua gg                                             82

<210> SEQ ID NO 181
<211> LENGTH: 99
<212> TYPE: RNA
<213> ORGANISM: Artificial Sequence
<220> FEATURE:
<223> OTHER INFORMATION: replicating RNA species

<400> SEQUENCE: 181
ggaaaaauca auucauuuga agaguuccaa aaucaauucu cuucaaauuc auugaagaga      60
auugauuuuu uggaacucuu caaaugaauu gauuuuggg                           99

<210> SEQ ID NO 182
<211> LENGTH: 75
<212> TYPE: RNA
```

```
<213> ORGANISM: Artificial Sequence
<220> FEATURE:
<223> OTHER INFORMATION: replicating RNA species

<400> SEQUENCE: 182
ggaaaauuau aucaaguaac acaaccagau auauuuuuu cuauaucugg uuguguuacu      60
ugauauaauu uuggg                                                      75

<210> SEQ ID NO 183
<211> LENGTH: 86
<212> TYPE: RNA
<213> ORGANISM: Artificial Sequence
<220> FEATURE:
<223> OTHER INFORMATION: replicating RNA species

<400> SEQUENCE: 183
ggaaugaaaa uuguuugaua agaaaggaua agcaacaauu uucugaaaau uguugcuuau      60
ccuuucuuau caaacaauuu ucuugg                                          86

<210> SEQ ID NO 184
<211> LENGTH: 85
<212> TYPE: RNA
<213> ORGANISM: Artificial Sequence
<220> FEATURE:
<223> OTHER INFORMATION: replicating RNA species

<400> SEQUENCE: 184
ggaaaauuga aaugaaaaaa uuccauuuca uuucauuuca aaaaauugaa augaaaugaa      60
auggaauuuu ucauuucaau uuugg                                           85

<210> SEQ ID NO 185
<211> LENGTH: 88
<212> TYPE: RNA
<213> ORGANISM: Artificial Sequence
<220> FEATURE:
<223> OTHER INFORMATION: replicating RNA species

<400> SEQUENCE: 185
ggaaauauac aauucuauau cauucagaua uagaaugaaa uugccaaauu uccuucuaua      60
ucugaaugau auagaauugu auauuugg                                        88

<210> SEQ ID NO 186
<211> LENGTH: 72
<212> TYPE: RNA
<213> ORGANISM: Artificial Sequence
<220> FEATURE:
<223> OTHER INFORMATION: replicating RNA species

<400> SEQUENCE: 186
ggaaauuaau ucaauuauca ucaauuaauu uggaugauuc caaauuaauu gaugauaauu      60
gaauuaauuu gg                                                         72

<210> SEQ ID NO 187
<211> LENGTH: 74
<212> TYPE: RNA
<213> ORGANISM: Artificial Sequence
<220> FEATURE:
<223> OTHER INFORMATION: replicating RNA species

<400> SEQUENCE: 187
ggaaaauuuc aaucaauucc auuccugauu gaaaauuuca aucaggaaug gaauugauug      60
aaauuuuggg gggg                                                       74
```

<210> SEQ ID NO 188
<211> LENGTH: 69
<212> TYPE: RNA
<213> ORGANISM: Artificial Sequence
<220> FEATURE:
<223> OTHER INFORMATION: replicating RNA species

<400> SEQUENCE: 188
ggaaaaaaau auaauauguc auuuccauau uauauauaau aauauggaaa ugacauauua      60
uauuuuggg                                                             69

<210> SEQ ID NO 189
<211> LENGTH: 83
<212> TYPE: RNA
<213> ORGANISM: Artificial Sequence
<220> FEATURE:
<223> OTHER INFORMATION: replicating RNA species

<400> SEQUENCE: 189
ggauuaauca aauccucaau auuuugauua auuaauauug aauuaauuaa ucaaaauauu      60
gaggauuuga uuaauuaauu cgg                                             83

<210> SEQ ID NO 190
<211> LENGTH: 69
<212> TYPE: RNA
<213> ORGANISM: Artificial Sequence
<220> FEATURE:
<223> OTHER INFORMATION: replicating RNA species

<400> SEQUENCE: 190
ggaaauuaga aucaaacguc ucaauucuaa uuccgaaauu agaauugaga cguuugauuc      60
uaauuuggg                                                             69

<210> SEQ ID NO 191
<211> LENGTH: 69
<212> TYPE: RNA
<213> ORGANISM: Artificial Sequence
<220> FEATURE:
<223> OTHER INFORMATION: replicating RNA species

<400> SEQUENCE: 191
ggauuauuag aagacaauua aacuaauaau aaucccuuua uuauuaguuu aauugucuuc      60
uaauaaagg                                                             69

<210> SEQ ID NO 192
<211> LENGTH: 69
<212> TYPE: RNA
<213> ORGANISM: Artificial Sequence
<220> FEATURE:
<223> OTHER INFORMATION: replicating RNA species

<400> SEQUENCE: 192
ggaaaauauu ugaauugcaa uucccaaaua uuuggccaaa uauuugggaa uugcaauuca      60
aauauuugg                                                             69

<210> SEQ ID NO 193
<211> LENGTH: 79
<212> TYPE: RNA
<213> ORGANISM: Artificial Sequence
<220> FEATURE:
<223> OTHER INFORMATION: replicating RNA species

<400> SEQUENCE: 193
ggaauuuaaa ucaaaguucu uauuaaauug cuuugaauuu aaaucaaagc aauuuaauaa          60
gaacuuugau uuaaauugg                                                        79

<210> SEQ ID NO 194
<211> LENGTH: 73
<212> TYPE: RNA
<213> ORGANISM: Artificial Sequence
<220> FEATURE:
<223> OTHER INFORMATION: replicating RNA species

<400> SEQUENCE: 194
ggauauuuau caucgaggug uugagagaua aaauccauua uuuaucucuc aacaccucga          60
ugauaaauaa ugg                                                             73

<210> SEQ ID NO 195
<211> LENGTH: 77
<212> TYPE: RNA
<213> ORGANISM: Artificial Sequence
<220> FEATURE:
<223> OTHER INFORMATION: replicating RNA species

<400> SEQUENCE: 195
ggaauauuca auuaauauug aaacaaaauu aauugauuua auucaauuaa uuuuguuuca          60
auauuaauug aauaugg                                                         77

<210> SEQ ID NO 196
<211> LENGTH: 61
<212> TYPE: RNA
<213> ORGANISM: Artificial Sequence
<220> FEATURE:
<223> OTHER INFORMATION: replicating RNA species

<400> SEQUENCE: 196
ggauauauuu caauauaugg uagauauauu ucaauauauc uaccauauau ugaaauauag          60
g                                                                          61

<210> SEQ ID NO 197
<211> LENGTH: 79
<212> TYPE: RNA
<213> ORGANISM: Artificial Sequence
<220> FEATURE:
<223> OTHER INFORMATION: replicating RNA species

<400> SEQUENCE: 197
ggaagaauuu guuauuuugc uucuuaacac aaauucuucc gaagaauuug uguuaagaag          60
caaaauaaca aauucuugg                                                        79

<210> SEQ ID NO 198
<211> LENGTH: 76
<212> TYPE: RNA
<213> ORGANISM: Artificial Sequence
<220> FEATURE:
<223> OTHER INFORMATION: replicating RNA species

<400> SEQUENCE: 198
ggaugaauua gagucuaccu guuaaccucc ucuaauucua cugaauuaga gguuaacagg          60
uagacucuaa uucagg                                                           76

<210> SEQ ID NO 199
<211> LENGTH: 67

-continued

```
<212> TYPE: RNA
<213> ORGANISM: Artificial Sequence
<220> FEATURE:
<223> OTHER INFORMATION: replicating RNA species

<400> SEQUENCE: 199
ggaaaauuuc aaauuucuuc acauuugaaa uuucaaauuu caaaugugaa gaaauuugaa        60
auuuggg                                                                  67

<210> SEQ ID NO 200
<211> LENGTH: 77
<212> TYPE: RNA
<213> ORGANISM: Artificial Sequence
<220> FEATURE:
<223> OTHER INFORMATION: replicating RNA species

<400> SEQUENCE: 200
ggauuucaua aacaaauucg aauguuuaug aaaucuaaga aauagauuuc auaaacauuc        60
gaauuuguuu auucugg                                                       77

<210> SEQ ID NO 201
<211> LENGTH: 81
<212> TYPE: RNA
<213> ORGANISM: Artificial Sequence
<220> FEATURE:
<223> OTHER INFORMATION: replicating RNA species

<400> SEQUENCE: 201
ggaugaauuu gauuuagauu uggcauuuau caaauucauc cgaugaauuu gauaaaugcc        60
aaaucuaaau caaauucaug g                                                  81

<210> SEQ ID NO 202
<211> LENGTH: 87
<212> TYPE: RNA
<213> ORGANISM: Artificial Sequence
<220> FEATURE:
<223> OTHER INFORMATION: replicating RNA species

<400> SEQUENCE: 202
ggaaacauug auuaauaaua cguucaauuu aucaaauguu uuccgaaaaa cauugauaaa        60
uugaacguau uauuaaucaa uguuugg                                            87

<210> SEQ ID NO 203
<211> LENGTH: 73
<212> TYPE: RNA
<213> ORGANISM: Artificial Sequence
<220> FEATURE:
<223> OTHER INFORMATION: replicating RNA species

<400> SEQUENCE: 203
ggauaaaaag aauuguuccu uucucuucuu uuuauguucc auaaaagaag agaaaggaac        60
aauucuuuua ugg                                                           73

<210> SEQ ID NO 204
<211> LENGTH: 73
<212> TYPE: RNA
<213> ORGANISM: Artificial Sequence
<220> FEATURE:
<223> OTHER INFORMATION: replicating RNA species

<400> SEQUENCE: 204
ggaaaaauac aaguuuccua uauucauugu auuuucucca aaauacaaug aauauaggaa        60
```

-continued acuuguauuu ugg                                                          73

<210> SEQ ID NO 205
<211> LENGTH: 71
<212> TYPE: RNA
<213> ORGANISM: Artificial Sequence
<220> FEATURE:
<223> OTHER INFORMATION: replicating RNA species

<400> SEQUENCE: 205
ggaaaauauu gaaucuaccg augucucaau auuuccgaaa uauugagaca ucgguagauu      60
caauauuuug g                                                           71

<210> SEQ ID NO 206
<211> LENGTH: 77
<212> TYPE: RNA
<213> ORGANISM: Artificial Sequence
<220> FEATURE:
<223> OTHER INFORMATION: replicating RNA species

<400> SEQUENCE: 206
ggaagaaaca auaauuuuuc ccuguucuuu auuguuuccc gaaacaauaa agaacaggga      60
aaauuauugu uucuugg                                                     77

<210> SEQ ID NO 207
<211> LENGTH: 68
<212> TYPE: RNA
<213> ORGANISM: Artificial Sequence
<220> FEATURE:
<223> OTHER INFORMATION: replicating RNA species

<400> SEQUENCE: 207
ggaaaauuga aauuucggaa auuuucaauu uuggaccaaa auugaaaauu uccgaaauuu      60
caauuugg                                                               68

<210> SEQ ID NO 208
<211> LENGTH: 65
<212> TYPE: RNA
<213> ORGANISM: Artificial Sequence
<220> FEATURE:
<223> OTHER INFORMATION: replicating RNA species

<400> SEQUENCE: 208
ggaauauuga auaugaauau ccauauucau gauucaugaa uauggauauu cauauucaau      60
auggg                                                                  65

<210> SEQ ID NO 209
<211> LENGTH: 75
<212> TYPE: RNA
<213> ORGANISM: Artificial Sequence
<220> FEATURE:
<223> OTHER INFORMATION: replicating RNA species

<400> SEQUENCE: 209
ggaaauuauc aauguguggu auggaucaac auugaaauua ucaauguuga uccauaccac      60
acauugauaa uuugg                                                       75

<210> SEQ ID NO 210
<211> LENGTH: 73
<212> TYPE: RNA
<213> ORGANISM: Artificial Sequence
<220> FEATURE:
<223> OTHER INFORMATION: replicating RNA species -continued

<400> SEQUENCE: 210
ggaauuuugg aauuugacaa cugguaucca aaauuccgaa uuuuggauac caguugucaa      60
auuccaaaau ugg                                                         73

<210> SEQ ID NO 211
<211> LENGTH: 71
<212> TYPE: RNA
<213> ORGANISM: Artificial Sequence
<220> FEATURE:
<223> OTHER INFORMATION: replicating RNA species

<400> SEQUENCE: 211
ggaaaaauug cuaauaucau cuugaaagca auuuucccaa auugcuuuca agaugauauu      60
agcaauuuug g                                                           71

<210> SEQ ID NO 212
<211> LENGTH: 83
<212> TYPE: RNA
<213> ORGANISM: Artificial Sequence
<220> FEATURE:
<223> OTHER INFORMATION: replicating RNA species

<400> SEQUENCE: 212
ggauaauaau cauuauuauu cccuauaaaa uaaugauuua ugaaauaauc auuauuuuau      60
agggaauaau aaugauuauu cgg                                              83

<210> SEQ ID NO 213
<211> LENGTH: 73
<212> TYPE: RNA
<213> ORGANISM: Artificial Sequence
<220> FEATURE:
<223> OTHER INFORMATION: replicating RNA species

<400> SEQUENCE: 213
ggaaaauugc aauuauuucc uuccauugca auuauuucca aauugcaaug gaaggaaaua      60
auugcaauuu ugg                                                         73

<210> SEQ ID NO 214
<211> LENGTH: 71
<212> TYPE: RNA
<213> ORGANISM: Artificial Sequence
<220> FEATURE:
<223> OTHER INFORMATION: replicating RNA species

<400> SEQUENCE: 214
ggaaauacau uuucauccaa aaaauguauu uuucauccaa aaauacauuu uuuggaugaa      60
aauguauuug g                                                           71

<210> SEQ ID NO 215
<211> LENGTH: 67
<212> TYPE: RNA
<213> ORGANISM: Artificial Sequence
<220> FEATURE:
<223> OTHER INFORMATION: replicating RNA species

<400> SEQUENCE: 215
ggaaaauuau ucaauaaau aauuggaauu auucaaauua uuccauuuau uuauuugaau       60
aauuugg                                                                67

<210> SEQ ID NO 216

```
<211> LENGTH: 63
<212> TYPE: RNA
<213> ORGANISM: Artificial Sequence
<220> FEATURE:
<223> OTHER INFORMATION: replicating RNA species

<400> SEQUENCE: 216
ggaaauaauu caauuauuua uuuaauugaa uaauucaauu aaauaaauaa uugaauuauu      60
ugg                                                                   63

<210> SEQ ID NO 217
<211> LENGTH: 72
<212> TYPE: RNA
<213> ORGANISM: Artificial Sequence
<220> FEATURE:
<223> OTHER INFORMATION: replicating RNA species

<400> SEQUENCE: 217 ggauaauua aucaacauca ugauuauuaa uuaauccaau aauuaauaau caugauguug       60
auuaauuauu gg                                                          72

<210> SEQ ID NO 218
<211> LENGTH: 89
<212> TYPE: RNA
<213> ORGANISM: Artificial Sequence
<220> FEATURE:
<223> OTHER INFORMATION: replicating RNA species

<400> SEQUENCE: 218
ggauaaucau uuauuuaugu cuuccccaau aaaauaaaug auuauccaau cauuuauuuu       60
auuggggaag acauaaauaa augauaugg                                        89

<210> SEQ ID NO 219
<211> LENGTH: 79
<212> TYPE: RNA
<213> ORGANISM: Artificial Sequence
<220> FEATURE:
<223> OTHER INFORMATION: replicating RNA species

<400> SEQUENCE: 219
ggaaaauuaa uaauccuaaa uuccaggggga uuauuuuaga aauuaauaau ccccuggaau      60
uuaggauuau uaauuucgg                                                   79

<210> SEQ ID NO 220
<211> LENGTH: 66
<212> TYPE: RNA
<213> ORGANISM: Artificial Sequence
<220> FEATURE:
<223> OTHER INFORMATION: replicating RNA species

<400> SEQUENCE: 220
ggaaaaaaau caaagagagc uuuucuuuga aucaaagaau caaagaaaag cucucuuuug      60
auuugg                                                                66

<210> SEQ ID NO 221
<211> LENGTH: 84
<212> TYPE: RNA
<213> ORGANISM: Artificial Sequence
<220> FEATURE:
<223> OTHER INFORMATION: replicating RNA species

<400> SEQUENCE: 221
ggaaaauuca acaaauucuu caauuucaaa uguugaauuu caacaaauuc aacauuugaa      60
```

-continued

```
auugaagaau uuguugaauu uugg                                         84

<210> SEQ ID NO 222
<211> LENGTH: 71
<212> TYPE: RNA
<213> ORGANISM: Artificial Sequence
<220> FEATURE:
<223> OTHER INFORMATION: replicating RNA species

<400> SEQUENCE: 222
ggaaaaauaa agauguagcu aaacgcuaua uauucccaau auauagcguu uagcuacauc   60
uuuauuuuug g                                                       71

<210> SEQ ID NO 223
<211> LENGTH: 77
<212> TYPE: RNA
<213> ORGANISM: Artificial Sequence
<220> FEATURE:
<223> OTHER INFORMATION: replicating RNA species

<400> SEQUENCE: 223
ggaauaauaa ucauugaacg gaauccucaa ugauuauuuc auuuaaucau ugaggauucc   60
guucaaugau uauucgg                                                 77

<210> SEQ ID NO 224
<211> LENGTH: 71
<212> TYPE: RNA
<213> ORGANISM: Artificial Sequence
<220> FEATURE:
<223> OTHER INFORMATION: replicating RNA species

<400> SEQUENCE: 224
ggaaaauaau uucuauuaaa uuauuugaua gaaauaauuu cuaucaaaua auuuaauaga   60
aauuauuuug g                                                       71

<210> SEQ ID NO 225
<211> LENGTH: 73
<212> TYPE: RNA
<213> ORGANISM: Artificial Sequence
<220> FEATURE:
<223> OTHER INFORMATION: replicating RNA species

<400> SEQUENCE: 225
ggauaauauu ucuaauuaac uacccauaau uagaaauauu ucuaauuaug gguaguuaau   60
uagaaauauu cgg                                                     73

<210> SEQ ID NO 226
<211> LENGTH: 67
<212> TYPE: RNA
<213> ORGANISM: Artificial Sequence
<220> FEATURE:
<223> OTHER INFORMATION: replicating RNA species

<400> SEQUENCE: 226
ggaaaaauuc aauaaucucu auuauuauug aaaaauucaa uaauaauaga gauuauugaa   60
uuuuugg                                                            67

<210> SEQ ID NO 227
<211> LENGTH: 76
<212> TYPE: RNA
<213> ORGANISM: Artificial Sequence
<220> FEATURE:
```

-continued

<223> OTHER INFORMATION: replicating RNA species

<400> SEQUENCE: 227
ggaaaaauuc aaaauuguug ucugaauuga auuauuuucc caaaauucaa uucagacaac        60
aauuuugaau uuuggg                                                         76

<210> SEQ ID NO 228
<211> LENGTH: 75
<212> TYPE: RNA
<213> ORGANISM: Artificial Sequence
<220> FEATURE:
<223> OTHER INFORMATION: replicating RNA species

<400> SEQUENCE: 228
ggaugaucaa uguguccugc aauucacaca cauugacaug aucaaugugu gaauugcagg        60
acacauugau cuugg                                                         75

<210> SEQ ID NO 229
<211> LENGTH: 75
<212> TYPE: RNA
<213> ORGANISM: Artificial Sequence
<220> FEATURE:
<223> OTHER INFORMATION: replicating RNA species

<400> SEQUENCE: 229
ggaaauauua uaaauacaua ugggagaagu uguauuauaa auacaacuuc ucccauaugu        60
auuuauaaua uuugg                                                         75

<210> SEQ ID NO 230
<211> LENGTH: 78
<212> TYPE: RNA
<213> ORGANISM: Artificial Sequence
<220> FEATURE:
<223> OTHER INFORMATION: replicating RNA species

<400> SEQUENCE: 230
ggaaaaauug gauucauaac uucgccuauc caauuuuccc gaaaauugga uaggcgaagu        60
uaugaaucca auuuuggg                                                      78

<210> SEQ ID NO 231
<211> LENGTH: 72
<212> TYPE: RNA
<213> ORGANISM: Artificial Sequence
<220> FEATURE:
<223> OTHER INFORMATION: replicating RNA species

<400> SEQUENCE: 231
ggaaaaaaau ucauucgaau gaaauugauu ucauucgaau gaaaucaauu ucauucgaau        60
gaauuuuuuu gg                                                            72

<210> SEQ ID NO 232
<211> LENGTH: 70
<212> TYPE: RNA
<213> ORGANISM: Artificial Sequence
<220> FEATURE:
<223> OTHER INFORMATION: replicating RNA species

<400> SEQUENCE: 232
ggaaaaucaa auacuugguc uauuuuauuu gauuuucuca aaauaaaaua gaccaaguau        60
uugauuuugg                                                               70

-continued

```
<210> SEQ ID NO 233
<211> LENGTH: 74
<212> TYPE: RNA
<213> ORGANISM: Artificial Sequence
<220> FEATURE:
<223> OTHER INFORMATION: replicating RNA species

<400> SEQUENCE: 233
ggaauaauuu caaacaucau uguccuuugu uugaauaauu ucaaacaaag gacaaugaug    60
uuugaaauua uugg                                                      74

<210> SEQ ID NO 234
<211> LENGTH: 67
<212> TYPE: RNA
<213> ORGANISM: Artificial Sequence
<220> FEATURE:
<223> OTHER INFORMATION: replicating RNA species

<400> SEQUENCE: 234
ggaauuuauu caauucaucu gcaauugaau uaauuuauuc aauugcagau gaauugaaua    60
aauuagg                                                              67

<210> SEQ ID NO 235
<211> LENGTH: 72
<212> TYPE: RNA
<213> ORGANISM: Artificial Sequence
<220> FEATURE:
<223> OTHER INFORMATION: replicating RNA species

<400> SEQUENCE: 235
ggauucaauu agguauucaa ucuuccccua auugaaucuc aauuaggga agauugaaua    60 ccuaauuucu gg                                                        72

<210> SEQ ID NO 236
<211> LENGTH: 67
<212> TYPE: RNA
<213> ORGANISM: Artificial Sequence
<220> FEATURE:
<223> OTHER INFORMATION: replicating RNA species

<400> SEQUENCE: 236
ggaauaucaa auuccaaua uguuuugauu uccaaauauc aaaaacauau uggaaauuug    60
auauugg                                                              67

<210> SEQ ID NO 237
<211> LENGTH: 78
<212> TYPE: RNA
<213> ORGANISM: Artificial Sequence
<220> FEATURE:
<223> OTHER INFORMATION: replicating RNA species

<400> SEQUENCE: 237
ggaaaauucc aauuuugguc gauggaaaca aaauuggaau uccaauuuug uuuccaucga    60
ccaaaauugg aauuuggg                                                  78

<210> SEQ ID NO 238
<211> LENGTH: 63
<212> TYPE: RNA
<213> ORGANISM: Artificial Sequence
<220> FEATURE:
<223> OTHER INFORMATION: replicating RNA species

<400> SEQUENCE: 238
```

-continued

```
ggaaaauauu ucucauauug ggcgauauuu cucaauaucg cccaauauga gaaauauuuu          60
ggg                                                                        63

<210> SEQ ID NO 239
<211> LENGTH: 72
<212> TYPE: RNA
<213> ORGANISM: Artificial Sequence
<220> FEATURE:
<223> OTHER INFORMATION: replicating RNA species

<400> SEQUENCE: 239
ggaaaaaaau uaucauuggu gugggaugau aauuucucga aauuaucauc ccacaccaau          60
gauaauuuuc gg                                                              72

<210> SEQ ID NO 240
<211> LENGTH: 73
<212> TYPE: RNA
<213> ORGANISM: Artificial Sequence
<220> FEATURE:
<223> OTHER INFORMATION: replicating RNA species

<400> SEQUENCE: 240
ggaaaaauuc aaauucaauc gagaauaauu ugaaucaaaa uucaaauuau ucucgauuga          60
auuugaauuu ugg                                                             73

<210> SEQ ID NO 241
<211> LENGTH: 66
<212> TYPE: RNA
<213> ORGANISM: Artificial Sequence
<220> FEATURE:
<223> OTHER INFORMATION: replicating RNA species

<400> SEQUENCE: 241
ggauuauuga uuuccaucaa caucaauaau cgcuauuauu gauguugaug gaaaucaaua          60
auaggg                                                                     66

<210> SEQ ID NO 242
<211> LENGTH: 74
<212> TYPE: RNA
<213> ORGANISM: Artificial Sequence
<220> FEATURE:
<223> OTHER INFORMATION: replicating RNA species

<400> SEQUENCE: 242
ggauuaauaa ucauuucgaa augauuucca auaaacgaaa ugauuauugg aaaucauuuc          60
gaaaugauua uugg                                                            74

<210> SEQ ID NO 243
<211> LENGTH: 70
<212> TYPE: RNA
<213> ORGANISM: Artificial Sequence
<220> FEATURE:
<223> OTHER INFORMATION: replicating RNA species

<400> SEQUENCE: 243
ggaauugaau ucaaaaucuc aauugauuuc auuccaauug aaaaucaauu gagauuuuga          60
auucaauugg                                                                 70

<210> SEQ ID NO 244
<211> LENGTH: 68
<212> TYPE: RNA
<213> ORGANISM: Artificial Sequence
```

-continued

```
<220> FEATURE:
<223> OTHER INFORMATION: replicating RNA species

<400> SEQUENCE: 244
gggaaaauuc aaaaguuucc ugaacuuuuu ugaaaauuca aaaguucagg aaacuuuuga     60
auuuuggg                                                              68

<210> SEQ ID NO 245
<211> LENGTH: 71
<212> TYPE: RNA
<213> ORGANISM: Artificial Sequence
<220> FEATURE:
<223> OTHER INFORMATION: replicating RNA species

<400> SEQUENCE: 245
ggaucauuaa uaucauuacu acagucuagu aaugauauca uuacuagacu guaguaauga     60
uauuaaucug g                                                         71

<210> SEQ ID NO 246
<211> LENGTH: 84
<212> TYPE: RNA
<213> ORGANISM: Artificial Sequence
<220> FEATURE:
<223> OTHER INFORMATION: replicating RNA species

<400> SEQUENCE: 246
ggaaaauaau ucuaauauuu gcauuuauuu uagaaaauaa uucuaauauu uucuaaaaua     60
aaugcaaaua uuagaauuau uugg                                           84

<210> SEQ ID NO 247
<211> LENGTH: 71
<212> TYPE: RNA
<213> ORGANISM: Artificial Sequence
<220> FEATURE:
<223> OTHER INFORMATION: replicating RNA species

<400> SEQUENCE: 247
ggaugaaauc uucauaauau uaucguauau auauuucaua auauauauac gauaauauua     60
ugaagauugg g                                                         71

<210> SEQ ID NO 248
<211> LENGTH: 61
<212> TYPE: RNA
<213> ORGANISM: Artificial Sequence
<220> FEATURE:
<223> OTHER INFORMATION: replicating RNA species

<400> SEQUENCE: 248
gggaauaauu aauugauuau uugaauuaau cgauuaauuc aaauaaucaa uuaauuauug     60
g                                                                    61

<210> SEQ ID NO 249
<211> LENGTH: 64
<212> TYPE: RNA
<213> ORGANISM: Artificial Sequence
<220> FEATURE:
<223> OTHER INFORMATION: replicating RNA species

<400> SEQUENCE: 249
ggaaaauuuc aaaguacuau caacuuugaa ucaaguucaa aguugauagu acuuugaauu     60
uugg                                                                 64
```

-continued

```
<210> SEQ ID NO 250
<211> LENGTH: 71
<212> TYPE: RNA
<213> ORGANISM: Artificial Sequence
<220> FEATURE:
<223> OTHER INFORMATION: replicating RNA species

<400> SEQUENCE: 250
ggaugaucaa uguguccugc aauucacauu gauucgauca augugaauug caggacacau      60
ugaucuuggg g                                                           71

<210> SEQ ID NO 251
<211> LENGTH: 61
<212> TYPE: RNA
<213> ORGANISM: Artificial Sequence
<220> FEATURE:
<223> OTHER INFORMATION: replicating RNA species

<400> SEQUENCE: 251
ggaauauuua ucaagcauuc gaaaauauau ccaauauuuu cgaaugcuug auaaauauug      60
g                                                                      61

<210> SEQ ID NO 252
<211> LENGTH: 88
<212> TYPE: RNA
<213> ORGANISM: Artificial Sequence
<220> FEATURE:
<223> OTHER INFORMATION: replicating RNA species

<400> SEQUENCE: 252
ggaaagaaau auuucuaauu aacuaccuag auuugaaaua uuucuaauau uucuaaucua      60
gguaguuaau uagaaauauu ucuuuggg                                         88

<210> SEQ ID NO 253
<211> LENGTH: 78
<212> TYPE: RNA
<213> ORGANISM: Artificial Sequence
<220> FEATURE:
<223> OTHER INFORMATION: replicating RNA species

<400> SEQUENCE: 253
gguuuaauuu aucugcauca aauucugaua aauuaauucc uuuaauuuau cagaauuuga      60
ugcagauaaa uuaaaggg                                                    78

<210> SEQ ID NO 254
<211> LENGTH: 87
<212> TYPE: RNA
<213> ORGANISM: Artificial Sequence
<220> FEATURE:
<223> OTHER INFORMATION: replicating RNA species

<400> SEQUENCE: 254
ggaugaucaa uguguccugc aauucacauu ccgugaauuc acauugaauu cacgaucaau      60
gugaauugca ggacacauug aucuugg                                          87

<210> SEQ ID NO 255
<211> LENGTH: 57
<212> TYPE: RNA
<213> ORGANISM: Artificial Sequence
<220> FEATURE:
<223> OTHER INFORMATION: replicating RNA species

<400> SEQUENCE: 255
```

```
ggaaaauauu ugaauugcaa uucccaaaua uuugggaauu gcaauucaaa uauuugg          57
```

```
<210> SEQ ID NO 256
<211> LENGTH: 73
<212> TYPE: RNA
<213> ORGANISM: Artificial Sequence
<220> FEATURE:
<223> OTHER INFORMATION: replicating RNA species

<400> SEQUENCE: 256
ggaaaaaaua auaugcaggu ggggcauauu auuuaauuaa aauaauaugc cccaccugca          60
uauuauuuuu ggg                                                            73
```

```
<210> SEQ ID NO 257
<211> LENGTH: 75
<212> TYPE: RNA
<213> ORGANISM: Artificial Sequence
<220> FEATURE:
<223> OTHER INFORMATION: replicating RNA species

<400> SEQUENCE: 257
ggauuuuauc ucucaacacc ucgaugauaa auauccccau uauuuaucau cgaggguug          60 agagauaaau aaugg                                                          75
```

```
<210> SEQ ID NO 258
<211> LENGTH: 67
<212> TYPE: RNA
<213> ORGANISM: Artificial Sequence
<220> FEATURE:
<223> OTHER INFORMATION: replicating RNA species

<400> SEQUENCE: 258
ggaaauuuca aagauuuagu aaccacuuug aaaauuucaa agugguuacu aaaucuuuga          60
aauuugg                                                                   67
```

```
<210> SEQ ID NO 259
<211> LENGTH: 70
<212> TYPE: RNA
<213> ORGANISM: Artificial Sequence
<220> FEATURE:
<223> OTHER INFORMATION: replicating RNA species

<400> SEQUENCE: 259
ggaaaauuca aaguccagug cacuuugaau uucaaaagaa auucaaagug cacuggacuu          60
ugaauucggg                                                                70
```

```
<210> SEQ ID NO 260
<211> LENGTH: 67
<212> TYPE: RNA
<213> ORGANISM: Artificial Sequence
<220> FEATURE:
<223> OTHER INFORMATION: replicating RNA species

<400> SEQUENCE: 260
ggaauauuua uauucaaacu cggaauauaa uauauauuua uauuccgagu uugaauauaa          60
auauugg                                                                   67
```

```
<210> SEQ ID NO 261
<211> LENGTH: 64
<212> TYPE: RNA
<213> ORGANISM: Artificial Sequence
<220> FEATURE:
```

<223> OTHER INFORMATION: replicating RNA species

<400> SEQUENCE: 261
ggaaauuuga uuucucaaau ucaaauuuag aauuccaaau uugaauuuga gaaaucaaau          60
uugg                                                                       64

<210> SEQ ID NO 262
<211> LENGTH: 83
<212> TYPE: RNA
<213> ORGANISM: Artificial Sequence
<220> FEATURE:
<223> OTHER INFORMATION: replicating RNA species

<400> SEQUENCE: 262
ggaauauuuc uuaauuuucu cguuguuuaa gaaauauuga uuccaauauu uucuuaaaca          60
acgagaaaau uaagaaauau ugg                                                   83

<210> SEQ ID NO 263
<211> LENGTH: 85
<212> TYPE: RNA
<213> ORGANISM: Artificial Sequence
<220> FEATURE:
<223> OTHER INFORMATION: replicating RNA species

<400> SEQUENCE: 263
ggaaugauga auucauucaa caucauugaa ugaaugauga auucauucaa uucauucaau          60
gauguugaau gaauucauca uuggg                                                 85

<210> SEQ ID NO 264
<211> LENGTH: 69
<212> TYPE: RNA
<213> ORGANISM: Artificial Sequence
<220> FEATURE:
<223> OTHER INFORMATION: replicating RNA species

<400> SEQUENCE: 264
ggaauaauuu caaucuaaau cuccagauug aauaauuuca aucuggagau uuagauugaa          60
auuauuggg                                                                   69

<210> SEQ ID NO 265
<211> LENGTH: 73
<212> TYPE: RNA
<213> ORGANISM: Artificial Sequence
<220> FEATURE:
<223> OTHER INFORMATION: replicating RNA species

<400> SEQUENCE: 265
ggaauaaaau ucaauauuuu ccuuauauau ugaauaaaau ucaauauaua aggaaaauau          60
ugaauuuuau ugg                                                              73

<210> SEQ ID NO 266
<211> LENGTH: 76
<212> TYPE: RNA
<213> ORGANISM: Artificial Sequence
<220> FEATURE:
<223> OTHER INFORMATION: replicating RNA species

<400> SEQUENCE: 266
ggaaaauuaa ucaaaucuac cugauuuuga uuugaaauua aucaaaucaa aaucagguag          60
auuugauuaa uuuugg                                                           76

<210> SEQ ID NO 267
<211> LENGTH: 81
<212> TYPE: RNA
<213> ORGANISM: Artificial Sequence
<220> FEATURE:
<223> OTHER INFORMATION: replicating RNA species

<400> SEQUENCE: 267
ggaaauaaag aauuucgauu ccuauauucu uauuuggaau uuccaaauaa agaauauagg       60
aaucgaaauu cuuuauuugg g                                                81

<210> SEQ ID NO 268
<211> LENGTH: 73
<212> TYPE: RNA
<213> ORGANISM: Artificial Sequence
<220> FEATURE:
<223> OTHER INFORMATION: replicating RNA species

<400> SEQUENCE: 268
ggaaaauuuc aauucaaauu ugccgaaauu gaaauuucaa uucaauucgg caaauuugaa       60
uugaaauuuu ggg                                                        73

<210> SEQ ID NO 269
<211> LENGTH: 76
<212> TYPE: RNA
<213> ORGANISM: Artificial Sequence
<220> FEATURE:
<223> OTHER INFORMATION: replicating RNA species

<400> SEQUENCE: 269
ggaaaaauau ucuucaaacu caauauugaa uauuuuucca aaaauauuca auauugaguu       60
ugaagaauau uuuugg                                                     76

<210> SEQ ID NO 270
<211> LENGTH: 71
<212> TYPE: RNA
<213> ORGANISM: Artificial Sequence
<220> FEATURE:
<223> OTHER INFORMATION: replicating RNA species

<400> SEQUENCE: 270
ggaauaaaua ucuguucaau uaguucccua auuuguucaa uuagggaacu aauugaacag       60
auauuuauug g                                                          71

<210> SEQ ID NO 271
<211> LENGTH: 66
<212> TYPE: RNA
<213> ORGANISM: Artificial Sequence
<220> FEATURE:
<223> OTHER INFORMATION: replicating RNA species

<400> SEQUENCE: 271
ggaaaauuca aagucaacaa uuugaauuuc uccaaaaauu caaauuguug acuuugaauu       60
uugggg                                                               66

<210> SEQ ID NO 272
<211> LENGTH: 84
<212> TYPE: RNA
<213> ORGANISM: Artificial Sequence
<220> FEATURE:
<223> OTHER INFORMATION: replicating RNA species

<400> SEQUENCE: 272

-continued

```
ggaaaauuua ucuuaucuac ccaaccugag auaaauuuug gaauuucaaa uuuaucucag      60
guuggguaga uaagauaaau uugg                                             84

<210> SEQ ID NO 273
<211> LENGTH: 70
<212> TYPE: RNA
<213> ORGANISM: Artificial Sequence
<220> FEATURE:
<223> OTHER INFORMATION: replicating RNA species

<400> SEQUENCE: 273
gggaaaaauu guuucaaaug cagcaaacaa uuuuggccaa aauuguuugc ugcauuugaa      60
acaauuuugg                                                            70

<210> SEQ ID NO 274
<211> LENGTH: 81
<212> TYPE: RNA
<213> ORGANISM: Artificial Sequence
<220> FEATURE:
<223> OTHER INFORMATION: replicating RNA species

<400> SEQUENCE: 274
ggaaaaacua uucauuuguc ucuaaucaga auagauuuuc caaaaaacua uucugauuag      60
agacaaauga auaguuuuug g                                                81

<210> SEQ ID NO 275
<211> LENGTH: 64
<212> TYPE: RNA
<213> ORGANISM: Artificial Sequence
<220> FEATURE:
<223> OTHER INFORMATION: replicating RNA species

<400> SEQUENCE: 275
ggaaaauuau caaaagucga ugauaauuuu gaccaaauua ucaucgacuu uuugauaauu      60
uugg                                                                  64

<210> SEQ ID NO 276
<211> LENGTH: 64
<212> TYPE: RNA
<213> ORGANISM: Artificial Sequence
<220> FEATURE:
<223> OTHER INFORMATION: replicating RNA species

<400> SEQUENCE: 276
ggaaaauuca aaauauuugg ugauauuuug aauucaaaau aucaccaaau auuuugaauu      60
uggg                                                                  64

<210> SEQ ID NO 277
<211> LENGTH: 93
<212> TYPE: RNA
<213> ORGANISM: Artificial Sequence
<220> FEATURE:
<223> OTHER INFORMATION: replicating RNA species

<400> SEQUENCE: 277
ggaaauacua uuucaucauu cuccugauga ugaugaaaga ugaauacuau uucaucuuuc      60
aucaucauca ggagaaugau gaaauaguau ugg                                   93

<210> SEQ ID NO 278
<211> LENGTH: 69
<212> TYPE: RNA
<213> ORGANISM: Artificial Sequence
```

<220> FEATURE:
<223> OTHER INFORMATION: replicating RNA species

<400> SEQUENCE: 278
gggaaaauua ucauuugaaa guggucaaau gaaaauuauc auuugaccac uuucaaauga        60
uaauuuugg                                                               69

<210> SEQ ID NO 279
<211> LENGTH: 74
<212> TYPE: RNA
<213> ORGANISM: Artificial Sequence
<220> FEATURE:
<223> OTHER INFORMATION: replicating RNA species

<400> SEQUENCE: 279
ggaaaauuaa acuuucacaa uccuccguga aagugauuaa acuuucacgg aggauuguga        60
aaguuuaauu uugg                                                         74

<210> SEQ ID NO 280
<211> LENGTH: 83
<212> TYPE: RNA
<213> ORGANISM: Artificial Sequence
<220> FEATURE:
<223> OTHER INFORMATION: replicating RNA species

<400> SEQUENCE: 280
ggaaauaaaa cuuuucauau ucauauugau gaaguuuuau ccaauaaaac uucaucaaua        60
ugaauaugaa aaguuuuauu ugg                                               83

<210> SEQ ID NO 281
<211> LENGTH: 72
<212> TYPE: RNA
<213> ORGANISM: Artificial Sequence
<220> FEATURE:
<223> OTHER INFORMATION: replicating RNA species

<400> SEQUENCE: 281
ggaaaaauuc aucaauggag aauguaugaa uuuuguccua aaauucauac auucuccauu        60
gaugaauuuu gg                                                           72

<210> SEQ ID NO 282
<211> LENGTH: 70
<212> TYPE: RNA
<213> ORGANISM: Artificial Sequence
<220> FEATURE:
<223> OTHER INFORMATION: replicating RNA species

<400> SEQUENCE: 282
ggggaaaauu gaucauagua guucaucaau uuuucuugca aaauugauga acuacuauga        60
ucaauuuugg                                                              70

<210> SEQ ID NO 283
<211> LENGTH: 77
<212> TYPE: RNA
<213> ORGANISM: Artificial Sequence
<220> FEATURE:
<223> OTHER INFORMATION: replicating RNA species

<400> SEQUENCE: 283
ggaaaauuug auggacuuau gcauacuuca aauuuucccg aaaauuugaa guaugcauaa        60
guccaucaaa uuuuggg                                                      77

<210> SEQ ID NO 284
<211> LENGTH: 84
<212> TYPE: RNA
<213> ORGANISM: Artificial Sequence
<220> FEATURE:
<223> OTHER INFORMATION: replicating RNA species

<400> SEQUENCE: 284
ggaaaauuaa uuugguacca uacuucaccc aaauuaauuu uugaaauuug aauuugguga      60 aguauggguac caaauuaauu uugg                                          84

<210> SEQ ID NO 285
<211> LENGTH: 66
<212> TYPE: RNA
<213> ORGANISM: Artificial Sequence
<220> FEATURE:
<223> OTHER INFORMATION: replicating RNA species

<400> SEQUENCE: 285
ggaauuaguu caauguauuu uugacaauga auuaguucaa ugucaaaaau acauugaacu      60
aauugg                                                              66

<210> SEQ ID NO 286
<211> LENGTH: 88
<212> TYPE: RNA
<213> ORGANISM: Artificial Sequence
<220> FEATURE:
<223> OTHER INFORMATION: replicating RNA species

<400> SEQUENCE: 286
ggaaaauuuc auauuguuaa uuacacaaua ugaacaauau gaaauuucau auuguucaua      60
uuguguaauu aacaauauga aauuucgg                                      88

<210> SEQ ID NO 287
<211> LENGTH: 93
<212> TYPE: RNA
<213> ORGANISM: Artificial Sequence
<220> FEATURE:
<223> OTHER INFORMATION: replicating RNA species

<400> SEQUENCE: 287
ggaaaguuaa auaaauaaau ucaaauucaa auucuauuua ucuuuuccaa aguuaaauag      60
aauuugaauu ugaauuuauu uauuuaacuu ugg                                93

<210> SEQ ID NO 288
<211> LENGTH: 79
<212> TYPE: RNA
<213> ORGANISM: Artificial Sequence
<220> FEATURE:
<223> OTHER INFORMATION: replicating RNA species

<400> SEQUENCE: 288
ggaaauauuu ccuauuuggg uaguuaggaa auauuuuacc caaauauuuc ccuaacuacc      60
caaauaggaa auauuuggg                                                79

<210> SEQ ID NO 289
<211> LENGTH: 68
<212> TYPE: RNA
<213> ORGANISM: Artificial Sequence
<220> FEATURE:
<223> OTHER INFORMATION: replicating RNA species

<400> SEQUENCE: 289

```
ggaaaaauua gauucugcua ucaaucuaau uuuccuaaau uagauugaua gcagaaucua      60
auuuuagg                                                              68

<210> SEQ ID NO 290
<211> LENGTH: 73
<212> TYPE: RNA
<213> ORGANISM: Artificial Sequence
<220> FEATURE:
<223> OTHER INFORMATION: replicating RNA species

<400> SEQUENCE: 290
ggaauaucaa aaucuaauua ggaggcuaga uuugaaauau caaaucuagc cuccuaauua      60
gauuugauau ugg                                                        73

<210> SEQ ID NO 291
<211> LENGTH: 65
<212> TYPE: RNA
<213> ORGANISM: Artificial Sequence
<220> FEATURE:
<223> OTHER INFORMATION: replicating RNA species

<400> SEQUENCE: 291
ggaaauucaa ucugaugacu uugaauuuca aucugaaaaa uucaaaguca ucagauugaa      60
uuugg                                                                65

<210> SEQ ID NO 292
<211> LENGTH: 67
<212> TYPE: RNA
<213> ORGANISM: Artificial Sequence
<220> FEATURE:
<223> OTHER INFORMATION: replicating RNA species

<400> SEQUENCE: 292
ggaauauuca aaugcguugg auuugaauau ucaaugcaau auucaaaucc aacgcauuga      60
auauugg                                                              67

<210> SEQ ID NO 293
<211> LENGTH: 80
<212> TYPE: RNA
<213> ORGANISM: Artificial Sequence
<220> FEATURE:
<223> OTHER INFORMATION: replicating RNA species

<400> SEQUENCE: 293
ggaaauuuga aagaagauuu gcuaaaauuc aaauuuccaa auugaaauuu gaauuuuuag      60
caaaucuucu uucaaauugg                                                 80

<210> SEQ ID NO 294
<211> LENGTH: 98
<212> TYPE: RNA
<213> ORGANISM: Artificial Sequence
<220> FEATURE:
<223> OTHER INFORMATION: replicating RNA species

<400> SEQUENCE: 294
ggauauuuuc aauuuguaua gcaagucaau acaaaacaaa auugacauau uuucaauuug      60
uuuuuguauu gacuugcuau acaaauugaa aauauggg                             98

<210> SEQ ID NO 295
<211> LENGTH: 84
<212> TYPE: RNA
```

-continued

<213> ORGANISM: Artificial Sequence
<220> FEATURE:
<223> OTHER INFORMATION: replicating RNA species

<400> SEQUENCE: 295
ggaugaugaa uacuucuaac auugugaucc caguauucau cggaugaaua cugggaucac    60
aauguuagaa guauucaucu uggg    84

<210> SEQ ID NO 296
<211> LENGTH: 85
<212> TYPE: RNA
<213> ORGANISM: Artificial Sequence
<220> FEATURE:
<223> OTHER INFORMATION: replicating RNA species

<400> SEQUENCE: 296
gggaaaacaa auugaaaauu guggcauuca caauuuguuu cccaaaaaca aauugugaau    60
gccacaauuu ucaauuuguu uuggg    85

<210> SEQ ID NO 297
<211> LENGTH: 65
<212> TYPE: RNA
<213> ORGANISM: Artificial Sequence
<220> FEATURE:
<223> OTHER INFORMATION: replicating RNA species

<400> SEQUENCE: 297
ggaaaauauu caaauuuuga augaauucaa auuuugaauu cauucaaaau uugaauauuu    60
ugggg    65

<210> SEQ ID NO 298
<211> LENGTH: 84
<212> TYPE: RNA
<213> ORGANISM: Artificial Sequence
<220> FEATURE:
<223> OTHER INFORMATION: replicating RNA species

<400> SEQUENCE: 298
ggaauaaaau uguuuauuu gguuauuuuu cacauuuuua uucccuaaaa augugaaaaa    60
uaaccaaaua aacacauuuu aggg    84

<210> SEQ ID NO 299
<211> LENGTH: 72
<212> TYPE: RNA
<213> ORGANISM: Artificial Sequence
<220> FEATURE:
<223> OTHER INFORMATION: replicating RNA species

<400> SEQUENCE: 299
ggaaaaauuc auauuauaga aaugaauaau augaaaaauu cauauuauuc auuucuauaa    60
uaugaauuuu gg    72

<210> SEQ ID NO 300
<211> LENGTH: 94
<212> TYPE: RNA
<213> ORGANISM: Artificial Sequence
<220> FEATURE:
<223> OTHER INFORMATION: replicating RNA species

<400> SEQUENCE: 300
ggaagaauca aaugaauacu gugaugaaca guguuuuagu ucuuccgaag aacuaaaaaa    60
cacuguucau cacaguauuc auuugauucu uggg    94

```
<210> SEQ ID NO 301
<211> LENGTH: 92
<212> TYPE: RNA
<213> ORGANISM: Artificial Sequence
<220> FEATURE:
<223> OTHER INFORMATION: replicating RNA species

<400> SEQUENCE: 301
ggaauauucu ucaaucuucu accuagauug auuggauuga uugcaauauu cuucaaucca      60
aucaaucuag guagaagauu gaagaauauu gg                                   92

<210> SEQ ID NO 302
<211> LENGTH: 98
<212> TYPE: RNA
<213> ORGANISM: Artificial Sequence
<220> FEATURE:
<223> OTHER INFORMATION: replicating RNA species

<400> SEQUENCE: 302
ggaaauauuu cauauuaugu auggaaucau aauuuuaaua ugaugaauau uucauauuaa      60
aaaaaauuau gauuccauac auaauaugaa auauuugg                             98

<210> SEQ ID NO 303
<211> LENGTH: 61
<212> TYPE: RNA
<213> ORGANISM: Artificial Sequence
<220> FEATURE:
<223> OTHER INFORMATION: replicating RNA species

<400> SEQUENCE: 303
ggaaauugca aauauacaau ucuauaucau ucgauauaga auuguauauu gaauuuuuug      60
g                                                                    61

<210> SEQ ID NO 304
<211> LENGTH: 98
<212> TYPE: RNA
<213> ORGANISM: Artificial Sequence
<220> FEATURE:
<223> OTHER INFORMATION: replicating RNA species

<400> SEQUENCE: 304
ggaaaaauca auaauaucuu uccaaucugg aaagauauua uugggauauu auuuccaaua      60
auaucuuucc agauuggaaa gauauuauug auuuuugg                             98

<210> SEQ ID NO 305
<211> LENGTH: 73
<212> TYPE: RNA
<213> ORGANISM: Artificial Sequence
<220> FEATURE:
<223> OTHER INFORMATION: replicating RNA species

<400> SEQUENCE: 305
ggaaauuuuc aauaauuaau ucccaaauua uugaaauuuu caauaauuug ggaauuaauu      60
auugaaaauu ugg                                                       73

<210> SEQ ID NO 306
<211> LENGTH: 71
<212> TYPE: RNA
<213> ORGANISM: Artificial Sequence
<220> FEATURE:
<223> OTHER INFORMATION: replicating RNA species
```

-continued

```
<400> SEQUENCE: 306 ggaauaaauau gaaauggaau ggauuccuau uauuccgaau aauaugaauc cauuccauuu      60
cauauuauug g                                                           71

<210> SEQ ID NO 307
<211> LENGTH: 73
<212> TYPE: RNA
<213> ORGANISM: Artificial Sequence
<220> FEATURE:
<223> OTHER INFORMATION: replicating RNA species

<400> SEQUENCE: 307
ggaauaaauc auuaaauauc auuaucgaug auuuauccau aaaucaucga uaaugauauu      60
uaaugauuua ugg                                                         73

<210> SEQ ID NO 308
<211> LENGTH: 75
<212> TYPE: RNA
<213> ORGANISM: Artificial Sequence
<220> FEATURE:
<223> OTHER INFORMATION: replicating RNA species

<400> SEQUENCE: 308
ggaauauuca uucaauauuc aucuauugaa uauauucauu caauauucaa uagaugaaua      60
uugaaugaau auugg                                                       75

<210> SEQ ID NO 309
<211> LENGTH: 70
<212> TYPE: RNA
<213> ORGANISM: Artificial Sequence
<220> FEATURE:
<223> OTHER INFORMATION: replicating RNA species

<400> SEQUENCE: 309
ggaaauuaua uugagcuucc aauccucaau auaauuuuau auugaggauu ggaagcucaa      60
uauaauuugg                                                             70

<210> SEQ ID NO 310
<211> LENGTH: 73
<212> TYPE: RNA
<213> ORGANISM: Artificial Sequence
<220> FEATURE:
<223> OTHER INFORMATION: replicating RNA species

<400> SEQUENCE: 310
ggaaauuauu ucuauguacc auuuugaauu aauuucccaa auuauuucaa aaugguacau      60
agaaauaauu ugg                                                         73

<210> SEQ ID NO 311
<211> LENGTH: 70
<212> TYPE: RNA
<213> ORGANISM: Artificial Sequence
<220> FEATURE:
<223> OTHER INFORMATION: replicating RNA species

<400> SEQUENCE: 311
ggaauauuau cacaauaauu uccauuuugu gaauauuauc acaaaugga aauuauugug      60 auaauauugg                                                             70

<210> SEQ ID NO 312
<211> LENGTH: 64
```

```
<212> TYPE: RNA
<213> ORGANISM: Artificial Sequence
<220> FEATURE:
<223> OTHER INFORMATION: replicating RNA species

<400> SEQUENCE: 312
ggaaauaauu aauuaagaag auuaauuauu accuaauaau uaaucuucuu aauuaauuau     60
uugg                                                                 64

<210> SEQ ID NO 313
<211> LENGTH: 67
<212> TYPE: RNA
<213> ORGANISM: Artificial Sequence
<220> FEATURE:
<223> OTHER INFORMATION: replicating RNA species

<400> SEQUENCE: 313
ggaaauauuc aaaugagaaa auaucauuug aaauauucaa augauauuuu cucauuugaa     60
uauuugg                                                              67

<210> SEQ ID NO 314
<211> LENGTH: 72
<212> TYPE: RNA
<213> ORGANISM: Artificial Sequence
<220> FEATURE:
<223> OTHER INFORMATION: replicating RNA species

<400> SEQUENCE: 314
ggaaauuaau caaauuaauu aauugauuug auuucaaauu aaucaaauca auuaauuaau     60
uugauuaauu gg                                                        72

<210> SEQ ID NO 315
<211> LENGTH: 77
<212> TYPE: RNA
<213> ORGANISM: Artificial Sequence
<220> FEATURE:
<223> OTHER INFORMATION: replicating RNA species

<400> SEQUENCE: 315
ggaaaauuuc auguugaauu ccaaucccaa caacaugaaa auuucauguu gggauuggaa     60
uucaacauga aauuugg                                                   77

<210> SEQ ID NO 316
<211> LENGTH: 74
<212> TYPE: RNA
<213> ORGANISM: Artificial Sequence
<220> FEATURE:
<223> OTHER INFORMATION: replicating RNA species

<400> SEQUENCE: 316
gggaaaauuc aauugaaauc aauuggaauc aauuaaaauu caauugauuc caauugauuu     60
caauugaauu uugg                                                      74

<210> SEQ ID NO 317
<211> LENGTH: 83
<212> TYPE: RNA
<213> ORGANISM: Artificial Sequence
<220> FEATURE:
<223> OTHER INFORMATION: replicating RNA species

<400> SEQUENCE: 317
ggaaugaauc aaauaauuca uucaaugaau caaauaauuc gaugaauuau uugauucauu     60
```

-continued auugaaugaa uuauuuugaa ugg                                                              83

<210> SEQ ID NO 318
<211> LENGTH: 76
<212> TYPE: RNA
<213> ORGANISM: Artificial Sequence
<220> FEATURE:
<223> OTHER INFORMATION: replicating RNA species

<400> SEQUENCE: 318
ggaaaaauag aauucaaguu aaacuauuuu cuauuuuucc aaaauagaaa auaguuuaac          60
uugaauucua uuuugg                                                                      76

<210> SEQ ID NO 319
<211> LENGTH: 81
<212> TYPE: RNA
<213> ORGANISM: Artificial Sequence
<220> FEATURE:
<223> OTHER INFORMATION: replicating RNA species

<400> SEQUENCE: 319
ggaaaauuau aauuggauuu ggauagacaa uuauaauuug caaaauuaua auugcuauc          60 caaauccaau uauaauuugg g                                                                81

<210> SEQ ID NO 320
<211> LENGTH: 67
<212> TYPE: RNA
<213> ORGANISM: Artificial Sequence
<220> FEATURE:
<223> OTHER INFORMATION: replicating RNA species

<400> SEQUENCE: 320
ggaaaauuau cuauacaucu ccgauaauuu ucuuuccaaa uuaucggaga uguauagaua          60
auuuggg                                                                                67

<210> SEQ ID NO 321
<211> LENGTH: 69
<212> TYPE: RNA
<213> ORGANISM: Artificial Sequence
<220> FEATURE:
<223> OTHER INFORMATION: replicating RNA species

<400> SEQUENCE: 321
ggaaauugaa ucaauuagau gauuuaauug aaauugaauc aauuaaauca ucuaauugau          60
ucaauuugg                                                                              69

<210> SEQ ID NO 322
<211> LENGTH: 70
<212> TYPE: RNA
<213> ORGANISM: Artificial Sequence
<220> FEATURE:
<223> OTHER INFORMATION: replicating RNA species

<400> SEQUENCE: 322
gggaauuuca uaaguucauc guuugcuuau gaaacaauuu cauaagcaaa cgaugaacuu          60
augaaauugg                                                                             70

<210> SEQ ID NO 323
<211> LENGTH: 60
<212> TYPE: RNA
<213> ORGANISM: Artificial Sequence
<220> FEATURE:
<223> OTHER INFORMATION: replicating RNA species -continued

<400> SEQUENCE: 323
gggaagauau aucaaagaaa uauauuuuc ccaaaaauau auuucuuuga uauaucuugg          60

<210> SEQ ID NO 324
<211> LENGTH: 71
<212> TYPE: RNA
<213> ORGANISM: Artificial Sequence
<220> FEATURE:
<223> OTHER INFORMATION: replicating RNA species

<400> SEQUENCE: 324
ggaaaauuua ucuuugguaa auuugauaaa uuuuaaucca aauuuaucaa auuuaccaaa          60
gauaaauuug g                                                             71

<210> SEQ ID NO 325
<211> LENGTH: 72
<212> TYPE: RNA
<213> ORGANISM: Artificial Sequence
<220> FEATURE:
<223> OTHER INFORMATION: replicating RNA species

<400> SEQUENCE: 325
ggaaauuuca auuucaauug gaauuaauug aaauuucaau uucaauuaau uccaauugaa          60
auugaaauuu gg                                                            72

<210> SEQ ID NO 326
<211> LENGTH: 68
<212> TYPE: RNA
<213> ORGANISM: Artificial Sequence
<220> FEATURE:
<223> OTHER INFORMATION: replicating RNA species

<400> SEQUENCE: 326
ggaaaauuug uuauguaugc auuggacaaa uuuucccaau uuguccaaug cauacauaac          60
aaauuggg                                                                 68

<210> SEQ ID NO 327
<211> LENGTH: 90
<212> TYPE: RNA
<213> ORGANISM: Artificial Sequence
<220> FEATURE:
<223> OTHER INFORMATION: replicating RNA species

<400> SEQUENCE: 327
ggaaauucaa uuucaauuac aauugaguug uaauugaauu ugguuaucca aauucaauua          60
caacucaauu guaauugaaa uugaauuugg                                          90

<210> SEQ ID NO 328
<211> LENGTH: 77
<212> TYPE: RNA
<213> ORGANISM: Artificial Sequence
<220> FEATURE:
<223> OTHER INFORMATION: replicating RNA species

<400> SEQUENCE: 328
ggaauaauau cuauuuauua uuauugauag auauuauuua auaauaucua ucaauaauaa          60
uaaauagaua uuauugg                                                       77

<210> SEQ ID NO 329
<211> LENGTH: 67
<212> TYPE: RNA

-continued

<213> ORGANISM: Artificial Sequence
<220> FEATURE:
<223> OTHER INFORMATION: replicating RNA species

<400> SEQUENCE: 329
ggaauuaauu ucaauucuau ucaguaauug auuaauuuca auuacugaau agaauugaaa        60
uuaaugg                                                                  67

<210> SEQ ID NO 330
<211> LENGTH: 82
<212> TYPE: RNA
<213> ORGANISM: Artificial Sequence
<220> FEATURE:
<223> OTHER INFORMATION: replicating RNA species

<400> SEQUENCE: 330
ggaaauuuau cauauucaug gggguagauca uauaugauga auuuaucaua uaugaucuac        60
cccaugaaua ugauaaauuu gg                                                  82

<210> SEQ ID NO 331
<211> LENGTH: 66
<212> TYPE: RNA
<213> ORGANISM: Artificial Sequence
<220> FEATURE:
<223> OTHER INFORMATION: replicating RNA species

<400> SEQUENCE: 331
ggauuuaauc uuugccucua aaaagauuaa uccauuuaau cuuuuuuaga ggcaaagauu        60
aaaugg                                                                   66

<210> SEQ ID NO 332
<211> LENGTH: 66
<212> TYPE: RNA
<213> ORGANISM: Artificial Sequence
<220> FEATURE:
<223> OTHER INFORMATION: replicating RNA species

<400> SEQUENCE: 332
gggauauuau cauauauguu ugaugacaua uaucauauau gucaucaaac auauaugaua        60
auaagg                                                                   66

<210> SEQ ID NO 333
<211> LENGTH: 76
<212> TYPE: RNA
<213> ORGANISM: Artificial Sequence
<220> FEATURE:
<223> OTHER INFORMATION: replicating RNA species

<400> SEQUENCE: 333
ggaaaauuau uuucaaauaa aggucucuau uaauuauuuu caaauaauag agaccuuuau        60
uugaaaauaa uuuugg                                                         76

<210> SEQ ID NO 334
<211> LENGTH: 65
<212> TYPE: RNA
<213> ORGANISM: Artificial Sequence
<220> FEATURE:
<223> OTHER INFORMATION: replicating RNA species

<400> SEQUENCE: 334
ggaaaauuuc aaauugaaaa ucaaauuuga aaauuucaaa uuugauuuuc aauuugaauu        60
uuugg                                                                    65

-continued

```
<210> SEQ ID NO 335
<211> LENGTH: 67
<212> TYPE: RNA
<213> ORGANISM: Artificial Sequence
<220> FEATURE:
<223> OTHER INFORMATION: replicating RNA species

<400> SEQUENCE: 335
ggaaaaauua ucauguacuc uaauccauga uaaaauuauc auggauuaga guacaugaua      60
auuuugg                                                              67

<210> SEQ ID NO 336
<211> LENGTH: 60
<212> TYPE: RNA
<213> ORGANISM: Artificial Sequence
<220> FEATURE:
<223> OTHER INFORMATION: replicating RNA species

<400> SEQUENCE: 336
ggaaaaauua gaaagaaaac cuaauuuuuc caaaaauuag guuuucuuuc uaauuuuugg      60

<210> SEQ ID NO 337
<211> LENGTH: 78
<212> TYPE: RNA
<213> ORGANISM: Artificial Sequence
<220> FEATURE:
<223> OTHER INFORMATION: replicating RNA species

<400> SEQUENCE: 337
gggaaauuug gauucucuuc ucuuccuaau ccaaauuucc caaauuugga uuaggaagag      60
aagagaaucc aaauuugg                                                  78

<210> SEQ ID NO 338
<211> LENGTH: 61
<212> TYPE: RNA
<213> ORGANISM: Artificial Sequence
<220> FEATURE:
<223> OTHER INFORMATION: replicating RNA species

<400> SEQUENCE: 338
ggaaauuuga uuaauucauu uggaaauuug auuaauuucc aaaugaauua aucaaauuug      60
g                                                                    61

<210> SEQ ID NO 339
<211> LENGTH: 72
<212> TYPE: RNA
<213> ORGANISM: Artificial Sequence
<220> FEATURE:
<223> OTHER INFORMATION: replicating RNA species

<400> SEQUENCE: 339
gggaaauuuc uuucaacaga gauaguuugu ugaauuucuu ucaacaaacu aucucuguug      60
aaagaaauuu gg                                                        72

<210> SEQ ID NO 340
<211> LENGTH: 73
<212> TYPE: RNA
<213> ORGANISM: Artificial Sequence
<220> FEATURE:
<223> OTHER INFORMATION: replicating RNA species

<400> SEQUENCE: 340
```

```
ggaaauuuca ucuugaauug uaaucccgag auuaaauuuc aucucgggau uacaauucaa      60
gaugaaauuu ggg                                                        73

<210> SEQ ID NO 341
<211> LENGTH: 95
<212> TYPE: RNA
<213> ORGANISM: Artificial Sequence
<220> FEATURE:
<223> OTHER INFORMATION: replicating RNA species

<400> SEQUENCE: 341
ggaaauuauc uuaauuaucu uaucaaauua gauaagauaa gauaauuauc uaucuuaucu      60
uaucuaauuu gauaagauaa uuaagauaau uuggg                                95

<210> SEQ ID NO 342
<211> LENGTH: 76
<212> TYPE: RNA
<213> ORGANISM: Artificial Sequence
<220> FEATURE:
<223> OTHER INFORMATION: replicating RNA species

<400> SEQUENCE: 342
ggauaauaau ggauuauugg ugauguucca uuauuauccg auaauaaugg aacaucacca      60
auaauccauu auuagg                                                     76

<210> SEQ ID NO 343
<211> LENGTH: 63
<212> TYPE: RNA
<213> ORGANISM: Artificial Sequence
<220> FEATURE:
<223> OTHER INFORMATION: replicating RNA species

<400> SEQUENCE: 343
ggauuugaau caaaucaaau caaaucaaau cauuugauuu gauuugauuu gcuaaucaaa      60
ugg                                                                   63

<210> SEQ ID NO 344
<211> LENGTH: 76
<212> TYPE: RNA
<213> ORGANISM: Artificial Sequence
<220> FEATURE:
<223> OTHER INFORMATION: replicating RNA species

<400> SEQUENCE: 344
ggaaaugaaa uaauauccau cauucuauua uuuuuuccaa augaaauaau agaaugaugg      60
auauuauuuc auuugg                                                     76

<210> SEQ ID NO 345
<211> LENGTH: 72
<212> TYPE: RNA
<213> ORGANISM: Artificial Sequence
<220> FEATURE:
<223> OTHER INFORMATION: replicating RNA species

<400> SEQUENCE: 345
ggaaaauuac aaaguuccag uguaauuuug uaauuuccaa uuacaaaauu acacuggaac      60
uuuguaauuu gg                                                         72

<210> SEQ ID NO 346
<211> LENGTH: 82
<212> TYPE: RNA
<213> ORGANISM: Artificial Sequence
```

US 12,612,658 B2

-continued

```
<220> FEATURE:
<223> OTHER INFORMATION: replicating RNA species

<400> SEQUENCE: 346
ggaaaauaau ggaucaaaua acuguaucau ucauuauuuu ccaaaauaau gaaugauaca      60
guuauuugau ccauuauuuu gg                                               82

<210> SEQ ID NO 347
<211> LENGTH: 81
<212> TYPE: RNA
<213> ORGANISM: Artificial Sequence
<220> FEATURE:
<223> OTHER INFORMATION: replicating RNA species

<400> SEQUENCE: 347
ggaaugaaua uacaggauaa auuauucacu ucauguauau ucauucccau gaagugaaua      60
auuuauccug uauauucaug g                                                81

<210> SEQ ID NO 348
<211> LENGTH: 82
<212> TYPE: RNA
<213> ORGANISM: Artificial Sequence
<220> FEATURE:
<223> OTHER INFORMATION: replicating RNA species

<400> SEQUENCE: 348
ggaaauaaau uagucuuucc uaaauaauua gacuaaauua aauaaauuag ucuaauuauu      60
uaggaaagac uaauuuauuu gg                                               82

<210> SEQ ID NO 349
<211> LENGTH: 74
<212> TYPE: RNA
<213> ORGANISM: Artificial Sequence
<220> FEATURE:
<223> OTHER INFORMATION: replicating RNA species

<400> SEQUENCE: 349
ggaaauauau auuugguuuu ucauccccaa auauauauuu auauuugggg augaaaacca      60
aauauauauu uggg                                                        74

<210> SEQ ID NO 350
<211> LENGTH: 81
<212> TYPE: RNA
<213> ORGANISM: Artificial Sequence
<220> FEATURE:
<223> OTHER INFORMATION: replicating RNA species

<400> SEQUENCE: 350
ggaaaauuua ggagugcuug uaaguuucca uccuaauuuu cccaauuuag gauggaaacu      60
uacaagcacu ccuaaauuug g                                                81

<210> SEQ ID NO 351
<211> LENGTH: 92
<212> TYPE: RNA
<213> ORGANISM: Artificial Sequence
<220> FEATURE:
<223> OTHER INFORMATION: replicating RNA species

<400> SEQUENCE: 351
ggaaauauuc aaaagauuuc auccuuuuga auauuuucuu ugaaauauuc aaaagaaaau      60
auucaaaagg augaaaucuu uugaauauuu gg                                    92
```

-continued

```
<210> SEQ ID NO 352
<211> LENGTH: 87
<212> TYPE: RNA
<213> ORGANISM: Artificial Sequence
<220> FEATURE:
<223> OTHER INFORMATION: replicating RNA species

<400> SEQUENCE: 352
ggagaaauaa auuugguaua cugcacauuu caauuuauuu cucgagaaau aaauugaaau    60
gugcaguaua ccaaauuuau uucuggg                                       87

<210> SEQ ID NO 353
<211> LENGTH: 63
<212> TYPE: RNA
<213> ORGANISM: Artificial Sequence
<220> FEATURE:
<223> OTHER INFORMATION: replicating RNA species

<400> SEQUENCE: 353
ggaaaauuug auucaaauac uucauauuug auucaaauau gaaguauuug aaucaaauuu    60
ugg                                                                 63

<210> SEQ ID NO 354
<211> LENGTH: 64
<212> TYPE: RNA
<213> ORGANISM: Artificial Sequence
<220> FEATURE:
<223> OTHER INFORMATION: replicating RNA species

<400> SEQUENCE: 354
gggaaaauuc auuucauuug caaaugaauu cauuucaauu cauuugcaaa ugaaaugaau    60
uugg                                                                64

<210> SEQ ID NO 355
<211> LENGTH: 83
<212> TYPE: RNA
<213> ORGANISM: Artificial Sequence
<220> FEATURE:
<223> OTHER INFORMATION: replicating RNA species

<400> SEQUENCE: 355
ggaaaucaaa uuaucuucau ccccauuuca gauaauuuga gaaucaaauu aucugaaaug    60
gggaugaaga uaauuugauu ugg                                           83

<210> SEQ ID NO 356
<211> LENGTH: 76
<212> TYPE: RNA
<213> ORGANISM: Artificial Sequence
<220> FEATURE:
<223> OTHER INFORMATION: replicating RNA species

<400> SEQUENCE: 356
ggaauauugg uuuugguauu ugcacuuucc aauauucccc aauauuggaa agugcaaaua    60
ccaaaaccaa uauugg                                                   76

<210> SEQ ID NO 357
<211> LENGTH: 84
<212> TYPE: RNA
<213> ORGANISM: Artificial Sequence
<220> FEATURE:
<223> OTHER INFORMATION: replicating RNA species

<400> SEQUENCE: 357
```

-continued

```
ggaaauugca auguuagauu cuuuccucaa auugcaauuu caguuuuuuc caauuugagg      60
aaagaaucua acauugcaau uugg                                            84

<210> SEQ ID NO 358
<211> LENGTH: 63
<212> TYPE: RNA
<213> ORGANISM: Artificial Sequence
<220> FEATURE:
<223> OTHER INFORMATION: replicating RNA species

<400> SEQUENCE: 358
gggaaauuau ucauaguucu gccuaugaaa auuauucaua ggcagaacua ugaauaauuu      60
agg                                                                   63

<210> SEQ ID NO 359
<211> LENGTH: 87
<212> TYPE: RNA
<213> ORGANISM: Artificial Sequence
<220> FEATURE:
<223> OTHER INFORMATION: replicating RNA species

<400> SEQUENCE: 359
ggauauucaa aucauuagca aauccuaaug augauuugaa auccauauuc aaaucaucau      60
uaggauuugc uaaugauuug aauaugg                                         87

<210> SEQ ID NO 360
<211> LENGTH: 73
<212> TYPE: RNA
<213> ORGANISM: Artificial Sequence
<220> FEATURE:
<223> OTHER INFORMATION: replicating RNA species

<400> SEQUENCE: 360
ggaaauuuug gaaauugaau ggaauccaaa auuuuccgaa auuuuggauu ccauucaauu      60
uccaaaauuu ggg                                                        73

<210> SEQ ID NO 361
<211> LENGTH: 74
<212> TYPE: RNA
<213> ORGANISM: Artificial Sequence
<220> FEATURE:
<223> OTHER INFORMATION: replicating RNA species

<400> SEQUENCE: 361 gggaaaugg aauugaaugg aaauuuccau uuuccaaaug gaaaaugaug aaauuuccau       60
ucaauuccau uugg                                                       74

<210> SEQ ID NO 362
<211> LENGTH: 91
<212> TYPE: RNA
<213> ORGANISM: Artificial Sequence
<220> FEATURE:
<223> OTHER INFORMATION: replicating RNA species

<400> SEQUENCE: 362
ggaaaauuca aauaauuaga gauugcauau uauuugaauu gauugcauau aaauucaaau      60
aauaugcaau cucuaauuau uugaauuuug g                                    91

<210> SEQ ID NO 363
<211> LENGTH: 66
<212> TYPE: RNA
```

<213> ORGANISM: Artificial Sequence
<220> FEATURE:
<223> OTHER INFORMATION: replicating RNA species

<400> SEQUENCE: 363
ggaaaauuca aaauucgaau uugaauuugg aaaauuucca aauucaaauu cgaauuuuga      60
auuugg                                                                66

<210> SEQ ID NO 364
<211> LENGTH: 63
<212> TYPE: RNA
<213> ORGANISM: Artificial Sequence
<220> FEATURE:
<223> OTHER INFORMATION: replicating RNA species

<400> SEQUENCE: 364
ggaaauuuca aauuucaauc aucgaaauuu caaauuucga ugauugaaau uugaaauuug      60
ggg                                                                   63

<210> SEQ ID NO 365
<211> LENGTH: 89
<212> TYPE: RNA
<213> ORGANISM: Artificial Sequence
<220> FEATURE:
<223> OTHER INFORMATION: replicating RNA species

<400> SEQUENCE: 365
ggauaaauuc auuaucuuca auucuccaga uaaugaauuu ugauuaucaa aaauucauua      60
ucuggagaau ugaagauaau gaauuucgg                                       89

<210> SEQ ID NO 366
<211> LENGTH: 98
<212> TYPE: RNA
<213> ORGANISM: Artificial Sequence
<220> FEATURE:
<223> OTHER INFORMATION: replicating RNA species

<400> SEQUENCE: 366
ggaaauauuc aauauuucac aggucacugu gaaauauuug gaauauuguc caaauuccaa      60
auauuucaca gugaccugug aaauauugaa uauuuggg                             98

<210> SEQ ID NO 367
<211> LENGTH: 78
<212> TYPE: RNA
<213> ORGANISM: Artificial Sequence
<220> FEATURE:
<223> OTHER INFORMATION: replicating RNA species

<400> SEQUENCE: 367
ggaaaauuga auacuucauu gcauuccauu caauuuuccc aaaauugaau ggaaugcaau      60
gaaguauuca auuuuggg                                                   78

<210> SEQ ID NO 368
<211> LENGTH: 77
<212> TYPE: RNA
<213> ORGANISM: Artificial Sequence
<220> FEATURE:
<223> OTHER INFORMATION: replicating RNA species

<400> SEQUENCE: 368
ggaaauuaau caauaaauuu agugcaauuc auuaaucaau aaauaaugaa uugcacuaaa      60
uuuauugauu aauuugg                                                    77

-continued

```
<210> SEQ ID NO 369
<211> LENGTH: 73
<212> TYPE: RNA
<213> ORGANISM: Artificial Sequence
<220> FEATURE:
<223> OTHER INFORMATION: replicating RNA species

<400> SEQUENCE: 369
ggaaauuugg ucucuuguca caucauccaa auuuccccca aauuuggaug augugacaag        60
agaccaaauu ugg                                                          73

<210> SEQ ID NO 370
<211> LENGTH: 72
<212> TYPE: RNA
<213> ORGANISM: Artificial Sequence
<220> FEATURE:
<223> OTHER INFORMATION: replicating RNA species

<400> SEQUENCE: 370
ggaaauuuga aauuucaaaa ucaaaugauu uugaaauuuc aaaaucauuu gauuuugaaa        60
uuucaaauuc gg                                                           72

<210> SEQ ID NO 371
<211> LENGTH: 93
<212> TYPE: RNA
<213> ORGANISM: Artificial Sequence
<220> FEATURE:
<223> OTHER INFORMATION: replicating RNA species

<400> SEQUENCE: 371
ggaaauauuu ucuuuucuag cauaucuaga aauauugaaa aauauuuucu uuuuucccaa        60
uauuucuaga uaugcuagaa aagaaaauau ugg                                    93

<210> SEQ ID NO 372
<211> LENGTH: 78
<212> TYPE: RNA
<213> ORGANISM: Artificial Sequence
<220> FEATURE:
<223> OTHER INFORMATION: replicating RNA species

<400> SEQUENCE: 372
ggaauauuga auuaauguaa uccacccaca uuaauucaca uugaauuaau gugguggauu        60
acauuaauuc aauauugg                                                     78

<210> SEQ ID NO 373
<211> LENGTH: 80
<212> TYPE: RNA
<213> ORGANISM: Artificial Sequence
<220> FEATURE:
<223> OTHER INFORMATION: replicating RNA species

<400> SEQUENCE: 373
ggaaauuuaa auacaauucc aagugccuug aauuguauuu aaauacaauu caaggcacuu        60
ggaauuguau uuaaauuugg                                                   80

<210> SEQ ID NO 374
<211> LENGTH: 63
<212> TYPE: RNA
<213> ORGANISM: Artificial Sequence
<220> FEATURE:
<223> OTHER INFORMATION: replicating RNA species
```

```
<400> SEQUENCE: 374
ggaaauuucu caaaauuuga cuugaaauuu cucaaaauuc aagucaaauu uugagaaauu     60
ugg                                                                   63

<210> SEQ ID NO 375
<211> LENGTH: 109
<212> TYPE: RNA
<213> ORGANISM: Artificial Sequence
<220> FEATURE:
<223> OTHER INFORMATION: replicating RNA species

<400> SEQUENCE: 375
ggaaaauauu cuucaacauu auauuugguu cauuacaagu ugaaauaaua uucuucaaca     60
uuauuucaac uuguaaugaa ccaaauauaa uguugaagaa uauuuuggg               109

<210> SEQ ID NO 376
<211> LENGTH: 85
<212> TYPE: RNA
<213> ORGANISM: Artificial Sequence
<220> FEATURE:
<223> OTHER INFORMATION: replicating RNA species

<400> SEQUENCE: 376
ggaauuauug gaauuuggcu aucuuauuaa uccaauaauu uggcauuau uggauuaaua     60 agauagccaa auuccaauaa uuggg                                          85

<210> SEQ ID NO 377
<211> LENGTH: 70
<212> TYPE: RNA
<213> ORGANISM: Artificial Sequence
<220> FEATURE:
<223> OTHER INFORMATION: replicating RNA species

<400> SEQUENCE: 377
ggaaauauca aucaaagccu uauauuugau uuuuccaaau aucaaauaua aggcuuugau     60
ugauauuugg                                                           70

<210> SEQ ID NO 378
<211> LENGTH: 85
<212> TYPE: RNA
<213> ORGANISM: Artificial Sequence
<220> FEATURE:
<223> OTHER INFORMATION: replicating RNA species

<400> SEQUENCE: 378
ggaauauuug cuuucuuuga uuauauucuu ugcaaauauu cccaaauauu ugcaaagaau     60
auaaucaaag aaagcaaaua uuggg                                          85

<210> SEQ ID NO 379
<211> LENGTH: 93
<212> TYPE: RNA
<213> ORGANISM: Artificial Sequence
<220> FEATURE:
<223> OTHER INFORMATION: replicating RNA species

<400> SEQUENCE: 379
ggaaauaaac uuccauauaa uauuggaaua uauuauauau ggaauaaacu uccauauaua     60
auauauucca auauuuauaug gaaguuuauu ggg                                93

<210> SEQ ID NO 380
<211> LENGTH: 76
```

<212> TYPE: RNA
<213> ORGANISM: Artificial Sequence
<220> FEATURE:
<223> OTHER INFORMATION: replicating RNA species

<400> SEQUENCE: 380
ggaaaaauug gauauugcug acucguuccc aauuuuuccc ggaaaauugg aacgagucag          60
caauauccaa uuuugg                                                          76

<210> SEQ ID NO 381
<211> LENGTH: 66
<212> TYPE: RNA
<213> ORGANISM: Artificial Sequence
<220> FEATURE:
<223> OTHER INFORMATION: replicating RNA species

<400> SEQUENCE: 381
gggaaauuug aaucucugcu ccauucaaau uuccaaauuu gaauggagca gagauucaaa          60
uuuggg                                                                    66

<210> SEQ ID NO 382
<211> LENGTH: 77
<212> TYPE: RNA
<213> ORGANISM: Artificial Sequence
<220> FEATURE:
<223> OTHER INFORMATION: replicating RNA species

<400> SEQUENCE: 382
ggaaauaauc aauaguuuua ccaacccuac uauugauuaa uaaucaauag uaggguuggu          60
aaacuauuga uuauugg                                                         77

<210> SEQ ID NO 383
<211> LENGTH: 87
<212> TYPE: RNA
<213> ORGANISM: Artificial Sequence
<220> FEATURE:
<223> OTHER INFORMATION: replicating RNA species

<400> SEQUENCE: 383
ggaaaauuag gaauuuugua gcauuuccau uuccuaauuu ucuacaaaau uaggaaaugg          60
aaaugcuaca aaauuccuaa uuuuggg                                              87

<210> SEQ ID NO 384
<211> LENGTH: 83
<212> TYPE: RNA
<213> ORGANISM: Artificial Sequence
<220> FEATURE:
<223> OTHER INFORMATION: replicating RNA species

<400> SEQUENCE: 384
ggaaauaaag aaguauuucu cuuuuccuua uuucucuuuu cuaaauaaag aaauaaggaa          60
aagagaaaua cuucuuuauu ugg                                                  83

<210> SEQ ID NO 385
<211> LENGTH: 65
<212> TYPE: RNA
<213> ORGANISM: Artificial Sequence
<220> FEATURE:
<223> OTHER INFORMATION: replicating RNA species

<400> SEQUENCE: 385
ggauaaauuc uauucgauuc cuagaauuuu cauuccauaa uucuaggaau cgaauagaau          60
uaugg                                                                                      65

<210> SEQ ID NO 386
<211> LENGTH: 73
<212> TYPE: RNA
<213> ORGANISM: Artificial Sequence
<220> FEATURE:
<223> OTHER INFORMATION: replicating RNA species

<400> SEQUENCE: 386
ggauugauua aaucaauaag gaauggcuuc uucauuuauu gaagaagcca uuccuuccuu        60
auugauuuca agg                                                           73

<210> SEQ ID NO 387
<211> LENGTH: 91
<212> TYPE: RNA
<213> ORGANISM: Artificial Sequence
<220> FEATURE:
<223> OTHER INFORMATION: replicating RNA species

<400> SEQUENCE: 387
ggaaaagaac uauuucaauu ccauucuuuu ggaaugaaau agauucuuuc uauuucauuc        60
caaaagaaug gaauugaaau aguucuuuug g                                       91

<210> SEQ ID NO 388
<211> LENGTH: 71
<212> TYPE: RNA
<213> ORGANISM: Artificial Sequence
<220> FEATURE:
<223> OTHER INFORMATION: replicating RNA species

<400> SEQUENCE: 388
ggaaaauugg aaaucaucau ucucauccaa uuuuccaaaa uuggaugaga augaugauuu        60
ccaauuuugg g                                                             71

<210> SEQ ID NO 389
<211> LENGTH: 70
<212> TYPE: RNA
<213> ORGANISM: Artificial Sequence
<220> FEATURE:
<223> OTHER INFORMATION: replicating RNA species

<400> SEQUENCE: 389
ggaauaaauu ggacuacuua auacacaauu uauuccaaua aauuguguau uaaguagucc        60
aauuuauugg                                                               70

<210> SEQ ID NO 390
<211> LENGTH: 79
<212> TYPE: RNA
<213> ORGANISM: Artificial Sequence
<220> FEATURE:
<223> OTHER INFORMATION: replicating RNA species

<400> SEQUENCE: 390
ggaaauaaca uuuucaucuc acaucagaaa uguuaauucc aaauaacauu ucugauguga        60
gaugaaaaug uuauuuggg                                                     79

<210> SEQ ID NO 391
<211> LENGTH: 66
<212> TYPE: RNA
<213> ORGANISM: Artificial Sequence
<220> FEATURE:
<223> OTHER INFORMATION: replicating RNA species -continued

<400> SEQUENCE: 391
ggaauaauuc aauaauuccu auauuauuga aauaauucaa uaauauagga auuauugaau          60
uauugg                                                                                                    66

<210> SEQ ID NO 392
<211> LENGTH: 82
<212> TYPE: RNA
<213> ORGANISM: Artificial Sequence
<220> FEATURE:
<223> OTHER INFORMATION: replicating RNA species

<400> SEQUENCE: 392
ggaauauuuc agaauucaau uacaucaauu ccgaauauuu uccaauauuc ggaauugaug          60
uaauugaauu cugaaauauu gg                                                                  82

<210> SEQ ID NO 393
<211> LENGTH: 65
<212> TYPE: RNA
<213> ORGANISM: Artificial Sequence
<220> FEATURE:
<223> OTHER INFORMATION: replicating RNA species

<400> SEQUENCE: 393
ggaaauuuca auguuaucau uacacauuga aaauuucaau guguaaugau aacauugaaa          60
uuugg                                                                                                       65

<210> SEQ ID NO 394
<211> LENGTH: 70
<212> TYPE: RNA
<213> ORGANISM: Artificial Sequence
<220> FEATURE:
<223> OTHER INFORMATION: replicating RNA species

<400> SEQUENCE: 394
ggauauuaca uuaucaaucc uugcgaugua auugauccua uuacaucgca aggauugaua          60
auguaauagg                                                                                           70

<210> SEQ ID NO 395
<211> LENGTH: 68
<212> TYPE: RNA
<213> ORGANISM: Artificial Sequence
<220> FEATURE:
<223> OTHER INFORMATION: replicating RNA species

<400> SEQUENCE: 395
ggaaauuauc auuucugauc aaagauauga uucaauuauc auaucuuuga ucagaaauga          60
uaauuugg                                                                                             68

<210> SEQ ID NO 396
<211> LENGTH: 79
<212> TYPE: RNA
<213> ORGANISM: Artificial Sequence
<220> FEATURE:
<223> OTHER INFORMATION: replicating RNA species

<400> SEQUENCE: 396
ggaaaauuuc aaauuauugu ggcugaaauu ugaaauuucc aaauuucaaa uuucagccac          60
aauaauuuga aauuuuggg                                                                         79

<210> SEQ ID NO 397

-continued

```
<211> LENGTH: 65
<212> TYPE: RNA
<213> ORGANISM: Artificial Sequence
<220> FEATURE:
<223> OTHER INFORMATION: replicating RNA species

<400> SEQUENCE: 397
ggaaaauuuc aaauaaugcc gauuauuuga aaauuucaaa uaaucggcau uauuugaaau        60
uuugg                                                                   65

<210> SEQ ID NO 398
<211> LENGTH: 85
<212> TYPE: RNA
<213> ORGANISM: Artificial Sequence
<220> FEATURE:
<223> OTHER INFORMATION: replicating RNA species

<400> SEQUENCE: 398
ggaaauuuca aacaaauuug uuguguguug uuugaauuuc aaacaaauuu caaaacaaca        60
cacaacaaau uuguuugaaa uuugg                                             85

<210> SEQ ID NO 399
<211> LENGTH: 66
<212> TYPE: RNA
<213> ORGANISM: Artificial Sequence
<220> FEATURE:
<223> OTHER INFORMATION: replicating RNA species

<400> SEQUENCE: 399
ggaaauuuac caauucaugg ggugguugaau uuaccaauuu accaccccau gaauuugguaa       60 auuggg                                                                  66

<210> SEQ ID NO 400
<211> LENGTH: 65
<212> TYPE: RNA
<213> ORGANISM: Artificial Sequence
<220> FEATURE:
<223> OTHER INFORMATION: replicating RNA species

<400> SEQUENCE: 400
ggggaauuuc auucaauuac ccgauugaug aaauuucauu caaucgggua auugaaugaa        60
auugg                                                                   65

<210> SEQ ID NO 401
<211> LENGTH: 77
<212> TYPE: RNA
<213> ORGANISM: Artificial Sequence
<220> FEATURE:
<223> OTHER INFORMATION: replicating RNA species

<400> SEQUENCE: 401
ggaauaauug auauaaugcg ucaaucaauu caauuauucc auaauugaau ugauugacgc        60
auuauaucaa uuauggg                                                      77

<210> SEQ ID NO 402
<211> LENGTH: 82
<212> TYPE: RNA
<213> ORGANISM: Artificial Sequence
<220> FEATURE:
<223> OTHER INFORMATION: replicating RNA species

<400> SEQUENCE: 402
ggaauauuuc aagaauguuu auccuuaucc auucuuuuga auauucaaga auggauaagg        60
```
auaaacauuc uugaaauauu gg                                                     82

<210> SEQ ID NO 403
<211> LENGTH: 70
<212> TYPE: RNA
<213> ORGANISM: Artificial Sequence
<220> FEATURE:
<223> OTHER INFORMATION: replicating RNA species

<400> SEQUENCE: 403
ggaaaauuuc gaaauuuccg aaauaucgaa auauccaaau uucgauauuu cggaaauuuc        60
gaaauuuugg                                                                  70

<210> SEQ ID NO 404
<211> LENGTH: 70
<212> TYPE: RNA
<213> ORGANISM: Artificial Sequence
<220> FEATURE:
<223> OTHER INFORMATION: replicating RNA species

<400> SEQUENCE: 404
ggaaaauuau caauugcacu cuugcaaauu gaaauuauca auuugcaaga gugcaauuga        60
uaauuuuggg                                                                  70

<210> SEQ ID NO 405
<211> LENGTH: 83
<212> TYPE: RNA
<213> ORGANISM: Artificial Sequence
<220> FEATURE:
<223> OTHER INFORMATION: replicating RNA species

<400> SEQUENCE: 405
ggaaauguuu auguuucuuu gcgauuuucc auaaacauuu ugcaaauguu uauggaaaau        60
cgcaaagaaa cauaaacauu ugg                                                    83

<210> SEQ ID NO 406
<211> LENGTH: 77
<212> TYPE: RNA
<213> ORGANISM: Artificial Sequence
<220> FEATURE:
<223> OTHER INFORMATION: replicating RNA species

<400> SEQUENCE: 406
ggaaaauuca aaucauuuag aguucggauu uaaauuuucc aaauucaaau ccgaacucua        60
aaugauuuga auuuugg                                                          77

<210> SEQ ID NO 407
<211> LENGTH: 70
<212> TYPE: RNA
<213> ORGANISM: Artificial Sequence
<220> FEATURE:
<223> OTHER INFORMATION: replicating RNA species

<400> SEQUENCE: 407
ggaaauugaa augcauuuca aauucaauuu uccaaauuga aaauugaauu gaaaugcauu        60
ucaauuuggg                                                                  70

<210> SEQ ID NO 408
<211> LENGTH: 69
<212> TYPE: RNA
<213> ORGANISM: Artificial Sequence
<220> FEATURE:

-continued

<223> OTHER INFORMATION: replicating RNA species

<400> SEQUENCE: 408
ggaaaauaau caauuccgga uuauugauua uuauuuccaa uaaucaauaa uccggaauug      60
auuauuugg                                                             69

<210> SEQ ID NO 409
<211> LENGTH: 64
<212> TYPE: RNA
<213> ORGANISM: Artificial Sequence
<220> FEATURE:
<223> OTHER INFORMATION: replicating RNA species

<400> SEQUENCE: 409
ggaaaaauug auucgaucau uucaauuuuu uccgaaaaau ugaaaugauc gaaucaauuu      60
uugg                                                                  64

<210> SEQ ID NO 410
<211> LENGTH: 89
<212> TYPE: RNA
<213> ORGANISM: Artificial Sequence
<220> FEATURE:
<223> OTHER INFORMATION: replicating RNA species

<400> SEQUENCE: 410
ggaauauuaa auacuuuauu cucccaauau uaaauacuuu auucggaaua aaguauuuaa      60
uauugggaga auaaaguauu uaauauugg                                        89

<210> SEQ ID NO 411
<211> LENGTH: 72
<212> TYPE: RNA
<213> ORGANISM: Artificial Sequence
<220> FEATURE:
<223> OTHER INFORMATION: replicating RNA species

<400> SEQUENCE: 411
ggaaaauauu uggcauauaa uauguauaau auuuucccaa auauuauaca uauuauaugc      60
caaauauuug gg                                                          72

<210> SEQ ID NO 412
<211> LENGTH: 71
<212> TYPE: RNA
<213> ORGANISM: Artificial Sequence
<220> FEATURE:
<223> OTHER INFORMATION: replicating RNA species

<400> SEQUENCE: 412
ggaaaauuaa uuaucaaaaa gcuguuccuu uaauuaucaa aaaggaacag cuuuuugaua      60
auuaauuuug g                                                          71

<210> SEQ ID NO 413
<211> LENGTH: 70
<212> TYPE: RNA
<213> ORGANISM: Artificial Sequence
<220> FEATURE:
<223> OTHER INFORMATION: replicating RNA species

<400> SEQUENCE: 413
ggaaauuauc auuucugauc aacccggaaa ugaauuauca uuuccggguu gaucagaaau      60
gauaauuugg                                                            70

-continued

```
<210> SEQ ID NO 414
<211> LENGTH: 63
<212> TYPE: RNA
<213> ORGANISM: Artificial Sequence
<220> FEATURE:
<223> OTHER INFORMATION: replicating RNA species

<400> SEQUENCE: 414
ggaauuuuuc aaacuuugga uccaguuuga auuuucaaac uggauccaaa guuugaaaau      60
ugg                                                                   63

<210> SEQ ID NO 415
<211> LENGTH: 67
<212> TYPE: RNA
<213> ORGANISM: Artificial Sequence
<220> FEATURE:
<223> OTHER INFORMATION: replicating RNA species

<400> SEQUENCE: 415
ggaaaauuuc aaugaucgau gggagcauug aaauuucaau gcucccaucg aucauugaaa      60
uuuuggg                                                               67

<210> SEQ ID NO 416
<211> LENGTH: 67
<212> TYPE: RNA
<213> ORGANISM: Artificial Sequence
<220> FEATURE:
<223> OTHER INFORMATION: replicating RNA species

<400> SEQUENCE: 416
ggaauauuug aaaaguuugg acuucuuuuc aaauauugaa aagaagucca aacuuuucaa      60
auauugg                                                               67

<210> SEQ ID NO 417
<211> LENGTH: 66
<212> TYPE: RNA
<213> ORGANISM: Artificial Sequence
<220> FEATURE:
<223> OTHER INFORMATION: replicating RNA species

<400> SEQUENCE: 417
ggaaauauuc aaaaucuacc cuugaauauu uuuccaaaua uucaagggua gauuuugaau      60
auuugg                                                               66

<210> SEQ ID NO 418
<211> LENGTH: 66
<212> TYPE: RNA
<213> ORGANISM: Artificial Sequence
<220> FEATURE:
<223> OTHER INFORMATION: replicating RNA species

<400> SEQUENCE: 418
ggaauauauc ugauugucua uuuagauauu uuccaauaua ucuaaauaga caaucagaua      60
uauugg                                                               66

<210> SEQ ID NO 419
<211> LENGTH: 73
<212> TYPE: RNA
<213> ORGANISM: Artificial Sequence
<220> FEATURE:
<223> OTHER INFORMATION: replicating RNA species

<400> SEQUENCE: 419
```

-continued ggaaaauugg auauucguag uugcuuccaa uuuucccgaa aaauuggaag caacuacgaa          60
uauccaauuu ugg                                                           73

<210> SEQ ID NO 420
<211> LENGTH: 79
<212> TYPE: RNA
<213> ORGANISM: Artificial Sequence
<220> FEATURE:
<223> OTHER INFORMATION: replicating RNA species

<400> SEQUENCE: 420
ggaacuuuuc auaaaucucc ucaacagugc gaugaacuuu ucauaaaucg cacuguugag          60
gagauuuaug aaaaguugg                                                      79

<210> SEQ ID NO 421
<211> LENGTH: 81
<212> TYPE: RNA
<213> ORGANISM: Artificial Sequence
<220> FEATURE:
<223> OTHER INFORMATION: replicating RNA species

<400> SEQUENCE: 421
ggauuuuuag ucauuuucaa aacgcgucug acuaaaaaag ccauuuuuag ucagacgcgu          60
uuugaaaaug acuaaaaaug g                                                   81

<210> SEQ ID NO 422
<211> LENGTH: 76
<212> TYPE: RNA
<213> ORGANISM: Artificial Sequence
<220> FEATURE:
<223> OTHER INFORMATION: replicating RNA species

<400> SEQUENCE: 422
ggaaaaauuc aacuuuuugu gcguugaguu gaauuuucca aaaauucaac ucaacgcaca          60
aaaaguugaa uuuugg                                                         76

<210> SEQ ID NO 423
<211> LENGTH: 71
<212> TYPE: RNA
<213> ORGANISM: Artificial Sequence
<220> FEATURE:
<223> OTHER INFORMATION: replicating RNA species

<400> SEQUENCE: 423
ggaaaauuuc augaucuuuu cucuugggaa auuucauaau uuuucccaag agaaaagauc          60
augaaauuug g                                                             71

<210> SEQ ID NO 424
<211> LENGTH: 74
<212> TYPE: RNA
<213> ORGANISM: Artificial Sequence
<220> FEATURE:
<223> OTHER INFORMATION: replicating RNA species

<400> SEQUENCE: 424
ggaauuaauc aaacucaucu uuucuauugu uugaauuaau caaacaauag aaaagaugag          60
uuugauuaau uggg                                                          74

<210> SEQ ID NO 425
<211> LENGTH: 81
<212> TYPE: RNA
<213> ORGANISM: Artificial Sequence

```
<220> FEATURE:
<223> OTHER INFORMATION: replicating RNA species

<400> SEQUENCE: 425
ggaaauucuc uuucaauauu caagaauuug agaauuucuu uccaaauucu caaauucuug      60
aauauugaaa gagaauuugg g                                                81

<210> SEQ ID NO 426
<211> LENGTH: 74
<212> TYPE: RNA
<213> ORGANISM: Artificial Sequence
<220> FEATURE:
<223> OTHER INFORMATION: replicating RNA species

<400> SEQUENCE: 426
ggaaaaauuc uaauaaguau caacuuucug aauuauucca aaauucagaa aguugauacu      60
uauuagaauu uugg                                                       74

<210> SEQ ID NO 427
<211> LENGTH: 69
<212> TYPE: RNA
<213> ORGANISM: Artificial Sequence
<220> FEATURE:
<223> OTHER INFORMATION: replicating RNA species

<400> SEQUENCE: 427
gggaaaucaa uuggaauaag cccaaaauug auuucaaauc aauuugggcu uauuccaauu      60
gauuugggg                                                            69

<210> SEQ ID NO 428
<211> LENGTH: 75
<212> TYPE: RNA
<213> ORGANISM: Artificial Sequence
<220> FEATURE:
<223> OTHER INFORMATION: replicating RNA species

<400> SEQUENCE: 428
gggggaaauu uguauuucau caaaugauga uuucaucaaa ugaugaaauc aucauuugau      60
gaaauacaaa uuugg                                                      75

<210> SEQ ID NO 429
<211> LENGTH: 71
<212> TYPE: RNA
<213> ORGANISM: Artificial Sequence
<220> FEATURE:
<223> OTHER INFORMATION: replicating RNA species

<400> SEQUENCE: 429
ggaaauucaa ucuauaacag ucauauaguu ugaaaaauuc aaucuauaug acguuauag      60 auugaauuug g                                                          71

<210> SEQ ID NO 430
<211> LENGTH: 90
<212> TYPE: RNA
<213> ORGANISM: Artificial Sequence
<220> FEATURE:
<223> OTHER INFORMATION: replicating RNA species

<400> SEQUENCE: 430
gggaaauauu guuguguauu ggauguugag uucguaacaa uauuccgaau auuguuacga      60
acucaacauc caauacacaa caauauuugg                                      90
```

```
<210> SEQ ID NO 431
<211> LENGTH: 72
<212> TYPE: RNA
<213> ORGANISM: Artificial Sequence
<220> FEATURE:
<223> OTHER INFORMATION: replicating RNA species

<400> SEQUENCE: 431
ggaaauugga auaaaugguu uauuacaauu uccaaauugg aaauuguaau aaaccauuua      60
uuccaauuug gg                                                        72

<210> SEQ ID NO 432
<211> LENGTH: 73
<212> TYPE: RNA
<213> ORGANISM: Artificial Sequence
<220> FEATURE:
<223> OTHER INFORMATION: replicating RNA species

<400> SEQUENCE: 432
ggaaaauugg aaauugagca acuguaccaa uuuucccgaa aauugguaca guugcucaau      60
uuccaauuuu ggg                                                       73

<210> SEQ ID NO 433
<211> LENGTH: 73
<212> TYPE: RNA
<213> ORGANISM: Artificial Sequence
<220> FEATURE:
<223> OTHER INFORMATION: replicating RNA species

<400> SEQUENCE: 433
ggaauaauug aauuacaacu ucaaaucaau uauucagcaa uaauugauuu gaaguuguaa      60
uucaauuauu ggg                                                       73

<210> SEQ ID NO 434
<211> LENGTH: 78
<212> TYPE: RNA
<213> ORGANISM: Artificial Sequence
<220> FEATURE:
<223> OTHER INFORMATION: replicating RNA species

<400> SEQUENCE: 434
ggaauaauuu gaaauuggca guuauuguuc aaauuauucu cccaaauuug aacaauaacu      60
gccaauuuca aauuuggg                                                  78

<210> SEQ ID NO 435
<211> LENGTH: 69
<212> TYPE: RNA
<213> ORGANISM: Artificial Sequence
<220> FEATURE:
<223> OTHER INFORMATION: replicating RNA species

<400> SEQUENCE: 435
ggaaaauuca aaacuuuucc gaaaaguuuu ugaaaauuca aaacuuuucg gaaaaguuuu      60
gaauuuugg                                                           69

<210> SEQ ID NO 436
<211> LENGTH: 78
<212> TYPE: RNA
<213> ORGANISM: Artificial Sequence
<220> FEATURE:
<223> OTHER INFORMATION: replicating RNA species

<400> SEQUENCE: 436
```

-continued

```
ggaauauuaa auacuuuauu cucccaauau aaaguauuaa auacuuuaua uugggagaau      60
aaaguauuua auauuggg                                                   78

<210> SEQ ID NO 437
<211> LENGTH: 92
<212> TYPE: RNA
<213> ORGANISM: Artificial Sequence
<220> FEATURE:
<223> OTHER INFORMATION: replicating RNA species

<400> SEQUENCE: 437
ggaaauauug guauuuaauu uuuacuguuu uucuaccaau auuucccaaa aauugguaga      60
aaaacaguaa aaauuaaaua ccaauauuug gg                                   92

<210> SEQ ID NO 438
<211> LENGTH: 89
<212> TYPE: RNA
<213> ORGANISM: Artificial Sequence
<220> FEATURE:
<223> OTHER INFORMATION: replicating RNA species

<400> SEQUENCE: 438
ggaaaaauaa augauauguu uccaucauuu aucauuuauu uuccuuaaaa auaaaugaua      60
aaugauggaa acauaucauu uauuuuugg                                       89

<210> SEQ ID NO 439
<211> LENGTH: 78
<212> TYPE: RNA
<213> ORGANISM: Artificial Sequence
<220> FEATURE:
<223> OTHER INFORMATION: replicating RNA species

<400> SEQUENCE: 439
ggaaauuuca aaguuacaag ucuccgacuu ugauuuugac aaauuucaaa gucggagacu      60
uguaacuuug aaauuugg                                                   78

<210> SEQ ID NO 440
<211> LENGTH: 79
<212> TYPE: RNA
<213> ORGANISM: Artificial Sequence
<220> FEATURE:
<223> OTHER INFORMATION: replicating RNA species

<400> SEQUENCE: 440
ggaagaauuu ugguagugaa agaugcuaca aauucuucga agaauuuuug uagcaucuuu      60
cacuaccaaa auucuuggg                                                  79

<210> SEQ ID NO 441
<211> LENGTH: 72
<212> TYPE: RNA
<213> ORGANISM: Artificial Sequence
<220> FEATURE:
<223> OTHER INFORMATION: replicating RNA species

<400> SEQUENCE: 441
ggaauaaauc uucaauaaau ccgaagauuu uauuuuucaa uaaaaucuuc ggauuuauug      60
aagauuuauu gg                                                         72

<210> SEQ ID NO 442
<211> LENGTH: 68
<212> TYPE: RNA
```

<213> ORGANISM: Artificial Sequence
<220> FEATURE:
<223> OTHER INFORMATION: replicating RNA species

<400> SEQUENCE: 442
gggaaaauca ucaaucgguu ccucugauga uuuuccaaau caucagagga accgauugau      60
gauuuggg                                                               68

<210> SEQ ID NO 443
<211> LENGTH: 75
<212> TYPE: RNA
<213> ORGANISM: Artificial Sequence
<220> FEATURE:
<223> OTHER INFORMATION: replicating RNA species

<400> SEQUENCE: 443
gggaaaauug gaaucgauac uccuauaucc aauuuucccc aaaauuggau auaggaguau      60
cgauuccaau uuugg                                                       75

<210> SEQ ID NO 444
<211> LENGTH: 69
<212> TYPE: RNA
<213> ORGANISM: Artificial Sequence
<220> FEATURE:
<223> OTHER INFORMATION: replicating RNA species

<400> SEQUENCE: 444
ggaaaauaug aauaucaauc cccauucaua uuucaaaaau augaaugggg auugauauuc      60
auauuuugg                                                              69

<210> SEQ ID NO 445
<211> LENGTH: 66
<212> TYPE: RNA
<213> ORGANISM: Artificial Sequence
<220> FEATURE:
<223> OTHER INFORMATION: replicating RNA species

<400> SEQUENCE: 445
ggauuaauuc aaauuaauua auggaauuaa uucaaauuaa uuccauuaau uaauuugaau      60
uaaugg                                                                 66

<210> SEQ ID NO 446
<211> LENGTH: 60
<212> TYPE: RNA
<213> ORGANISM: Artificial Sequence
<220> FEATURE:
<223> OTHER INFORMATION: replicating RNA species

<400> SEQUENCE: 446
ggaaaaauuc aaaucaagua ucgauuugaa auucaaaucg auacuugauu ugaauuuugg      60

<210> SEQ ID NO 447
<211> LENGTH: 69
<212> TYPE: RNA
<213> ORGANISM: Artificial Sequence
<220> FEATURE:
<223> OTHER INFORMATION: replicating RNA species

<400> SEQUENCE: 447
ggaaauuuga auugcaacca acgauucaaa uucucccaau uugaaucguu gguugcaauu      60
caaauuggg                                                              69

-continued

```
<210> SEQ ID NO 448
<211> LENGTH: 73
<212> TYPE: RNA
<213> ORGANISM: Artificial Sequence
<220> FEATURE:
<223> OTHER INFORMATION: replicating RNA species

<400> SEQUENCE: 448
gggaggagau ucaaauuuca gaaggacgau uugaauuuca gauucaaauc guccuucuga        60
aauuugaauc ugg                                                           73

<210> SEQ ID NO 449
<211> LENGTH: 68
<212> TYPE: RNA
<213> ORGANISM: Artificial Sequence
<220> FEATURE:
<223> OTHER INFORMATION: replicating RNA species

<400> SEQUENCE: 449
ggaaaaaagu ucuauucagu ccuagacuuu uuucuuccaa aagucuagga cugaauagaa        60
cuuuuggg                                                                 68

<210> SEQ ID NO 450
<211> LENGTH: 73
<212> TYPE: RNA
<213> ORGANISM: Artificial Sequence
<220> FEATURE:
<223> OTHER INFORMATION: replicating RNA species

<400> SEQUENCE: 450
ggauuauuuc uagauuauug aaauaaugaa auaacccauu auuucauuau uucaauaauc        60
uagaaauaau ggg                                                           73

<210> SEQ ID NO 451
<211> LENGTH: 55
<212> TYPE: RNA
<213> ORGANISM: Artificial Sequence
<220> FEATURE:
<223> OTHER INFORMATION: replicating RNA species

<400> SEQUENCE: 451
ggagaaauau ucauucucau auucaauagc auugcaauau gagaaugaau auugg            55

<210> SEQ ID NO 452
<211> LENGTH: 61
<212> TYPE: RNA
<213> ORGANISM: Artificial Sequence
<220> FEATURE:
<223> OTHER INFORMATION: replicating RNA species

<400> SEQUENCE: 452
ggaaaauuuc uaauaauucu agaaauuucu aauaaauuuc uagaauuauu agaaauuuug        60
g                                                                        61

<210> SEQ ID NO 453
<211> LENGTH: 78
<212> TYPE: RNA
<213> ORGANISM: Artificial Sequence
<220> FEATURE:
<223> OTHER INFORMATION: replicating RNA species

<400> SEQUENCE: 453
ggaaaucauu ggaauuuugu uggcuuucca augauccuc aucaucauug gaaagccaac         60
```

-continued aaaauuccaa ugauuugg                                                                          78

<210> SEQ ID NO 454
<211> LENGTH: 72
<212> TYPE: RNA
<213> ORGANISM: Artificial Sequence
<220> FEATURE:
<223> OTHER INFORMATION: replicating RNA species

<400> SEQUENCE: 454
ggaauaauuc aaaauaauuc uaucucauuu ugaaauaauu caaaaugaga uagaauuauu          60
uugaauuauu gg                                                              72

<210> SEQ ID NO 455
<211> LENGTH: 78
<212> TYPE: RNA
<213> ORGANISM: Artificial Sequence
<220> FEATURE:
<223> OTHER INFORMATION: replicating RNA species

<400> SEQUENCE: 455
ggaauucaau ucaaaaguuu ccuuuugacu uuugaauuca auucaaaagu caaaaggaaa          60
cuuuugaauu gaauuggg                                                        78

<210> SEQ ID NO 456
<211> LENGTH: 67
<212> TYPE: RNA
<213> ORGANISM: Artificial Sequence
<220> FEATURE:
<223> OTHER INFORMATION: replicating RNA species

<400> SEQUENCE: 456
ggaaaauuuc aaacuaccau ucccuguuug aaaauuucaa acagggaaug guaguuugaa          60
auuuggg                                                                    67

<210> SEQ ID NO 457
<211> LENGTH: 104
<212> TYPE: RNA
<213> ORGANISM: Artificial Sequence
<220> FEATURE:
<223> OTHER INFORMATION: replicating RNA species

<400> SEQUENCE: 457
ggaacauaau guuuguuucc acauaauguu acaugugugg aaacauuauu acacauaaug          60
uuuccacaca uguaacauua uguggaaaca aacauuaugu uggg                          104

<210> SEQ ID NO 458
<211> LENGTH: 70
<212> TYPE: RNA
<213> ORGANISM: Artificial Sequence
<220> FEATURE:
<223> OTHER INFORMATION: replicating RNA species

<400> SEQUENCE: 458
ggaaaaauau aaauauaaga gaguauuuau auuuagaaaa uauaaauacu cucuuauauu          60
uauauuuugg                                                                 70

<210> SEQ ID NO 459
<211> LENGTH: 88
<212> TYPE: RNA
<213> ORGANISM: Artificial Sequence
<220> FEATURE:
<223> OTHER INFORMATION: replicating RNA species

<400> SEQUENCE: 459
ggauugaauu caauuucacu gaauucagug aaauucgaau uuuggauuga auucaauuuc          60
acugaauuca gugaaauucg aauuuugg                                            88

<210> SEQ ID NO 460
<211> LENGTH: 76
<212> TYPE: RNA
<213> ORGANISM: Artificial Sequence
<220> FEATURE:
<223> OTHER INFORMATION: replicating RNA species

<400> SEQUENCE: 460
ggaaaauuca auucuaucua uucaacaaua gaaaauucaa uucuaucuau uguugaauag          60
auagaauuga auuugg                                                         76

<210> SEQ ID NO 461
<211> LENGTH: 74
<212> TYPE: RNA
<213> ORGANISM: Artificial Sequence
<220> FEATURE:
<223> OTHER INFORMATION: replicating RNA species

<400> SEQUENCE: 461
ggaauuuuca gauauuuauu gccucuauau cugauaaauu ucagauauag aggcaauaaa          60
uaucugaaau uugg                                                           74

<210> SEQ ID NO 462
<211> LENGTH: 84
<212> TYPE: RNA
<213> ORGANISM: Artificial Sequence
<220> FEATURE:
<223> OTHER INFORMATION: replicating RNA species

<400> SEQUENCE: 462
gggaaaaauu caauugauaa uacaauguuu ccauugaauu ucaaaaauuc aauggaaaca          60
uuguauuauc aauugaauuu uugg                                                84

<210> SEQ ID NO 463
<211> LENGTH: 72
<212> TYPE: RNA
<213> ORGANISM: Artificial Sequence
<220> FEATURE:
<223> OTHER INFORMATION: replicating RNA species

<400> SEQUENCE: 463
ggaaaaauuc aaugaugcuu cguuucauug aauucaaaau ucaggaaac gaagcaucau           60 ugaauuuugg gg                                                             72

<210> SEQ ID NO 464
<211> LENGTH: 75
<212> TYPE: RNA
<213> ORGANISM: Artificial Sequence
<220> FEATURE:
<223> OTHER INFORMATION: replicating RNA species

<400> SEQUENCE: 464
ggggaaaauu gauauugcag acuuuuuuuu caauaucaaa uugauauuga aaaaaagucu          60
gcaauaucaa uuugg                                                          75

<210> SEQ ID NO 465

<211> LENGTH: 69
<212> TYPE: RNA
<213> ORGANISM: Artificial Sequence
<220> FEATURE:
<223> OTHER INFORMATION: replicating RNA species

<400> SEQUENCE: 465
ggggaugaaa uucaauucga dacgaauuuc auuucaauga aauucgucuc gaauugaauu    60
ucauugggg                                                          69

<210> SEQ ID NO 466
<211> LENGTH: 73
<212> TYPE: RNA
<213> ORGANISM: Artificial Sequence
<220> FEATURE:
<223> OTHER INFORMATION: replicating RNA species

<400> SEQUENCE: 466
ggaaaaaauc aauucaauuc aauugauuuu ugaaucaauc ccaaaaauca auugaauuga    60
auugauuuuu ggg                                                      73

<210> SEQ ID NO 467
<211> LENGTH: 79
<212> TYPE: RNA
<213> ORGANISM: Artificial Sequence
<220> FEATURE:
<223> OTHER INFORMATION: replicating RNA species

<400> SEQUENCE: 467
ggauuaaaau caaaugaucc uauucuccau cauuugaauu aaaaucaaau gauggagaau    60
aggaucauuu gauuuucgg                                                79

<210> SEQ ID NO 468
<211> LENGTH: 77
<212> TYPE: RNA
<213> ORGANISM: Artificial Sequence
<220> FEATURE:
<223> OTHER INFORMATION: replicating RNA species

<400> SEQUENCE: 468
ggggaaaauu gauuuucaau ucaauuucga aauugauuuc uuucaauuuc gaaauugaau    60
ugaaaaucaa uuuuggg                                                  77

<210> SEQ ID NO 469
<211> LENGTH: 88
<212> TYPE: RNA
<213> ORGANISM: Artificial Sequence
<220> FEATURE:
<223> OTHER INFORMATION: replicating RNA species

<400> SEQUENCE: 469
ggggaauauu ucauuucuua uauccaauau uuccgaaaua uuucccaaua uuucggaaau    60
auuggauaua agaaaugaaa uauuggggg                                     88

<210> SEQ ID NO 470
<211> LENGTH: 68
<212> TYPE: RNA
<213> ORGANISM: Artificial Sequence
<220> FEATURE:
<223> OTHER INFORMATION: replicating RNA species

<400> SEQUENCE: 470
ggaauaauaa aggauucaaa uaucauuauu auaccaauaa uaaugauauu ugaauccuuu    60
auuauugg                                                              68

<210> SEQ ID NO 471
<211> LENGTH: 70
<212> TYPE: RNA
<213> ORGANISM: Artificial Sequence
<220> FEATURE:
<223> OTHER INFORMATION: replicating RNA species

<400> SEQUENCE: 471
gguauaauaa ugauauuuga auccuuuauu auuccccaau aauaaaggau ucaaauauca      60
uuauuauugg                                                            70

<210> SEQ ID NO 472
<211> LENGTH: 78
<212> TYPE: RNA
<213> ORGANISM: Artificial Sequence
<220> FEATURE:
<223> OTHER INFORMATION: replicating RNA species

<400> SEQUENCE: 472
ggaauaauaa aggauucaaa uaucauuauu auaccaauaa uaaugauauu uaaugauauu      60
ugaauccuuu auuauugg                                                   78

<210> SEQ ID NO 473
<211> LENGTH: 59
<212> TYPE: RNA
<213> ORGANISM: Artificial Sequence
<220> FEATURE:
<223> OTHER INFORMATION: replicating RNA species

<400> SEQUENCE: 473
ggaauaauaa aggauucaaa uaucauuauu auaaugauau uugaauccuu uauuauugg       59

<210> SEQ ID NO 474
<211> LENGTH: 74
<212> TYPE: RNA
<213> ORGANISM: Artificial Sequence
<220> FEATURE:
<223> OTHER INFORMATION: replicating RNA species

<400> SEQUENCE: 474
ggaugaaauc uuucagacgu uuucucugau uuuuugucca agaaaucaga gaaaacgucu      60
gaaagauuuc uugg                                                       74

<210> SEQ ID NO 475
<211> LENGTH: 66
<212> TYPE: RNA
<213> ORGANISM: Artificial Sequence
<220> FEATURE:
<223> OTHER INFORMATION: replicating RNA species

<400> SEQUENCE: 475
ggaugaaauc uuucagacgu uuucucugau uuuuuuuca gagaaaacgu cugaaagauu       60
ucuugg                                                                66

<210> SEQ ID NO 476
<211> LENGTH: 71
<212> TYPE: RNA
<213> ORGANISM: Artificial Sequence
<220> FEATURE:
<223> OTHER INFORMATION: replicating RNA species -continued

<400> SEQUENCE: 476
ggaaaauuuc uauaucacau uacauaugua auuuucuaua uuacauaugu aaugugauau        60
agaaauuuug g                                                             71

<210> SEQ ID NO 477
<211> LENGTH: 78
<212> TYPE: RNA
<213> ORGANISM: Artificial Sequence
<220> FEATURE:
<223> OTHER INFORMATION: replicating RNA species

<400> SEQUENCE: 477
ggaaaaauaa aucuuuauca uuuuaccuga agauuuauga aauaaaucuu cagguaaaau        60
gauaaagauu uauuuugg                                                      78

<210> SEQ ID NO 478
<211> LENGTH: 64
<212> TYPE: RNA
<213> ORGANISM: Artificial Sequence
<220> FEATURE:
<223> OTHER INFORMATION: replicating RNA species

<400> SEQUENCE: 478
ggaagaauua augguauuuc uauuauaauu ugcaaauuau aauagaaaua ccauuaauuc        60
uugg                                                                     64

<210> SEQ ID NO 479
<211> LENGTH: 73
<212> TYPE: RNA
<213> ORGANISM: Artificial Sequence
<220> FEATURE:
<223> OTHER INFORMATION: replicating RNA species

<400> SEQUENCE: 479
ggaaaaauuc aaugaagcgc uuccuugaau uugaaaguga agaaauucaa ugaagcgcuu        60
cauugaauuu ugg                                                           73

<210> SEQ ID NO 480
<211> LENGTH: 78
<212> TYPE: RNA
<213> ORGANISM: Artificial Sequence
<220> FEATURE:
<223> OTHER INFORMATION: replicating RNA species

<400> SEQUENCE: 480
ggacaaaaaa ucagagaaaa cgucugaaag auuucauccc caagaaaucu uucagacguu        60
uuucucugau uucuuggg                                                      78

<210> SEQ ID NO 481
<211> LENGTH: 80
<212> TYPE: RNA
<213> ORGANISM: Artificial Sequence
<220> FEATURE:
<223> OTHER INFORMATION: replicating RNA species

<400> SEQUENCE: 481
ggaagaauua augguauuuc uauuauaauu ugcggauaaa aaauugugca aauuauaaua        60
gaaauaccau uaauucuugg                                                    80

<210> SEQ ID NO 482
<211> LENGTH: 88

-continued

```
<212> TYPE: RNA
<213> ORGANISM: Artificial Sequence
<220> FEATURE:
<223> OTHER INFORMATION: replicating RNA species

<400> SEQUENCE: 482
ggaugaaauc uuucagacgu uuucucugau uuuuuugucc aagaaaucag agaaaaaaau      60
cagagaaaac gucugaaaga uuucuugg                                        88

<210> SEQ ID NO 483
<211> LENGTH: 65
<212> TYPE: RNA
<213> ORGANISM: Artificial Sequence
<220> FEATURE:
<223> OTHER INFORMATION: replicating RNA species

<400> SEQUENCE: 483
ggaugaaauc uuucagacgu uuucucugau uaaaucagag aaaaaacguc ugaaagauuu      60
cuugg                                                                 65

<210> SEQ ID NO 484
<211> LENGTH: 50
<212> TYPE: RNA
<213> ORGANISM: Artificial Sequence
<220> FEATURE:
<223> OTHER INFORMATION: replicating RNA species

<400> SEQUENCE: 484
ggaagaauua augguauuuc uauuauaaua gaaauaccau uaauucaugg                50

<210> SEQ ID NO 485
<211> LENGTH: 67
<212> TYPE: RNA
<213> ORGANISM: Artificial Sequence
<220> FEATURE:
<223> OTHER INFORMATION: replicating RNA species

<400> SEQUENCE: 485
ggaauauuuc uucaauucaa caugaaauaa uauuccaaua uuucauguug aauugaagaa      60
auauugg                                                               67

<210> SEQ ID NO 486
<211> LENGTH: 80
<212> TYPE: RNA
<213> ORGANISM: Artificial Sequence
<220> FEATURE:
<223> OTHER INFORMATION: replicating RNA species

<400> SEQUENCE: 486
ggauaauaau aauugaauuc cauuuuccaa uuauuaucca aauauaauaa uuggaaaaug      60
gaauucaauu auuauuuugg                                                 80

<210> SEQ ID NO 487
<211> LENGTH: 92
<212> TYPE: RNA
<213> ORGANISM: Artificial Sequence
<220> FEATURE:
<223> OTHER INFORMATION: replicating RNA species

<400> SEQUENCE: 487
ggauaauucu aauagucaau ucucccuauu uagaauuaua auauauauua uauauaauuc      60 uaauaggggga gaauugacua uuagaauuau gg                                  92
```

-continued

```
<210> SEQ ID NO 488
<211> LENGTH: 87
<212> TYPE: RNA
<213> ORGANISM: Artificial Sequence
<220> FEATURE:
<223> OTHER INFORMATION: replicating RNA species

<400> SEQUENCE: 488
ggaaaauuau aguucuacuu cgauauuuga aaacuauaaa auuccaaauu auaguuuuca      60
aauaucgaag uagaacuaua auuuggg                                         87

<210> SEQ ID NO 489
<211> LENGTH: 80
<212> TYPE: RNA
<213> ORGANISM: Artificial Sequence
<220> FEATURE:
<223> OTHER INFORMATION: replicating RNA species

<400> SEQUENCE: 489
ggaaauuuca auaugaauau uuuguuucgu auuugauuuu aaauuucaau acgaaacaaa      60
auauucauau ugaaauuugg                                                 80

<210> SEQ ID NO 490
<211> LENGTH: 68
<212> TYPE: RNA
<213> ORGANISM: Artificial Sequence
<220> FEATURE:
<223> OTHER INFORMATION: replicating RNA species

<400> SEQUENCE: 490
gggagauuau acucauucga acccagagua uaugauuaua cucuggguuc gaaugaguau      60
aaucaugg                                                             68

<210> SEQ ID NO 491
<211> LENGTH: 68
<212> TYPE: RNA
<213> ORGANISM: Artificial Sequence
<220> FEATURE:
<223> OTHER INFORMATION: replicating RNA species

<400> SEQUENCE: 491
ggaaaauuuc aaauucaagc cugaaugaaa uuuuucaaau ucauucaggc uugaauuuga      60
aauuuugg                                                             68

<210> SEQ ID NO 492
<211> LENGTH: 42
<212> TYPE: RNA
<213> ORGANISM: Artificial Sequence
<220> FEATURE:
<223> OTHER INFORMATION: replicating RNA species

<400> SEQUENCE: 492
ggaauauuuc uucaauucaa uguugaauug aagaaauauu gg                       42

<210> SEQ ID NO 493
<211> LENGTH: 77
<212> TYPE: RNA
<213> ORGANISM: Artificial Sequence
<220> FEATURE:
<223> OTHER INFORMATION: replicating RNA species

<400> SEQUENCE: 493
ggaaaauaua auucauauug gaagacagaa uuauuuauac aaauauaauu cugucuucca      60
```

-continued auaugaauua uauuugg                                                              77

<210> SEQ ID NO 494
<211> LENGTH: 81
<212> TYPE: RNA
<213> ORGANISM: Artificial Sequence
<220> FEATURE:
<223> OTHER INFORMATION: replicating RNA species

<400> SEQUENCE: 494
ggaaaaauua aacaaaaaug cuuuguaugu uuaauuuuca uccaaaauua aacauacaaa        60
gcauuuuugu uuaauuuugg g                                                          81

<210> SEQ ID NO 495
<211> LENGTH: 81
<212> TYPE: RNA
<213> ORGANISM: Artificial Sequence
<220> FEATURE:
<223> OTHER INFORMATION: replicating RNA species

<400> SEQUENCE: 495
ggaaaaauaa ucgaaauauu uugaucgauu auuuugauua aguucaaaaa uaaucgauca        60
aaauauuucg auuauuuugg g                                                          81

<210> SEQ ID NO 496
<211> LENGTH: 67
<212> TYPE: RNA
<213> ORGANISM: Artificial Sequence
<220> FEATURE:
<223> OTHER INFORMATION: replicating RNA species

<400> SEQUENCE: 496
gggaaaauau uuguuucaga ucuccaaaua uuugccaaau auuuggagau cugaaacaaa        60
uauuugg                                                                         67

<210> SEQ ID NO 497
<211> LENGTH: 73
<212> TYPE: RNA
<213> ORGANISM: Artificial Sequence
<220> FEATURE:
<223> OTHER INFORMATION: replicating RNA species

<400> SEQUENCE: 497
ggaaaauuug aauucaauuc ucugaagaau ucaaauuuug aauucuucag agaauugaau        60
ucaaauuugg ggg                                                                  73

<210> SEQ ID NO 498
<211> LENGTH: 73
<212> TYPE: RNA
<213> ORGANISM: Artificial Sequence
<220> FEATURE:
<223> OTHER INFORMATION: replicating RNA species

<400> SEQUENCE: 498
ggaauuaaua uuauucauau ucaauugaug aauuaauauu auucaucaau ugaauaugaa        60
uaauauuaau ugg                                                                  73

<210> SEQ ID NO 499
<211> LENGTH: 75
<212> TYPE: RNA
<213> ORGANISM: Artificial Sequence
<220> FEATURE:

<223> OTHER INFORMATION: replicating RNA species

<400> SEQUENCE: 499
ggauauaaua guacaucuuc aauuccuacu auuaauaucc aauaauagua ggaauugaag        60
auguacuauu auugg                                                        75

<210> SEQ ID NO 500
<211> LENGTH: 30
<212> TYPE: DNA
<213> ORGANISM: Artificial Sequence
<220> FEATURE:
<223> OTHER INFORMATION: AF-NJ-269 oligo
<220> FEATURE:
<221> NAME/KEY: misc_feature
<222> LOCATION: (1)..(8)
<223> OTHER INFORMATION: n is a, c, g, or t
<220> FEATURE:
<221> NAME/KEY: misc_feature
<222> LOCATION: (30)..(30)
<223> OTHER INFORMATION: Dideoxycytidine

<400> SEQUENCE: 500
nnnnnnnnag atcggaagag cacacgtctc                                        30

<210> SEQ ID NO 501
<211> LENGTH: 102
<212> TYPE: DNA
<213> ORGANISM: Artificial Sequence
<220> FEATURE:
<223> OTHER INFORMATION: AF-NJ-200 oligo
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (82)..(85)
<223> OTHER INFORMATION: n is a, c, g, or t

<400> SEQUENCE: 501
ccaaaattng tangtagtag tacnaaattt tggaaaattt ngtactacta cntacnaatt        60
ttcctatagt gagtcgtatt annnntaata cgactcacta ta                         102

<210> SEQ ID NO 502
<211> LENGTH: 102
<212> TYPE: DNA
<213> ORGANISM: Artificial Sequence
<220> FEATURE:
<223> OTHER INFORMATION: AF-NJ-201 oligo
<220> FEATURE:
<221> NAME/KEY: misc_feature

```
<222> LOCATION: (10)..(10)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (82)..(85)
<223> OTHER INFORMATION: n is a, c, g, or t

<400> SEQUENCE: 502
ccaaaattan tagntagtag tantaaattt tggaaaattt antactacta nctantaatt      60
ttcctatagt gagtcgtatt annnntaata cgactcacta ta                       102

<210> SEQ ID NO 503
<211> LENGTH: 102
<212> TYPE: DNA
<213> ORGANISM: Artificial Sequence
<220> FEATURE:
<223> OTHER INFORMATION: AF-JTG-11 oligo
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (82)..(85)
<223> OTHER INFORMATION: n is a, c, g, or t

<400> SEQUENCE: 503
ccaaaattag taggtantag tantaaattt tgnaaaattt antactanta cctactaatt      60
ttcctatagt gagtcgtatt annnntaata cgactcacta ta                       102

<210> SEQ ID NO 504
<211> LENGTH: 102
<212> TYPE: DNA
<213> ORGANISM: Artificial Sequence
<220> FEATURE:
<223> OTHER INFORMATION: AF-JTG-13 oligo
<220> FEATURE:
```

```
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (82)..(85)
<223> OTHER INFORMATION: n is a, c, g, or t

<400> SEQUENCE: 504
ccaaaatttn aagatcaggg cttnaaattt tgnaaaattt naagccctga tcttnaaatt      60
ttcctatagt gagtcgtatt annnntaata cgactcacta ta                       102

<210> SEQ ID NO 505
<211> LENGTH: 70
<212> TYPE: DNA
<213> ORGANISM: Artificial Sequence
<220> FEATURE:
<223> OTHER INFORMATION: AF-KLA-67 oligo

<400> SEQUENCE: 505
aatgatacgg cgaccaccga gatctacact atagcctaca ctctttccct acacgacgct      60
cttccgatct                                                           70

<210> SEQ ID NO 506
<211> LENGTH: 70
<212> TYPE: DNA
<213> ORGANISM: Artificial Sequence
<220> FEATURE:
<223> OTHER INFORMATION: AF-KLA-68 oligo

<400> SEQUENCE: 506
aatgatacgg cgaccaccga gatctacaca tagaggcaca ctctttccct acacgacgct      60
cttccgatct                                                           70

<210> SEQ ID NO 507
<211> LENGTH: 70
<212> TYPE: DNA
<213> ORGANISM: Artificial Sequence
<220> FEATURE:
<223> OTHER INFORMATION: AF-KLA-69 oligo

<400> SEQUENCE: 507
aatgatacgg cgaccaccga gatctacacc ctatcctaca ctctttccct acacgacgct      60
cttccgatct                                                           70

<210> SEQ ID NO 508
<211> LENGTH: 68
<212> TYPE: DNA
<213> ORGANISM: Artificial Sequence
<220> FEATURE:
<223> OTHER INFORMATION: AF-KLA-70 oligo
```

-continued

<400> SEQUENCE: 508
aatgatacgg cgaccaccga gatctacacg gctctgaaca ctctttccct acacgacgct    60
cttccgat                                                             68

<210> SEQ ID NO 509
<211> LENGTH: 70
<212> TYPE: DNA
<213> ORGANISM: Artificial Sequence
<220> FEATURE:
<223> OTHER INFORMATION: AF-KLA-71 oligo

<400> SEQUENCE: 509
aatgatacgg cgaccaccga gatctacaca ggcgaagaca ctctttccct acacgacgct    60
cttccgatct                                                           70

<210> SEQ ID NO 510
<211> LENGTH: 70
<212> TYPE: DNA
<213> ORGANISM: Artificial Sequence
<220> FEATURE:
<223> OTHER INFORMATION: AF-KLA-72 oligo

<400> SEQUENCE: 510
aatgatacgg cgaccaccga gatctacact aatcttaaca ctctttccct acacgacgct    60
cttccgatct                                                           70

<210> SEQ ID NO 511
<211> LENGTH: 70
<212> TYPE: DNA
<213> ORGANISM: Artificial Sequence
<220> FEATURE:
<223> OTHER INFORMATION: AF-KLA-73 olgio

<400> SEQUENCE: 511
aatgatacgg cgaccaccga gatctacacc aggacgtaca ctctttccct acacgacgct    60
cttccgatct                                                           70

<210> SEQ ID NO 512
<211> LENGTH: 70
<212> TYPE: DNA
<213> ORGANISM: Artificial Sequence
<220> FEATURE:
<223> OTHER INFORMATION: AF-KLA-74 oligo

<400> SEQUENCE: 512
aatgatacgg cgaccaccga gatctacacg tactgacaca ctctttccct acacgacgct    60
cttccgatct                                                           70

<210> SEQ ID NO 513
<211> LENGTH: 66
<212> TYPE: DNA
<213> ORGANISM: Artificial Sequence
<220> FEATURE:
<223> OTHER INFORMATION: AF-ZF-838 oligo

<400> SEQUENCE: 513
caagcagaag acggcatacg agatcgagta atgtgactgg agttcagacg tgtgctcttc    60
cgatct                                                               66

<210> SEQ ID NO 514

```
<211> LENGTH: 66
<212> TYPE: DNA
<213> ORGANISM: Artificial Sequence
<220> FEATURE:
<223> OTHER INFORMATION: AF-ZF-839 oligo

<400> SEQUENCE: 514
caagcagaag acggcatacg agattctccg gagtgactgg agttcagacg tgtgctcttc      60
cgatct                                                                 66

<210> SEQ ID NO 515
<211> LENGTH: 66
<212> TYPE: DNA
<213> ORGANISM: Artificial Sequence
<220> FEATURE:
<223> OTHER INFORMATION: AF-ZF-840 oligo

<400> SEQUENCE: 515
caagcagaag acggcatacg agataatgag cggtgactgg agttcagacg tgtgctcttc      60
cgatct                                                                 66

<210> SEQ ID NO 516
<211> LENGTH: 66
<212> TYPE: DNA
<213> ORGANISM: Artificial Sequence
<220> FEATURE:
<223> OTHER INFORMATION: AF-ZF-841 oligo

<400> SEQUENCE: 516
caagcagaag acggcatacg agatggaatc tcgtgactgg agttcagacg tgtgctcttc      60
cgatct                                                                 66

<210> SEQ ID NO 517
<211> LENGTH: 66
<212> TYPE: DNA
<213> ORGANISM: Artificial Sequence
<220> FEATURE:
<223> OTHER INFORMATION: AF-ZF-842 oligo

<400> SEQUENCE: 517
caagcagaag acggcatacg agatttctga atgtgactgg agttcagacg tgtgctcttc      60
cgatct                                                                 66

<210> SEQ ID NO 518
<211> LENGTH: 66
<212> TYPE: DNA
<213> ORGANISM: Artificial Sequence
<220> FEATURE:
<223> OTHER INFORMATION: AF-ZF-843 oligo

<400> SEQUENCE: 518
caagcagaag acggcatacg agatacgaat tcgtgactgg agttcagacg tgtgctcttc      60
cgatct                                                                 66
```

-continued

```
<210> SEQ ID NO 519
<211> LENGTH: 84
<212> TYPE: RNA
<213> ORGANISM: Artificial Sequence
<220> FEATURE:
<223> OTHER INFORMATION: 2A RNA

<400> SEQUENCE: 519
ggaaaauuuc aaacauuaug uuguaauuug uuugaaaauu ucaaacaaau uacaacauaa          60
uguuugaaau uuugggggga aaau                                                84

<210> SEQ ID NO 520
<211> LENGTH: 68
<212> TYPE: RNA
<213> ORGANISM: Artificial Sequence
<220> FEATURE:
<223> OTHER INFORMATION: 2B RNA

<400> SEQUENCE: 520
cccaauauca ucaauugcug acgaagauga uauugauaau aucaucuucg ucagcaauug          60
augauauu                                                                  68

<210> SEQ ID NO 521
<211> LENGTH: 67
<212> TYPE: RNA
<213> ORGANISM: Artificial Sequence
<220> FEATURE:
<223> OTHER INFORMATION: 2C RNA

<400> SEQUENCE: 521
ggaaaaucaa ugacugguca aucucauuga uuuuugaaau caaugagauu gaccagucau          60
ugauuuu                                                                   67
```